US007425544B2

(12) United States Patent
Dobie et al.

(10) Patent No.: US 7,425,544 B2
(45) Date of Patent: Sep. 16, 2008

(54) MODULATION OF EIF4E EXPRESSION

(75) Inventors: Kenneth Dobie, Del Mar, CA (US); Eric G. Marcusson, San Francisco, CA (US); Eric E. Swayze, Carlsbad, CA (US); Balkrishen Bhat, Carlsbad, CA (US); Jeremy Richard Graff, Indianapolis, IN (US)

(73) Assignees: Eli Lilly and Company, Indianapolis, IN (US); ISIS Pharmaceuticals, Inc., Carlsbad, CA (US)

( * ) Notice: Subject to any disclaimer, the term of this patent is extended or adjusted under 35 U.S.C. 154(b) by 143 days.

(21) Appl. No.: 10/571,339

(22) PCT Filed: Sep. 17, 2004

(86) PCT No.: PCT/US2004/030436

§ 371 (c)(1),
(2), (4) Date: Nov. 29, 2006

(87) PCT Pub. No.: WO2005/028628

PCT Pub. Date: Mar. 31, 2005

(65) Prior Publication Data

US 2007/0066549 A1    Mar. 22, 2007

(51) Int. Cl.
*A61K 31/70* (2006.01)
*C07H 21/02* (2006.01)
*C07H 21/04* (2006.01)
*C12N 5/00* (2006.01)
*C12Q 1/68* (2006.01)

(52) U.S. Cl. .................. 514/44; 536/24.1; 536/24.5; 536/23.1; 435/6; 435/375; 435/377

(58) Field of Classification Search .................. None
See application file for complete search history.

(56) References Cited

FOREIGN PATENT DOCUMENTS

| WO | WO 02/44321 | 6/2000 |
| WO | WO 01/96388 A2 | 12/2001 |
| WO | WO 02/10409 | 2/2002 |
| WO | WO 2004113496 A2 * | 12/2004 |

OTHER PUBLICATIONS

Rychlik, et al., "Amino acid sequence of the mRNA cap-binding protein from human tissues," *Proc. Natl. Acad. Sci.*, 84:945-949 (Feb. 1987).
Altmann, K-H, et al., "Novel Chemistry", *Applied Antisense Oligonucleotide Technology* (Stein & Krieg, Eds.), pp. 73-107, Wiley-Liss: New York (1998).
De Benedetti, Arrigo, et al., "eIF4E expression in tumors: Its possible role in progression of malignancies", *Int'l Journal of Biochemistry and Cell Biology*, 31(1):59-72 (Jan. 1999).
Vickers, Timothy, et al., "Efficient Reduction of Target RNAs by Small Interfering RNA and RNase H-dependent Antisense Agents," *Journal of Biological Chemistry*, 278(9):7108-7118 (2003).

Yamagiwa, Yoko, et al., "Translational regulation by p38 mitogen-activated protein kinase signaling during human cholangiocarcinoma growth," *Hepatology*, 38(1):158-166 (Jul. 2003).
Yang, Yu-Jie, et al., "Contribution of eIF-4E inhibition to the expression and activity of heparanase in human colon adenocarcinoma cell line : LS-174T," *World J. Gastroenterol*, 9(8):1707-1712 (2003).
Zimmer, S., et al., "Translational Control of Malignancy: the mRNA cap-Binding Protein, eIF-4E, as a Central Regulator of Tumor Formation, Growth, Invasion and Metastasis," *Anticancer Research*, 20:1343-1352 (2000).
J.R. Graff et al., Therapeutic suppression of translation initiation factor eIF4E expression reduces tumor growth without toxicity, *The Journal of Clinical Investigation*, Sep. 2007, pp. 2638-2648, vol. 117, No. 9.
B.C. Barnhart et al., Taking aim at translation for tumor therapy, *The Journal of Clinical Investigation*, Sep. 2007, pp. 2385-2388, vol. 117, No. 9.
S.T. Crooke, Progress in Antisense Technology, *Annual Review of Medicine: Selected Topics in the Clinical Sciences*, 2004, pp. 61-95, vol. 55.
De Benedetti, A., et al., "Expression of antisense RNA against Initiation Factor eIF-4E mRNA in HeLa Cells Results in Lengthened Cell Division Times, Diminished Translation Rates, and Reduced Levels of Both eIF-4E and the p220 Component of eIF-4F," *Molecular and Cellular Biology* 11(11):5435-5445 (1991).
De Benedetti, A., et al., "Expression of Antisense RNA Against eIF-4E mRNA in HeLa Cells Results in Diminished Translation Rates, Lengthened Doubling Time, and a Requirement for eIF-4F in vitro," *FASEB Journal*, 75th Annual Meeting, Atlanta, GA, Apr. 21-25, 1991 Abstracts Part III, Abstract 6760:A1536 (1991).
De Benedetti, A., et al., "eIF-4E expression and its role in malignancies and metastases," *Oncogene* 23:3189-3199 (2004).
Meric, F., et al., "Translation Initiation in Cancer: A Novel Target for Therapy," *Molecular Cancer Therapeutics* 1:971-979 (2002).
eIF-4E Antisense Oligonucleotide Sequence Search Results (2003; 2004).
GenBank Record for Accession No. BU747458 (2002).
GenBank Record for Accession No. BG074412 (2001).
GenBank Record for Accession No. M15353.1 (1987).
GenBank Record for Accession No. NM_007917.1 (1991).
Jaramillo, M. et al., "Multiple mRNAs Encode the Murine Translation Initiation Factor eIF-4E," *The Journal of Biological Chemistry* 266(16):10446-10451 (1991).

(Continued)

*Primary Examiner*—Sean R McGarry
(74) *Attorney, Agent, or Firm*—Charles E. Cohen

(57) ABSTRACT

Oligomeric compounds, compositions and methods are provided for modulating the expression of eIF4E. The antisense compounds may be single- or double-stranded and are targeted to nucleic acid encoding eIF4E. Methods of using these compounds for modulation of eIF4E expression and for diagnosis and treatment of diseases and conditions associated with expression of eIF4E are provided.

16 Claims, No Drawings

OTHER PUBLICATIONS

Scherer et al., Approaches for the sequence-specific knockdown of mRNA, *Nature Biotechnology* 21(12):1457-1465 (2003).

Mahato et al., Modulation of gene expression by antisense and antigene oligodeoxynucleotides and small interfering RNA, *Expert Opinion on Drug Delivery* 2(1):3-28 (2005).

Groothuis, The blood-brain and blood-tumor barriers: A review of strategies for increasing drug delivery, *Neuro-Oncology* 2(1):45-59 (2000).

Jen et al., Suppression of Gene Expression by Targeted Disruption of Messenger RNA: Available Options and Current Strategies, *Stem Cells* 18:307-319 (2000).

Matzura et al., RNAdraw; an integrated program for RNA secondary structure calculation and analysis under 32-bit Microsoft Windows, *Computer Applications in the Biosciences* 12(3):247-249 (1996).

Olie et al., A Novel Antisense Oligonucleotide Targeting Survivin Expression Induces Apoptosis and Sensitizes Lung Cancer Cells to Chemotherapy, *Cancer Research* 60:2805-2809 (2000).

* cited by examiner

SEQUENCE LISTING

<160> NUMBER OF SEQ ID NOS: 459

<210> SEQ ID NO 1
<211> LENGTH: 20
<212> TYPE: DNA
<213> ORGANISM: Artificial Sequence
<220> FEATURE:

-continued

```
<223> OTHER INFORMATION: Antisense Compound

<400> SEQUENCE: 1
tccgtcatcg ctcctcaggg                                               20

<210> SEQ ID NO 2
<211> LENGTH: 20
<212> TYPE: DNA
<213> ORGANISM: Artificial Sequence
<220> FEATURE:
<223> OTHER INFORMATION: Antisense Compound

<400> SEQUENCE: 2
gtgcgcgcga gcccgaaatc                                               20

<210> SEQ ID NO 3
<211> LENGTH: 20
<212> TYPE: DNA
<213> ORGANISM: Artificial Sequence
<220> FEATURE:
<223> OTHER INFORMATION: Antisense Compound

<400> SEQUENCE: 3
atgcattctg cccccaagga                                               20

<210> SEQ ID NO 4
<211> LENGTH: 1842
<212> TYPE: DNA
<213> ORGANISM: H. sapiens
<220> FEATURE:
<220> FEATURE:
<221> NAME/KEY: CDS
<222> LOCATION: (19)...(672)

<400> SEQUENCE: 4
cgatcagatc gatctaag atg gcg act gtc gaa ccg gaa acc acc cct act        51
                    Met Ala Thr Val Glu Pro Glu Thr Thr Pro Thr
                     1               5                  10 cct aat ccc ccg act aca gaa gag gag aaa acg gaa tct aat cag gag        99
Pro Asn Pro Pro Thr Thr Glu Glu Glu Lys Thr Glu Ser Asn Gln Glu
             15                  20                  25 gtt gct aac cca gaa cac tat att aaa cat ccc cta cag aac aga tgg       147
Val Ala Asn Pro Glu His Tyr Ile Lys His Pro Leu Gln Asn Arg Trp
         30                  35                  40 gca ctc tgg ttt ttt aaa aat gat aaa agc aaa act tgg caa gca aac       195
Ala Leu Trp Phe Phe Lys Asn Asp Lys Ser Lys Thr Trp Gln Ala Asn
     45                  50                  55 ctg cgg ctg atc tcc aag ttt gat act gtt gaa gac ttt tgg gct ctg       243
Leu Arg Leu Ile Ser Lys Phe Asp Thr Val Glu Asp Phe Trp Ala Leu
 60                  65                  70                  75 tac aac cat atc cag ttg tct agt aat tta atg cct ggc tgt gac tac       291
Tyr Asn His Ile Gln Leu Ser Ser Asn Leu Met Pro Gly Cys Asp Tyr
                 80                  85                  90 tca ctt ttt aag gat ggt att gag cct atg tgg gaa gat gag aaa aac       339
Ser Leu Phe Lys Asp Gly Ile Glu Pro Met Trp Glu Asp Glu Lys Asn
             95                 100                 105 aaa cgg gga gga cga tgg cta att aca ttg aac aaa cag cag aga cga       387
Lys Arg Gly Gly Arg Trp Leu Ile Thr Leu Asn Lys Gln Gln Arg Arg
        110                 115                 120 agt gac ctc gat cgc ttt tgg cta gag aca ctt ctg tgc ctt att gga       435
Ser Asp Leu Asp Arg Phe Trp Leu Glu Thr Leu Leu Cys Leu Ile Gly
    125                 130                 135 gaa tct ttt gat gac tac agt gat gat gta tgt ggc gct gtt gtt aat       483
```

```
                                    -continued

Glu Ser Phe Asp Asp Tyr Ser Asp Asp Val Cys Gly Ala Val Val Asn
140                 145                 150                 155 gtt aga gct aaa ggt gat aag ata gca ata tgg act act gaa tgt gaa       531
Val Arg Ala Lys Gly Asp Lys Ile Ala Ile Trp Thr Thr Glu Cys Glu
                160                 165                 170 aac aga gaa gct gtt aca cat ata ggg agg gta tac aag gaa agg tta       579
Asn Arg Glu Ala Val Thr His Ile Gly Arg Val Tyr Lys Glu Arg Leu
            175                 180                 185 gga ctt cct cca aag ata gtg att ggt tat cag tcc cac gca gac aca       627
Gly Leu Pro Pro Lys Ile Val Ile Gly Tyr Gln Ser His Ala Asp Thr
        190                 195                 200 gct act aag agc ggc tcc acc act aaa aat agg ttt gtt gtt taa           672
Ala Thr Lys Ser Gly Ser Thr Thr Lys Asn Arg Phe Val Val *
    205                 210                 215 gaagacacct tctgagtatt ctcataggag actgcgtcaa gcaatcgaga tttgggagct     732
gaaccaaagc ctcttcaaaa agcagagtgg actgcattta aatttgattt ccatcttaat     792
gttactcaga tataagagaa gtctcattcg cctttgtctt gtacttctgt gttcattttt     852
tttttttttt tttggctaga gtttccacta tcccaatcaa agaattacag tacacatccc     912
cagaatccat aaatgtgttc ctggcccact ctgtaatagt tcagtagaat taccattaat     972
tacatacaga ttttacctat ccacaatagt cagaaaacaa cttggcattt ctatacttta   1032
caggaaaaaa aattctgttg ttccatttta tgcagaagca tattttgctg gtttgaaaga   1092
ttatgatgca tacagttttc tagcaatttt ctttgtttct ttttacagca ttgtctttgc   1152
tgtactcttg ctgatggctg ctagatttta atttatttgt ttccctactt gataatatta   1212
gtgattctga tttcagtttt tcatttgttt tgcttaaatt tttttttttt ttttcctcat   1272
gtaacattgg tgaaggatcc aggaatatga cacaaaggtg gaataaacat taattttgtg   1332
cattctttgg taattttttt tgttttttgt aactacaaag ctttgctaca aatttatgca   1392
tttcattcaa atcagtgatc tatgtttgtg tgatttccta aacataattg tggattataa   1452
aaaatgtaac atcataatta cattcctaac tagaattagt atgtctgttt ttgtatcttt   1512
atgctgtatt ttaacacttt gtattactta ggttattttg ctttggttaa aaatggctca   1572
agtagaaaag cagtcccatt catattaaga cagtgtacaa aactgtaaat aaaatgtgta   1632
cagtgaattg tcttttagac aactagattt gtccttttat ttctccatct ttatagaagg   1692
aatttgtact tcttattgca ggcaagtctc tatattatgt cctcttttgt ggtgtcttcc   1752
atgtgaacag cataagtttg gagcactagt ttgattatta tgtttattac aatttttaat   1812
aaattgaata ggtagtatca tatatatgga                                   1842

<210> SEQ ID NO 5
<211> LENGTH: 17
<212> TYPE: DNA
<213> ORGANISM: Artificial Sequence
<220> FEATURE:
<223> OTHER INFORMATION: PCR Primer

<400> SEQUENCE: 5
tggcgactgt cgaaccg                                                    17

<210> SEQ ID NO 6
<211> LENGTH: 26
<212> TYPE: DNA
<213> ORGANISM: Artificial Sequence
<220> FEATURE:
<223> OTHER INFORMATION: PCR Primer
```

-continued

<400> SEQUENCE: 6
agattccgtt ttctcctctt ctgtag                                          26

<210> SEQ ID NO 7
<211> LENGTH: 26
<212> TYPE: DNA
<213> ORGANISM: Artificial Sequence
<220> FEATURE:
<223> OTHER INFORMATION: PCR Probe

<400> SEQUENCE: 7
aaaccacccc tactcctaat cccccg                                          26

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                                  19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                                 20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                                 20

<210> SEQ ID NO 11
<211> LENGTH: 2763
<212> TYPE: DNA
<213> ORGANISM: M. musculus
<220> FEATURE:
<220> FEATURE:
<221> NAME/KEY: CDS
<222> LOCATION: (15)...(668)

<400> SEQUENCE: 11

```
gagatcgatc taag atg gcg act gtg gaa ccg gaa acc acc cct acc act        50
              Met Ala Thr Val Glu Pro Glu Thr Thr Pro Thr Thr
                1               5                  10 aat ccc cca cct gca gaa gag gaa aaa aca gag tct aat caa gag gtt        98
Asn Pro Pro Pro Ala Glu Glu Glu Lys Thr Glu Ser Asn Gln Glu Val
             15                  20                  25 gct aac cca gag cac tat att aaa cac cct cta cag aac agg tgg gca       146
Ala Asn Pro Glu His Tyr Ile Lys His Pro Leu Gln Asn Arg Trp Ala
     30                  35                  40 ctc tgg ttt ttt aaa aat gat aaa agc aaa act tgg caa gca aac ctt       194
Leu Trp Phe Phe Lys Asn Asp Lys Ser Lys Thr Trp Gln Ala Asn Leu
 45                  50                  55                  60
```

```
cga ttg atc tct aag ttt gat act gtt gaa gac ttt tgg gct cta tac        242
Arg Leu Ile Ser Lys Phe Asp Thr Val Glu Asp Phe Trp Ala Leu Tyr
                65                  70                  75 aac cat atc cag ttg tct agt aat tta atg cct ggc tgt gac tac tca        290
Asn His Ile Gln Leu Ser Ser Asn Leu Met Pro Gly Cys Asp Tyr Ser
        80                  85                  90 ctt ttt aag gac ggg att gag cct atg tgg gaa gat gag aaa aac aaa        338
Leu Phe Lys Asp Gly Ile Glu Pro Met Trp Glu Asp Glu Lys Asn Lys
    95                  100                 105 cga gga gga cgg tgg ctg atc aca ctg aac aag cag cag aga cgg agt        386
Arg Gly Gly Arg Trp Leu Ile Thr Leu Asn Lys Gln Gln Arg Arg Ser
110                 115                 120 gac ctc gat cgc ttc tgg cta gag aca ctg ctg tgc ctt att gga gaa        434
Asp Leu Asp Arg Phe Trp Leu Glu Thr Leu Leu Cys Leu Ile Gly Glu
125                 130                 135                 140 tct ttc gat gac tac agt gat gat gtg tgt gga gct gtt gtt aat gtt        482
Ser Phe Asp Asp Tyr Ser Asp Asp Val Cys Gly Ala Val Val Asn Val
                145                 150                 155 aga gct aaa ggc gat aag ata gca ata tgg act act gag agt gaa aac        530
Arg Ala Lys Gly Asp Lys Ile Ala Ile Trp Thr Thr Glu Ser Glu Asn
                160                 165                 170 aga gat gca gtc aca cac ata ggg agg gta tac aag gaa agg tta gga        578
Arg Asp Ala Val Thr His Ile Gly Arg Val Tyr Lys Glu Arg Leu Gly
            175                 180                 185 ctt cct ccg aag ata gtg att ggt tat cag tcc cac gca gac aca gct        626
Leu Pro Pro Lys Ile Val Ile Gly Tyr Gln Ser His Ala Asp Thr Ala
        190                 195                 200 aca aag agc ggc tcc acc act aaa aat agg ttt gtt gtt taa                668
Thr Lys Ser Gly Ser Thr Thr Lys Asn Arg Phe Val Val  *
205                 210                 215 aaagacacct tctgagtatt ctcacaggag actgcgtcac gcaatcgaga ttgggagctg      728
aaccaaagcc tcatcaaagc agagtggact gcactgaagt tgattccatc caagtgttgc      788
taagatataa gagaagtctc attcgccttt gtcttgtact tctgtgttca ttctcctccc      848 ccaccccaa ttttgctag tgtgtccact atcccaatca agaattaca gtatacgtca         908 ccccagaacc cgcagatgtg ttcctggccc gctctgtaac agccggttag aattaccatg      968
acacacacat ttgcctttcc acagtattcg aaaaagaact tgcatttcta ttccttagc      1028 aggaaagatc tggttttgct ccactccatg caggagcgga ctttgctggt gtgagagtct     1088
gagtacagct ttctagcaac cttctgtttc ctttcacagc attgtccttg ctgtcctctt     1148
gctgatggct gctagattta atttatttgc ttccctcctt gataacatta gtgattctga     1208
tttcagtttt tcatttgttt tgcttttgtt ttttcctcg tgtaacattg gtgaaggatc      1268
caggaatatg acagaaaggt ggaataaaca ttaaatttgt gcattctttg gtaatttttt     1328
tgtttcttgt aactacaaag ctttgctaca aatttatgca tttcattcaa atcagtgatc     1388
tatgtctgtg tgatccctaa acataattgt ggactataaa aatgtaacac cataattaca     1448
ttcctaacta gaattagtat gtctgccttt gtatctctat gctgtacttt aacactttgt     1508
attcttaggt tattttgctt tggttacaat ggctcaagta gaaaagcggt cccatccata     1568
ttaagacagt gtacaaaact gtaaataaaa tgtgtacagt gaattgtctt ttagacaact     1628
agatttgtcc tttatttctc catctctaga aggaatctgt acttcgtatt gcaaggcagt     1688
ctcttgtgtc ttcttagagt gtcttcccca tgcacagcct cagtttggag cactagttta     1748
ttatgtttat tacaatttttt aataaattga ctaggtagta tcacatgtaa ttacactgat    1808
```

-continued

```
gtggctatct ttttaataaa gttaaggcac agttgctcag tcctaggttg agtgatggac    1868
tttgactatg ttacagttga tgaggattgg ggttttggtg catcaccatt cggtaggaac    1928
agcggctaga aactgattgt tgggtttaag atgtttttac ttaatggcca gaaaattagc    1988
gtaaggaaag tatatagaga aacatgcgtt agggacatta gtgttactat ctgaataaaa    2048
cacaataaac aagtattaag aactacttat attggtcaat tgttgcagta tggttttctg    2108
taaacttgaa accttgatct attctttgta tcatttaaag caaacatgaa gacattttgt    2168
ctgcagtacg taattgtata gttcagatcc tgtgagatga ggtgtggctg ttaacgccga    2228
agggtaagct gaactgtggg tagcagagtg gaaaccattg gctgagagaa aaatgctctt    2288
taagtggtgg ttgttatgaa ttcacactga taacttgata agatcctta taaaatacat    2348 acggaattaa tagcattgct cttattatgt acgtcaagaa tgtataaccg cctgctcttg    2408
ttgtcacaga taactccctg ttcagtgctt tggaaatagc gatgctcacg atctcagcat    2468
tctgtacccT acatctactg tgtggatcat tgagagatct tttgacattg caacatgata    2528
tggtctatgt tgggctgcat tcctggctgt cttgtatgag accccggttg gctccctgaa    2588
gctgattgat acagtgtaca ggcatgaagg tggctgatga ggctttctta ccaacatgtg    2648
ggattctagt agttgtatct attagagatt aattctcata ttcctttca ttcatttgta    2708 agaagtatca actttagaag tgaaaaaaga atcataaaat acagttttta aagtt         2763
```

<210> SEQ ID NO 12
<211> LENGTH: 19
<212> TYPE: DNA
<213> ORGANISM: Artificial Sequence
<220> FEATURE:
<223> OTHER INFORMATION: PCR Primer

<400> SEQUENCE: 12
aggacggtgg ctgatcaca                                                   19

<210> SEQ ID NO 13
<211> LENGTH: 21
<212> TYPE: DNA
<213> ORGANISM: Artificial Sequence
<220> FEATURE:
<223> OTHER INFORMATION: PCR Primer

<400> SEQUENCE: 13
tctctagcca gaagcgatcg a                                                21

<210> SEQ ID NO 14
<211> LENGTH: 25
<212> TYPE: DNA
<213> ORGANISM: Artificial Sequence
<220> FEATURE:
<223> OTHER INFORMATION: PCR Probe

<400> SEQUENCE: 14
tgaacaagca gcagagacgg agtga                                            25

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
ggcaaattca acggcacagt                                                  20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
gggtctcgct cctggaagat                                          20

<210> SEQ ID NO 17
<211> LENGTH: 27
<212> TYPE: DNA
<213> ORGANISM: Artificial Sequence
<220> FEATURE:
<223> OTHER INFORMATION: PCR Probe

<400> SEQUENCE: 17
aaggccgaga atgggaagct tgtcatc                                  27

<210> SEQ ID NO 18
<211> LENGTH: 20
<212> TYPE: DNA
<213> ORGANISM: Artificial Sequence
<220> FEATURE:
<223> OTHER INFORMATION: Antisense Compound

<400> SEQUENCE: 18
aatggtaatt ctactgaact                                          20

<210> SEQ ID NO 19
<211> LENGTH: 20
<212> TYPE: DNA
<213> ORGANISM: Artificial Sequence
<220> FEATURE:
<223> OTHER INFORMATION: Antisense Compound

<400> SEQUENCE: 19
atattatcaa gtagggaaac                                          20

<210> SEQ ID NO 20
<211> LENGTH: 20
<212> TYPE: DNA
<213> ORGANISM: Artificial Sequence
<220> FEATURE:
<223> OTHER INFORMATION: Antisense Compound

<400> SEQUENCE: 20
tttcacattc agtagtccat                                          20

<210> SEQ ID NO 21
<211> LENGTH: 20
<212> TYPE: DNA
<213> ORGANISM: Artificial Sequence
<220> FEATURE:
<223> OTHER INFORMATION: Antisense Compound

<400> SEQUENCE: 21
cgtgggactg ataaccaatc                                          20

<210> SEQ ID NO 22
<211> LENGTH: 20
<212> TYPE: DNA
<213> ORGANISM: Artificial Sequence
<220> FEATURE:

```
<223> OTHER INFORMATION: Antisense Compound

<400> SEQUENCE: 22
atgccaagtt gttttctgac                                              20

<210> SEQ ID NO 23
<211> LENGTH: 20
<212> TYPE: DNA
<213> ORGANISM: Artificial Sequence
<220> FEATURE:
<223> OTHER INFORMATION: Antisense Compound

<400> SEQUENCE: 23
cacctttagc tctaacatta                                              20

<210> SEQ ID NO 24
<211> LENGTH: 20
<212> TYPE: DNA
<213> ORGANISM: Artificial Sequence
<220> FEATURE:
<223> OTHER INFORMATION: Antisense Compound

<400> SEQUENCE: 24
aacctatttt tagtggtgga                                              20

<210> SEQ ID NO 25
<211> LENGTH: 20
<212> TYPE: DNA
<213> ORGANISM: Artificial Sequence
<220> FEATURE:
<223> OTHER INFORMATION: Antisense Compound

<400> SEQUENCE: 25
tagcagccat cagcaagagt                                              20

<210> SEQ ID NO 26
<211> LENGTH: 20
<212> TYPE: DNA
<213> ORGANISM: Artificial Sequence
<220> FEATURE:
<223> OTHER INFORMATION: Antisense Compound

<400> SEQUENCE: 26
attaaaatct agcagccatc                                              20

<210> SEQ ID NO 27
<211> LENGTH: 20
<212> TYPE: DNA
<213> ORGANISM: Artificial Sequence
<220> FEATURE:
<223> OTHER INFORMATION: Antisense Compound

<400> SEQUENCE: 27
aatcactatc tttggaggaa                                              20

<210> SEQ ID NO 28
<211> LENGTH: 20
<212> TYPE: DNA
<213> ORGANISM: Artificial Sequence
<220> FEATURE:
<223> OTHER INFORMATION: Antisense Compound

<400> SEQUENCE: 28
tcttaatatg aatgggactg                                              20
```

```
<210> SEQ ID NO 29
<211> LENGTH: 20
<212> TYPE: DNA
<213> ORGANISM: Artificial Sequence
<220> FEATURE:
<223> OTHER INFORMATION: Antisense Compound

<400> SEQUENCE: 29
gaaggtgtct tcttaaacaa                                               20

<210> SEQ ID NO 30
<211> LENGTH: 20
<212> TYPE: DNA
<213> ORGANISM: Artificial Sequence
<220> FEATURE:
<223> OTHER INFORMATION: Antisense Compound

<400> SEQUENCE: 30
tctgcgtggg actgataacc                                               20

<210> SEQ ID NO 31
<211> LENGTH: 20
<212> TYPE: DNA
<213> ORGANISM: Artificial Sequence
<220> FEATURE:
<223> OTHER INFORMATION: Antisense Compound

<400> SEQUENCE: 31
tctcgattgc ttgacgcagt                                               20

<210> SEQ ID NO 32
<211> LENGTH: 20
<212> TYPE: DNA
<213> ORGANISM: Artificial Sequence
<220> FEATURE:
<223> OTHER INFORMATION: Antisense Compound

<400> SEQUENCE: 32
aacagcttct ctgttttcac                                               20

<210> SEQ ID NO 33
<211> LENGTH: 20
<212> TYPE: DNA
<213> ORGANISM: Artificial Sequence
<220> FEATURE:
<223> OTHER INFORMATION: Antisense Compound

<400> SEQUENCE: 33
aaaatctagc agccatcagc                                               20

<210> SEQ ID NO 34
<211> LENGTH: 20
<212> TYPE: DNA
<213> ORGANISM: Artificial Sequence
<220> FEATURE:
<223> OTHER INFORMATION: Antisense Compound

<400> SEQUENCE: 34
ggatgtttaa tatagtgttc                                               20

<210> SEQ ID NO 35
<211> LENGTH: 20
<212> TYPE: DNA
<213> ORGANISM: Artificial Sequence
<220> FEATURE:
<223> OTHER INFORMATION: Antisense Compound
```

-continued

```
<400> SEQUENCE: 35
actgtcttaa tatgaatggg                                                  20

<210> SEQ ID NO 36
<211> LENGTH: 20
<212> TYPE: DNA
<213> ORGANISM: Artificial Sequence
<220> FEATURE:
<223> OTHER INFORMATION: Antisense Compound

<400> SEQUENCE: 36
tcaatttatt aaaaattgta                                                  20

<210> SEQ ID NO 37
<211> LENGTH: 20
<212> TYPE: DNA
<213> ORGANISM: Artificial Sequence
<220> FEATURE:
<223> OTHER INFORMATION: Antisense Compound

<400> SEQUENCE: 37
ataaatttgt agcaaagctt                                                  20

<210> SEQ ID NO 38
<211> LENGTH: 20
<212> TYPE: DNA
<213> ORGANISM: Artificial Sequence
<220> FEATURE:
<223> OTHER INFORMATION: Antisense Compound

<400> SEQUENCE: 38
aaaactgtat gcatcataat                                                  20

<210> SEQ ID NO 39
<211> LENGTH: 20
<212> TYPE: DNA
<213> ORGANISM: Artificial Sequence
<220> FEATURE:
<223> OTHER INFORMATION: Antisense Compound

<400> SEQUENCE: 39
aaaagcgatc gaggtcactt                                                  20

<210> SEQ ID NO 40
<211> LENGTH: 20
<212> TYPE: DNA
<213> ORGANISM: Artificial Sequence
<220> FEATURE:
<223> OTHER INFORMATION: Antisense Compound

<400> SEQUENCE: 40
tgtcatattc ctggatcctt                                                  20

<210> SEQ ID NO 41
<211> LENGTH: 20
<212> TYPE: DNA
<213> ORGANISM: Artificial Sequence
<220> FEATURE:
<223> OTHER INFORMATION: Antisense Compound

<400> SEQUENCE: 41
tataatccac aattatgttt                                                  20

<210> SEQ ID NO 42
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 42
tatgcttctg cataaaatgg                                              20

<210> SEQ ID NO 43
<211> LENGTH: 20
<212> TYPE: DNA
<213> ORGANISM: Artificial Sequence
<220> FEATURE:
<223> OTHER INFORMATION: Antisense Compound

<400> SEQUENCE: 43
gtggtggagc cgctcttagt                                              20

<210> SEQ ID NO 44
<211> LENGTH: 20
<212> TYPE: DNA
<213> ORGANISM: Artificial Sequence
<220> FEATURE:
<223> OTHER INFORMATION: Antisense Compound

<400> SEQUENCE: 44
agaaaactgt atgcatcata                                              20

<210> SEQ ID NO 45
<211> LENGTH: 20
<212> TYPE: DNA
<213> ORGANISM: Artificial Sequence
<220> FEATURE:
<223> OTHER INFORMATION: Antisense Compound

<400> SEQUENCE: 45
aagacaattc actgtacaca                                              20

<210> SEQ ID NO 46
<211> LENGTH: 20
<212> TYPE: DNA
<213> ORGANISM: Artificial Sequence
<220> FEATURE:
<223> OTHER INFORMATION: Antisense Compound

<400> SEQUENCE: 46
cgacagtcgc catcttagat                                              20

<210> SEQ ID NO 47
<211> LENGTH: 20
<212> TYPE: DNA
<213> ORGANISM: Artificial Sequence
<220> FEATURE:
<223> OTHER INFORMATION: Antisense Compound

<400> SEQUENCE: 47
ttttcctgta aagtatagaa                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense Compound

<400> SEQUENCE: 48
```
ctagttgtct aaaagacaat                                               20

<210> SEQ ID NO 49
<211> LENGTH: 20
<212> TYPE: DNA
<213> ORGANISM: Artificial Sequence
<220> FEATURE:
<223> OTHER INFORMATION: Antisense Compound

<400> SEQUENCE: 49
tgtagtcatc aaaagattct                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Compound

<400> SEQUENCE: 50
attgtggata ggtaaaatct                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Compound

<400> SEQUENCE: 51
tgctgttcac atggaagaca                                               20

<210> SEQ ID NO 52
<211> LENGTH: 20
<212> TYPE: DNA
<213> ORGANISM: Artificial Sequence
<220> FEATURE:
<223> OTHER INFORMATION: Antisense Compound

<400> SEQUENCE: 52
atcaaactag tgctccaaac                                               20

<210> SEQ ID NO 53
<211> LENGTH: 20
<212> TYPE: DNA
<213> ORGANISM: Artificial Sequence
<220> FEATURE:
<223> OTHER INFORMATION: Antisense Compound

<400> SEQUENCE: 53
aaatttaaat gcagtccact                                               20

<210> SEQ ID NO 54
<211> LENGTH: 20
<212> TYPE: DNA
<213> ORGANISM: Artificial Sequence
<220> FEATURE:
<223> OTHER INFORMATION: Antisense Compound

<400> SEQUENCE: 54
cgctcttagt agctgtgtct                                               20

<210> SEQ ID NO 55
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 55
atcttagatc gatctgatcg                                                    20

<210> SEQ ID NO 56
<211> LENGTH: 20
<212> TYPE: DNA
<213> ORGANISM: Artificial Sequence
<220> FEATURE:
<223> OTHER INFORMATION: Antisense Compound

<400> SEQUENCE: 56
acagtcgcca tcttagatcg                                                    20

<210> SEQ ID NO 57
<211> LENGTH: 20
<212> TYPE: DNA
<213> ORGANISM: Artificial Sequence
<220> FEATURE:
<223> OTHER INFORMATION: Antisense Compound

<400> SEQUENCE: 57
ttagcaacct cctgattaga                                                    20

<210> SEQ ID NO 58
<211> LENGTH: 20
<212> TYPE: DNA
<213> ORGANISM: Artificial Sequence
<220> FEATURE:
<223> OTHER INFORMATION: Antisense Compound

<400> SEQUENCE: 58
tctgggttag caacctcctg                                                    20

<210> SEQ ID NO 59
<211> LENGTH: 20
<212> TYPE: DNA
<213> ORGANISM: Artificial Sequence
<220> FEATURE:
<223> OTHER INFORMATION: Antisense Compound

<400> SEQUENCE: 59
gccaagtttt gcttttatca                                                    20

<210> SEQ ID NO 60
<211> LENGTH: 20
<212> TYPE: DNA
<213> ORGANISM: Artificial Sequence
<220> FEATURE:
<223> OTHER INFORMATION: Antisense Compound

<400> SEQUENCE: 60
gtttgcttgc caagttttgc                                                    20

<210> SEQ ID NO 61
<211> LENGTH: 20
<212> TYPE: DNA
<213> ORGANISM: Artificial Sequence
<220> FEATURE:
<223> OTHER INFORMATION: Antisense Compound

<400> SEQUENCE: 61
tcttcaacag tatcaaactt                                                    20
```

```
<210> SEQ ID NO 62
<211> LENGTH: 20
<212> TYPE: DNA
<213> ORGANISM: Artificial Sequence
<220> FEATURE:
<223> OTHER INFORMATION: Antisense Compound

<400> SEQUENCE: 62
aaaagtcttc aacagtatca                                                   20

<210> SEQ ID NO 63
<211> LENGTH: 20
<212> TYPE: DNA
<213> ORGANISM: Artificial Sequence
<220> FEATURE:
<223> OTHER INFORMATION: Antisense Compound

<400> SEQUENCE: 63
agagcccaaa agtcttcaac                                                   20

<210> SEQ ID NO 64
<211> LENGTH: 20
<212> TYPE: DNA
<213> ORGANISM: Artificial Sequence
<220> FEATURE:
<223> OTHER INFORMATION: Antisense Compound

<400> SEQUENCE: 64
gacaactgga tatggttgta                                                   20

<210> SEQ ID NO 65
<211> LENGTH: 20
<212> TYPE: DNA
<213> ORGANISM: Artificial Sequence
<220> FEATURE:
<223> OTHER INFORMATION: Antisense Compound

<400> SEQUENCE: 65
tactagacaa ctggatatgg                                                   20

<210> SEQ ID NO 66
<211> LENGTH: 20
<212> TYPE: DNA
<213> ORGANISM: Artificial Sequence
<220> FEATURE:
<223> OTHER INFORMATION: Antisense Compound

<400> SEQUENCE: 66
taaattacta gacaactgga                                                   20

<210> SEQ ID NO 67
<211> LENGTH: 20
<212> TYPE: DNA
<213> ORGANISM: Artificial Sequence
<220> FEATURE:
<223> OTHER INFORMATION: Antisense Compound

<400> SEQUENCE: 67
ggcattaaat tactagacaa                                                   20

<210> SEQ ID NO 68
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 68
agccaggcat taaattacta                                          20

<210> SEQ ID NO 69
<211> LENGTH: 20
<212> TYPE: DNA
<213> ORGANISM: Artificial Sequence
<220> FEATURE:
<223> OTHER INFORMATION: Antisense Compound

<400> SEQUENCE: 69
gtcacagcca ggcattaaat                                          20

<210> SEQ ID NO 70
<211> LENGTH: 20
<212> TYPE: DNA
<213> ORGANISM: Artificial Sequence
<220> FEATURE:
<223> OTHER INFORMATION: Antisense Compound

<400> SEQUENCE: 70
gagtagtcac agccaggcat                                          20

<210> SEQ ID NO 71
<211> LENGTH: 20
<212> TYPE: DNA
<213> ORGANISM: Artificial Sequence
<220> FEATURE:
<223> OTHER INFORMATION: Antisense Compound

<400> SEQUENCE: 71
aaagtgagta gtcacagcca                                          20

<210> SEQ ID NO 72
<211> LENGTH: 20
<212> TYPE: DNA
<213> ORGANISM: Artificial Sequence
<220> FEATURE:
<223> OTHER INFORMATION: Antisense Compound

<400> SEQUENCE: 72
tccttaaaaa gtgagtagtc                                          20

<210> SEQ ID NO 73
<211> LENGTH: 20
<212> TYPE: DNA
<213> ORGANISM: Artificial Sequence
<220> FEATURE:
<223> OTHER INFORMATION: Antisense Compound

<400> SEQUENCE: 73
tcttcccaca taggctcaat                                          20

<210> SEQ ID NO 74
<211> LENGTH: 20
<212> TYPE: DNA
<213> ORGANISM: Artificial Sequence
<220> FEATURE:
<223> OTHER INFORMATION: Antisense Compound

<400> SEQUENCE: 74
tctcatcttc ccacataggc                                          20

<210> SEQ ID NO 75
```

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 75
gtttttctca tcttcccaca                                                     20

<210> SEQ ID NO 76
<211> LENGTH: 20
<212> TYPE: DNA
<213> ORGANISM: Artificial Sequence
<220> FEATURE:
<223> OTHER INFORMATION: Antisense Compound

<400> SEQUENCE: 76
aaagattctc caataaggca                                                     20

<210> SEQ ID NO 77
<211> LENGTH: 20
<212> TYPE: DNA
<213> ORGANISM: Artificial Sequence
<220> FEATURE:
<223> OTHER INFORMATION: Antisense Compound

<400> SEQUENCE: 77
acatcatcac tgtagtcatc                                                     20

<210> SEQ ID NO 78
<211> LENGTH: 20
<212> TYPE: DNA
<213> ORGANISM: Artificial Sequence
<220> FEATURE:
<223> OTHER INFORMATION: Antisense Compound

<400> SEQUENCE: 78
gctctaacat taacaacagc                                                     20

<210> SEQ ID NO 79
<211> LENGTH: 20
<212> TYPE: DNA
<213> ORGANISM: Artificial Sequence
<220> FEATURE:
<223> OTHER INFORMATION: Antisense Compound

<400> SEQUENCE: 79
tcttatcacc tttagctcta                                                     20

<210> SEQ ID NO 80
<211> LENGTH: 20
<212> TYPE: DNA
<213> ORGANISM: Artificial Sequence
<220> FEATURE:
<223> OTHER INFORMATION: Antisense Compound

<400> SEQUENCE: 80
tgctatctta tcacctttag                                                     20

<210> SEQ ID NO 81
<211> LENGTH: 20
<212> TYPE: DNA
<213> ORGANISM: Artificial Sequence
<220> FEATURE:
<223> OTHER INFORMATION: Antisense Compound

<400> SEQUENCE: 81
```

-continued

```
gtccatattg ctatcttatc                                               20

<210> SEQ ID NO 82
<211> LENGTH: 20
<212> TYPE: DNA
<213> ORGANISM: Artificial Sequence
<220> FEATURE:
<223> OTHER INFORMATION: Antisense Compound

<400> SEQUENCE: 82
tcagtagtcc atattgctat                                               20

<210> SEQ ID NO 83
<211> LENGTH: 20
<212> TYPE: DNA
<213> ORGANISM: Artificial Sequence
<220> FEATURE:
<223> OTHER INFORMATION: Antisense Compound

<400> SEQUENCE: 83
tccttgtata ccctccctat                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense Compound

<400> SEQUENCE: 84
acctttcctt gtataccctc                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Compound

<400> SEQUENCE: 85
tcctaacctt tccttgtata                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense Compound

<400> SEQUENCE: 86
ggaggaagtc ctaacctttc                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Compound

<400> SEQUENCE: 87
tgataaccaa tcactatctt                                               20

<210> SEQ ID NO 88
<211> LENGTH: 20
<212> TYPE: DNA
```

```
<213> ORGANISM: Artificial Sequence
<220> FEATURE:
<223> OTHER INFORMATION: Antisense Compound

<400> SEQUENCE: 88
gtagctgtgt ctgcgtggga                                              20

<210> SEQ ID NO 89
<211> LENGTH: 20
<212> TYPE: DNA
<213> ORGANISM: Artificial Sequence
<220> FEATURE:
<223> OTHER INFORMATION: Antisense Compound

<400> SEQUENCE: 89
ttagtggtgg agccgctctt                                              20

<210> SEQ ID NO 90
<211> LENGTH: 20
<212> TYPE: DNA
<213> ORGANISM: Artificial Sequence
<220> FEATURE:
<223> OTHER INFORMATION: Antisense Compound

<400> SEQUENCE: 90
acaacaaacc tattttagt                                               20

<210> SEQ ID NO 91
<211> LENGTH: 20
<212> TYPE: DNA
<213> ORGANISM: Artificial Sequence
<220> FEATURE:
<223> OTHER INFORMATION: Antisense Compound

<400> SEQUENCE: 91
gtcttcttaa acaacaaacc                                              20

<210> SEQ ID NO 92
<211> LENGTH: 20
<212> TYPE: DNA
<213> ORGANISM: Artificial Sequence
<220> FEATURE:
<223> OTHER INFORMATION: Antisense Compound

<400> SEQUENCE: 92
atactcagaa ggtgtcttct                                              20

<210> SEQ ID NO 93
<211> LENGTH: 20
<212> TYPE: DNA
<213> ORGANISM: Artificial Sequence
<220> FEATURE:
<223> OTHER INFORMATION: Antisense Compound

<400> SEQUENCE: 93
tgagaatact cagaaggtgt                                              20

<210> SEQ ID NO 94
<211> LENGTH: 20
<212> TYPE: DNA
<213> ORGANISM: Artificial Sequence
<220> FEATURE:
<223> OTHER INFORMATION: Antisense Compound

<400> SEQUENCE: 94
agctcccaaa tctcgattgc                                              20
```

```
<210> SEQ ID NO 95
<211> LENGTH: 20
<212> TYPE: DNA
<213> ORGANISM: Artificial Sequence
<220> FEATURE:
<223> OTHER INFORMATION: Antisense Compound

<400> SEQUENCE: 95
ggctttggtt cagctcccaa                                                    20

<210> SEQ ID NO 96
<211> LENGTH: 20
<212> TYPE: DNA
<213> ORGANISM: Artificial Sequence
<220> FEATURE:
<223> OTHER INFORMATION: Antisense Compound

<400> SEQUENCE: 96
atgagacttc tcttatatct                                                    20

<210> SEQ ID NO 97
<211> LENGTH: 20
<212> TYPE: DNA
<213> ORGANISM: Artificial Sequence
<220> FEATURE:
<223> OTHER INFORMATION: Antisense Compound

<400> SEQUENCE: 97
ggcgaatgag acttctctta                                                    20

<210> SEQ ID NO 98
<211> LENGTH: 20
<212> TYPE: DNA
<213> ORGANISM: Artificial Sequence
<220> FEATURE:
<223> OTHER INFORMATION: Antisense Compound

<400> SEQUENCE: 98
agacaaaggc gaatgagact                                                    20

<210> SEQ ID NO 99
<211> LENGTH: 20
<212> TYPE: DNA
<213> ORGANISM: Artificial Sequence
<220> FEATURE:
<223> OTHER INFORMATION: Antisense Compound

<400> SEQUENCE: 99
gtacaagaca aaggcgaatg                                                    20

<210> SEQ ID NO 100
<211> LENGTH: 20
<212> TYPE: DNA
<213> ORGANISM: Artificial Sequence
<220> FEATURE:
<223> OTHER INFORMATION: Antisense Compound

<400> SEQUENCE: 100
tctttgattg ggatagtgga                                                    20

<210> SEQ ID NO 101
<211> LENGTH: 20
<212> TYPE: DNA
<213> ORGANISM: Artificial Sequence
<220> FEATURE:
```

```
<223> OTHER INFORMATION: Antisense Compound

<400> SEQUENCE: 101
ctgtaattct ttgattggga                                               20

<210> SEQ ID NO 102
<211> LENGTH: 20
<212> TYPE: DNA
<213> ORGANISM: Artificial Sequence
<220> FEATURE:
<223> OTHER INFORMATION: Antisense Compound

<400> SEQUENCE: 102
ctagcagcca tcagcaagag                                               20

<210> SEQ ID NO 103
<211> LENGTH: 20
<212> TYPE: DNA
<213> ORGANISM: Artificial Sequence
<220> FEATURE:
<223> OTHER INFORMATION: Antisense Compound

<400> SEQUENCE: 103
ctgaaatcag aatcactaat                                               20

<210> SEQ ID NO 104
<211> LENGTH: 20
<212> TYPE: DNA
<213> ORGANISM: Artificial Sequence
<220> FEATURE:
<223> OTHER INFORMATION: Antisense Compound

<400> SEQUENCE: 104
gatccttcac caatgttaca                                               20

<210> SEQ ID NO 105
<211> LENGTH: 20
<212> TYPE: DNA
<213> ORGANISM: Artificial Sequence
<220> FEATURE:
<223> OTHER INFORMATION: Antisense Compound

<400> SEQUENCE: 105
tcctggatcc ttcaccaatg                                               20

<210> SEQ ID NO 106
<211> LENGTH: 20
<212> TYPE: DNA
<213> ORGANISM: Artificial Sequence
<220> FEATURE:
<223> OTHER INFORMATION: Antisense Compound

<400> SEQUENCE: 106
aagctttgta gttacaaaaa                                               20

<210> SEQ ID NO 107
<211> LENGTH: 20
<212> TYPE: DNA
<213> ORGANISM: Artificial Sequence
<220> FEATURE:
<223> OTHER INFORMATION: Antisense Compound

<400> SEQUENCE: 107
tagcaaagct ttgtagttac                                               20
```

```
<210> SEQ ID NO 108
<211> LENGTH: 20
<212> TYPE: DNA
<213> ORGANISM: Artificial Sequence
<220> FEATURE:
<223> OTHER INFORMATION: Antisense Compound

<400> SEQUENCE: 108
aaatgcataa atttgtagca                                               20

<210> SEQ ID NO 109
<211> LENGTH: 20
<212> TYPE: DNA
<213> ORGANISM: Artificial Sequence
<220> FEATURE:
<223> OTHER INFORMATION: Antisense Compound

<400> SEQUENCE: 109
gaatgaaatg cataaatttg                                               20

<210> SEQ ID NO 110
<211> LENGTH: 20
<212> TYPE: DNA
<213> ORGANISM: Artificial Sequence
<220> FEATURE:
<223> OTHER INFORMATION: Antisense Compound

<400> SEQUENCE: 110
gatttgaatg aaatgcataa                                               20

<210> SEQ ID NO 111
<211> LENGTH: 20
<212> TYPE: DNA
<213> ORGANISM: Artificial Sequence
<220> FEATURE:
<223> OTHER INFORMATION: Antisense Compound

<400> SEQUENCE: 111
tcactgattt gaatgaaatg                                               20

<210> SEQ ID NO 112
<211> LENGTH: 20
<212> TYPE: DNA
<213> ORGANISM: Artificial Sequence
<220> FEATURE:
<223> OTHER INFORMATION: Antisense Compound

<400> SEQUENCE: 112
catagatcac tgatttgaat                                               20

<210> SEQ ID NO 113
<211> LENGTH: 20
<212> TYPE: DNA
<213> ORGANISM: Artificial Sequence
<220> FEATURE:
<223> OTHER INFORMATION: Antisense Compound

<400> SEQUENCE: 113
ctagttagga atgtaattat                                               20

<210> SEQ ID NO 114
<211> LENGTH: 20
<212> TYPE: DNA
<213> ORGANISM: Artificial Sequence
<220> FEATURE:
<223> OTHER INFORMATION: Antisense Compound
```

<400> SEQUENCE: 114
taattctagt taggaatgta                                               20

<210> SEQ ID NO 115
<211> LENGTH: 20
<212> TYPE: DNA
<213> ORGANISM: Artificial Sequence
<220> FEATURE:
<223> OTHER INFORMATION: Antisense Compound

<400> SEQUENCE: 115
cagacatact aattctagtt                                               20

<210> SEQ ID NO 116
<211> LENGTH: 20
<212> TYPE: DNA
<213> ORGANISM: Artificial Sequence
<220> FEATURE:
<223> OTHER INFORMATION: Antisense Compound

<400> SEQUENCE: 116
gcttttctac ttgagccatt                                               20

<210> SEQ ID NO 117
<211> LENGTH: 20
<212> TYPE: DNA
<213> ORGANISM: Artificial Sequence
<220> FEATURE:
<223> OTHER INFORMATION: Antisense Compound

<400> SEQUENCE: 117
ttgtacactg tcttaatatg                                               20

<210> SEQ ID NO 118
<211> LENGTH: 20
<212> TYPE: DNA
<213> ORGANISM: Artificial Sequence
<220> FEATURE:
<223> OTHER INFORMATION: Antisense Compound

<400> SEQUENCE: 118
cagttttgta cactgtctta                                               20

<210> SEQ ID NO 119
<211> LENGTH: 20
<212> TYPE: DNA
<213> ORGANISM: Artificial Sequence
<220> FEATURE:
<223> OTHER INFORMATION: Antisense Compound

<400> SEQUENCE: 119
atttacagtt ttgtacactg                                               20

<210> SEQ ID NO 120
<211> LENGTH: 20
<212> TYPE: DNA
<213> ORGANISM: Artificial Sequence
<220> FEATURE:
<223> OTHER INFORMATION: Antisense Compound

<400> SEQUENCE: 120
gtacacattt tatttacagt                                               20

<210> SEQ ID NO 121
<211> LENGTH: 20

```
<212> TYPE: DNA
<213> ORGANISM: Artificial Sequence
<220> FEATURE:
<223> OTHER INFORMATION: Antisense Compound

<400> SEQUENCE: 121
aaggacaaat ctagttgtct                                              20

<210> SEQ ID NO 122
<211> LENGTH: 20
<212> TYPE: DNA
<213> ORGANISM: Artificial Sequence
<220> FEATURE:
<223> OTHER INFORMATION: Antisense Compound

<400> SEQUENCE: 122
tttcacactc agtagtccat                                              20

<210> SEQ ID NO 123
<211> LENGTH: 20
<212> TYPE: DNA
<213> ORGANISM: H. sapiens
<220> FEATURE:

<400> SEQUENCE: 123
atggactact gaatgtgaaa                                              20

<210> SEQ ID NO 124
<211> LENGTH: 20
<212> TYPE: DNA
<213> ORGANISM: H. sapiens
<220> FEATURE:

<400> SEQUENCE: 124
gattggttat cagtcccacg                                              20

<210> SEQ ID NO 125
<211> LENGTH: 20
<212> TYPE: DNA
<213> ORGANISM: H. sapiens
<220> FEATURE:

<400> SEQUENCE: 125
gtcagaaaac aacttggcat                                              20

<210> SEQ ID NO 126
<211> LENGTH: 20
<212> TYPE: DNA
<213> ORGANISM: H. sapiens
<220> FEATURE:

<400> SEQUENCE: 126
taatgttaga gctaaaggtg                                              20

<210> SEQ ID NO 127
<211> LENGTH: 20
<212> TYPE: DNA
<213> ORGANISM: H. sapiens
<220> FEATURE:

<400> SEQUENCE: 127
tccaccacta aaaataggtt                                              20

<210> SEQ ID NO 128
<211> LENGTH: 20
```

```
<212> TYPE: DNA
<213> ORGANISM: H. sapiens
<220> FEATURE:

<400> SEQUENCE: 128
actcttgctg atggctgcta                                              20

<210> SEQ ID NO 129
<211> LENGTH: 20
<212> TYPE: DNA
<213> ORGANISM: H. sapiens
<220> FEATURE:

<400> SEQUENCE: 129
gatggctgct agattttaat                                              20

<210> SEQ ID NO 130
<211> LENGTH: 20
<212> TYPE: DNA
<213> ORGANISM: H. sapiens
<220> FEATURE:

<400> SEQUENCE: 130
cagtcccatt catattaaga                                              20

<210> SEQ ID NO 131
<211> LENGTH: 20
<212> TYPE: DNA
<213> ORGANISM: H. sapiens
<220> FEATURE:

<400> SEQUENCE: 131
ttgtttaaga agacaccttc                                              20

<210> SEQ ID NO 132
<211> LENGTH: 20
<212> TYPE: DNA
<213> ORGANISM: H. sapiens
<220> FEATURE:

<400> SEQUENCE: 132
ggttatcagt cccacgcaga                                              20

<210> SEQ ID NO 133
<211> LENGTH: 20
<212> TYPE: DNA
<213> ORGANISM: H. sapiens
<220> FEATURE:

<400> SEQUENCE: 133
actgcgtcaa gcaatcgaga                                              20

<210> SEQ ID NO 134
<211> LENGTH: 20
<212> TYPE: DNA
<213> ORGANISM: H. sapiens
<220> FEATURE:

<400> SEQUENCE: 134
gtgaaaacag agaagctgtt                                              20

<210> SEQ ID NO 135
<211> LENGTH: 20
<212> TYPE: DNA
<213> ORGANISM: H. sapiens
```

```
<220> FEATURE:

<400> SEQUENCE: 135
gctgatggct gctagatttt                                          20

<210> SEQ ID NO 136
<211> LENGTH: 20
<212> TYPE: DNA
<213> ORGANISM: H. sapiens
<220> FEATURE:

<400> SEQUENCE: 136
gaacactata ttaaacatcc                                          20

<210> SEQ ID NO 137
<211> LENGTH: 20
<212> TYPE: DNA
<213> ORGANISM: H. sapiens
<220> FEATURE:

<400> SEQUENCE: 137
aagctttgct acaaatttat                                          20

<210> SEQ ID NO 138
<211> LENGTH: 20
<212> TYPE: DNA
<213> ORGANISM: H. sapiens
<220> FEATURE:

<400> SEQUENCE: 138
attatgatgc atacagtttt                                          20

<210> SEQ ID NO 139
<211> LENGTH: 20
<212> TYPE: DNA
<213> ORGANISM: H. sapiens
<220> FEATURE:

<400> SEQUENCE: 139
aagtgacctc gatcgctttt                                          20

<210> SEQ ID NO 140
<211> LENGTH: 20
<212> TYPE: DNA
<213> ORGANISM: H. sapiens
<220> FEATURE:

<400> SEQUENCE: 140
aaggatccag gaatatgaca                                          20

<210> SEQ ID NO 141
<211> LENGTH: 20
<212> TYPE: DNA
<213> ORGANISM: H. sapiens
<220> FEATURE:

<400> SEQUENCE: 141
ccattttatg cagaagcata                                          20

<210> SEQ ID NO 142
<211> LENGTH: 20
<212> TYPE: DNA
<213> ORGANISM: H. sapiens
<220> FEATURE:
```

```
<400> SEQUENCE: 142
actaagagcg gctccaccac                                          20

<210> SEQ ID NO 143
<211> LENGTH: 20
<212> TYPE: DNA
<213> ORGANISM: H. sapiens
<220> FEATURE:

<400> SEQUENCE: 143
tatgatgcat acagttttct                                          20

<210> SEQ ID NO 144
<211> LENGTH: 20
<212> TYPE: DNA
<213> ORGANISM: H. sapiens
<220> FEATURE:

<400> SEQUENCE: 144
atctaagatg gcgactgtcg                                          20

<210> SEQ ID NO 145
<211> LENGTH: 20
<212> TYPE: DNA
<213> ORGANISM: H. sapiens
<220> FEATURE:

<400> SEQUENCE: 145
ttctatactt tacaggaaaa                                          20

<210> SEQ ID NO 146
<211> LENGTH: 20
<212> TYPE: DNA
<213> ORGANISM: H. sapiens
<220> FEATURE:

<400> SEQUENCE: 146
tgtcttccat gtgaacagca                                          20

<210> SEQ ID NO 147
<211> LENGTH: 20
<212> TYPE: DNA
<213> ORGANISM: H. sapiens
<220> FEATURE:

<400> SEQUENCE: 147
gtttggagca ctagtttgat                                          20

<210> SEQ ID NO 148
<211> LENGTH: 20
<212> TYPE: DNA
<213> ORGANISM: H. sapiens
<220> FEATURE:

<400> SEQUENCE: 148
agacacagct actaagagcg                                          20

<210> SEQ ID NO 149
<211> LENGTH: 20
<212> TYPE: DNA
<213> ORGANISM: H. sapiens
<220> FEATURE:

<400> SEQUENCE: 149
```

-continued

```
cgatctaaga tggcgactgt                                          20

<210> SEQ ID NO 150
<211> LENGTH: 20
<212> TYPE: DNA
<213> ORGANISM: H. sapiens
<220> FEATURE:

<400> SEQUENCE: 150
tctaatcagg aggttgctaa                                          20

<210> SEQ ID NO 151
<211> LENGTH: 20
<212> TYPE: DNA
<213> ORGANISM: H. sapiens
<220> FEATURE:

<400> SEQUENCE: 151
caggaggttg ctaacccaga                                          20

<210> SEQ ID NO 152
<211> LENGTH: 20
<212> TYPE: DNA
<213> ORGANISM: H. sapiens
<220> FEATURE:

<400> SEQUENCE: 152
tgataaaagc aaaacttggc                                          20

<210> SEQ ID NO 153
<211> LENGTH: 20
<212> TYPE: DNA
<213> ORGANISM: H. sapiens
<220> FEATURE:

<400> SEQUENCE: 153
gcaaaacttg gcaagcaaac                                          20

<210> SEQ ID NO 154
<211> LENGTH: 20
<212> TYPE: DNA
<213> ORGANISM: H. sapiens
<220> FEATURE:

<400> SEQUENCE: 154
gttgaagact tttgggctct                                          20

<210> SEQ ID NO 155
<211> LENGTH: 20
<212> TYPE: DNA
<213> ORGANISM: H. sapiens
<220> FEATURE:

<400> SEQUENCE: 155
tacaaccata tccagttgtc                                          20

<210> SEQ ID NO 156
<211> LENGTH: 20
<212> TYPE: DNA
<213> ORGANISM: H. sapiens
<220> FEATURE:

<400> SEQUENCE: 156
ccatatccag ttgtctagta                                          20
```

```
<210> SEQ ID NO 157
<211> LENGTH: 20
<212> TYPE: DNA
<213> ORGANISM: H. sapiens
<220> FEATURE:

<400> SEQUENCE: 157
tccagttgtc tagtaattta                                               20

<210> SEQ ID NO 158
<211> LENGTH: 20
<212> TYPE: DNA
<213> ORGANISM: H. sapiens
<220> FEATURE:

<400> SEQUENCE: 158
ttgtctagta atttaatgcc                                               20

<210> SEQ ID NO 159
<211> LENGTH: 20
<212> TYPE: DNA
<213> ORGANISM: H. sapiens
<220> FEATURE:

<400> SEQUENCE: 159
atttaatgcc tggctgtgac                                               20

<210> SEQ ID NO 160
<211> LENGTH: 20
<212> TYPE: DNA
<213> ORGANISM: H. sapiens
<220> FEATURE:

<400> SEQUENCE: 160
atgcctggct gtgactactc                                               20

<210> SEQ ID NO 161
<211> LENGTH: 20
<212> TYPE: DNA
<213> ORGANISM: H. sapiens
<220> FEATURE:

<400> SEQUENCE: 161
tggctgtgac tactcacttt                                               20

<210> SEQ ID NO 162
<211> LENGTH: 20
<212> TYPE: DNA
<213> ORGANISM: H. sapiens
<220> FEATURE:

<400> SEQUENCE: 162
gactactcac tttttaagga                                               20

<210> SEQ ID NO 163
<211> LENGTH: 20
<212> TYPE: DNA
<213> ORGANISM: H. sapiens
<220> FEATURE:

<400> SEQUENCE: 163
attgagccta tgtgggaaga                                               20

<210> SEQ ID NO 164
```

```
<211> LENGTH: 20
<212> TYPE: DNA
<213> ORGANISM: H. sapiens
<220> FEATURE:

<400> SEQUENCE: 164
gcctatgtgg gaagatgaga                                            20

<210> SEQ ID NO 165
<211> LENGTH: 20
<212> TYPE: DNA
<213> ORGANISM: H. sapiens
<220> FEATURE:

<400> SEQUENCE: 165
tgtgggaaga tgagaaaaac                                            20

<210> SEQ ID NO 166
<211> LENGTH: 20
<212> TYPE: DNA
<213> ORGANISM: H. sapiens
<220> FEATURE:

<400> SEQUENCE: 166
tgccttattg gagaatcttt                                            20

<210> SEQ ID NO 167
<211> LENGTH: 20
<212> TYPE: DNA
<213> ORGANISM: H. sapiens
<220> FEATURE:

<400> SEQUENCE: 167
gatgactaca gtgatgatgt                                            20

<210> SEQ ID NO 168
<211> LENGTH: 20
<212> TYPE: DNA
<213> ORGANISM: H. sapiens
<220> FEATURE:

<400> SEQUENCE: 168
gctgttgtta atgttagagc                                            20

<210> SEQ ID NO 169
<211> LENGTH: 20
<212> TYPE: DNA
<213> ORGANISM: H. sapiens
<220> FEATURE:

<400> SEQUENCE: 169
tagagctaaa ggtgataaga                                            20

<210> SEQ ID NO 170
<211> LENGTH: 20
<212> TYPE: DNA
<213> ORGANISM: H. sapiens
<220> FEATURE:

<400> SEQUENCE: 170
ctaaaggtga taagatagca                                            20

<210> SEQ ID NO 171
<211> LENGTH: 20
<212> TYPE: DNA
```

```
<213> ORGANISM: H. sapiens
<220> FEATURE:

<400> SEQUENCE: 171
gataagatag caatatggac                                                 20

<210> SEQ ID NO 172
<211> LENGTH: 20
<212> TYPE: DNA
<213> ORGANISM: H. sapiens
<220> FEATURE:

<400> SEQUENCE: 172
atagcaatat ggactactga                                                 20

<210> SEQ ID NO 173
<211> LENGTH: 20
<212> TYPE: DNA
<213> ORGANISM: H. sapiens
<220> FEATURE:

<400> SEQUENCE: 173
atagggaggg tatacaagga                                                 20

<210> SEQ ID NO 174
<211> LENGTH: 20
<212> TYPE: DNA
<213> ORGANISM: H. sapiens
<220> FEATURE:

<400> SEQUENCE: 174
gagggtatac aaggaaaggt                                                 20

<210> SEQ ID NO 175
<211> LENGTH: 20
<212> TYPE: DNA
<213> ORGANISM: H. sapiens
<220> FEATURE:

<400> SEQUENCE: 175
tatacaagga aaggttagga                                                 20

<210> SEQ ID NO 176
<211> LENGTH: 20
<212> TYPE: DNA
<213> ORGANISM: H. sapiens
<220> FEATURE:

<400> SEQUENCE: 176
gaaaggttag gacttcctcc                                                 20

<210> SEQ ID NO 177
<211> LENGTH: 20
<212> TYPE: DNA
<213> ORGANISM: H. sapiens
<220> FEATURE:

<400> SEQUENCE: 177
aagatagtga ttggttatca                                                 20

<210> SEQ ID NO 178
<211> LENGTH: 20
<212> TYPE: DNA
<213> ORGANISM: H. sapiens
<220> FEATURE:
```

```
<400> SEQUENCE: 178
tcccacgcag acacagctac                                              20

<210> SEQ ID NO 179
<211> LENGTH: 20
<212> TYPE: DNA
<213> ORGANISM: H. sapiens
<220> FEATURE:

<400> SEQUENCE: 179
aagagcggct ccaccactaa                                              20

<210> SEQ ID NO 180
<211> LENGTH: 20
<212> TYPE: DNA
<213> ORGANISM: H. sapiens
<220> FEATURE:

<400> SEQUENCE: 180
ggtttgttgt ttaagaagac                                              20

<210> SEQ ID NO 181
<211> LENGTH: 20
<212> TYPE: DNA
<213> ORGANISM: H. sapiens
<220> FEATURE:

<400> SEQUENCE: 181
agaagacacc ttctgagtat                                              20

<210> SEQ ID NO 182
<211> LENGTH: 20
<212> TYPE: DNA
<213> ORGANISM: H. sapiens
<220> FEATURE:

<400> SEQUENCE: 182
acaccttctg agtattctca                                              20

<210> SEQ ID NO 183
<211> LENGTH: 20
<212> TYPE: DNA
<213> ORGANISM: H. sapiens
<220> FEATURE:

<400> SEQUENCE: 183
gcaatcgaga tttgggagct                                              20

<210> SEQ ID NO 184
<211> LENGTH: 20
<212> TYPE: DNA
<213> ORGANISM: H. sapiens
<220> FEATURE:

<400> SEQUENCE: 184
ttgggagctg aaccaaagcc                                              20

<210> SEQ ID NO 185
<211> LENGTH: 20
<212> TYPE: DNA
<213> ORGANISM: H. sapiens
<220> FEATURE:

<400> SEQUENCE: 185
```

-continued agatataaga gaagtctcat                      20

<210> SEQ ID NO 186
<211> LENGTH: 20
<212> TYPE: DNA
<213> ORGANISM: H. sapiens
<220> FEATURE:

<400> SEQUENCE: 186
taagagaagt ctcattcgcc                      20

<210> SEQ ID NO 187
<211> LENGTH: 20
<212> TYPE: DNA
<213> ORGANISM: H. sapiens
<220> FEATURE:

<400> SEQUENCE: 187
agtctcattc gcctttgtct                      20

<210> SEQ ID NO 188
<211> LENGTH: 20
<212> TYPE: DNA
<213> ORGANISM: H. sapiens
<220> FEATURE:

<400> SEQUENCE: 188
cattcgcctt tgtcttgtac                      20

<210> SEQ ID NO 189
<211> LENGTH: 20
<212> TYPE: DNA
<213> ORGANISM: H. sapiens
<220> FEATURE:

<400> SEQUENCE: 189
tccactatcc caatcaaaga                      20

<210> SEQ ID NO 190
<211> LENGTH: 20
<212> TYPE: DNA
<213> ORGANISM: H. sapiens
<220> FEATURE:

<400> SEQUENCE: 190
tcccaatcaa agaattacag                      20

<210> SEQ ID NO 191
<211> LENGTH: 20
<212> TYPE: DNA
<213> ORGANISM: H. sapiens
<220> FEATURE:

<400> SEQUENCE: 191
ctcttgctga tggctgctag                      20

<210> SEQ ID NO 192
<211> LENGTH: 20
<212> TYPE: DNA
<213> ORGANISM: H. sapiens
<220> FEATURE:

<400> SEQUENCE: 192
attagtgatt ctgatttcag                      20

```
<210> SEQ ID NO 193
<211> LENGTH: 20
<212> TYPE: DNA
<213> ORGANISM: H. sapiens
<220> FEATURE:

<400> SEQUENCE: 193
tgtaacattg gtgaaggatc                                              20

<210> SEQ ID NO 194
<211> LENGTH: 20
<212> TYPE: DNA
<213> ORGANISM: H. sapiens
<220> FEATURE:

<400> SEQUENCE: 194
cattggtgaa ggatccagga                                              20

<210> SEQ ID NO 195
<211> LENGTH: 20
<212> TYPE: DNA
<213> ORGANISM: H. sapiens
<220> FEATURE:

<400> SEQUENCE: 195
gtaactacaa agctttgcta                                              20

<210> SEQ ID NO 196
<211> LENGTH: 20
<212> TYPE: DNA
<213> ORGANISM: H. sapiens
<220> FEATURE:

<400> SEQUENCE: 196
ttatgcattt cattcaaatc                                              20

<210> SEQ ID NO 197
<211> LENGTH: 20
<212> TYPE: DNA
<213> ORGANISM: H. sapiens
<220> FEATURE:

<400> SEQUENCE: 197
catttcattc aaatcagtga                                              20

<210> SEQ ID NO 198
<211> LENGTH: 20
<212> TYPE: DNA
<213> ORGANISM: H. sapiens
<220> FEATURE:

<400> SEQUENCE: 198
attcaaatca gtgatctatg                                              20

<210> SEQ ID NO 199
<211> LENGTH: 20
<212> TYPE: DNA
<213> ORGANISM: H. sapiens
<220> FEATURE:

<400> SEQUENCE: 199
tacattccta actagaatta                                              20
```

```
<210> SEQ ID NO 200
<211> LENGTH: 20
<212> TYPE: DNA
<213> ORGANISM: H. sapiens
<220> FEATURE:

<400> SEQUENCE: 200
aactagaatt agtatgtctg                                                 20

<210> SEQ ID NO 201
<211> LENGTH: 20
<212> TYPE: DNA
<213> ORGANISM: H. sapiens
<220> FEATURE:

<400> SEQUENCE: 201
aatggctcaa gtagaaaagc                                                 20

<210> SEQ ID NO 202
<211> LENGTH: 20
<212> TYPE: DNA
<213> ORGANISM: H. sapiens
<220> FEATURE:

<400> SEQUENCE: 202
catattaaga cagtgtacaa                                                 20

<210> SEQ ID NO 203
<211> LENGTH: 20
<212> TYPE: DNA
<213> ORGANISM: H. sapiens
<220> FEATURE:

<400> SEQUENCE: 203
taagacagtg tacaaaactg                                                 20

<210> SEQ ID NO 204
<211> LENGTH: 20
<212> TYPE: DNA
<213> ORGANISM: H. sapiens
<220> FEATURE:

<400> SEQUENCE: 204
cagtgtacaa aactgtaaat                                                 20

<210> SEQ ID NO 205
<211> LENGTH: 20
<212> TYPE: DNA
<213> ORGANISM: H. sapiens
<220> FEATURE:

<400> SEQUENCE: 205
actgtaaata aaatgtgtac                                                 20

<210> SEQ ID NO 206
<211> LENGTH: 20
<212> TYPE: DNA
<213> ORGANISM: M. musculus
<220> FEATURE:

<400> SEQUENCE: 206
atggactact gagtgtgaaa                                                 20

<210> SEQ ID NO 207
<211> LENGTH: 20
```

```
<212> TYPE: DNA
<213> ORGANISM: Artificial Sequence
<220> FEATURE:
<221> NAME/KEY: n is any base
<222> LOCATION: positions 1-20
<223> OTHER INFORMATION: Antisense Compound

<400> SEQUENCE: 207
nnnnnnnnnn nnnnnnnnnn                                              20

<210> SEQ ID NO 208
<211> LENGTH: 20
<212> TYPE: DNA
<213> ORGANISM: Artificial Sequence
<220> FEATURE:
<223> OTHER INFORMATION: Antisense Compound

<400> SEQUENCE: 208
ttcgcggctg gacgattcag                                              20

<210> SEQ ID NO 209
<211> LENGTH: 20
<212> TYPE: DNA
<213> ORGANISM: Artificial Sequence
<220> FEATURE:
<223> OTHER INFORMATION: Antisense Compound

<400> SEQUENCE: 209
ggatagaacg cgaaagcttg                                              20

<210> SEQ ID NO 210
<211> LENGTH: 20
<212> TYPE: DNA
<213> ORGANISM: Artificial Sequence
<220> FEATURE:
<223> OTHER INFORMATION: Antisense Compound

<400> SEQUENCE: 210
tgttacagtc ttgtaccctt                                              20

<210> SEQ ID NO 211
<211> LENGTH: 20
<212> TYPE: DNA
<213> ORGANISM: Artificial Sequence
<220> FEATURE:
<223> OTHER INFORMATION: Antisense Compound

<400> SEQUENCE: 211
ccttccctga aggttcctcc                                              20

<210> SEQ ID NO 212
<211> LENGTH: 19
<212> TYPE: RNA
<213> ORGANISM: Artificial Sequence
<220> FEATURE:
<223> OTHER INFORMATION: Antisense Compound

<400> SEQUENCE: 212
cagaugggca cucugguuu                                               19

<210> SEQ ID NO 213
<211> LENGTH: 19
<212> TYPE: RNA
<213> ORGANISM: Artificial Sequence
<220> FEATURE:
<223> OTHER INFORMATION: Antisense Compound
```

```
<400> SEQUENCE: 213
gucuacccgu gagaccaaa                                                     19

<210> SEQ ID NO 214
<211> LENGTH: 19
<212> TYPE: RNA
<213> ORGANISM: Artificial Sequence
<220> FEATURE:
<223> OTHER INFORMATION: Antisense Compound

<400> SEQUENCE: 214
ccugcggcug aucuccaag                                                     19

<210> SEQ ID NO 215
<211> LENGTH: 19
<212> TYPE: RNA
<213> ORGANISM: Artificial Sequence
<220> FEATURE:
<223> OTHER INFORMATION: Antisense Compound

<400> SEQUENCE: 215
ggacgccgac uagagguuc                                                     19

<210> SEQ ID NO 216
<211> LENGTH: 19
<212> TYPE: RNA
<213> ORGANISM: Artificial Sequence
<220> FEATURE:
<223> OTHER INFORMATION: Antisense Compound

<400> SEQUENCE: 216
caacuuggca uuucuauac                                                     19

<210> SEQ ID NO 217
<211> LENGTH: 19
<212> TYPE: RNA
<213> ORGANISM: Artificial Sequence
<220> FEATURE:
<223> OTHER INFORMATION: Antisense Compound

<400> SEQUENCE: 217
guugaaccgu aaagauaug                                                     19

<210> SEQ ID NO 218
<211> LENGTH: 19
<212> TYPE: RNA
<213> ORGANISM: Artificial Sequence
<220> FEATURE:
<223> OTHER INFORMATION: Antisense Compound

<400> SEQUENCE: 218
cuuacgcuga guacuucga                                                     19

<210> SEQ ID NO 219
<211> LENGTH: 19
<212> TYPE: RNA
<213> ORGANISM: Artificial Sequence
<220> FEATURE:
<223> OTHER INFORMATION: Antisense Compound

<400> SEQUENCE: 219
gaaugcgacu caugaagcu                                                     19

<210> SEQ ID NO 220
<211> LENGTH: 20
```

<212> TYPE: RNA
<213> ORGANISM: Artificial Sequence
<220> FEATURE:
<223> OTHER INFORMATION: Antisense Compound

<400> SEQUENCE: 220 ugcauauuc cuggauccuu                                                    20

<210> SEQ ID NO 221
<211> LENGTH: 20
<212> TYPE: RNA
<213> ORGANISM: Artificial Sequence
<220> FEATURE:
<223> OTHER INFORMATION: Antisense Compound

<400> SEQUENCE: 221
aaggauccag gaauaugaca                                                   20

<210> SEQ ID NO 222
<211> LENGTH: 20
<212> TYPE: RNA
<213> ORGANISM: Artificial Sequence
<220> FEATURE:
<223> OTHER INFORMATION: Antisense Compound

<400> SEQUENCE: 222
ggaggaaguc cuaaccuuuc                                                   20

<210> SEQ ID NO 223
<211> LENGTH: 20
<212> TYPE: RNA
<213> ORGANISM: Artificial Sequence
<220> FEATURE:
<223> OTHER INFORMATION: Antisense Compound

<400> SEQUENCE: 223
gaaagguuag gacuuccucc                                                   20

<210> SEQ ID NO 224
<211> LENGTH: 20
<212> TYPE: RNA
<213> ORGANISM: Artificial Sequence
<220> FEATURE:
<223> OTHER INFORMATION: Antisense Compound

<400> SEQUENCE: 224
ggcuuugguu cagcucccaa                                                   20

<210> SEQ ID NO 225
<211> LENGTH: 20
<212> TYPE: RNA
<213> ORGANISM: Artificial Sequence
<220> FEATURE:
<223> OTHER INFORMATION: Antisense Compound

<400> SEQUENCE: 225
uugggagcug aaccaaagcc                                                   20

<210> SEQ ID NO 226
<211> LENGTH: 20
<212> TYPE: RNA
<213> ORGANISM: Artificial Sequence
<220> FEATURE:
<223> OTHER INFORMATION: Antisense Compound

<400> SEQUENCE: 226

```
ggcgaaugag acuucucuua                                        20

<210> SEQ ID NO 227
<211> LENGTH: 20
<212> TYPE: RNA
<213> ORGANISM: Artificial Sequence
<220> FEATURE:
<223> OTHER INFORMATION: Antisense Compound

<400> SEQUENCE: 227
uaagagaagu cucauucgcc                                        20

<210> SEQ ID NO 228
<211> LENGTH: 20
<212> TYPE: RNA
<213> ORGANISM: Artificial Sequence
<220> FEATURE:
<223> OTHER INFORMATION: Antisense Compound

<400> SEQUENCE: 228
uccuggaucc uucaccaaug                                        20

<210> SEQ ID NO 229
<211> LENGTH: 20
<212> TYPE: RNA
<213> ORGANISM: Artificial Sequence
<220> FEATURE:
<223> OTHER INFORMATION: Antisense Compound

<400> SEQUENCE: 229
cauuggugaa ggauccagga                                        20

<210> SEQ ID NO 230
<211> LENGTH: 20
<212> TYPE: RNA
<213> ORGANISM: Artificial Sequence
<220> FEATURE:
<223> OTHER INFORMATION: Antisense Compound

<400> SEQUENCE: 230
gcuuuucuac uugagccauu                                        20

<210> SEQ ID NO 231
<211> LENGTH: 20
<212> TYPE: RNA
<213> ORGANISM: Artificial Sequence
<220> FEATURE:
<223> OTHER INFORMATION: Antisense Compound

<400> SEQUENCE: 231
aauggcucaa guagaaaagc                                        20

<210> SEQ ID NO 232
<211> LENGTH: 20
<212> TYPE: RNA
<213> ORGANISM: Artificial Sequence
<220> FEATURE:
<223> OTHER INFORMATION: Antisense Compound

<400> SEQUENCE: 232
acaucaucac uguagucauc                                        20

<210> SEQ ID NO 233
<211> LENGTH: 20
<212> TYPE: RNA
<213> ORGANISM: Artificial Sequence
```

```
<220> FEATURE:
<223> OTHER INFORMATION: Antisense Compound

<400> SEQUENCE: 233
gaugacuaca gugaugaugu                                                       20

<210> SEQ ID NO 234
<211> LENGTH: 20
<212> TYPE: RNA
<213> ORGANISM: Artificial Sequence
<220> FEATURE:
<223> OTHER INFORMATION: Antisense Compound

<400> SEQUENCE: 234
caccuuuagc ucuaacauua                                                       20

<210> SEQ ID NO 235
<211> LENGTH: 20
<212> TYPE: RNA
<213> ORGANISM: Artificial Sequence
<220> FEATURE:
<223> OTHER INFORMATION: Antisense Compound

<400> SEQUENCE: 235
uaauguuaga gcuaaaggug                                                       20

<210> SEQ ID NO 236
<211> LENGTH: 20
<212> TYPE: RNA
<213> ORGANISM: Artificial Sequence
<220> FEATURE:
<223> OTHER INFORMATION: Antisense Compound

<400> SEQUENCE: 236
ucuuaucacc uuuagcucua                                                       20

<210> SEQ ID NO 237
<211> LENGTH: 20
<212> TYPE: RNA
<213> ORGANISM: Artificial Sequence
<220> FEATURE:
<223> OTHER INFORMATION: Antisense Compound

<400> SEQUENCE: 237
uagagcuaaa ggugauaaga                                                       20

<210> SEQ ID NO 238
<211> LENGTH: 20
<212> TYPE: RNA
<213> ORGANISM: Artificial Sequence
<220> FEATURE:
<223> OTHER INFORMATION: Antisense Compound

<400> SEQUENCE: 238
ugcuaucuua ucaccuuuag                                                       20

<210> SEQ ID NO 239
<211> LENGTH: 20
<212> TYPE: RNA
<213> ORGANISM: Artificial Sequence
<220> FEATURE:
<223> OTHER INFORMATION: Antisense Compound

<400> SEQUENCE: 239
cuaaagguga uaagauagca                                                       20
```

```
<210> SEQ ID NO 240
<211> LENGTH: 20
<212> TYPE: RNA
<213> ORGANISM: Artificial Sequence
<220> FEATURE:
<223> OTHER INFORMATION: Antisense Compound

<400> SEQUENCE: 240
guccauauug cuaucuuauc                                                  20

<210> SEQ ID NO 241
<211> LENGTH: 20
<212> TYPE: RNA
<213> ORGANISM: Artificial Sequence
<220> FEATURE:
<223> OTHER INFORMATION: Antisense Compound

<400> SEQUENCE: 241
gauaagauag caauauggac                                                  20

<210> SEQ ID NO 242
<211> LENGTH: 20
<212> TYPE: RNA
<213> ORGANISM: Artificial Sequence
<220> FEATURE:
<223> OTHER INFORMATION: Antisense Compound

<400> SEQUENCE: 242
gccaaguuuu gcuuuuauca                                                  20

<210> SEQ ID NO 243
<211> LENGTH: 20
<212> TYPE: RNA
<213> ORGANISM: Artificial Sequence
<220> FEATURE:
<223> OTHER INFORMATION: Antisense Compound

<400> SEQUENCE: 243
ugauaaaagc aaaacuuggc                                                  20

<210> SEQ ID NO 244
<211> LENGTH: 20
<212> TYPE: RNA
<213> ORGANISM: Artificial Sequence
<220> FEATURE:
<223> OTHER INFORMATION: Antisense Compound

<400> SEQUENCE: 244
ucuucaacag uaucaaacuu                                                  20

<210> SEQ ID NO 245
<211> LENGTH: 20
<212> TYPE: RNA
<213> ORGANISM: Artificial Sequence
<220> FEATURE:
<223> OTHER INFORMATION: Antisense Compound

<400> SEQUENCE: 245
aaguuugaua cuguugaaga                                                  20

<210> SEQ ID NO 246
<211> LENGTH: 20
<212> TYPE: RNA
<213> ORGANISM: Artificial Sequence
<220> FEATURE:
<223> OTHER INFORMATION: Antisense Compound
```

```
<400> SEQUENCE: 246
gucacagcca ggcauuaaau                                            20

<210> SEQ ID NO 247
<211> LENGTH: 20
<212> TYPE: RNA
<213> ORGANISM: Artificial Sequence
<220> FEATURE:
<223> OTHER INFORMATION: Antisense Compound

<400> SEQUENCE: 247
auuuaaugcc uggcugugac                                            20

<210> SEQ ID NO 248
<211> LENGTH: 20
<212> TYPE: RNA
<213> ORGANISM: Artificial Sequence
<220> FEATURE:
<223> OTHER INFORMATION: Antisense Compound

<400> SEQUENCE: 248
ucucaucuuc ccacauaggc                                            20

<210> SEQ ID NO 249
<211> LENGTH: 20
<212> TYPE: RNA
<213> ORGANISM: Artificial Sequence
<220> FEATURE:
<223> OTHER INFORMATION: Antisense Compound

<400> SEQUENCE: 249
gccuaugugg gaagaugaga                                            20

<210> SEQ ID NO 250
<211> LENGTH: 20
<212> TYPE: RNA
<213> ORGANISM: Artificial Sequence
<220> FEATURE:
<223> OTHER INFORMATION: Antisense Compound

<400> SEQUENCE: 250
accuuuccuu guauacccuc                                            20

<210> SEQ ID NO 251
<211> LENGTH: 20
<212> TYPE: RNA
<213> ORGANISM: Artificial Sequence
<220> FEATURE:
<223> OTHER INFORMATION: Antisense Compound

<400> SEQUENCE: 251
gaggguauac aaggaaaggu                                            20

<210> SEQ ID NO 252
<211> LENGTH: 20
<212> TYPE: RNA
<213> ORGANISM: Artificial Sequence
<220> FEATURE:
<223> OTHER INFORMATION: Antisense Compound

<400> SEQUENCE: 252
guagcugugu cugcguggga                                            20

<210> SEQ ID NO 253
```

```
<211> LENGTH: 20
<212> TYPE: RNA
<213> ORGANISM: Artificial Sequence
<220> FEATURE:
<223> OTHER INFORMATION: Antisense Compound

<400> SEQUENCE: 253
ucccacgcag acacagcuac                                               20

<210> SEQ ID NO 254
<211> LENGTH: 20
<212> TYPE: RNA
<213> ORGANISM: Artificial Sequence
<220> FEATURE:
<223> OTHER INFORMATION: Antisense Compound

<400> SEQUENCE: 254
auacucagaa ggugucuucu                                               20

<210> SEQ ID NO 255
<211> LENGTH: 20
<212> TYPE: RNA
<213> ORGANISM: Artificial Sequence
<220> FEATURE:
<223> OTHER INFORMATION: Antisense Compound

<400> SEQUENCE: 255
agaagacacc uucugaguau                                               20

<210> SEQ ID NO 256
<211> LENGTH: 20
<212> TYPE: RNA
<213> ORGANISM: Artificial Sequence
<220> FEATURE:
<223> OTHER INFORMATION: Antisense Compound

<400> SEQUENCE: 256
cuguaauucu uugauuggga                                               20

<210> SEQ ID NO 257
<211> LENGTH: 20
<212> TYPE: RNA
<213> ORGANISM: Artificial Sequence
<220> FEATURE:
<223> OTHER INFORMATION: Antisense Compound

<400> SEQUENCE: 257
ucccaaucaa agaauuacag                                               20

<210> SEQ ID NO 258
<211> LENGTH: 20
<212> TYPE: RNA
<213> ORGANISM: Artificial Sequence
<220> FEATURE:
<223> OTHER INFORMATION: Antisense Compound

<400> SEQUENCE: 258
gaaugaaaug cauaaauuug                                               20

<210> SEQ ID NO 259
<211> LENGTH: 20
<212> TYPE: RNA
<213> ORGANISM: Artificial Sequence
<220> FEATURE:
<223> OTHER INFORMATION: Antisense Compound

<400> SEQUENCE: 259
```
caaauuuaug cauuucauuc                                        20

<210> SEQ ID NO 260
<211> LENGTH: 20
<212> TYPE: RNA
<213> ORGANISM: Artificial Sequence
<220> FEATURE:
<223> OTHER INFORMATION: Antisense Compound

<400> SEQUENCE: 260
ucacugauuu gaaugaaaug                                        20

<210> SEQ ID NO 261
<211> LENGTH: 20
<212> TYPE: RNA
<213> ORGANISM: Artificial Sequence
<220> FEATURE:
<223> OTHER INFORMATION: Antisense Compound

<400> SEQUENCE: 261
cauuucauuc aaaucaguga                                        20

<210> SEQ ID NO 262
<211> LENGTH: 20
<212> TYPE: RNA
<213> ORGANISM: Artificial Sequence
<220> FEATURE:
<223> OTHER INFORMATION: Antisense Compound

<400> SEQUENCE: 262
auuuacaguu uuguacacug                                        20

<210> SEQ ID NO 263
<211> LENGTH: 20
<212> TYPE: RNA
<213> ORGANISM: Artificial Sequence
<220> FEATURE:
<223> OTHER INFORMATION: Antisense Compound

<400> SEQUENCE: 263
caguguacaa aacuguaaau                                        20

<210> SEQ ID NO 264
<211> LENGTH: 20
<212> TYPE: RNA
<213> ORGANISM: Artificial Sequence
<220> FEATURE:
<223> OTHER INFORMATION: Antisense Compound

<400> SEQUENCE: 264
aaaaccagag ugcccaucug                                        20

<210> SEQ ID NO 265
<211> LENGTH: 20
<212> TYPE: RNA
<213> ORGANISM: Artificial Sequence
<220> FEATURE:
<223> OTHER INFORMATION: Antisense Compound

<400> SEQUENCE: 265
cagaugggca cucugguuuu                                        20

<210> SEQ ID NO 266
<211> LENGTH: 20
<212> TYPE: RNA

-continued

```
<213> ORGANISM: Artificial Sequence
<220> FEATURE:
<223> OTHER INFORMATION: Antisense Compound

<400> SEQUENCE: 266
acuuggagau cagccgcagg                                                    20

<210> SEQ ID NO 267
<211> LENGTH: 20
<212> TYPE: RNA
<213> ORGANISM: Artificial Sequence
<220> FEATURE:
<223> OTHER INFORMATION: Antisense Compound

<400> SEQUENCE: 267
ccugcggcug aucuccaagu                                                    20

<210> SEQ ID NO 268
<211> LENGTH: 20
<212> TYPE: RNA
<213> ORGANISM: Artificial Sequence
<220> FEATURE:
<223> OTHER INFORMATION: Antisense Compound

<400> SEQUENCE: 268
aguauagaaa ugccaaguug                                                    20

<210> SEQ ID NO 269
<211> LENGTH: 20
<212> TYPE: RNA
<213> ORGANISM: Artificial Sequence
<220> FEATURE:
<223> OTHER INFORMATION: Antisense Compound

<400> SEQUENCE: 269
caacuuggca uuucuauacu                                                    20

<210> SEQ ID NO 270
<211> LENGTH: 21
<212> TYPE: DNA
<213> ORGANISM: Artificial Sequence
<220> FEATURE:
<223> OTHER INFORMATION: Antisense Compound

<400> SEQUENCE: 270
aaaccagagu gcccaucugt t                                                  21

<210> SEQ ID NO 271
<211> LENGTH: 21
<212> TYPE: DNA
<213> ORGANISM: Artificial Sequence
<220> FEATURE:
<223> OTHER INFORMATION: Antisense Compound

<400> SEQUENCE: 271
cagaugggca cucugguuut t                                                  21

<210> SEQ ID NO 272
<211> LENGTH: 21
<212> TYPE: DNA
<213> ORGANISM: Artificial Sequence
<220> FEATURE:
<223> OTHER INFORMATION: Antisense Compound

<400> SEQUENCE: 272
cuuggagauc agccgcaggt t                                                  21
```

<210> SEQ ID NO 273
<211> LENGTH: 21
<212> TYPE: DNA
<213> ORGANISM: Artificial Sequence
<220> FEATURE:
<223> OTHER INFORMATION: Antisense Compound

<400> SEQUENCE: 273
ccugcggcug aucuccaagt t                                             21

<210> SEQ ID NO 274
<211> LENGTH: 21
<212> TYPE: DNA
<213> ORGANISM: Artificial Sequence
<220> FEATURE:
<223> OTHER INFORMATION: Antisense Compound

<400> SEQUENCE: 274
guauagaaau gccaaguugt t                                             21

<210> SEQ ID NO 275
<211> LENGTH: 21
<212> TYPE: DNA
<213> ORGANISM: Artificial Sequence
<220> FEATURE:
<223> OTHER INFORMATION: Antisense Compound

<400> SEQUENCE: 275
caacuuggca uuucuauact t                                             21

<210> SEQ ID NO 276
<211> LENGTH: 20
<212> TYPE: RNA
<213> ORGANISM: Artificial Sequence
<220> FEATURE:
<223> OTHER INFORMATION: Antisense Compound

<400> SEQUENCE: 276 uuugcucug guccuuacuu                                                20

<210> SEQ ID NO 277
<211> LENGTH: 20
<212> TYPE: RNA
<213> ORGANISM: Artificial Sequence
<220> FEATURE:
<223> OTHER INFORMATION: Antisense Compound

<400> SEQUENCE: 277
aaguaaggac cagagacaaa                                               20

<210> SEQ ID NO 278
<211> LENGTH: 21
<212> TYPE: RNA
<213> ORGANISM: Artificial Sequence
<220> FEATURE:
<223> OTHER INFORMATION: Antisense Compound

<400> SEQUENCE: 278
cuucuggcau ccgguuuagu u                                             21

<210> SEQ ID NO 279
<211> LENGTH: 21
<212> TYPE: RNA
<213> ORGANISM: Artificial Sequence
<220> FEATURE:

<223> OTHER INFORMATION: Antisense Compound

<400> SEQUENCE: 279
cuaaaccgga ugccagaagu u                                             21

<210> SEQ ID NO 280
<211> LENGTH: 20
<212> TYPE: DNA
<213> ORGANISM: Artificial Sequence
<220> FEATURE:
<223> OTHER INFORMATION: Antisense Compound

<400> SEQUENCE: 280
ctgctagcct ctggatttga                                               20

<210> SEQ ID NO 281
<211> LENGTH: 20
<212> TYPE: DNA
<213> ORGANISM: Artificial Sequence
<220> FEATURE:
<223> OTHER INFORMATION: Antisense Compound

<400> SEQUENCE: 281
cgttattaac ctccgttgaa                                               20

<210> SEQ ID NO 282
<211> LENGTH: 20
<212> TYPE: DNA
<213> ORGANISM: Artificial Sequence
<220> FEATURE:
<223> OTHER INFORMATION: Antisense Compound

<400> SEQUENCE: 282
atgcatacta cgaaaggccg                                               20

<210> SEQ ID NO 283
<211> LENGTH: 20
<212> TYPE: RNA
<213> ORGANISM: Artificial Sequence
<220> FEATURE:
<223> OTHER INFORMATION: Antisense Compound

<400> SEQUENCE: 283
uuaaaaaacc agagugccca                                               20

<210> SEQ ID NO 284
<211> LENGTH: 20
<212> TYPE: RNA
<213> ORGANISM: Artificial Sequence
<220> FEATURE:
<223> OTHER INFORMATION: Antisense Compound

<400> SEQUENCE: 284
ugggcacucu gguuuuuuaa                                               20

<210> SEQ ID NO 285
<211> LENGTH: 20
<212> TYPE: RNA
<213> ORGANISM: Artificial Sequence
<220> FEATURE:
<223> OTHER INFORMATION: Antisense Compound

<400> SEQUENCE: 285
uuuaaaaaac cagagugccc                                               20

```
<210> SEQ ID NO 286
<211> LENGTH: 20
<212> TYPE: RNA
<213> ORGANISM: Artificial Sequence
<220> FEATURE:
<223> OTHER INFORMATION: Antisense Compound

<400> SEQUENCE: 286
gggcacucug guuuuuaaa                                           20

<210> SEQ ID NO 287
<211> LENGTH: 20
<212> TYPE: RNA
<213> ORGANISM: Artificial Sequence
<220> FEATURE:
<223> OTHER INFORMATION: Antisense Compound

<400> SEQUENCE: 287
uuuuaaaaaa ccagagugcc                                          20

<210> SEQ ID NO 288
<211> LENGTH: 20
<212> TYPE: RNA
<213> ORGANISM: Artificial Sequence
<220> FEATURE:
<223> OTHER INFORMATION: Antisense Compound

<400> SEQUENCE: 288
ggcacucugg uuuuuuaaaa                                          20

<210> SEQ ID NO 289
<211> LENGTH: 20
<212> TYPE: RNA
<213> ORGANISM: Artificial Sequence
<220> FEATURE:
<223> OTHER INFORMATION: Antisense Compound

<400> SEQUENCE: 289
auuuuuaaaa aaccagagug                                          20

<210> SEQ ID NO 290
<211> LENGTH: 20
<212> TYPE: RNA
<213> ORGANISM: Artificial Sequence
<220> FEATURE:
<223> OTHER INFORMATION: Antisense Compound

<400> SEQUENCE: 290
cacucugguu uuuaaaaaau                                          20

<210> SEQ ID NO 291
<211> LENGTH: 20
<212> TYPE: RNA
<213> ORGANISM: Artificial Sequence
<220> FEATURE:
<223> OTHER INFORMATION: Antisense Compound

<400> SEQUENCE: 291
agagcccaaa agucuucaac                                          20

<210> SEQ ID NO 292
<211> LENGTH: 20
<212> TYPE: RNA
<213> ORGANISM: Artificial Sequence
<220> FEATURE:
<223> OTHER INFORMATION: Antisense Compound
```

```
<400> SEQUENCE: 292
guugaagacu uuugggcucu                                              20

<210> SEQ ID NO 293
<211> LENGTH: 20
<212> TYPE: RNA
<213> ORGANISM: Artificial Sequence
<220> FEATURE:
<223> OTHER INFORMATION: Antisense Compound

<400> SEQUENCE: 293
uacuagacaa cuggauaugg                                              20

<210> SEQ ID NO 294
<211> LENGTH: 20
<212> TYPE: RNA
<213> ORGANISM: Artificial Sequence
<220> FEATURE:
<223> OTHER INFORMATION: Antisense Compound

<400> SEQUENCE: 294
ccauauccag uugucuagua                                              20

<210> SEQ ID NO 295
<211> LENGTH: 20
<212> TYPE: RNA
<213> ORGANISM: Artificial Sequence
<220> FEATURE:
<223> OTHER INFORMATION: Antisense Compound

<400> SEQUENCE: 295
ggcauuaaau uacuagacaa                                              20

<210> SEQ ID NO 296
<211> LENGTH: 20
<212> TYPE: RNA
<213> ORGANISM: Artificial Sequence
<220> FEATURE:
<223> OTHER INFORMATION: Antisense Compound

<400> SEQUENCE: 296
uugucuagua auuuaaugcc                                              20

<210> SEQ ID NO 297
<211> LENGTH: 20
<212> TYPE: RNA
<213> ORGANISM: Artificial Sequence
<220> FEATURE:
<223> OTHER INFORMATION: Antisense Compound

<400> SEQUENCE: 297
aaagugagua gucacagcca                                              20

<210> SEQ ID NO 298
<211> LENGTH: 20
<212> TYPE: RNA
<213> ORGANISM: Artificial Sequence
<220> FEATURE:
<223> OTHER INFORMATION: Antisense Compound

<400> SEQUENCE: 298
uggcugugac uacucacuuu                                              20

<210> SEQ ID NO 299
<211> LENGTH: 20
```

```
<212> TYPE: RNA
<213> ORGANISM: Artificial Sequence
<220> FEATURE:
<223> OTHER INFORMATION: Antisense Compound

<400> SEQUENCE: 299
guuuuucuca ucuucccaca                                                   20

<210> SEQ ID NO 300
<211> LENGTH: 20
<212> TYPE: RNA
<213> ORGANISM: Artificial Sequence
<220> FEATURE:
<223> OTHER INFORMATION: Antisense Compound

<400> SEQUENCE: 300
ugugggaaga ugagaaaaac                                                   20

<210> SEQ ID NO 301
<211> LENGTH: 19
<212> TYPE: RNA
<213> ORGANISM: Artificial Sequence
<220> FEATURE:
<223> OTHER INFORMATION: Antisense Compound

<400> SEQUENCE: 301
ucuuaucacc uuuagcucu                                                    19

<210> SEQ ID NO 302
<211> LENGTH: 19
<212> TYPE: RNA
<213> ORGANISM: Artificial Sequence
<220> FEATURE:
<223> OTHER INFORMATION: Antisense Compound

<400> SEQUENCE: 302
agagcuaaag gugauaaga                                                    19

<210> SEQ ID NO 303
<211> LENGTH: 20
<212> TYPE: RNA
<213> ORGANISM: Artificial Sequence
<220> FEATURE:
<223> OTHER INFORMATION: Antisense Compound

<400> SEQUENCE: 303
uccuuguaua cccucccuau                                                   20

<210> SEQ ID NO 304
<211> LENGTH: 20
<212> TYPE: RNA
<213> ORGANISM: Artificial Sequence
<220> FEATURE:
<223> OTHER INFORMATION: Antisense Compound

<400> SEQUENCE: 304
auagggaggg uauacaagga                                                   20

<210> SEQ ID NO 305
<211> LENGTH: 20
<212> TYPE: RNA
<213> ORGANISM: Artificial Sequence
<220> FEATURE:
<223> OTHER INFORMATION: Antisense Compound

<400> SEQUENCE: 305
```
ugauaaccaa ucacuaucuu                                              20

<210> SEQ ID NO 306
<211> LENGTH: 20
<212> TYPE: RNA
<213> ORGANISM: Artificial Sequence
<220> FEATURE:
<223> OTHER INFORMATION: Antisense Compound

<400> SEQUENCE: 306
aagauaguga uugguuauca                                              20

<210> SEQ ID NO 307
<211> LENGTH: 20
<212> TYPE: RNA
<213> ORGANISM: Artificial Sequence
<220> FEATURE:
<223> OTHER INFORMATION: Antisense Compound

<400> SEQUENCE: 307
acaacaaacc uauuuuuagu                                              20

<210> SEQ ID NO 308
<211> LENGTH: 20
<212> TYPE: RNA
<213> ORGANISM: Artificial Sequence
<220> FEATURE:
<223> OTHER INFORMATION: Antisense Compound

<400> SEQUENCE: 308
acuaaaaaua gguuuguugu                                              20

<210> SEQ ID NO 309
<211> LENGTH: 20
<212> TYPE: RNA
<213> ORGANISM: Artificial Sequence
<220> FEATURE:
<223> OTHER INFORMATION: Antisense Compound

<400> SEQUENCE: 309
augagacuuc ucuuauaucu                                              20

<210> SEQ ID NO 310
<211> LENGTH: 20
<212> TYPE: RNA
<213> ORGANISM: Artificial Sequence
<220> FEATURE:
<223> OTHER INFORMATION: Antisense Compound

<400> SEQUENCE: 310
agauauaaga gaagucucau                                              20

<210> SEQ ID NO 311
<211> LENGTH: 20
<212> TYPE: RNA
<213> ORGANISM: Artificial Sequence
<220> FEATURE:
<223> OTHER INFORMATION: Antisense Compound

<400> SEQUENCE: 311
guacaagaca aaggcgaaug                                              20

<210> SEQ ID NO 312
<211> LENGTH: 20
<212> TYPE: RNA
<213> ORGANISM: Artificial Sequence

```
<220> FEATURE:
<223> OTHER INFORMATION: Antisense Compound

<400> SEQUENCE: 312
cauucgccuu ugucuuguac                                               20

<210> SEQ ID NO 313
<211> LENGTH: 20
<212> TYPE: RNA
<213> ORGANISM: Artificial Sequence
<220> FEATURE:
<223> OTHER INFORMATION: Antisense Compound

<400> SEQUENCE: 313
cuagcagcca ucagcaagag                                               20

<210> SEQ ID NO 314
<211> LENGTH: 20
<212> TYPE: RNA
<213> ORGANISM: Artificial Sequence
<220> FEATURE:
<223> OTHER INFORMATION: Antisense Compound

<400> SEQUENCE: 314
cucuugcuga uggcugcuag                                               20

<210> SEQ ID NO 315
<211> LENGTH: 20
<212> TYPE: RNA
<213> ORGANISM: Artificial Sequence
<220> FEATURE:
<223> OTHER INFORMATION: Antisense Compound

<400> SEQUENCE: 315
uagcaaagcu uuguaguuac                                               20

<210> SEQ ID NO 316
<211> LENGTH: 20
<212> TYPE: RNA
<213> ORGANISM: Artificial Sequence
<220> FEATURE:
<223> OTHER INFORMATION: Antisense Compound

<400> SEQUENCE: 316
guaacuacaa agcuuugcua                                               20

<210> SEQ ID NO 317
<211> LENGTH: 20
<212> TYPE: RNA
<213> ORGANISM: Artificial Sequence
<220> FEATURE:
<223> OTHER INFORMATION: Antisense Compound

<400> SEQUENCE: 317
cuaguuagga auguaauuau                                               20

<210> SEQ ID NO 318
<211> LENGTH: 20
<212> TYPE: RNA
<213> ORGANISM: Artificial Sequence
<220> FEATURE:
<223> OTHER INFORMATION: Antisense Compound

<400> SEQUENCE: 318
auaauuacau uccuaacuag                                               20
```

```
<210> SEQ ID NO 319
<211> LENGTH: 20
<212> TYPE: RNA
<213> ORGANISM: Artificial Sequence
<220> FEATURE:
<223> OTHER INFORMATION: Antisense Compound

<400> SEQUENCE: 319
uuguacacug ucuuaauaug                                              20

<210> SEQ ID NO 320
<211> LENGTH: 20
<212> TYPE: RNA
<213> ORGANISM: Artificial Sequence
<220> FEATURE:
<223> OTHER INFORMATION: Antisense Compound

<400> SEQUENCE: 320
cauauuaaga caguguacaa                                              20

<210> SEQ ID NO 321
<211> LENGTH: 20
<212> TYPE: RNA
<213> ORGANISM: Artificial Sequence
<220> FEATURE:
<223> OTHER INFORMATION: Antisense Compound

<400> SEQUENCE: 321
guacacauuu uauuuacagu                                              20

<210> SEQ ID NO 322
<211> LENGTH: 20
<212> TYPE: RNA
<213> ORGANISM: Artificial Sequence
<220> FEATURE:
<223> OTHER INFORMATION: Antisense Compound

<400> SEQUENCE: 322
acuguaaaua aaauguguac                                              20

<210> SEQ ID NO 323
<211> LENGTH: 19
<212> TYPE: RNA
<213> ORGANISM: Artificial Sequence
<220> FEATURE:
<223> OTHER INFORMATION: Antisense Compound

<400> SEQUENCE: 323
ugucauauuc cuggauccu                                               19

<210> SEQ ID NO 324
<211> LENGTH: 19
<212> TYPE: RNA
<213> ORGANISM: Artificial Sequence
<220> FEATURE:
<223> OTHER INFORMATION: Antisense Compound

<400> SEQUENCE: 324
aggauccagg aauaugaca                                               19

<210> SEQ ID NO 325
<211> LENGTH: 19
<212> TYPE: RNA
<213> ORGANISM: Artificial Sequence
<220> FEATURE:
<223> OTHER INFORMATION: Antisense Compound
```

```
<400> SEQUENCE: 325
uccuggaucc uucaccaau                                              19

<210> SEQ ID NO 326
<211> LENGTH: 19
<212> TYPE: RNA
<213> ORGANISM: Artificial Sequence
<220> FEATURE:
<223> OTHER INFORMATION: Antisense Compound

<400> SEQUENCE: 326
auuggugaag gauccagga                                              19

<210> SEQ ID NO 327
<211> LENGTH: 19
<212> TYPE: RNA
<213> ORGANISM: Artificial Sequence
<220> FEATURE:
<223> OTHER INFORMATION: Antisense Compound

<400> SEQUENCE: 327
auacucagaa ggugucuuc                                              19

<210> SEQ ID NO 328
<211> LENGTH: 19
<212> TYPE: RNA
<213> ORGANISM: Artificial Sequence
<220> FEATURE:
<223> OTHER INFORMATION: Antisense Compound

<400> SEQUENCE: 328
gaagacaccu ucugaguau                                              19

<210> SEQ ID NO 329
<211> LENGTH: 19
<212> TYPE: RNA
<213> ORGANISM: Artificial Sequence
<220> FEATURE:
<223> OTHER INFORMATION: Antisense Compound

<400> SEQUENCE: 329
aaaccagagu gcccaucug                                              19

<210> SEQ ID NO 330
<211> LENGTH: 19
<212> TYPE: RNA
<213> ORGANISM: Artificial Sequence
<220> FEATURE:
<223> OTHER INFORMATION: Antisense Compound

<400> SEQUENCE: 330
cagaugggca cucugguuu                                              19

<210> SEQ ID NO 331
<211> LENGTH: 19
<212> TYPE: RNA
<213> ORGANISM: Artificial Sequence
<220> FEATURE:
<223> OTHER INFORMATION: Antisense Compound

<400> SEQUENCE: 331
aaaaccagag ugcccaucu                                              19

<210> SEQ ID NO 332
```

```
<211> LENGTH: 19
<212> TYPE: RNA
<213> ORGANISM: Artificial Sequence
<220> FEATURE:
<223> OTHER INFORMATION: Antisense Compound

<400> SEQUENCE: 332
agaugggcac ucugguuuu                                                  19

<210> SEQ ID NO 333
<211> LENGTH: 19
<212> TYPE: RNA
<213> ORGANISM: Artificial Sequence
<220> FEATURE:
<223> OTHER INFORMATION: Antisense Compound

<400> SEQUENCE: 333
aaaaaccaga gugcccauc                                                  19

<210> SEQ ID NO 334
<211> LENGTH: 19
<212> TYPE: RNA
<213> ORGANISM: Artificial Sequence
<220> FEATURE:
<223> OTHER INFORMATION: Antisense Compound

<400> SEQUENCE: 334
gaugggcacu cugguuuuu                                                  19

<210> SEQ ID NO 335
<211> LENGTH: 21
<212> TYPE: RNA
<213> ORGANISM: Artificial Sequence
<220> FEATURE:
<223> OTHER INFORMATION: Antisense Compound

<400> SEQUENCE: 335
aaaaccagag ugcccaucug u                                               21

<210> SEQ ID NO 336
<211> LENGTH: 21
<212> TYPE: RNA
<213> ORGANISM: Artificial Sequence
<220> FEATURE:
<223> OTHER INFORMATION: Antisense Compound

<400> SEQUENCE: 336
acagaugggc acucugguuu u                                               21

<210> SEQ ID NO 337
<211> LENGTH: 21
<212> TYPE: RNA
<213> ORGANISM: Artificial Sequence
<220> FEATURE:
<223> OTHER INFORMATION: Antisense Compound

<400> SEQUENCE: 337
aaaaaccaga gugcccaucu g                                               21

<210> SEQ ID NO 338
<211> LENGTH: 21
<212> TYPE: RNA
<213> ORGANISM: Artificial Sequence
<220> FEATURE:
<223> OTHER INFORMATION: Antisense Compound

<400> SEQUENCE: 338
```
cagaugggca cucugguuuu u                                      21

<210> SEQ ID NO 339
<211> LENGTH: 19
<212> TYPE: RNA
<213> ORGANISM: Artificial Sequence
<220> FEATURE:
<223> OTHER INFORMATION: Antisense Compound

<400> SEQUENCE: 339 gcuugguuc agcucccaa                                          19

<210> SEQ ID NO 340
<211> LENGTH: 19
<212> TYPE: RNA
<213> ORGANISM: Artificial Sequence
<220> FEATURE:
<223> OTHER INFORMATION: Antisense Compound

<400> SEQUENCE: 340
ggcgaaugag acuucucuu                                         19

<210> SEQ ID NO 341
<211> LENGTH: 19
<212> TYPE: RNA
<213> ORGANISM: Artificial Sequence
<220> FEATURE:
<223> OTHER INFORMATION: Antisense Compound

<400> SEQUENCE: 341 cuuucuacu ugagccauu                                          19

<210> SEQ ID NO 342
<211> LENGTH: 19
<212> TYPE: RNA
<213> ORGANISM: Artificial Sequence
<220> FEATURE:
<223> OTHER INFORMATION: Antisense Compound

<400> SEQUENCE: 342
caucaucacu guagucauc                                         19

<210> SEQ ID NO 343
<211> LENGTH: 19
<212> TYPE: RNA
<213> ORGANISM: Artificial Sequence
<220> FEATURE:
<223> OTHER INFORMATION: Antisense Compound

<400> SEQUENCE: 343
ugcuaucuua ucaccuuua                                         19

<210> SEQ ID NO 344
<211> LENGTH: 19
<212> TYPE: RNA
<213> ORGANISM: Artificial Sequence
<220> FEATURE:
<223> OTHER INFORMATION: Antisense Compound

<400> SEQUENCE: 344
uccauauugc uaucuuauc                                         19

<210> SEQ ID NO 345
<211> LENGTH: 19
<212> TYPE: RNA

```
<213> ORGANISM: Artificial Sequence
<220> FEATURE:
<223> OTHER INFORMATION: Antisense Compound

<400> SEQUENCE: 345
ucacagccag gcauuaaau                                                    19

<210> SEQ ID NO 346
<211> LENGTH: 19
<212> TYPE: RNA
<213> ORGANISM: Artificial Sequence
<220> FEATURE:
<223> OTHER INFORMATION: Antisense Compound

<400> SEQUENCE: 346 accuuccuu guauacccu                                                     19

<210> SEQ ID NO 347
<211> LENGTH: 19
<212> TYPE: RNA
<213> ORGANISM: Artificial Sequence
<220> FEATURE:
<223> OTHER INFORMATION: Antisense Compound

<400> SEQUENCE: 347
uguaauucuu ugauuggga                                                    19

<210> SEQ ID NO 348
<211> LENGTH: 19
<212> TYPE: RNA
<213> ORGANISM: Artificial Sequence
<220> FEATURE:
<223> OTHER INFORMATION: Antisense Compound

<400> SEQUENCE: 348
ucacugauuu gaaugaaau                                                    19

<210> SEQ ID NO 349
<211> LENGTH: 19
<212> TYPE: RNA
<213> ORGANISM: Artificial Sequence
<220> FEATURE:
<223> OTHER INFORMATION: Antisense Compound

<400> SEQUENCE: 349
uuuacaguuu uguacacug                                                    19

<210> SEQ ID NO 350
<211> LENGTH: 19
<212> TYPE: RNA
<213> ORGANISM: Artificial Sequence
<220> FEATURE:
<223> OTHER INFORMATION: Antisense Compound

<400> SEQUENCE: 350
uuaaaaaacc agagugccc                                                    19

<210> SEQ ID NO 351
<211> LENGTH: 19
<212> TYPE: RNA
<213> ORGANISM: Artificial Sequence
<220> FEATURE:
<223> OTHER INFORMATION: Antisense Compound

<400> SEQUENCE: 351
uuuaaaaaac cagagugcc                                                    19
```

```
<210> SEQ ID NO 352
<211> LENGTH: 19
<212> TYPE: RNA
<213> ORGANISM: Artificial Sequence
<220> FEATURE:
<223> OTHER INFORMATION: Antisense Compound

<400> SEQUENCE: 352
uuuuaaaaaa ccagagugc                                              19

<210> SEQ ID NO 353
<211> LENGTH: 19
<212> TYPE: RNA
<213> ORGANISM: Artificial Sequence
<220> FEATURE:
<223> OTHER INFORMATION: Antisense Compound

<400> SEQUENCE: 353
auuuuuaaaa aaccagagu                                              19

<210> SEQ ID NO 354
<211> LENGTH: 19
<212> TYPE: RNA
<213> ORGANISM: Artificial Sequence
<220> FEATURE:
<223> OTHER INFORMATION: Antisense Compound

<400> SEQUENCE: 354
agagcccaaa agucuucaa                                              19

<210> SEQ ID NO 355
<211> LENGTH: 19
<212> TYPE: RNA
<213> ORGANISM: Artificial Sequence
<220> FEATURE:
<223> OTHER INFORMATION: Antisense Compound

<400> SEQUENCE: 355
uacuagacaa cuggauaug                                              19

<210> SEQ ID NO 356
<211> LENGTH: 19
<212> TYPE: RNA
<213> ORGANISM: Artificial Sequence
<220> FEATURE:
<223> OTHER INFORMATION: Antisense Compound

<400> SEQUENCE: 356
aaagugagua gucacagcc                                              19

<210> SEQ ID NO 357
<211> LENGTH: 19
<212> TYPE: RNA
<213> ORGANISM: Artificial Sequence
<220> FEATURE:
<223> OTHER INFORMATION: Antisense Compound

<400> SEQUENCE: 357
uuuuucucau cuucccaca                                              19

<210> SEQ ID NO 358
<211> LENGTH: 19
<212> TYPE: RNA
<213> ORGANISM: Artificial Sequence
<220> FEATURE:
```

-continued

<223> OTHER INFORMATION: Antisense Compound

<400> SEQUENCE: 358
uccuuguaua cccucccua                                                 19

<210> SEQ ID NO 359
<211> LENGTH: 19
<212> TYPE: RNA
<213> ORGANISM: Artificial Sequence
<220> FEATURE:
<223> OTHER INFORMATION: Antisense Compound

<400> SEQUENCE: 359
ugauaaccaa ucacuaucu                                                 19

<210> SEQ ID NO 360
<211> LENGTH: 19
<212> TYPE: RNA
<213> ORGANISM: Artificial Sequence
<220> FEATURE:
<223> OTHER INFORMATION: Antisense Compound

<400> SEQUENCE: 360
augagacuuc ucuuauauc                                                 19

<210> SEQ ID NO 361
<211> LENGTH: 19
<212> TYPE: RNA
<213> ORGANISM: Artificial Sequence
<220> FEATURE:
<223> OTHER INFORMATION: Antisense Compound

<400> SEQUENCE: 361
uacaagacaa aggcgaaug                                                 19

<210> SEQ ID NO 362
<211> LENGTH: 19
<212> TYPE: RNA
<213> ORGANISM: Artificial Sequence
<220> FEATURE:
<223> OTHER INFORMATION: Antisense Compound

<400> SEQUENCE: 362
uagcagccau cagcaagag                                                 19

<210> SEQ ID NO 363
<211> LENGTH: 19
<212> TYPE: RNA
<213> ORGANISM: Artificial Sequence
<220> FEATURE:
<223> OTHER INFORMATION: Antisense Compound

<400> SEQUENCE: 363
uagcaaagcu uuguaguua                                                 19

<210> SEQ ID NO 364
<211> LENGTH: 19
<212> TYPE: RNA
<213> ORGANISM: Artificial Sequence
<220> FEATURE:
<223> OTHER INFORMATION: Antisense Compound

<400> SEQUENCE: 364
uaguuaggaa uguaauuau                                                 19

```
<210> SEQ ID NO 365
<211> LENGTH: 19
<212> TYPE: RNA
<213> ORGANISM: Artificial Sequence
<220> FEATURE:
<223> OTHER INFORMATION: Antisense Compound

<400> SEQUENCE: 365
uuguacacug ucuuaauau                                                  19

<210> SEQ ID NO 366
<211> LENGTH: 19
<212> TYPE: RNA
<213> ORGANISM: Artificial Sequence
<220> FEATURE:
<223> OTHER INFORMATION: Antisense Compound

<400> SEQUENCE: 366
uuaucaccuu uagcucuaa                                                  19

<210> SEQ ID NO 367
<211> LENGTH: 19
<212> TYPE: RNA
<213> ORGANISM: Artificial Sequence
<220> FEATURE:
<223> OTHER INFORMATION: Antisense Compound

<400> SEQUENCE: 367
uuuagcucua acauuaaca                                                  19

<210> SEQ ID NO 368
<211> LENGTH: 19
<212> TYPE: RNA
<213> ORGANISM: Artificial Sequence
<220> FEATURE:
<223> OTHER INFORMATION: Antisense Compound

<400> SEQUENCE: 368
cuuuagcucu aacauuaac                                                  19

<210> SEQ ID NO 369
<211> LENGTH: 19
<212> TYPE: RNA
<213> ORGANISM: Artificial Sequence
<220> FEATURE:
<223> OTHER INFORMATION: Antisense Compound

<400> SEQUENCE: 369
cucuaacauu aacaacagc                                                  19

<210> SEQ ID NO 370
<211> LENGTH: 19
<212> TYPE: RNA
<213> ORGANISM: Artificial Sequence
<220> FEATURE:
<223> OTHER INFORMATION: Antisense Compound

<400> SEQUENCE: 370
uuacuagaca acuggauau                                                  19

<210> SEQ ID NO 371
<211> LENGTH: 19
<212> TYPE: RNA
<213> ORGANISM: Artificial Sequence
<220> FEATURE:
<223> OTHER INFORMATION: Antisense Compound
```

```
<400> SEQUENCE: 371
cuagacaacu ggauauggu                                              19

<210> SEQ ID NO 372
<211> LENGTH: 19
<212> TYPE: RNA
<213> ORGANISM: Artificial Sequence
<220> FEATURE:
<223> OTHER INFORMATION: Antisense Compound

<400> SEQUENCE: 372
uuaaauuacu agacaacug                                              19

<210> SEQ ID NO 373
<211> LENGTH: 19
<212> TYPE: RNA
<213> ORGANISM: Artificial Sequence
<220> FEATURE:
<223> OTHER INFORMATION: Antisense Compound

<400> SEQUENCE: 373
auuaaauuac uagacaacu                                              19

<210> SEQ ID NO 374
<211> LENGTH: 19
<212> TYPE: RNA
<213> ORGANISM: Artificial Sequence
<220> FEATURE:
<223> OTHER INFORMATION: Antisense Compound

<400> SEQUENCE: 374
aaaaagugag uagucacag                                              19

<210> SEQ ID NO 375
<211> LENGTH: 19
<212> TYPE: RNA
<213> ORGANISM: Artificial Sequence
<220> FEATURE:
<223> OTHER INFORMATION: Antisense Compound

<400> SEQUENCE: 375
uuaaaaagug aguagucac                                              19

<210> SEQ ID NO 376
<211> LENGTH: 19
<212> TYPE: RNA
<213> ORGANISM: Artificial Sequence
<220> FEATURE:
<223> OTHER INFORMATION: Antisense Compound

<400> SEQUENCE: 376
ugaguaguca cagccaggc                                              19

<210> SEQ ID NO 377
<211> LENGTH: 19
<212> TYPE: RNA
<213> ORGANISM: Artificial Sequence
<220> FEATURE:
<223> OTHER INFORMATION: Antisense Compound

<400> SEQUENCE: 377
aagugaguag ucacagcca                                              19

<210> SEQ ID NO 378
<211> LENGTH: 19
```

```
<212> TYPE: RNA
<213> ORGANISM: Artificial Sequence
<220> FEATURE:
<223> OTHER INFORMATION: Antisense Compound

<400> SEQUENCE: 378
uuuugcuuuu aucauuuuu                                                  19

<210> SEQ ID NO 379
<211> LENGTH: 19
<212> TYPE: RNA
<213> ORGANISM: Artificial Sequence
<220> FEATURE:
<223> OTHER INFORMATION: Antisense Compound

<400> SEQUENCE: 379
guuuugcuuu uaucauuuu                                                  19

<210> SEQ ID NO 380
<211> LENGTH: 19
<212> TYPE: RNA
<213> ORGANISM: Artificial Sequence
<220> FEATURE:
<223> OTHER INFORMATION: Antisense Compound

<400> SEQUENCE: 380
uuuuauuuac aguuugua                                                   19

<210> SEQ ID NO 381
<211> LENGTH: 19
<212> TYPE: RNA
<213> ORGANISM: Artificial Sequence
<220> FEATURE:
<223> OTHER INFORMATION: Antisense Compound

<400> SEQUENCE: 381 cauuuauuu acaguuuug                                                   19

<210> SEQ ID NO 382
<211> LENGTH: 19
<212> TYPE: RNA
<213> ORGANISM: Artificial Sequence
<220> FEATURE:
<223> OTHER INFORMATION: Antisense Compound

<400> SEQUENCE: 382
uuaaaaauug uaauaaaca                                                  19

<210> SEQ ID NO 383
<211> LENGTH: 19
<212> TYPE: RNA
<213> ORGANISM: Artificial Sequence
<220> FEATURE:
<223> OTHER INFORMATION: Antisense Compound

<400> SEQUENCE: 383
uuuauuaaaa auuguaaua                                                  19

<210> SEQ ID NO 384
<211> LENGTH: 19
<212> TYPE: RNA
<213> ORGANISM: Artificial Sequence
<220> FEATURE:
<223> OTHER INFORMATION: Antisense Compound

<400> SEQUENCE: 384
```

|  |  |
|---|---|
| uuuguuuuuc ucaucuucc | 19 |

<210> SEQ ID NO 385
<211> LENGTH: 19
<212> TYPE: RNA
<213> ORGANISM: Artificial Sequence
<220> FEATURE:
<223> OTHER INFORMATION: Antisense Compound

<400> SEQUENCE: 385

|  |  |
|---|---|
| aaaaaauuac caaagaaug | 19 |

<210> SEQ ID NO 386
<211> LENGTH: 19
<212> TYPE: RNA
<213> ORGANISM: Artificial Sequence
<220> FEATURE:
<223> OTHER INFORMATION: Antisense Compound

<400> SEQUENCE: 386

|  |  |
|---|---|
| aaugaaaugc auaaauuug | 19 |

<210> SEQ ID NO 387
<211> LENGTH: 19
<212> TYPE: RNA
<213> ORGANISM: Artificial Sequence
<220> FEATURE:
<223> OTHER INFORMATION: Antisense Compound

<400> SEQUENCE: 387

|  |  |
|---|---|
| aaacugaaau cagaaucac | 19 |

<210> SEQ ID NO 388
<211> LENGTH: 19
<212> TYPE: RNA
<213> ORGANISM: Artificial Sequence
<220> FEATURE:
<223> OTHER INFORMATION: Antisense Compound

<400> SEQUENCE: 388

|  |  |
|---|---|
| uuaauguuua uuccaccuu | 19 |

<210> SEQ ID NO 389
<211> LENGTH: 19
<212> TYPE: RNA
<213> ORGANISM: Artificial Sequence
<220> FEATURE:
<223> OTHER INFORMATION: Antisense Compound

<400> SEQUENCE: 389

|  |  |
|---|---|
| uaaauuugua gcaaagcuu | 19 |

<210> SEQ ID NO 390
<211> LENGTH: 19
<212> TYPE: RNA
<213> ORGANISM: Artificial Sequence
<220> FEATURE:
<223> OTHER INFORMATION: Antisense Compound

<400> SEQUENCE: 390

|  |  |
|---|---|
| uaauucuagu uaggaaugu | 19 |

<210> SEQ ID NO 391
<211> LENGTH: 19
<212> TYPE: RNA
<213> ORGANISM: Artificial Sequence

```
<220> FEATURE:
<223> OTHER INFORMATION: Antisense Compound

<400> SEQUENCE: 391
uaaccaaagc aaaauaacc                                                  19

<210> SEQ ID NO 392
<211> LENGTH: 19
<212> TYPE: RNA
<213> ORGANISM: Artificial Sequence
<220> FEATURE:
<223> OTHER INFORMATION: Antisense Compound

<400> SEQUENCE: 392
uguacacauu uuauuuaca                                                  19

<210> SEQ ID NO 393
<211> LENGTH: 19
<212> TYPE: RNA
<213> ORGANISM: Artificial Sequence
<220> FEATURE:
<223> OTHER INFORMATION: Antisense Compound

<400> SEQUENCE: 393
uaguugucua aaagacaau                                                  19

<210> SEQ ID NO 394
<211> LENGTH: 19
<212> TYPE: RNA
<213> ORGANISM: Artificial Sequence
<220> FEATURE:
<223> OTHER INFORMATION: Antisense Compound

<400> SEQUENCE: 394
ucaauuuauu aaaaauugu                                                  19

<210> SEQ ID NO 395
<211> LENGTH: 15
<212> TYPE: DNA
<213> ORGANISM: Artificial Sequence
<220> FEATURE:
<223> OTHER INFORMATION: Antisense Compound

<400> SEQUENCE: 395
gatcgatctg atcgc                                                      15

<210> SEQ ID NO 396
<211> LENGTH: 15
<212> TYPE: DNA
<213> ORGANISM: Artificial Sequence
<220> FEATURE:
<223> OTHER INFORMATION: Antisense Compound

<400> SEQUENCE: 396
agatcgatct gatcg                                                      15

<210> SEQ ID NO 397
<211> LENGTH: 15
<212> TYPE: DNA
<213> ORGANISM: Artificial Sequence
<220> FEATURE:
<223> OTHER INFORMATION: Antisense Compound

<400> SEQUENCE: 397
tagatcgatc tgatc                                                      15
```

```
<210> SEQ ID NO 398
<211> LENGTH: 15
<212> TYPE: DNA
<213> ORGANISM: Artificial Sequence
<220> FEATURE:
<223> OTHER INFORMATION: Antisense Compound

<400> SEQUENCE: 398
ttagatcgat ctgat                                                     15

<210> SEQ ID NO 399
<211> LENGTH: 19
<212> TYPE: RNA
<213> ORGANISM: Artificial Sequence
<220> FEATURE:
<223> OTHER INFORMATION: Antisense Compound

<400> SEQUENCE: 399
uugggagcug aaccaaagc                                                 19

<210> SEQ ID NO 400
<211> LENGTH: 19
<212> TYPE: RNA
<213> ORGANISM: Artificial Sequence
<220> FEATURE:
<223> OTHER INFORMATION: Antisense Compound

<400> SEQUENCE: 400
aagagaaguc ucauucgcc                                                 19

<210> SEQ ID NO 401
<211> LENGTH: 19
<212> TYPE: RNA
<213> ORGANISM: Artificial Sequence
<220> FEATURE:
<223> OTHER INFORMATION: Antisense Compound

<400> SEQUENCE: 401
aauggcucaa guagaaaag                                                 19

<210> SEQ ID NO 402
<211> LENGTH: 19
<212> TYPE: RNA
<213> ORGANISM: Artificial Sequence
<220> FEATURE:
<223> OTHER INFORMATION: Antisense Compound

<400> SEQUENCE: 402
gaugacuaca gugaugaug                                                 19

<210> SEQ ID NO 403
<211> LENGTH: 19
<212> TYPE: RNA
<213> ORGANISM: Artificial Sequence
<220> FEATURE:
<223> OTHER INFORMATION: Antisense Compound

<400> SEQUENCE: 403
uaaaggugau aagauagca                                                 19

<210> SEQ ID NO 404
<211> LENGTH: 19
<212> TYPE: RNA
<213> ORGANISM: Artificial Sequence
<220> FEATURE:
<223> OTHER INFORMATION: Antisense Compound
```

```
<400> SEQUENCE: 404
gauaagauag caauaugga                                    19

<210> SEQ ID NO 405
<211> LENGTH: 19
<212> TYPE: RNA
<213> ORGANISM: Artificial Sequence
<220> FEATURE:
<223> OTHER INFORMATION: Antisense Compound

<400> SEQUENCE: 405
auuuaaugcc uggcuguga                                    19

<210> SEQ ID NO 406
<211> LENGTH: 19
<212> TYPE: RNA
<213> ORGANISM: Artificial Sequence
<220> FEATURE:
<223> OTHER INFORMATION: Antisense Compound

<400> SEQUENCE: 406
aggguauaca aggaaaggu                                    19

<210> SEQ ID NO 407
<211> LENGTH: 19
<212> TYPE: RNA
<213> ORGANISM: Artificial Sequence
<220> FEATURE:
<223> OTHER INFORMATION: Antisense Compound

<400> SEQUENCE: 407
ucccaaucaa agaauuaca                                    19

<210> SEQ ID NO 408
<211> LENGTH: 19
<212> TYPE: RNA
<213> ORGANISM: Artificial Sequence
<220> FEATURE:
<223> OTHER INFORMATION: Antisense Compound

<400> SEQUENCE: 408
auuucauuca aaucaguga                                    19

<210> SEQ ID NO 409
<211> LENGTH: 19
<212> TYPE: RNA
<213> ORGANISM: Artificial Sequence
<220> FEATURE:
<223> OTHER INFORMATION: Antisense Compound

<400> SEQUENCE: 409
caguguacaa aacuguaaa                                    19

<210> SEQ ID NO 410
<211> LENGTH: 19
<212> TYPE: RNA
<213> ORGANISM: Artificial Sequence
<220> FEATURE:
<223> OTHER INFORMATION: Antisense Compound

<400> SEQUENCE: 410
gggcacucug guuuuuaa                                     19

<210> SEQ ID NO 411
```

-continued

```
<211> LENGTH: 19
<212> TYPE: RNA
<213> ORGANISM: Artificial Sequence
<220> FEATURE:
<223> OTHER INFORMATION: Antisense Compound

<400> SEQUENCE: 411
ggcacucugg uuuuuaaa                                                    19

<210> SEQ ID NO 412
<211> LENGTH: 19
<212> TYPE: RNA
<213> ORGANISM: Artificial Sequence
<220> FEATURE:
<223> OTHER INFORMATION: Antisense Compound

<400> SEQUENCE: 412
gcacucuggu uuuuaaaa                                                    19

<210> SEQ ID NO 413
<211> LENGTH: 19
<212> TYPE: RNA
<213> ORGANISM: Artificial Sequence
<220> FEATURE:
<223> OTHER INFORMATION: Antisense Compound

<400> SEQUENCE: 413
acucugguuu uuaaaaau                                                    19

<210> SEQ ID NO 414
<211> LENGTH: 19
<212> TYPE: RNA
<213> ORGANISM: Artificial Sequence
<220> FEATURE:
<223> OTHER INFORMATION: Antisense Compound

<400> SEQUENCE: 414
uugaagacuu uugggcucu                                                   19

<210> SEQ ID NO 415
<211> LENGTH: 19
<212> TYPE: RNA
<213> ORGANISM: Artificial Sequence
<220> FEATURE:
<223> OTHER INFORMATION: Antisense Compound

<400> SEQUENCE: 415 cauaccagu ugucuagua                                                    19

<210> SEQ ID NO 416
<211> LENGTH: 19
<212> TYPE: RNA
<213> ORGANISM: Artificial Sequence
<220> FEATURE:
<223> OTHER INFORMATION: Antisense Compound

<400> SEQUENCE: 416
ggcugugacu acucacuuu                                                   19

<210> SEQ ID NO 417
<211> LENGTH: 19
<212> TYPE: RNA
<213> ORGANISM: Artificial Sequence
<220> FEATURE:
<223> OTHER INFORMATION: Antisense Compound

<400> SEQUENCE: 417
```

```
uguggaaga ugagaaaaa                                              19

<210> SEQ ID NO 418
<211> LENGTH: 19
<212> TYPE: RNA
<213> ORGANISM: Artificial Sequence
<220> FEATURE:
<223> OTHER INFORMATION: Antisense Compound

<400> SEQUENCE: 418
uagggagggu auacaagga                                             19

<210> SEQ ID NO 419
<211> LENGTH: 19
<212> TYPE: RNA
<213> ORGANISM: Artificial Sequence
<220> FEATURE:
<223> OTHER INFORMATION: Antisense Compound

<400> SEQUENCE: 419
agauagugau ugguuauca                                             19

<210> SEQ ID NO 420
<211> LENGTH: 19
<212> TYPE: RNA
<213> ORGANISM: Artificial Sequence
<220> FEATURE:
<223> OTHER INFORMATION: Antisense Compound

<400> SEQUENCE: 420
gauauaagag aagucucau                                             19

<210> SEQ ID NO 421
<211> LENGTH: 19
<212> TYPE: RNA
<213> ORGANISM: Artificial Sequence
<220> FEATURE:
<223> OTHER INFORMATION: Antisense Compound

<400> SEQUENCE: 421
cauucgccuu ugucuugua                                             19

<210> SEQ ID NO 422
<211> LENGTH: 19
<212> TYPE: RNA
<213> ORGANISM: Artificial Sequence
<220> FEATURE:
<223> OTHER INFORMATION: Antisense Compound

<400> SEQUENCE: 422
cucuugcuga uggcugcua                                             19

<210> SEQ ID NO 423
<211> LENGTH: 19
<212> TYPE: RNA
<213> ORGANISM: Artificial Sequence
<220> FEATURE:
<223> OTHER INFORMATION: Antisense Compound

<400> SEQUENCE: 423
uaacuacaaa gcuuugcua                                             19

<210> SEQ ID NO 424
<211> LENGTH: 19
<212> TYPE: RNA
```

```
<213> ORGANISM: Artificial Sequence
<220> FEATURE:
<223> OTHER INFORMATION: Antisense Compound

<400> SEQUENCE: 424
auaauuacau uccuaacua                                                    19

<210> SEQ ID NO 425
<211> LENGTH: 19
<212> TYPE: RNA
<213> ORGANISM: Artificial Sequence
<220> FEATURE:
<223> OTHER INFORMATION: Antisense Compound

<400> SEQUENCE: 425
auauuaagac aguguacaa                                                    19

<210> SEQ ID NO 426
<211> LENGTH: 19
<212> TYPE: RNA
<213> ORGANISM: Artificial Sequence
<220> FEATURE:
<223> OTHER INFORMATION: Antisense Compound

<400> SEQUENCE: 426
uuagagcuaa aggugauaa                                                    19

<210> SEQ ID NO 427
<211> LENGTH: 19
<212> TYPE: RNA
<213> ORGANISM: Artificial Sequence
<220> FEATURE:
<223> OTHER INFORMATION: Antisense Compound

<400> SEQUENCE: 427
uguuaauguu agagcuaaa                                                    19

<210> SEQ ID NO 428
<211> LENGTH: 19
<212> TYPE: RNA
<213> ORGANISM: Artificial Sequence
<220> FEATURE:
<223> OTHER INFORMATION: Antisense Compound

<400> SEQUENCE: 428
guuaauguua gagcuaaag                                                    19

<210> SEQ ID NO 429
<211> LENGTH: 19
<212> TYPE: RNA
<213> ORGANISM: Artificial Sequence
<220> FEATURE:
<223> OTHER INFORMATION: Antisense Compound

<400> SEQUENCE: 429
gcuguuguua auguuagag                                                    19

<210> SEQ ID NO 430
<211> LENGTH: 19
<212> TYPE: RNA
<213> ORGANISM: Artificial Sequence
<220> FEATURE:
<223> OTHER INFORMATION: Antisense Compound

<400> SEQUENCE: 430 auaccaguu gucuaguaa                                                     19
```

<210> SEQ ID NO 431
<211> LENGTH: 19
<212> TYPE: RNA
<213> ORGANISM: Artificial Sequence
<220> FEATURE:
<223> OTHER INFORMATION: Antisense Compound

<400> SEQUENCE: 431
accauaucca guugucuag                                                    19

<210> SEQ ID NO 432
<211> LENGTH: 19
<212> TYPE: RNA
<213> ORGANISM: Artificial Sequence
<220> FEATURE:
<223> OTHER INFORMATION: Antisense Compound

<400> SEQUENCE: 432
caguugucua guaauuuaa                                                    19

<210> SEQ ID NO 433
<211> LENGTH: 19
<212> TYPE: RNA
<213> ORGANISM: Artificial Sequence
<220> FEATURE:
<223> OTHER INFORMATION: Antisense Compound

<400> SEQUENCE: 433
aguugucuag uaauuuaau                                                    19

<210> SEQ ID NO 434
<211> LENGTH: 19
<212> TYPE: RNA
<213> ORGANISM: Artificial Sequence
<220> FEATURE:
<223> OTHER INFORMATION: Antisense Compound

<400> SEQUENCE: 434
cugugacuac ucacuuuuu                                                    19

<210> SEQ ID NO 435
<211> LENGTH: 19
<212> TYPE: RNA
<213> ORGANISM: Artificial Sequence
<220> FEATURE:
<223> OTHER INFORMATION: Antisense Compound

<400> SEQUENCE: 435
gugacuacuc acuuuuuaa                                                    19

<210> SEQ ID NO 436
<211> LENGTH: 19
<212> TYPE: RNA
<213> ORGANISM: Artificial Sequence
<220> FEATURE:
<223> OTHER INFORMATION: Antisense Compound

<400> SEQUENCE: 436
gccuggcugu gacuacuca                                                    19

<210> SEQ ID NO 437
<211> LENGTH: 19
<212> TYPE: RNA
<213> ORGANISM: Artificial Sequence
<220> FEATURE:

<223> OTHER INFORMATION: Antisense Compound

<400> SEQUENCE: 437
uggcugugac uacucacuu 19

<210> SEQ ID NO 438
<211> LENGTH: 19
<212> TYPE: RNA
<213> ORGANISM: Artificial Sequence
<220> FEATURE:
<223> OTHER INFORMATION: Antisense Compound

<400> SEQUENCE: 438
aaaaaugaua aaagcaaaa 19

<210> SEQ ID NO 439
<211> LENGTH: 19
<212> TYPE: RNA
<213> ORGANISM: Artificial Sequence
<220> FEATURE:
<223> OTHER INFORMATION: Antisense Compound

<400> SEQUENCE: 439
aaaaugauaa aagcaaaac 19

<210> SEQ ID NO 440
<211> LENGTH: 19
<212> TYPE: RNA
<213> ORGANISM: Artificial Sequence
<220> FEATURE:
<223> OTHER INFORMATION: Antisense Compound

<400> SEQUENCE: 440
uacaaaacug uaaauaaaa 19

<210> SEQ ID NO 441
<211> LENGTH: 19
<212> TYPE: RNA
<213> ORGANISM: Artificial Sequence
<220> FEATURE:
<223> OTHER INFORMATION: Antisense Compound

<400> SEQUENCE: 441
caaaacugua aauaaaaug 19

<210> SEQ ID NO 442
<211> LENGTH: 19
<212> TYPE: RNA
<213> ORGANISM: Artificial Sequence
<220> FEATURE:
<223> OTHER INFORMATION: Antisense Compound

<400> SEQUENCE: 442
uguuuauuac aauuuuuaa 19

<210> SEQ ID NO 443
<211> LENGTH: 19
<212> TYPE: RNA
<213> ORGANISM: Artificial Sequence
<220> FEATURE:
<223> OTHER INFORMATION: Antisense Compound

<400> SEQUENCE: 443
uauuacaauu uuuaauaaa 19

```
<210> SEQ ID NO 444
<211> LENGTH: 19
<212> TYPE: RNA
<213> ORGANISM: Artificial Sequence
<220> FEATURE:
<223> OTHER INFORMATION: Antisense Compound

<400> SEQUENCE: 444
ggaagaugag aaaaacaaa                                              19

<210> SEQ ID NO 445
<211> LENGTH: 19
<212> TYPE: RNA
<213> ORGANISM: Artificial Sequence
<220> FEATURE:
<223> OTHER INFORMATION: Antisense Compound

<400> SEQUENCE: 445
cauucuuugg uaauuuuuu                                              19

<210> SEQ ID NO 446
<211> LENGTH: 19
<212> TYPE: RNA
<213> ORGANISM: Artificial Sequence
<220> FEATURE:
<223> OTHER INFORMATION: Antisense Compound

<400> SEQUENCE: 446
caaauuuaug cauuucauu                                              19

<210> SEQ ID NO 447
<211> LENGTH: 19
<212> TYPE: RNA
<213> ORGANISM: Artificial Sequence
<220> FEATURE:
<223> OTHER INFORMATION: Antisense Compound

<400> SEQUENCE: 447
gugauucuga uuucaguuu                                              19

<210> SEQ ID NO 448
<211> LENGTH: 20
<212> TYPE: RNA
<213> ORGANISM: Artificial Sequence
<220> FEATURE:
<223> OTHER INFORMATION: Antisense Compound

<400> SEQUENCE: 448
uuguccucaa ccauggucag                                             20

<210> SEQ ID NO 449
<211> LENGTH: 20
<212> TYPE: RNA
<213> ORGANISM: Artificial Sequence
<220> FEATURE:
<223> OTHER INFORMATION: Antisense Compound

<400> SEQUENCE: 449
cugcccuagg cuggcagggc                                             20

<210> SEQ ID NO 450
<211> LENGTH: 20
<212> TYPE: RNA
<213> ORGANISM: Artificial Sequence
<220> FEATURE:
<223> OTHER INFORMATION: Antisense Compound
```

```
<400> SEQUENCE: 450
uuggcaugga gugggagag                                                  20

<210> SEQ ID NO 451
<211> LENGTH: 20
<212> TYPE: RNA
<213> ORGANISM: Artificial Sequence
<220> FEATURE:
<223> OTHER INFORMATION: Antisense Compound

<400> SEQUENCE: 451
ggcauuccaa aacauucuuu                                                 20

<210> SEQ ID NO 452
<211> LENGTH: 20
<212> TYPE: RNA
<213> ORGANISM: Artificial Sequence
<220> FEATURE:
<223> OTHER INFORMATION: Antisense Compound

<400> SEQUENCE: 452
ugcgcccuca ggaguuccgg                                                 20

<210> SEQ ID NO 453
<211> LENGTH: 20
<212> TYPE: RNA
<213> ORGANISM: Artificial Sequence
<220> FEATURE:
<223> OTHER INFORMATION: Antisense Compound

<400> SEQUENCE: 453
auugucacag ggucucacag                                                 20

<210> SEQ ID NO 454
<211> LENGTH: 20
<212> TYPE: DNA
<213> ORGANISM: Artificial Sequence
<220> FEATURE:
<223> OTHER INFORMATION: Antisense Compound

<400> SEQUENCE: 454
agtcgccatc ttagatcgat                                                 20

<210> SEQ ID NO 455
<211> LENGTH: 20
<212> TYPE: RNA
<213> ORGANISM: Artificial Sequence
<220> FEATURE:
<223> OTHER INFORMATION: Antisense Compound

<400> SEQUENCE: 455
agucgccauc uuagaucgau                                                 20

<210> SEQ ID NO 456
<211> LENGTH: 19
<212> TYPE: DNA
<213> ORGANISM: Artificial Sequence
<220> FEATURE:
<223> OTHER INFORMATION: Antisense Compound

<400> SEQUENCE: 456
cgagaggcgg acgggaccg                                                  19

<210> SEQ ID NO 457
<211> LENGTH: 21
```

```
<212> TYPE: DNA
<213> ORGANISM: Artificial Sequence
<220> FEATURE:
<223> OTHER INFORMATION: Antisense Compound

<400> SEQUENCE: 457
cgagaggcgg acgggaccgt t                                              21

<210> SEQ ID NO 458
<211> LENGTH: 21
<212> TYPE: DNA
<213> ORGANISM: Artificial Sequence
<220> FEATURE:
<223> OTHER INFORMATION: Sense Compound

<400> SEQUENCE: 458
cggtcccgtc cgcctctcgt t                                              21

<210> SEQ ID NO 459
<211> LENGTH: 19
<212> TYPE: DNA
<213> ORGANISM: Artificial Sequence
<220> FEATURE:
<223> OTHER INFORMATION: Sense Compound

<400> SEQUENCE: 459
cggtcccgtc cgcctctcg                                                 19
```

MODULATION OF EIF4E EXPRESSION

FIELD OF THE INVENTION

The present invention provides compositions and methods for modulating the expression of eIF4E. In particular, this invention relates to single- or double-stranded antisense compounds, particularly oligonucleotide compounds, which hybridize with nucleic acid molecules encoding eIF4E. Such compounds are shown herein to modulate the expression of eIF4E.

BACKGROUND OF THE INVENTION

Eukaryotic gene expression must be regulated such that cells can rapidly respond to a wide range of different conditions. The process of mRNA translation is one step at which gene expression is highly regulated. In response to hormones, growth factors, cytokines and nutrients, animal cells generally activate translation in preparation for the proliferative response. The rate of protein synthesis typically decreases under stressful conditions, such as oxidative or osmotic stress, DNA damage or nutrient withdrawal. Activation or suppression of mRNA translation occurs within minutes and control over this process is thought to be exerted at the initiation phase of protein synthesis (Rosenwald et al., Oncogene, 1999, 18, 2507-2517; Strudwick and Borden, Differentiation, 2002, 70, 10-22).

Translation initiation necessitates the coordinated activities of several eukaryotic initiation factors (eIFs), proteins which are classically defined by their cytoplasmic location and ability to regulate the initiation phase of protein synthesis. One of these factors, eukaryotic initiation factor 4E (eIF4E) (also known as eukaryotic translation initiation factor 4E, eukaryotic translation initiation factor 4E-like 1 (eIF4EL1), cap-binding protein (CBP) and messenger RNA cap-binding protein) was initially isolated as a 25 kDa mRNA cap-binding protein involved in translation (Rychlik et al., Proc. Natl. Acad. Sci. USA, 1987, 84, 945-949) and has since become one of the most highly-characterized eIFs. eIF4E, present in limiting amounts relative to other initiation factors, is one component of the eIF4F initiation complex, which is also comprised of a scaffold protein eIF4G and the RNA helicase eIF4A. In the cytoplasm, eIF4E catalyzes the rate-limiting step of cap-dependent protein synthesis by specifically binding to the 5' terminal 7-methyl GpppX cap structure present on nearly all mature cellular mRNAs, which serves to deliver the mRNAs to the eIF4F complex. Once bound, the eIF4F complex scans from the 5' to the 3' end of the cap, permitting the RNA helicase activity of eIF4A to resolve any secondary structure present in the 5' untranslated region (UTR), thus revealing the translation initiation codon and facilitating ribosome loading onto the mRNA (Graff et al., Clin. Exp. Metastasis, 2003, 20, 265-273; Strudwick et al., Differentiation, 2002, 70, 10-22).

eIF4E availability for incorporation into the eIF4E complex is regulated through phosphorylation as well as through the binding of inhibitory proteins. eIF4E is a phosphoprotein that is phosphorylated on serine 209 by the mitogen-activated protein kinase-interacting kinase Mnk1 (Flynn et al., J. Biol. Chem., 1995, 270, 21684-21688; Wang et al., J. Biol. Chem., 1998, 273, 9373-9377; and Waskiewicz et al., Embo J., 1997, 16, 1909-1920). Phosphorylation of eIF4E increases its affinity for mRNA caps, thus elevating translation rates (Waskiewicz et al., Mol. Cell Biol., 1999, 19, 1871-1880). Increased phosphorylation of eIF4E by phorbol esters, cell stresses and cytokines involves the p38 mitogen-activated (MAP) kinase and/or Erk signaling pathways, which in turn stimulate Mnk1 activity. Other stresses such as heat shock, sorbitol and hydrogen peroxide stimulate p38 MAP kinase and increase Mnk1 activity, however, these stimuli increase the binding of eIF4E to the eIF4E-binding protein 1 (4E-BP1) (Wang et al., J. Biol. Chem., 1998, 273, 9373-9377). Binding of 4E-BP1 to eIF4E blocks the phosphorylation of eIF4E by Mnk1 (Wang et al., J. Biol. Chem., 1998, 273, 9373-9377). The 4E-binding proteins 1 and 2 act as effective inhibitors of translation by competing with eIF4G for binding to the dorsal surface of eIF4E (Ptushkina et al., Embo J., 1999, 18, 4068-4075). Phosphorylation of the binding proteins by MTOR causes them to dissociate from eIF4E, allowing eIF4E activity.

A growing number of observations suggest that translation factors localize and function in the nucleus, as well as in the cytoplasm. Transcription and translation are traditionally considered to be spatially separated in eukaryotes; however, coupled transcription and translation is observed within the nuclei of mammalian cells (Iborra et al., Science, 2001, 293, 1139-1142). A fraction of eIF4E localizes to the nucleus, suggesting that this translation factor may exhibit some of its control over translation in the nucleus (Lejbkowicz et al., Proc. Natl. Acad. Sci. U S A, 1992, 89, 9612-9616). eIF4E is imported into the nucleus through the importin alpha/beta pathway by the nucleoplasmic shuttling protein eIF4E-transporter (4E-T) (Dostie et al., Embo J., 2000, 19, 3142-3156). In the nucleus, eIF4E can be directly bound by the promyelocytic leukemia protein (PML), an important regulator of mammalian cell growth and apoptosis (Cohen et al., Embo J., 2001, 20, 4547-4559). PML, through its RING domain, modulates eIF4E activity by greatly reducing its affinity for the 5' cap structure of mRNAs (Cohen et al., Embo J., 2001, 20, 4547-4559).

An excess of eIF4E does not lead to global elevated translation rates, but rather selectively increases the synthesis of proteins encoded by mRNAs that are classified as eIF4E-sensitive, including growth stimulatory proteins such as vascular endothelial growth factor (VEGF), ornithine decarboxylase (ODC) and cyclin D1 (Kevil et al., Int. J. Cancer, 1996, 65, 785-790; Rosenwald, Cancer Lett., 1995, 98, 77-82; and Shantz et al., Cancer Res., 1994, 54, 2313-2316). While ODC and VEGF protein levels are elevated through increased translation initiation, cyclin D1 levels are elevated due to greater transport of cyclin D1 mRNA into the cytoplasm (Kevil et al., Int. J. Cancer, 1996, 65, 785-790; Rosenwald, Cancer Lett., 1995, 98, 77-82; Rousseau et al., Proc. Natl. Acad. Sci. USA, 1996, 93, 1065-1070). Thus, in addition to having a role in translation initiation, eIF4E can also affect mRNA nucleocytoplasmic transport.

eIF4E function is an essential determinant of overall cell protein synthesis and growth (De Benedetti et al., Mol. Cell. Biol., 1991, 11, 5435-5445). In normal cells, eIF4E is present in limiting amounts, which restricts translation. mRNAs which encode proteins necessary for cell growth and survival typically contain a complex, highly structured 5' UTR, which renders these mRNAs poor substrates for translation. Many of these mRNAs, however, are well translated in the presence of excess eIF4E and are also upregulated by tumors (Graff and Zimmer, Clin. Exp. Metastasis, 2003, 20, 265-273). The translation of mRNAs related to cell differentiation may also be enhanced by eIF4E, as increased levels of eIF4E are found in some differentiating cell lines, including epithelial lung tumor cell lines (Walsh et al., Differentiation, 2003, 71, 126-134).

Overexpression of eIF4E has been reported in many human cancers and cancer-derived cell lines and also leads to oncogenic transformation of cells and invasive/metastatic phenotype in animal models. Unlike non-transformed, cultured cells, transformed cell lines express eIF4E independently of the presence of serum growth factors (Rosenwald, Cancer Lett., 1995, 98, 77-82). Excess eIF4E leads to aberrant growth and neoplastic morphology in HeLa cells and also causes tumorigenic transformation in NIH 3T3 and Rat2 fibroblasts, as judged by anchorage-independent growth, formation of transformed foci in culture and tumor formation in nude mice (De Benedetti et al., Proc. Natl. Acad. Sci. USA, 1990, 87, 8212-8216; and Lazaris-Karatzas et al., Nature, 1990, 345, 544-547). Furthermore, neoplastic transformation exhibited by cells overexpressing eIF4E is associated with the increased translation of ODC (Lazaris-Karatzas et al., Nature, 1990, 345, 544-547). Additionally, the elevated nuclear export of cyclin D1 associated with increased eIF4E expression is directly linked to transformation activity (Cohen et al., Embo J., 2001, 20, 4547-4559). These findings demonstrate that when present in excess, eIF4E can increase the expression or nuclear export of growth regulatory mRNAs. As a consequence, the affected cells can proliferate independently of normal growth control mechanisms. Enhanced eIF4E phosphorylation is observed in cells transformed with the src tyrosine kinase oncoprotein, suggesting that elevated eIF4E activity, in addition to overexpression, contributes to the loss of growth regulation in transformed cells (Frederickson et al., Mol. Cell. Biol., 1991, 11, 2896-2900).

eIF4E is found elevated in several human cancers, including but not limited to non-Hodgkin's lymphomas, colon adenomas and carcinomas and larynx, head and neck, prostate, breast and bladder cancers (Crew et al., Br. J. Cancer, 2000, 82, 161-166; Graff et al., Clin. Exp. Metastasis, 2003, 20, 265-273; Haydon et al., Cancer, 2000, 88, 2803-2810; Kerekatte et al., Int. J. Cancer, 1995, 64, 27-31; Rosenwald et al., Oncogene, 1999, 18, 2507-2517; Wang et al., Am. J. Pathol., 1999, 155, 247-255). Upregulation of eIF4E is an early event in colon carcinogenesis, and is frequently accompanied by an increase in cyclin D1 levels (Rosenwald et al., Oncogene, 1999, 18, 2507-2517). Excess eIF4E is also a reliable predictor of tumor recurrence in head and neck carcinomas, is selectively upregulated in invasive bladder carcinomas and is correlated with poor histological grades and more advanced states of metastasis in laryngeal squamous cell carcinoma (Crew et al., Br. J. Cancer, 2000, 82, 161-166; Liang et al., Laryngoscope, 2003, 113, 1238-1243; and Nathan et al., Oncogene, 1997, 15, 579-584). These findings suggest that elevated levels of eIF4E participate in the advancement as well as initiation of cancer.

Inhibition of eIF4E expression and activity has been accomplished through the use of antisense mechanisms. Antisense oligonucleotides equipped with 3'-overhanging nucleotides modulate the binding of eIF4E to 5'-capped oligoribonucleotides (Baker et al., J. Biol. Chem., 1992, 267, 11495-11499). Introduction into HeLa cells of an episomal vector engineered to express an oligonucleotide complementary to 20 nucleotides in the translation start region of eIF4E reduces levels of eIF4E and concomitantly decreases the rates of cell growth and protein synthesis, demonstrating that eIF4E is required for cell proliferation (Bommer et al., Cell. Mol. Biol. Res., 1994, 40, 633-641; De Benedetti et al., Mol. Cell. Biol., 1991, 11, 5435-5445). Levels of eIF4G, the scaffold protein component of the eIF4F complex, are also reduced. Despite the diminished levels of translation following inhibition of eIF4E, certain proteins continue to be synthesized, and many of these have been identified as stress-inducible or heat-shock proteins (Joshi-Barve et al., J. Biol. Chem., 1992, 267, 21038-21043). The same vector reduces eIF4E by 50 to 60 percent in rat embryo fibroblasts, which is sufficient to inhibit ras-mediated transformation and tumorigenesis of these cells (Graff et al., Int. J. Cancer, 1995, 60, 255-263; Rinker-Schaeffer et al., Int. J. Cancer, 1993, 55, 841-847). Furthermore, ODC translation and polyamine transport are diminished, an observation that provides a link between ras-induced malignancy, eIF4E activity and polyamine metabolism (Graff et al., Biochem. Biophys. Res. Commun., 1997, 240, 15-20). Stable transformation of a mammary carcinoma line and a head and neck squamous cell carcinoma cell line with the eIF4E antisense vector results in reduction fibroblast growth factor-2 (FGF-2) expression and in inhibition of tumorigenic and angiogenic capacity of the cells in mice, suggesting a causal role for eIF4E in tumor vascularization (DeFatta et al., Laryngoscope, 2000, 110, 928-933; Nathan et al., Oncogene, 1997, 15, 1087-1094).

Targeted inactivation of a *Caenorhabditis elegans* homolog of human eIF4E, IFE-3, with small interfering RNA injected into young adult worms leads to embryonic lethality in 100% of the progeny (Keiper et al., J. Biol. Chem., 2000, 275, 10590-10596). Small interfering double-stranded RNA targeted to eIF4E has also revealed that lack of eIF4E regulation participates in cellular transformation. Functional inactivation of eIF4E using a gene-specific 21-nucleotide small interfering RNA targeted to a portion of the coding region of human eIF4E results in a significant reduction of anchorage-independent growth of malignant cholangiocytes, a phenotype associated with transformed cells. In addition, phosphorylation of eIF4E in malignant cholangiocytes is dependent upon p38 MAP kinase signaling, demonstrating a link between p38 MAP kinase signaling and the regulation of protein synthesis in the process of cholangiocarcinoma growth (Yamagiwa et al., Hepatology, 2003, 38, 158-166).

Further evidence that inhibition of eIF4E activity reduces the tumorigenic potential of cells is seen in breast cancer cells that express a constitutively active form of the eIF4E inhibitor 4EBP-1, which leads to cell cycle arrest associated with downregulation of cyclin D1 and upregulation of the cyclin-dependent kinase $p27^{Kip1}$ (Jiang et al., Cancer Cell Int., 2003, 3, 2). The overexpression of 4E-BP1 in gastrointestinal cancers, where eIF4E levels are significantly higher than in normal tissue, is correlated with a reduction in distant metastases (Martin et al., Int. J. Biochem. Cell. Biol., 2000, 32, 633-642).

U.S. Pat. No. 5,646,009 claims and discloses a hybrid vector in which one DNA segment encodes a cap-binding protein consisting of eIF4E, eIF4E factor or a mutant thereof. This patent also discloses a nucleic acid sequence encoding a human eIF4E.

Disclosed in U.S. Pat. No. 6,171,798 is a method for treating cancer in a patient by administering to cancer cells an antisense construct comprising at least 12 nucleotides of a coding sequence of a gene selected from a group containing a human eIF4E, in 3' to 5' orientation with respect to a promotor controlling its expression.

U.S. Pat. No. 6,596,854 claims and discloses isolated nucleic acid molecules encoding variants of human eIF4E, wherein said variants have amino acid substitutions in the regions of amino acids 112 and 114-121, or position 118, or position 119, or position 115 or position 121.

European patent application 1 033 401 and Japanese patent application 2001269182 claim a purified nucleic acid comprising at least 10 consecutive nucleotides of a sequence selected from a group of EST-related sequences which includes a portion of a nucleic acid molecule encoding human eIF4E. These publications also disclose the preparation and use of antisense constructs and oligonucleotides to be used in gene therapy.

PCT publications WO 01/96388 and WO 01/96389 disclose and claim isolated polynucleotides comprising a sequence selected from: sequences, complements of sequences, sequences consisting of at least 20 contiguous residues of a sequence, sequences that hybridize to a sequence, or sequences having at least 75% or at least 95% identity to a sequence, provided in the sequence listing, which includes a nucleic acid molecule encoding a human eIF4E. This publication also claims a method for the treatment of a cancer in a patient, comprising administering to the patient a composition of the claimed polynucleotides.

PCT publication WO 03/039443 claims and discloses a method for the preparation of a pharmaceutical composition for the treatment of leukemia characterized in that an antisense oligonucleotide complementary to a polynucleotide encoding a protein corresponding to marker, selected from a group including a human eIF4E nucleic acid molecule, is admixed with pharmaceutical compounds.

U.S. pre-grant publication 20030087852 discloses a plasmid encoding eIF4E antisense mRNA and cultured mouse cells transfected with this plasmid.

Disclosed in U.S. pre-grant publication 20030144190 are antisense molecules which may be used to decrease or abrogate the expression of a nucleic acid sequence or protein of the invention, including eIF4E. Also disclosed are a plasmid encoding eIF4E antisense mRNA and cultured rat fibroblasts constitutively expressing this plasmid.

As a consequence of eIF4E involvement in many diseases, there remains a long felt need for additional agents capable of effectively regulating eIF4E. As such, inhibition is especially important in the treatment of cancer, given that the upregulation of expression of eIF4E is associated with so many different types of cancer.

Antisense technology is an effective means for reducing the expression of specific gene products and has been proven to be uniquely useful in a number of therapeutic, diagnostic, and research applications. The present invention provides compositions and methods for modulating eIF4E expression.

SUMMARY OF THE INVENTION

The present invention is directed to oligomeric compounds, such as antisense compounds, and pharmaceutically acceptable salts thereof, which are targeted to a nucleic acid molecule encoding eIF4E and which inhibit the expression of eIF4E. The oligomeric compounds may be RNA-like or DNA-like oligomeric compounds, including oligonucleotides. The oligomeric compounds may be single-stranded or partially or wholly double-stranded oligomeric compounds, and may be chemically modified or unmodified. Pharmaceutical and other compositions comprising these compounds are also provided.

Further provided are methods of screening for modulators of eIF4E and methods of modulating the expression of eIF4E in cells, tissues or animals comprising contacting said cells, tissues or animals with one or more of the compounds or compositions of the invention. Methods of treating an animal, particularly a human are also set forth herein. Such methods comprise administering a therapeutically or prophylactically effective amount of one or more of the compounds or compositions of the invention.

DETAILED DESCRIPTION OF THE INVENTION

A. Overview of the Invention

The present invention employs oligomeric compounds, such as antisense compounds, single- or double-stranded oligonucleotides and similar species, for use in modulating the function or effect of nucleic acid molecules encoding eIF4E. This is accomplished by providing oligomeric compounds which specifically hybridize with one or more nucleic acid molecules encoding eIF4E. As used herein, the terms "target nucleic acid" and "nucleic acid molecule encoding eIF4E" have been used for convenience to encompass DNA encoding eIF4E, RNA (including pre-mRNA and mRNA or portions thereof) transcribed from such DNA, and also cDNA derived from such RNA. This modulation of function of a target nucleic acid by compounds that hybridize to it is generally referred to as "antisense".

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, and catalytic activity or complex formation involving the RNA which may be engaged in or facilitated by the RNA. One result of such interference with target nucleic acid function is modulation of the expression of eIF4E. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is one form of modulation of expression and mRNA is often a target nucleic acid.

In the context of this invention, "hybridization" means the pairing of substantially complementary strands of oligomeric compounds. In the present invention, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is "specifically hybridizable" when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as Na++ or K++ (i.e., low ionic strength), temperature higher than 20°-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SDS at 60° C. for 30 minutes.

"Complementary," as used herein, refers to the capacity for precise pairing between two nucleobases on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense compound. These compounds are then tested using the methods described herein to determine their ability to inhibit expression of eIF4E mRNA.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

B. Compounds of the Invention

In the context of the present invention, the term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular and may also include branching. Oligomeric compounds can include double-stranded constructs such as, for example, two strands hybridized to form double-stranded compounds or a single strand with sufficient self complementarity to allow for hybridization and formation of a fully or partially double-stranded compound. In one embodiment of the invention, double-stranded antisense compounds encompass short interfering RNAs (siRNAs). As used herein, the term "siRNA" is defined as a double-stranded compound having a first and second strand and comprises a central complementary portion between said first and second strands and terminal portions that are optionally complementary between said first and second strands or with the target mRNA. Each strand may be from about 8 to about 80 nucleobases in length, 10 to 50 nucleobases in length, 12 or 13 to 30 nucleobases in length, 12 or 13 to 24 nucleobases in length or 19 to 23 nucleobases in length. The central complementary portion may be from about 8 to about 80 nucleobases in length, 10 to 50 nucleobases in length, 12 or 13 to 30 nucleobases in length, 12 or 13 to 24 nucleobases in length or 19 to 23 nucleobases in length. The terminal portions can be from 1 to 6 nucleobases in length. The siRNAs may also have no terminal portions. The two strands of an siRNA can be linked internally leaving free 3' or 5' termini or can be linked to form a continuous hairpin structure or loop. The hairpin structure may contain an overhang on either the 5' or 3' terminus producing an extension of single-stranded character.

In one embodiment of the invention, double-stranded antisense compounds are canonical siRNAs. As used herein, the term "canonical siRNA" is defined as a double-stranded oligomeric compound having a first strand and a second strand each strand being 21 nucleobases in length with the strands being complementary over 19 nucleobases and having on each 3' termini of each strand a deoxy thymidine dimer (dTdT) which in the double-stranded compound acts as a 3' overhang.

In another embodiment, the double-stranded antisense compounds are blunt-ended siRNAs. As used herein the term "blunt-ended siRNA" is defined as an siRNA having no terminal overhangs. That is, at least one end of the double-stranded compound is blunt. siRNAs whether canonical or blunt act to elicit dsRNAse enzymes and trigger the recruitment or activation of the RNAi antisense mechanism. In a further embodiment, single-stranded RNAi (ssRNAi) compounds that act via the RNAi antisense mechanism are contemplated.

Further modifications can be made to the double-stranded compounds and may include conjugate groups attached to one of the termini, selected nucleobase positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double-stranded. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

According to the present invention, "antisense compounds" include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleobase positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific inhibition of gene expression can be achieved by stable expression of dsRNA hairpins in transgenic cell lines (Hammond et al., Nat. Rev. Genet., 1991, 2, 110-119; Matzke et al., Curr. Opin. Genet. Dev., 2001, 11, 221-227; Sharp, Genes Dev., 2001, 15, 485-490). When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-form-like structure are "RNA-like." In some (chimeric) embodiments, an antisense compound may contain both A- and B-form regions.

One example of an enzyme that modifies the target nucleic acid is RNAse H, a cellular endonuclease which cleaves the RNA strand of an RNA:DNA duplex. It is known in the art that single-stranded antisense compounds which contain "DNA-like" regions (e.g., 2'-deoxy regions) longer than about 3 or 4 consecutive nucleobases are able to recruit RNAse H. Activation of RNase H, therefore, results in cleavage of the RNA target, thereby greatly enhancing the efficiency of oligonucleotide-mediated inhibition of gene expression. More recently, a dsRNAse has been postulated to be involved in the cleavage of the RNA strand in the RNA:RNA duplex observed in the RNA interference (RNAi) process.

While one well accepted form of antisense compound is a single-stranded antisense oligonucleotide, in other contexts, double-stranded RNA or analogs thereof are useful. In many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing (Guo et al., Cell, 1995, 81, 611-620; Montgomery et al., Proc. Natl. Acad. Sci. USA, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., Nature, 1998, 391, 806-811). The RNAi compounds are often referred to as short interfering RNAs or siRNAs. Recently, it has been shown that it is, in fact, the single-stranded RNA oligomers of antisense polarity of the dsRNAs which are the potent inducers of RNAi (Tijsterman et al., Science, 2002, 295, 694-697). Both RNAi compounds (i.e., single- or double-stranded RNA or RNA-like compounds) and single-stranded RNase H-dependent antisense compounds bind to their RNA target by base pairing (i.e., hybridization) and induce site-specific cleavage of the target RNA by specific RNAses; i.e., both work via an antisense mechanism. Vickers et al., J. Biol. Chem., 2003, 278, 7108-7118.

In the context of this invention, the term "oligonucleotide" refers to an oligomer or polymer of ribonucleic acid (RNA) and/or deoxyribonucleic acid (DNA), or a mimetic, chimera, analog or homolog thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

The antisense compounds in accordance with this invention can comprise an antisense portion from about 8 to about 80 nucleobases (i.e. from about 8 to about 80 linked nucleosides) in length. This refers to the length of the antisense strand or portion of the antisense compound. In other words, a single-stranded antisense compound of the invention comprises from 8 to about 80 nucleobases, and a double-stranded antisense compound of the invention (such as a dsRNA, for example) comprises an antisense strand or portion of 8 to about 80 nucleobases in length. One of ordinary skill in the art will appreciate that this comprehends antisense portions of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length, or any range therewithin.

In one embodiment, the antisense compounds of the invention have antisense portions of 10 to 50 nucleobases in length. One having ordinary skill in the art will appreciate that this embodies antisense compounds having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length, or any range therewithin.

In one embodiment, the antisense compounds of the invention have antisense portions of 12 or 13 to 30 nucleobases in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleobases in length, or any range therewithin.

In some embodiments, the antisense compounds of the invention have antisense portions of 12 or 13 to 24 nucleobases in length. One having ordinary skill in the art will appreciate that this embodies antisense compounds having antisense portions of 12, 13, 14, 15, 16, 17, 18, 19, 20, 21, 22, 23 or 24 nucleobases in length, or any range therewithin.

In some embodiments, the antisense compounds of the invention have antisense portions of 19 to 23 nucleobases in length. One having ordinary skill in the art will appreciate that this embodies antisense compounds having antisense portions of 19, 20, 21, 22 or 23 nucleobases in length, or any range therewithin.

Antisense compounds 8-80 nucleobases in length comprising a stretch of at least eight (8) consecutive nucleobases selected from within the illustrative antisense compounds are considered to be suitable antisense compounds as well.

Exemplary compounds include oligonucleotide sequences that comprise at least the 8 consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Other compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). It is also understood that compounds may be represented by oligonucleotide sequences that comprise at least 8 consecutive nucleobases from an internal portion of the sequence of an illustrative compound, and may extend in either or both directions until the oligonucleotide contains about 8 about 80 nucleobases.

It should be noted that oligomeric compounds or pharmaceutically acceptable salts thereof of the present invention do not include the nucleobase sequence 5'-AGTCGCCATCT-TAGATCGAT-3' (SEQ ID NO:454) or 5'-AGUCGCCAU-CUUAGAUCGAU-3' (SEQ ID NO:455). Furthermore, oligomeric compounds or pharmaceutically acceptable salts thereof encompassed by the present invention can consist of, consist essentially of, or comprise, the specific nucleotide sequences disclosed herein. The phrases "consist essentially of," "consists essentially of," "consisting essentially of," or the like when applied to oligomeric compounds or pharmaceutically acceptable salts thereof encompassed by the present invention refer to nucleotide sequences like those disclosed herein, but which contain additional nucleotides (ribonucleotides, deoxyribonucleotides, or analogs or derivatives thereof as discussed herein). Such additional nucleotides, however, do not materially affect the basic and novel characteristic(s) of these oligomeric compounds or pharmaceutically acceptable salts thereof in modulating, attenuating, or inhibiting eIF4E gene expression or RNA function, including the specific quantitative effects of these molecules, compared to the corresponding parameters of the corresponding oligomeric compounds or pharmaceutically acceptable salts thereof disclosed herein.

One having skill in the art armed with the antisense compounds illustrated herein will be able, without undue experimentation, to identify further antisense compounds.

C. Targets of the Invention

"Targeting" an oligomeric compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes eIF4E.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes)

or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding eIF4E, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, one region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. The 5' cap region is also a target.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also suitable target sites. mRNA transcripts produced via the process of splicing of two (or more) mRNAs from different gene sources are known as "fusion transcripts." It is also known that introns can be effectively targeted using antisense compounds targeted to, for example, DNA or pre-mRNA. Single-stranded antisense compounds such as oligonucleotide compounds that work via an RNase H mechanism are effective for targeting pre-mRNA.

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants." Consequently, mRNA variants are processed pre-mRNA variants and each unique pre-mRNA variant must always produce a unique mRNA variant as a result of splicing. These mRNA variants are also known as "alternative splice variants." If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also suitable target nucleic acids.

The locations on the target nucleic acid to which the suitable oligomeric compounds hybridize are hereinbelow referred to as "suitable target segments." As used herein the term "suitable target segment" is defined as at least an 8-nucleobase portion of a target region to which an active oligomeric compound is targeted. While not wishing to be bound by theory, it is presently believed that these target segments represent portions of the target nucleic acid which are accessible for hybridization.

While the specific sequences of certain suitable target segments are set forth herein, one of skill in the art will recognize that these serve to illustrate and describe particular embodiments within the scope of the present invention. Additional suitable target segments may be identified by one having ordinary skill. It is not necessary that the "suitable target segment" be identified by this term or included in a "suitable target segment" table, if any.

Target segments 8-80 nucleobases in length comprising a stretch of at least eight (8) consecutive nucleobases selected from within the illustrative suitable target segments are considered to be suitable for targeting as well.

Target segments can include DNA or RNA sequences that comprise at least the 8 consecutive nucleobases from the 5'-terminus of one of the illustrative suitable target segments (the remaining nucleobases being a consecutive stretch of the same DNA or RNA beginning immediately upstream of the 5'-terminus of the target segment and continuing until the DNA or RNA contains about 8 to about 80 nucleobases). Similarly suitable target segments are represented by DNA or RNA sequences that comprise at least the 8 consecutive nucleobases from the 3'-terminus of one of the illustrative suitable target segments (the remaining nucleobases being a consecutive stretch of the same DNA or RNA beginning immediately downstream of the 3'-terminus of the target segment and continuing until the DNA or RNA contains about 8 to about 80 nucleobases). It is also understood that suitable oligomeric target segments may be represented by DNA or RNA sequences that comprise at least 8 consecutive nucleobases from an internal portion of the sequence of an illustrative suitable target segments, and may extend in either or both directions until the oligonucleotide contains about 8 about 80 nucleobases. One having skill in the art armed with the suitable target segments illustrated herein will be able, without undue experimentation, to identify further suitable target segments.

Once one or more target regions, segments or sites have been identified, oligomeric compounds are chosen which are sufficiently complementary to the target, i.e., hybridize sufficiently well and with sufficient specificity, to give the desired effect.

The oligomeric compounds may also be targeted to regions of the target nucleobase sequence (e.g., such as those disclosed in Examples below) comprising nucleobases 1-80, 81-160, 161-240, 241-320, 321-400, 401-480, 481-560, 561-640, 641-720, 721-800, 801-880, 881-960, 961-1040, 1041-1120, 1121-1200, 1201-1280, 1281-1360, 1361-1440, 1441-1520, 1521-1600, 1601-1680, 1681-1760, or 1761-1842, or any combination thereof.

D. Screening and Target Validation

In a further embodiment, the "suitable target segments" identified herein may be employed in a screen for additional compounds that modulate the expression of eIF4E. "Modulators" are those compounds that decrease or increase the expression of a nucleic acid molecule encoding eIF4E and which comprise at least an 8-nucleobase portion which is complementary (i.e., antisense) to a suitable target segment. The screening method comprises the steps of contacting a suitable target segment of a nucleic acid molecule encoding eIF4E with one or more candidate modulators, and selecting for one or more candidate modulators which decrease or increase the expression of a nucleic acid molecule encoding eIF4E. Once it is shown that the candidate modulator or modulators are capable of modulating (e.g. either decreasing or increasing) the expression of a nucleic acid molecule encoding eIF4E, the modulator may then be employed in further investigative studies of the function of eIF4E, or for use as a research, diagnostic, or therapeutic agent in accordance with the present invention.

In general, activity of dsRNA constructs correlated with the activity of RNase H-dependent single-stranded antisense compounds targeted to the same site. Vickers et al., J. Biol. Chem., 2003, 278, 7108. Thus sequences which are active as either single-stranded antisense compounds (e.g., RNase H-dependent compounds) can be used to design double-stranded (e.g. siRNA) antisense compounds and vice versa. The suitable target segments of the present invention may be combined with their respective complementary antisense compounds to form stabilized double-stranded (duplexed) compounds. Such double stranded oligomeric compounds moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697). Both RNase H-based antisense (usually using single-stranded compounds) and siRNA (usually using double-stranded compounds) are antisense mechanisms, typically resulting in loss of target RNA function. Optimized siRNA and RNase H-dependent oligomeric compounds behave similarly in terms of potency, maximal effects, specificity and duration of action, and efficiency. Moreover it has been shown that in general, activity of dsRNA constructs correlated with the activity of RNase H-dependent single-stranded antisense compounds targeted to the same site. One major exception is that RNase H-dependent antisense compounds were generally active against target sites in pre-mRNA whereas siRNAs were not. Vickers et al., J. Biol. Chem., 203, 278, 7108.

The oligomeric compounds of the present invention can also be applied in the areas of drug discovery and target validation. The present invention comprehends the use of the compounds and suitable target segments identified herein in drug discovery efforts to elucidate relationships that exist between eIF4E and a disease state, phenotype, or condition. These methods include detecting or modulating eIF4E comprising contacting a sample, tissue, cell, or organism with one or more antisense compounds of the present invention, measuring the nucleic acid or protein level of eIF4E and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The oligomeric compounds of the present invention can be utilized for diagnostics, therapeutics, prophylaxis and as research reagents and kits. Furthermore, oligomeric compounds, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma et al., FEBS Lett., 2000, 480, 17-24; Celis et al., FEBS Lett., 2000, 480, 2-16), SAGE (serial analysis of gene expression) (Madden et al., Drug Discov. Today, 2000, 5, 415-425), READS (restriction enzyme amplification of digested cDNAs) (Prashar et al., Methods Enzymol., 1999, 303, 258-72), TOGA (total gene expression analysis) (Sutcliffe et al., Proc. Natl. Acad. Sci. U.S.A., 2000, 97, 1976-81), protein arrays and proteomics (Celis et al., FEBS Lett., 2000, 480, 2-16; Jungblut et al., Electrophoresis, 1999, 20, 2100-10), expressed sequence tag (EST) sequencing (Celis et al., FEBS Lett., 2000, 480, 2-16; Larsson et al., J. Biotechnol., 2000, 80, 143-57), subtractive RNA fingerprinting (SuRF) (Fuchs et al., Anal. Biochem., 2000, 286, 91-98; Larson et al., Cytometry, 2000, 41, 203-208), subtractive cloning, differential display (DD) (Jurecic et al., Curr. Opin. Microbiol., 2000, 3, 316-21), comparative genomic hybridization (Carulli et al., J. Cell Biochem. Suppl., 1998, 31, 286-96), FISH (fluorescent in situ hybridization) techniques (Going et al., Eur. J. Cancer, 1999, 35, 1895-904) and mass spectrometry methods (To, Comb. Chem. High Throughput Screen, 2000, 3, 235-41).

The specificity and sensitivity of antisense is also harnessed by those of skill in the art for therapeutic uses. Antisense compounds have been employed as therapeutic moieties in the treatment of disease states in animals, including humans. Antisense drugs, including ribozymes, have been safely and effectively administered to humans and numerous clinical trials are presently underway. It is thus established that antisense compounds are useful therapeutic modalities that can be configured to be useful in treatment regimes for the treatment of cells, tissues and animals, especially humans. Treatment of animals selected from companion, zoo, and farm animals, including, but not limited to, cats, dogs, rodents, horses, cows, sheep, pigs, goats, etc. is contemplated by the present invention.

For therapeutics, an animal, such as a human, suspected of having a disease or disorder which can be treated by modulating the expression of eIF4E is treated by administering compounds in accordance with this invention. For example, in one non-limiting embodiment, the methods comprise the step of administering to the animal in need of treatment, a therapeutically effective amount of an oligomeric compound that inhibits eIF4E. The eIF4E compounds of the present invention effectively inhibit the activity or expression of a nucleic acid encoding eIF4E RNA. Because reduction in eIF4E RNA levels can lead to reduction in eIF4E protein levels as well, reduction in protein expression or levels can also be measured. In some embodiments, the animal is diagnosed for the disease or disorder prior to treatment. In one embodiment, the oligomeric compounds modulate the activity or expression of eIF4E mRNA by at least about 10%, by at least about 20%, by at least about 25%, by at least about 30%, by at least about 40%, by at least about 50%, by at least about 60%, by at least about 70%, by at least about 75%, by at least about 80%, by at least about 85%, by at least about 90%, by at least about 95%, by at least about 98%, by at least about 99%, or by 100%.

For example, the reduction of the expression of eIF4E may be measured in serum, adipose tissue, liver or any other body fluid, tissue or organ of the animal. The cells contained within said fluids, tissues or organs being analyzed can contain a nucleic acid molecule encoding eIF4E protein and/or the eIF4E protein itself.

The compounds of the invention can be utilized in pharmaceutical compositions by adding an effective amount of a compound to a suitable pharmaceutically or physiologically acceptable excipient, diluent or carrier. Use of the compounds and methods of the invention may also be useful prophylactically. Thus, the present invention encompasses the use of the compounds disclosed herein as pharmaceuticals, as well as the use of the presently disclosed compounds for the preparation of medicaments for the treatment of disorders as disclosed herein.

The compounds of the present invention inhibit the expression of eIF4E. Because these compounds inhibit the effects of eIF4E activation, the compounds are useful in the treatment of disorders related to eIF4E expression. Thus, the compounds of the present invention are antineoplastic agents.

The present compounds are believed to be useful in treating carcinomas such as neoplasms of the central nervous system: glioblastoma multiforme, astrocytoma, oligodendroglial tumors, ependymal and choroid plexus tumors, pineal tumors, neuronal tumors, medulloblastoma, schwannoma, meningioma, meningeal sarcoma; neoplasms of the eye: basal cell carcinoma, squamous cell carcinoma, melanoma, rhabdomyosarcoma, retinoblastoma; neoplasms of the endocrine glands: pituitary neoplasms, neoplasms of the thyroid, neoplasms of the adrenal cortex, neoplasms of the neuroendocrine system, neoplasms of the gastroenteropancreatic endocrine system, neoplasms of the gonads; neoplasms of the head and neck: head and neck cancer, oral cavity, pharynx, larynx, odontogenic tumors; neoplasms of the thorax: large cell lung carcinoma, small cell lung carcinoma, non-small cell lung carcinoma, neoplasms of the thorax, malignant mesothelioma, thymomas, primary germ cell tumors of the thorax; neoplasms of the alimentary canal: neoplasms of the esophagus, neoplasms of the stomach, neoplasms of the liver, neoplasms of the gallbladder, neoplasms of the exocrine pancreas, neoplasms of the small intestine, veriform appendix and peritoneum, adneocarcinoma of the colon and rectum, neoplasms of the anus; neoplasms of the genitourinary tract: renal cell carcinoma, neoplasms of the renal pelvis and ureter, neoplasms of the bladder, neoplasms of the urethra, neoplasms of the prostate, neoplasms of the penis, neoplasms of the testis; neoplasms of the female reproductive organs: neoplasms of the vulva and vagina, neoplasms of the cervix, addenocarcinoma of the uterine corpus, ovarian cancer, gynecologic sarcomas; neoplasms of the breast; neoplasms of the skin: basal cell carcinoma, squamous cell carcinoma, dermatofibrosarcoma, Merkel cell tumor; malignant melanoma; neoplasms of the bone and soft tissue: osteogenic sarcoma, malignant fibrous histiocytoma, chondrosarcoma, Ewing's sarcoma, primitive neuroectodermal tumor, angiosarcoma; neoplasms of the hematopoietic system: myelodysplastic sydromes, acute myeloid leukemia, chronic myeloid leukemia, acute lymphocytic leukemia, HTLV-1 and T-cell leukemia/lymphoma, chronic lymphocytic leukemia, hairy cell leukemia, Hodgkin's disease, non-Hodgkin's lymphomas, mast cell leukemia; and neoplasms of children: acute lymphoblastic leukemia, acute myelocytic leukemias, neuroblastoma, bone tumors, rhabdomyosarcoma, lymphomas, renal tumors.

Thus, in one embodiment, the present invention provides a method for the treatment of susceptible neoplasms comprising administering to a patient in need thereof an effective amount of an isolated single stranded RNA or double stranded RNA oligonucleotide directed to eIF4E. The ssRNA or dsRNA oligonucleotide may be modified or unmodified. That is, the present invention provides for the use of an isolated double stranded RNA oligonucleotide targeted to eIF4E, or a pharmaceutical composition thereof, for the treatment of susceptible neoplasms.

In another aspect, the present invention provides for the use of a compound of an isolated double stranded RNA oligonucleotide in the manufacture of a medicament for inhibiting eIF4E expression or overexpression. Thus, the present invention provides for the use of an isolated double stranded RNA oligonucleotide targeted to eIF4E in the manufacture of a medicament for the treatment of susceptible neoplasms by means of the method described above.

The compounds of the present invention are useful for the treatment of hyperproliferative disorders. Specifically, the compounds of the present invention are useful for the treatment of cancer. The compounds of the present invention are particularly useful for the treatment of solid tumors. Thus, the compounds of the present invention are especially useful for the treatment of breast cancer, colon cancer, prostate cancer, lung cancer, liver cancer, bladder cancer, ovarian cancer, renal cancer and glioblastoma. The antisense compounds of the present invention are particularly useful for the treatment of solid tumors.

F. Modifications

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally desired. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Sugar and Internucleoside Linkages

Specific examples of oligomeric antisense compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Oligomeric compounds of the invention can have one or more modified internucleoside linkages. One phosphorus-containing modified internucleoside linkage is the phosphorothioate internucleoside linkage. Other modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkyl-phosphoramidates, thionophosphoramidates, thionoalkylphosphonates, thionoalkyl-phosphotriesters, phosphonoacetate and thiophosphonoacetate (see Sheehan et al., Nucleic Acids Research, 2003, 31(14), 4109-4118 and Dellinger et al., J. Am. Chem. Soc., 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., J. Am. Chem. Soc., 1994, 116, 3143-3144). N3'-P5'-phosphoramidates have been studied with some success in vivo to specifically down regulate the expression of the c-myc gene (Skorski et al., Proc. Natl. Acad. Sci., 1997, 94, 3966-3971; and Faira et al., Nat. Biotechnol., 2001, 19, 40-44).

Representative U.S. patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In some embodiments of the invention, oligomeric compounds may have one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). The MMI type internucleoside linkages are disclosed in the above referenced U.S. Pat. No. 5,489,677. Amide internucleoside linkages are disclosed in the above referenced U.S. Pat. No. 5,602,240.

Some oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Another group of oligomeric compounds amenable to the present invention includes oligonucleotide mimetics. The term mimetic as it is applied to oligonucleotides is intended to include oligomeric compounds wherein the furanose ring or the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid.

One such oligomeric compound, an oligonucleotide mimetic that has been shown to have excellent hybridization properties, is referred to as a peptide nucleic acid (PNA). Nielsen et al., Science, 1991, 254, 1497-1500. PNAs have favorable hybridization properties, high biological stability and are electrostatically neutral molecules. In one recent study PNA compounds were used to correct aberrant splicing in a transgenic mouse model (Sazani et al., Nat. Biotechnol., 2002, 20, 1228-1233). In PNA oligomeric compounds, the sugar-backbone of an oligonucleotide is replaced with an amide containing backbone, in particular an aminoethylglycine backbone. The nucleobases are bound directly or indirectly (—C(=O)—CH$_2$— as shown below) to aza nitrogen atoms of the amide portion of the backbone. Representative United States patents that teach the preparation of PNA oligomeric compounds include, but are not limited to, U.S. Pat. Nos.: 5,539,082; 5,714,331; and 5,719,262, each of which is herein incorporated by reference. PNA compounds can be obtained commercially from Applied Biosystems (Foster City, Calif., USA). Numerous modifications to the basic PNA backbone are known in the art; particularly useful are PNA compounds with one or more amino acids conjugated to one or both termini. In particular, 1-8 lysine or arginine residues are useful when conjugated to the end of a PNA molecule.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Braasch et al., Biochemistry, 2002, 41(14), 4503-4510). Morpholino-based oligomeric compounds have been studied in zebrafish embryos (see: Genesis, volume 30, issue 3, 2001 and Heasman, J., Dev. Biol., 2002, 243, 209-214). Further studies of morpholino-based oligomeric compounds have also been reported (see: Nasevicius et al., Nat. Genet., 2000, 26, 216-220; and Lacerra et al., Proc. Natl. Acad. Sci., 2000, 97, 9591-9596). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits. Linking groups can be varied from chiral to achiral, and from charged to neutral. U.S. Pat. No. 5,166,315 discloses linkages including —O—P(=O)(N(CH$_3$)$_2$)—O—; U.S. Pat. No. 5,034,506 discloses achiral intermorpholino linkages; and U.S. Pat. No. 5,185,444 discloses phosphorus containing chiral intermorpholino linkages.

A further class of oligonucleotide mimetic is referred to as cyclohexenyl nucleic acids (CeNA). The furanose ring normally present in a DNA or RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate E. coli RNase resulting in cleavage of the target RNA strand.

A further modification includes bicyclic sugar moieties such as "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos.: 6,268,490 and 6,670,461). The linkage can be a methylene (—CH$_2$—) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., Bioorganic Medicinal Chemistry, 2003, 11, 2211-2226). LNA and other bicyclic sugar analogs display very high duplex thermal stabilities with complementary DNA and RNA (Tm= +3 to +10 C), stability towards 3'-exonucleolytic degradation and good solubility properties. LNAs are commercially available from ProLigo (Paris, France and Boulder, Colo., USA).

An isomer of LNA that has also been studied is ∀-L-LNA which has been shown to have superior stability against a 3'-exonuclease (Frieden et al., Nucleic Acids Research, 2003, 21, 6365-6372). The ∀-L-LNAs were incorporated into antisense gapmers and chimeras that showed potent antisense activity.

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA: LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm= +15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD)

spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DNA LNA chimeras have been shown to efficiently inhibit gene expression when targeted to a variety of regions (5'-untranslated region, region of the start codon or coding region) within the luciferase mRNA (Braasch et al., Nucleic Acids Research, 2002, 30, 5160-5167).

Potent and nontoxic antisense oligonucleotides containing LNAs have been described (Wahlestedt et al., Proc. Natl. Acad. Sci. U.S.A., 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished. Further successful in vivo studies involving LNA's have shown knock-down of the rat delta opioid receptor without toxicity (Wahlestedt et al., Proc. Natl. Acad. Sci., 2000, 97, 5633-5638) and in another study showed a blockage of the translation of the large subunit of RNA polymerase II (Fluiter et al., Nucleic Acids Res., 2003, 31, 953-962).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Another oligonucleotide mimetic amenable to the present invention that has been prepared and studied is threose nucleic acid. This oligonucleotide mimetic is based on threose nucleosides instead of ribose nucleosides. Initial interest in (3',2')-∀-L-threose nucleic acid (TNA) was directed to the question of whether a DNA polymerase existed that would copy the TNA. It was found that certain DNA polymerases are able to copy limited stretches of a TNA template (reported in C&EN/Jan. 13, 2003). In another study it was determined that TNA is capable of antiparallel Watson-Crick base pairing with complementary DNA, RNA and TNA oligonucleotides (Chaput et al., J. Am. Chem. Soc., 2003, 125, 856-857).

In one study (3',2')-∀-L-threose nucleic acid was prepared and compared to the 2' and 3' amidate analogs (Wu et al., Organic Letters, 2002, 4(8), 1279-1282). The amidate analogs were shown to bind to RNA and DNA with comparable strength to that of RNA/DNA.

Further oligonucleotide mimetics have been prepared to include bicyclic and tricyclic nucleoside analogs (see Steffens et al., Helv. Chim. Acta, 1997, 80, 2426-2439; Steffens et al., J. Am. Chem. Soc., 1999, 121, 3249-3255; Renneberg et al., J. Am. Chem. Soc., 2002, 124, 5993-6002; and Renneberg et al., Nucleic Acids Res., 2002, 30, 2751-2757). These modified nucleoside analogs have been oligomerized using the phosphoramidite approach and the resulting oligomeric compounds containing tricyclic nucleoside analogs have shown increased thermal stabilities (Tms) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology. Further oligonucleotide mimetics amenable to the present invention have been prepared wherein a cyclobutyl ring replaces the naturally occurring furanosyl ring.

Oligomeric compounds may also contain one or more substituted sugar moieties. Suitable compounds can comprise one of the following at the 2' position: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_m CH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O—(2-methoxyethyl) or 2'-MOE) (Martin et al., Helv. Chim. Acta, 1995, 78, 486-504) i.e., an alkoxyalkoxy group. A further modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$, also described in examples hereinbelow.

Other modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the C. elegans system. Properties that are enhanced by using more stable 3'-endo nucleosides include but are not limited to: modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as illustrated in FIG. 2, below (Gallo et al., Tetrahedron, 2001, 57, 5707-5713. Harry-O'kuru et al., J. Org. Chem., 1997, 62(6), 1754-1759 and Tang et al., J. Org. Chem., 1999, 64, 747-754.)

Alternatively, preference for the 3'-endo conformation can be achieved by deletion of the 2'-OH as exemplified by 2'deoxy-2'F-nucleosides (Kawasaki et al., J. Med. Chem., 1993, 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters, 1995, 5, 1455-1460; and Owen et al., J. Org. Chem., 1976, 41, 3010-3017), or for example modification to yield methanocarba nucleoside analogs (Jacobson et al., J. Med. Chem. Lett., 2000, 43, 2196-2203; and Lee et al., Bioorganic and Medicinal Chemistry Letters, 2001, 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun., 1998, 4, 455-456), and ethylene bridged Nucleic Acids (ENA, Morita et al, Bioorganic & Medicinal Chemistry Letters, 2002, 12, 73-76.)

One conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligonucleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press, and the examples section below.)

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, Biochem. Biophys. Res. Comm., 1970, 47, 1504.) In general, RNA:RNA duplexes are more stable and have higher melting temperatures (Tms) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., Nucleic Acids Research, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., Nucleic Acids Res., 1993, 21, 2051-2056). The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). The stability of the duplex formed between a target RNA and a synthetic sequence is central to therapies such as but not limited to antisense and RNA interference as these mechanisms require the binding of a synthetic oligomer strand to an RNA target strand. In the case of antisense, effective inhibition of the mRNA requires that the antisense DNA have a very high binding affinity with the mRNA. Otherwise the desired interaction between the synthetic oligomer strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

Increasing the percentage of C3'-endo sugars in a modified oligonucleotide targeted to an RNA target strand should preorganize this strand for binding to RNA. Of the several sugar modifications that have been reported and studied in the literature, the incorporation of electronegative substituents such as 2'-fluoro or 2'-alkoxy shift the sugar conformation towards the 3' endo (northern) pucker conformation. This preorganizes an oligonucleotide that incorporates such modifications to have an A-form conformational geometry. This A-form conformation results in increased binding affinity of the oligonucleotide to a target RNA strand.

Representative 2'-substituent groups amenable to the present invention that give A-form conformational properties (3'-endo) to the resultant duplexes include 2'-O-alkyl, 2'-O-substituted alkyl and 2'-fluoro substituent groups. Suitable for the substituent groups are various alkyl and aryl ethers and thioethers, amines and monoalkyl and dialkyl substituted amines. It is further intended that multiple modifications can be made to one or more of the oligomeric compounds of the invention at multiple sites of one or more monomeric subunits (nucleosides are suitable) and or internucleoside linkages to enhance properties such as but not limited to activity in a selected application.

Natural and Modified Nucleobases

Oligomeric compounds may also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($—C{\equiv}C—CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-b)(1,4)benzoxazin-2 (3H)-one), carbazole cytidine (2H-pyrimido(4,5-b)indol-2-one), pyridoindole cytidine (H-pyrido(3',2':4,5)pyrrolo(2,3-d)pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently suitable base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, each of which is herein incorporated by reference, and U.S. Pat. No. 5,750,692, which is herein incorporated by reference.

Oligomeric compounds of the present invention can also include polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Representative cytosine analogs that make 3 hydrogen bonds with a guanosine in a second strand include 1,3-diazaphenoxazine-2-one ($R_{10}$=O, $R_{11}$-$R_{14}$=H) (Kurchavov et al., Nucleosides and Nucleotides, 1997, 16, 1837-1846), 1,3-diazaphenothiazine-2-one ($R_{10}$=S, $R_{11}$-$R_{14}$=H), (Lin et al, J. Am. Chem. Soc., 1995, 117, 3873-3874) and 6,7,8,9-tetrafluoro-1,3-diazaphenoxazine-2-one ($R_{10}$=O, $R_{11}$-$R_{14}$=F) (Wang et al, Tetrahedron Lett., 1998, 39, 8385-8388). Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155,920; and U.S. patent application entitled "Nuclease Resistant Chimeric Oligonucleotides" filed May 24, 2002, Ser. No. 10/013,295, both of which are commonly herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) (Lin et al, J. Am. Chem. Soc., 1998, 120, 8531-8532). Binding studies demonstrated that a single incorporation could enhance the binding affinity of a model oligonucleotide to its complementary target DNA or RNA with a $\Delta T_m$ of up to 18° relative to 5-methyl cytosine ($dC5^{me}$), which is the highest known affinity enhancement for a single modification, yet. On the other hand, the gain in helical stability does not compromise the specificity of the oligonucleotides.

Further tricyclic heterocyclic compounds and methods of using them that are amenable to use in the present invention are disclosed in U.S. Pat. No. 6,028,183, which issued on May 22, 2000, and U.S. Pat. No. 6,007,992, which issued on Dec. 28, 1999, the contents of which are incorporated herein in their entirety.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNase H, enhance cellular uptake and exhibit an increased antisense activity (Lin et al, J. Am. Chem. Soc., 1998, 120, 8531-8532). The activity enhancement was even more pronounced in case of G-clamp, as a single substitution was shown to significantly improve the in vitro potency of a 20mer 2'-deoxyphosphorothioate oligonucleotides (Flanagan et al, Proc. Natl. Acad. Sci. USA, 1999, 96, 3513-3518). Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocyclic bases are disclosed in but not limited to, the above noted U.S. Pat. No. 3,687,808, as well as U.S. Pat. Nos.: 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. patent application Ser. No. 09/996,292 filed Nov. 28, 2001, each of which is herein incorporated by reference.

Conjugates

Another modification of the antisense compounds of the invention involves chemically linking to the oligomeric compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Antisense compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative U.S. patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Oligomeric compounds can also be modified to have one or more stabilizing groups that are generally attached to one or both termini of an oligomeric strand to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein. These terminal modifications protect the oligomeric compounds having terminal nucleic acid molecules from exonuclease degradation, and can help in delivery and/or localization within a cell. The cap can be present at either the 5'-terminus (5'-cap) or at the 3'-terminus (3'-cap) or can be present on both termini of a single strand, or one or more termini of both strands of a double-stranded compound. This cap structure is not to be confused with the inverted methylguanosine "5'cap" present at the 5' end of native mRNA molecules. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein). For siRNA constructs, the 5' end (5' cap) is commonly but not limited to 5'-hydroxyl or 5'-phosphate.

Particularly suitable 3'-cap structures include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in WO 03/004602 published on Jan. 16, 2003.

Chimeric Compounds

It is not necessary for all positions in a given antisense compound to be uniformly modified, and in fact more than one of the aforementioned modifications may be incorporated in a single compound or even within a single nucleoside within an antisense compound.

The present invention also includes antisense compounds which are chimeric compounds. "Chimeric" antisense compounds or "chimeras," in the context of this invention, are single- or double-stranded antisense compounds, such as oligonucleotides, which contain two or more chemically distinct regions, each made up of at least one monomer unit, i.e., a nucleotide in the case of an oligonucleotide compound. Chimeric antisense oligonucleotides are one form of antisense compound. These oligonucleotides typically contain at least one region which is modified so as to confer upon the oligonucleotide increased resistance to nuclease degradation, increased cellular uptake, alteration of charge, increased stability and/or increased binding affinity for the target nucleic acid. An additional region of the oligonucleotide may serve as a substrate for RNAses or other enzymes. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNase III or RNAseL which cleaves both cellular and viral RNA. Cleavage products of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

Salts, Prodrugs and Bioequivalents

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes or other chemicals and/or conditions. In particular, prodrug versions of the oligonucleotides of the invention are prepared as SATE ((S-acetyl-2-thioethyl) phosphate) derivatives according to the methods disclosed in WO 93/24510 to Gosselin et al., published Dec. 9, 1993 or in WO 94/26764 to Imbach et al. The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoc acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. Sodium salts of antisense oligonucleotides are useful and are well accepted for therapeutic administration to humans. In another embodiment, sodium salts of dsRNA compounds are also provided.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Penetration enhancers have been found to enhance bioavailability of orally administered oligonucleotides. Penetration enhancers include surfactants, bile salts, fatty acids, chelating agents or non-chelating surfactants. Capric acid (C10) and/or lauric acid (C12) and their salts are among those shown to be effective fatty acids for enhancing biavailability of oligonucleotides; ursodeoxycholic acid (UDCA) and chenodeoxycholic acid (CDCA) are among those shown to be effective bile salts for enhancing biavailability of oligonucleotides. Delayed-release (for example pulsed or pulsatile-release) formulations and sustained-release formulations are also useful for enhancing bioavailability. Bioadhesive materials may be added to adhere drug carrier particles to mucosal membranes to enhance uptake.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety. Various fatty acids and their derivatives which act as penetration enhancers include, for example, oleic acid, lauric acid (C12), capric acid (C10), myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., Critical Reviews in Therapeutic Drug Carrier Systems, 1991, 8:2, 91-192; Muranishi, Critical Reviews in Therapeutic Drug Carrier Systems, 1990, 7:1, 1-33; El-Hariri et al., J. Pharm. Pharmacol., 1992, 44, 651-654). Examples of some fatty acids are sodium caprate (C10) and sodium laurate (C12), used singly or in combination at concentrations of 0.5 to 5%.

Exemplary bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxy-cholate), chenodeoxycholic acid (sodium chenodeoxy-cholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583). UDCA and CDCA have been used effectively as penetration enhancers for oligonucleotides, and even more effectively when combined.

Complex formulations containing one or more bile salts and one or more fatty acids were even more effective, particularly CDCA (with or without UDCA), in combination with laurate and caprate (U.S. application Ser. No. 09/108,673, Teng and Hardee, filed Jul. 1, 1998).

One of skill in the art will recognize that formulations are routinely designed according to their intended use, i.e. route of administration.

Formulations for topical administration include those in which the oligonucleotides of the invention are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations are those in which oligonucleotides of the invention are administered in conjunction with one or more penetration enhancers surfactants and chelators. Surfactants include fatty acids and/or esters or salts thereof, bile acids and/or salts thereof. Bile acids/salts and fatty acids and their uses are further described in U.S. Pat. No. 6,287,860, which is incorporated herein in its entirety. Also suitable are combinations of penetration enhancers, for example, fatty acids/salts in combination with bile acids/salts. One combination is the sodium salt of lauric acid, capric acid and UDCA. Further penetration enhancers include polyoxyethylene-9-lauryl ether, polyoxyethylene- 20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. Nos. 09/108,673 (filed Jul. 1, 1998), 09/315,298 (filed May 20, 1999) and 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin, pemetrexed and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

As used herein, the term "patient" refers to a mammal that is afflicted with one or more disorders associated with eIF4E expression or overexpression. It will be understood that the most desired patient is a human. It is also understood that this invention relates specifically to the inhibition of mammalian eIF4E expression or overexpression.

It is recognized that one skilled in the art may affect the disorders associated with eIF4E expression or overexpression by treating a patient presently afflicted with the disorders with an effective amount of a compound of the present invention. Thus, the terms "treatment" and "treating" are intended to refer to all processes wherein there may be a slowing, interrupting, arresting, controlling, delaying or stopping of the progression of the disorders described herein, but does not necessarily indicate a total elimination of all symptoms.

As used herein, the term "effective amount" or "therapeutically effective amount" of a compound of the present invention refers to an amount that is effective in treating or preventing the disorders described herein.

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.0001 µg to 100 g per kg of body weight, and may be given once or more daily, weekly, monthly or yearly, or even once every 2 to 20 years. In some embodiments, dosage is from 0.0001 µg to 100 g per kg of body weight, from 0.001 µg to 10 g per kg of body weight, from 0.01 µg to 1 g per kg of body weight, from 0.1 µg to 100 mg per kg of body weight, from 1 µg to 10 mg per kg of body weight, from 10 µg to 1 mg per kg of body weight, or from 100 µg to 500 µg per kg of body weight, and may be given once or more daily, weekly, monthly or yearly, or even once every 2 to 20 years. For double-stranded compounds, the dose must be calculated to account for the increased nucleic acid load of the second strand (for compounds comprising two strands) or additional nucleic acid length (for a self-complementary compound). Persons of ordinary skill in the art can easily estimate repetition rates for dosing based on measured residence times and concentrations of the drug in bodily fluids or tissues.

Much work has been done on the absorbance, distribution, metabolism and excretion (collectively known as ADME) of oligonucleotides. ADME is sequence independent because all sequences of a given chemistry (e.g., all 2' MOE gapmers with a P=S backbone) have similar physical/chemical properties such as water solubility, molecular weight (approx. 7000) and pKa. Oligonucleotides are eliminated relatively rapidly from plasma (distribution half life approximately 1 hour, distribution complete by 24 hours) by distribution to tissues, primarily but not limited to liver, kidney, spleen and bone marrow. A strong correlation between pharmacokinetics and pharmacodynamics has been demonstrated in tissues including kidney, liver, bone marrow, adipose tissue, spleen, lymph nodes, lung (via aerosol) and central nervous system (given intracerebroventricularly). The tissue half life is 1-5 days for first generation antisense drugs (2'-deoxy with phosphorothioate backbone) and 10-28 days for 2'-MOE gapped oligonucleotides with phosphorothioate backbones. Henry et al., Curr. Opin. Invest. Drugs, 2001, 2, 1444-1449.

Following successful treatment, it may be desirable to have the patient undergo maintenance therapy to prevent the recurrence of the disease state, wherein the oligonucleotide is administered in maintenance doses, ranging from 0.0001 μg to 100 g per kg of body weight, once or more daily, to once every 20 years.

While the present invention has been described with specificity in accordance with certain of its embodiments, the following examples serve only to illustrate the invention and are not intended to limit the same. Each of the references, GenBank accession numbers, and the like recited in the present application is incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, (5'-O-(4,4'-Dimethoxytriphenylmethyl)-2'-deoxy-N$^4$-benzoyl-5-methylcytidin-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N$^4$-benzoyl-5-methyl-cytidine penultimate intermediate, (5'-O-(4,4'-Dimethoxytriphenylmethyl)-2'-O-(2-methoxyethyl)-N$^4$-benzoyl-5-methylcytidin-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-N$^6$-benzoyladenosin-3'-O-yl)-2-cyanoethyl-N,N-diisopropylphosphoramidite (MOE A amdite), (5'-O-(4,4'-Dimethoxytriphenylmethyl)-2'-O-(2-methoxyethyl)-N$^4$-isobutyrylguanosin-3'-O-yl)-2-cyanoethyl-N,N-diisopropylphosphormidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-O$^2$-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O—(N,N dimethylaminooxyethyl)-5-methyluridine, 2'-β-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy) nucleoside amidites, N2-isobutyryl-6-O-diphenylcarbomoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy (2'-DMAEOE) nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl))-5-methyl uridine-3'-O-(cyanoethyl-N,N-diisopropyl) phosphoramidite.

2'-Deoxy and 2'-methoxy Amidites

2'-Deoxy and 2'-methoxy beta-cyanoethyldiisopropyl phosphoramidites were purchased from commercial sources (e.g. Chemgenes, Needham, Mass. or Glen Research, Inc. Sterling, Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods (Sanghvi et. al., Nucleic Acids Research, 1993, 21, 3197-3203) using commercially available phosphoramidites (Glen Research, Sterling Va. or ChemGenes, Needham, Mass.).

2'-Fluoro Amidites

2'-fluoro oligonucleotides were synthesized as described previously (Kawasaki et. al., J. Med. Chem., 1993, 36, 831-841) and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as per the methods of Martin, Helvetica Chimica Acta, 1995, 78, 486-504.

2'-(Aminooxyethyl) Nucleoside Amidites and 2'-(dimethylaminooxyethyl) Nucleoside Amidites Aminooxyethyl and dimethylaminooxyethyl amidites are prepared as per the methods of U.S. Pat. No. 6,127,533 which is herein incorporated by reference.

Example 2

Oligonucleotide and Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

4'-thio-containing oligonucleotides are synthesized as described in U.S. Pat. No. 5,639,873, the contents of which are herein incorporated by reference in their entirety.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

PNA Synthesis

Peptide nucleic acids (PNAs) are prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. Nos. 5,539,082, 5,700,922, and 5,719,262, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe et al., J. Am. Chem. Soc., 1998, 120, 11820-11821; Matteucci et al., J. Am. Chem. Soc., 1981, 103, 3185-3191; Beaucage et al, Tetrahedron Lett., 1981, 22, 1859-1862; Dahl et al., Acta Chem. Scand., 1990, 44, 639-641; Reddy et al., Tetrahedrom Lett., 1994, 25, 4311-4314; Wincott et al., Nucleic Acids Res., 1995, 23, 2677-2684; Griffin et al., Tetrahedron, 1967, 23, 2301-2313; Griffin et al., Tetrahedron, 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 uM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid, or for diagnostic or therapeutic purposes.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

(2'-O—Me)—(2'-deoxy)—(2'-O—Me) Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for the 2'-O-alkyl portion. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

(2'-O-(2-Methoxyethyl))—(2'-deoxy)—(2'-O-(Methoxyethyl)) Chimeric Phosphorothioate Oligonucleotides (2'-O-(2-methoxyethyl))—(2'-deoxy)—(-2'-O-(methoxyethyl)) chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

(2'-O-(2-Methoxyethyl)Phosphodiester)—(2'-deoxy Phosphorothioate)—(2'-O-(2-Methoxyethyl) Phosphodiester) Chimeric Oligonucleotides (2'-O-(2-methoxyethyl phosphodiester)—(2'-deoxy phosphorothioate)—(2'-O-(methoxyethyl) phosphodiester) chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting eIF4E

In accordance with the present invention, a series of nucleic acid duplexes comprising the antisense compounds of the present invention and their complements can be designed to target eIF4E. The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini. It is possible for one end of a duplex to be blunt and the other to have overhanging nucleobases. In one embodiment, the number of overhanging nucleobases is from 1 to 6 on the 3' end of each strand of the duplex. In another embodiment, the number of overhanging nucleobases is from 1 to 6 on the 3' end of only one strand of the duplex. In a further embodiment, the number of overhanging nucleobases is from 1 to 6 on one or both 5' ends of the duplexed strands. In another embodiment, the number of overhanging nucleobases is zero.

By way of example, a duplex comprising an antisense strand having the sequence CGAGAGGCGGACGGGACCG (SEQ ID NO:456) and having a two-nucleobase overhang of deoxythymidine(dT) would have the following structure:

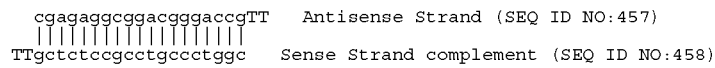

In another embodiment, a duplex comprising an antisense strand having the same sequence CGAGAGGCGGACGG-GACCG may be prepared with blunt ends (no single stranded overhang) as shown:

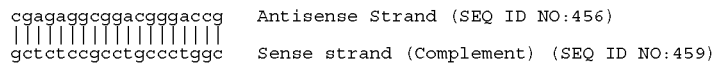

The duplex may be unimolecular or bimolecular, i.e., the sense and antisense strands may be part of the same molecule (which forms a hairpin or other self structure) or two (or even more) separate molecules.

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate eIF4E expression.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32 +/−48). For some studies oligonucleotides were purified by HPLC, as described by Chiang et al., J. Biol. Chem. 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment—Single Stranded Antisense Compounds

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

b.END Cells:

The mouse brain endothelial cell line b.END was obtained from Dr. Werner Risau at the Max Plank Instititute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis. For Northern blotting or other analyses, cells may be seeded onto 100 mm or other standard tissue culture plates and treated similarly, using appropriate volumes of medium and oligonucleotide.

HeLa Cells:

The human epitheloid carcinoma cell line HeLa was obtained from the American Tissue Type Culture Collection (Manassas, Va.). HeLa cells were routinely cultured in DMEM, high glucose (Invitrogen Corporation, Carlsbad, Calif.) supplemented with 10% fetal bovine serum (Invitrogen Corporation, Carlsbad, Calif.). Cells were routinely passaged by trypsinization and dilution when they reached approximately 90% confluence. Cells were seeded into 24-well plates (Falcon-Primaria #3846) at a density of approximately 50,000 cells/well or in 96-well plates at a density of approximately 5,000 cells/well for use in RT-PCR analysis. For Northern blotting or other analyses, cells were harvested when they reached approximately 90% confluence.

U-87 MG Cells:

The human glioblastoma U-87 MG cell line was obtained from the American Type Culture Collection (Manassas, Va.). U-87 MG cells were cultured in DMEM (Invitrogen Life Technologies, Carlsbad, Calif.) supplemented with 10% fetal bovine serum (Invitrogen Life Technologies, Carlsbad, Calif.) and antibiotics. Cells were routinely passaged by trypsinization and dilution when they reached appropriate confluence. Cells were seeded into 96-well plates (Falcon-Primaria #3872) at a density of about 10,000 cells/well for use in RT-PCR analysis.

For Northern blotting or other analyses, cells may be seeded onto 100 mm or other standard tissue culture plates and treated similarly, using appropriate volumes of medium and oligonucleotide. For Northern blotting or other analyses, cells may be seeded onto 100 mm or other standard tissue culture plates and treated similarly, using appropriate volumes of medium and oligonucleotide.

MH-S Cells:

Mouse MH-S cells were purchased from the American Type Culture Collection (Manassas, Va.). The cells were maintained in RPMI 1640 medium containing 10% heat-inactivated fetal calf serum (FCS) (Hyclone Laboratories, Logan, Utah). Cells were plated in 96-well plates at a density of 5000 cells/well and grown in DMEM with high glucose, 10% FBS, 1% penicillin/streptomycin.

Treatment with Antisense Compounds:

When cells reached 65-75% confluency, they were treated with oligonucleotide. For cells grown in 96-well plates, wells were washed once with 100 µL OPTI-MEM™-1™ reduced-serum medium (Invitrogen Corporation, Carlsbad, Calif.) and then treated with 130 µL of OPTI-MEM™-1 containing 3.75 µg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO:1) which is targeted to human H-ras, or ISIS 18078, (GTGCGCGCGAGCCCGAAATC, SEQ ID NO:2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO:3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of eIF4E Expression

Antisense modulation of eIF4E expression can be assayed in a variety of ways known in the art. For example, eIF4E mRNA levels can be quantitated by, e.g., Northern blot analysis, competitive polymerase chain reaction (PCR), or real-time PCR (RT-PCR). Real-time quantitative PCR is presently suitable. RNA analysis can be performed on total cellular RNA or poly(A)+ mRNA. One method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of eIF4E can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to eIF4E can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays for the Use of eIF4E Inhibitors

Once eIF4E inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of eIF4E in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with eIF4E inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the eIF4E inhibitors. Hallmark genes, or those genes suspected to be associated with a specific disease state, condition, or phenotype, are measured in both treated and untreated cells.

Example 12

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 μL cold PBS. 150 μL Buffer RLT was added to each well and the plate vigorously agitated for 20 seconds. 150 μL of 70% ethanol was then added to each well and the contents mixed by pipetting three times up and down. The samples were then transferred to the RNEASY 96™ well plate attached to a QIA-VAC™ manifold fitted with a waste collection tray and attached to a vacuum source. Vacuum was applied for 1 minute. 500 μL of Buffer RW1 was added to each well of the RNEASY 96™ plate and incubated for 15 minutes and the vacuum was again applied for 1 minute. An additional 500 μL of Buffer RW1 was added to each well of the RNEASY 96™ and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of eIF4E mRNA Levels

Quantitation of eIF4E mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5× PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATI- NUM® Taq, 5 Units MuLV reverse transcriptase, and 2.5× ROX dye) to 96-well plates containing 30 µL total RNA solution (20-200 ng). The RT reaction was carried out by incubation for 30 minutes at 48° C. Following a 10 minute incubation at 95° C. to activate the PLATINUM™ Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and primers to human eIF4E were designed to hybridize to a human eIF4E sequence, using published sequence information (GenBank accession number M15353.1, incorporated herein as SEQ ID NO: 4). For human eIF4E the PCR primers were:

forward primer: TGGCGACTGTCGAACCG (SEQ ID NO:5)

reverse primer: AGATTCCGTTTTCTCCTCTTCTGTAG (SEQ ID NO:6)

and the PCR probe was: FAM-AAACCACCCCTACTC-CTAATCCCCCG-TAMRA (SEQ ID NO:7) where FAM is the fluorescent dye and TAMRA is the quencher dye. For human GAPDH the PCR primers were:

forward primer: GAAGGTGAAGGTCGGAGTC(SEQ ID NO:8)

reverse primer: GAAGATGGTGATGGGATTTC (SEQ ID NO:9)

and the PCR probe was: 5' JOE-CAAGCTTCCCGTTCT-CAGCC-TAMRA 3' (SEQ ID NO:10) where JOE is the fluorescent reporter dye and TAMRA is the quencher dye.

Probes and primers to mouse eIF4E were designed to hybridize to a mouse eIF4E sequence, using published sequence information (GenBank accession number NM_007917.1, incorporated herein as SEQ ID NO:11). For mouse eIF4E the PCR primers were:

forward primer: AGGACGGTGGCTGATCACA (SEQ ID NO:12)

reverse primer: TCTCTAGCCAGAAGCGATCGA (SEQ ID NO:13)

and the PCR probe was: FAM-TGAACAAGCAGCA-GAGACGGAGTGA-TAMRA (SEQ ID NO:14) where FAM is the fluorescent reporter dye and TAMRA is the quencher dye. For mouse GAPDH the PCR primers were:

forward primer: GGCAAATTCAACGGCACAGT (SEQ ID NO:15)

reverse primer: GGGTCTCGCTCCTGGAAGAT (SEQ ID NO:16)

and the PCR probe was: 5' JOE-AAGGCCGAGAATGG-GAAGCTTGTCATC-TAMRA 3' (SEQ ID NO:17) where JOE is the fluorescent reporter dye and TAMRA is the quencher dye.

Example 14

Northern Blot Analysis of eIF4E mRNA Levels

Eighteen hours after antisense treatment, cell monolayers are washed twice with cold PBS and lysed in 1 mL RNA-ZOL™ (TEL-TEST "B" Inc., Friendswood, Tex.). Total RNA is prepared following manufacturer's recommended protocols. Twenty micrograms of total RNA is fractionated by electrophoresis through 1.2% agarose gels containing 1.1% formaldehyde using a MOPS buffer system (AMRESCO, Inc. Solon, Ohio). RNA is transferred from the gel to HYBOND™–N+nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer is confirmed by UV visualization. Membranes are fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human eIF4E, a human eIF4E specific probe is prepared by PCR using the forward primer TGGCGACT-GTCGAACCG (SEQ ID NO:5) and the reverse primer AGATTCCGTTTTCTCCTCTTCTGTAG (SEQ ID NO:6). To normalize for variations in loading and transfer efficiency membranes are stripped and probed for human glyceraldehyde-3-phosphate dehydrogenase (GAPDH) RNA (Clontech, Palo Alto, Calif.).

To detect mouse eIF4E, a mouse eIF4E specific probe is prepared by PCR using the forward primer AGGACGGTG-GCTGATCACA (SEQ ID NO:12) and the reverse primer TCTCTAGCCAGAAGCGATCGA (SEQ ID NO:13). To normalize for variations in loading and transfer efficiency membranes are stripped and probed for mouse glyceraldehyde-3-phosphate dehydrogenase (GAPDH) RNA (Clontech, Palo Alto, Calif.).

Hybridized membranes are visualized and quantitated using a PHOSPHORFMAGER™ and IMAGEQUAN™ Software V3.3 (Molecular Dynamics, Sunnyvale, Calif.). Data are normalized to GAPDH levels in untreated controls.

Example 15

Antisense Inhibition of Human eIF4E Expression by Chimeric Phosphorothioate Oligonucleotides Having 2'-MOE Wings and a Deoxy Gap In accordance with the present invention, a series of antisense compounds were designed to target different regions of the human eIF4E RNA, using published sequences (GenBank accession number M15353.1, incorporated herein as SEQ ID NO:4). The compounds are shown in Table 1. "Target site" indicates the first (5'-most) nucleotide number on the particular human eIF4E target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines.

A second series of antisense compounds were designed to target different regions of the mouse eIF4E RNA, using published sequences (GenBank accession number NM_007917.1, incorporated herein as SEQ ID NO:11). The compounds are shown in Table 1. "Target site" indicates the first (5'-most) nucleotide number on the particular human eIF4E target nucleic acid to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

As compounds in Table 1 are complementary to both human and mouse eIF4E sequences, the compounds were analyzed for their effect on human eIF4E mRNA levels by quantitative real-time PCR as described in other examples herein. Data are averages from three experiments in which A549 cells were treated with the antisense oligonucleotides of the present invention. The positive control for each datapoint is identified in the table by sequence ID number. If present, "N.D." indicates "no data".

TABLE 1

Inhibition of human eIF4E mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 183728 | 3'UTR | 4 | 950 | aatggtaattctactgaact | 42 | 18 | 1 |
| 183729 | 3'UTR | 4 | 1191 | atattatcaagtagggaaac | 0 | 19 | 1 |
| 183730 | Coding | 4 | 513 | tttcacattcagtagtccat | 73 | 20 | 1 |
| 183731 | Coding | 4 | 600 | cgtgggactgataaccaatc | 84 | 21 | 1 |
| 183732 | 3'UTR | 4 | 1001 | atgccaagttgttttctgac | 68 | 22 | 1 |
| 183733 | Coding | 4 | 480 | cacctttagctctaacatta | 81 | 23 | 1 |
| 183734 | Coding | 4 | 643 | aacctattttagtggtgga | 76 | 24 | 1 |
| 183735 | 3'UTR | 4 | 1156 | tagcagccatcagcaagagt | 76 | 25 | 1 |
| 183736 | 3'UTR | 4 | 1165 | attaaaatctagcagccatc | 56 | 26 | 1 |
| 183737 | Coding | 4 | 584 | aatcactatctttggaggaa | 18 | 27 | 1 |
| 183738 | 3'UTR | 4 | 1583 | tcttaatatgaatgggactg | 75 | 28 | 1 |
| 183739 | Stop Codon | 4 | 665 | gaaggtgtcttcttaaacaa | 78 | 29 | 1 |
| 183740 | Coding | 4 | 604 | tctgcgtgggactgataacc | 81 | 30 | 1 |
| 183741 | 3'UTR | 4 | 703 | tctcgattgcttgacgcagt | 83 | 31 | 1 |
| 183742 | Coding | 4 | 527 | aacagcttctctgttttcac | 51 | 32 | 1 |
| 183743 | 3'UTR | 4 | 1162 | aaaatctagcagccatcagc | 75 | 33 | 1 |
| 183744 | Coding | 4 | 112 | ggatgtttaatatagtgttc | 61 | 34 | 1 |
| 183745 | 3'UTR | 4 | 1587 | actgtcttaatatgaatggg | 45 | 35 | 1 |
| 183746 | 3'UTR | 4 | 1800 | tcaatttattaaaaattgta | 7 | 36 | 1 |
| 183747 | 3'UTR | 4 | 1370 | ataaatttgtagcaaagctt | 53 | 37 | 1 |
| 183748 | 3'UTR | 4 | 1092 | aaaactgtatgcatcataat | 54 | 38 | 1 |
| 183749 | Coding | 4 | 387 | aaaagcgatcgaggtcactt | 62 | 39 | 1 |
| 183750 | 3'UTR | 4 | 1285 | tgtcatattcctggatcctt | 84 | 40 | 1 |
| 183751 | 3'UTR | 4 | 1432 | tataatccacaattatgttt | 41 | 41 | 1 |
| 183752 | 3'UTR | 4 | 1055 | tatgcttctgcataaaatgg | 55 | 42 | 1 |
| 183753 | Coding | 4 | 631 | gtggtggagccgctcttagt | 68 | 43 | 1 |
| 183754 | 3'UTR | 4 | 1094 | agaaaactgtatgcatcata | 67 | 44 | 1 |
| 183755 | 3'UTR | 4 | 1627 | aagacaattcactgtacaca | 41 | 45 | 1 |

TABLE 1-continued

Inhibition of human eIF4E mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 183756 | Start Codon | 4 | 12 | cgacagtcgccatcttagat | 82 | 46 | 1 |
| 183757 | 3'UTR | 4 | 1021 | ttttcctgtaaagtatagaa | 55 | 47 | 1 |
| 183758 | 3'UTR | 4 | 1639 | ctagttgtctaaaagacaat | 17 | 48 | 1 |
| 183759 | Coding | 4 | 435 | tgtagtcatcaaaagattct | 42 | 49 | 1 |
| 183760 | 3'UTR | 4 | 980 | attgtggataggtaaaatct | 0 | 50 | 1 |
| 183761 | 3'UTR | 4 | 1745 | tgctgttcacatggaagaca | 65 | 51 | 1 |
| 183762 | 3'UTR | 4 | 1768 | atcaaactagtgctccaaac | 61 | 52 | 1 |
| 183763 | 3'UTR | 4 | 758 | aaatttaaatgcagtccact | 42 | 53 | 1 |
| 183764 | Codong | 4 | 621 | cgctcttagtagctgtgtct | 66 | 54 | 1 |
| 298772 | 5' Cap/UTR | 4 | 1 | atcttagatcgatctgatcg | 15 | 55 | 1 |
| 298773 | Start Codon | 4 | 10 | acagtcgccatcttagatcg | 73 | 56 | 1 |
| 298774 | Coding | 4 | 88 | ttagcaacctcctgattaga | 82 | 57 | 1 |
| 298775 | Coding | 4 | 94 | tctgggttagcaacctcctg | 76 | 58 | 1 |
| 298776 | Coding | 4 | 168 | gccaagttttgcttttatca | 88 | 59 | 1 |
| 298777 | Coding | 4 | 176 | gtttgcttgccaagttttgc | 72 | 60 | 1 |
| 298778 | Coding | 4 | 211 | tcttcaacagtatcaaactt | 40 | 61 | 1 |
| 298779 | Coding | 4 | 216 | aaaagtcttcaacagtatca | 31 | 62 | 1 |
| 298780 | Coding | 4 | 223 | agagcccaaaagtcttcaac | 55 | 63 | 1 |
| 298781 | Coding | 4 | 244 | gacaactggatatggttgta | 83 | 64 | 1 |
| 298782 | Coding | 4 | 249 | tactagacaactggatatgg | 88 | 65 | 1 |
| 298783 | Coding | 4 | 254 | taaattactagacaactgga | 84 | 66 | 1 |
| 298784 | Coding | 4 | 259 | ggcattaaattactagacaa | 71 | 67 | 1 |
| 298785 | Coding | 4 | 264 | agccaggcattaaattacta | 33 | 68 | 1 |
| 298786 | Coding | 4 | 269 | gtcacagccaggcattaaat | 68 | 69 | 1 |
| 298787 | Coding | 4 | 274 | gagtagtcacagccaggcat | 74 | 70 | 1 |
| 298788 | Coding | 4 | 279 | aaagtgagtagtcacagcca | 64 | 71 | 1 |
| 298789 | Coding | 4 | 286 | tccttaaaagtgagtagtc | 58 | 72 | 1 |
| 298790 | Coding | 4 | 310 | tcttcccacataggctcaat | 70 | 73 | 1 |
| 298791 | Coding | 4 | 315 | tctcatcttcccacataggc | 73 | 74 | 1 |
| 298792 | Coding | 4 | 320 | gtttttctcatcttcccaca | 79 | 75 | 1 |
| 298793 | Coding | 4 | 424 | aaagattctccaataaggca | 70 | 76 | 1 |
| 298794 | Coding | 4 | 445 | acatcatcactgtagtcatc | 87 | 77 | 1 |
| 298795 | Coding | 4 | 472 | gctctaacattaacaacagc | 84 | 78 | 1 |
| 298796 | Coding | 4 | 486 | tcttatcacctttagctcta | 84 | 79 | 1 |

TABLE 1-continued

Inhibition of human eIF4E mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 298797 | Coding | 4 | 491 | tgctatcttatcacctttag | 91 | 80 | 1 |
| 298798 | Coding | 4 | 499 | gtccatattgctatcttatc | 82 | 81 | 1 |
| 298799 | Coding | 4 | 505 | tcagtagtccatattgctat | 78 | 82 | 1 |
| 298801 | Coding | 4 | 553 | tccttgtataccctccctat | 57 | 83 | 1 |
| 298802 | Coding | 4 | 558 | acctttccttgtataccctc | 59 | 84 | 1 |
| 298803 | Coding | 4 | 563 | tcctaacctttccttgtata | 71 | 85 | 1 |
| 298804 | Coding | 4 | 571 | ggaggaagtcctaacctttc | 86 | 86 | 1 |
| 298805 | Coding | 4 | 592 | tgataaccaatcactatctt | 66 | 87 | 1 |
| 298806 | Coding | 4 | 613 | gtagctgtgtctgcgtggga | 56 | 88 | 1 |
| 298807 | Coding | 4 | 634 | ttagtggtggagccgctctt | 74 | 89 | 1 |
| 298808 | Coding | 4 | 649 | acaacaaacctatttttagt | 43 | 90 | 1 |
| 298809 | Stop Codon | 4 | 659 | gtcttcttaaacaacaaacc | 52 | 91 | 1 |
| 298810 | Stop Codon | 4 | 672 | atactcagaaggtgtcttct | 73 | 92 | 1 |
| 298811 | 3'UTR | 4 | 677 | tgagaatactcagaaggtgt | 70 | 93 | 1 |
| 298812 | 3'UTR | 4 | 713 | agctcccaaatctcgattgc | 84 | 94 | 1 |
| 298813 | 3'UTR | 4 | 724 | ggctttggttcagctcccaa | 79 | 95 | 1 |
| 298814 | 3'UTR | 4 | 800 | atgagacttctcttatatct | 78 | 96 | 1 |
| 298815 | 3'UTR | 4 | 805 | ggcgaatgagacttctctta | 88 | 97 | 1 |
| 298816 | 3'UTR | 4 | 812 | agacaaaggcgaatgagact | 78 | 98 | 1 |
| 298817 | 3'UTR | 4 | 817 | gtacaagacaaaggcgaatg | 78 | 99 | 1 |
| 298818 | 3'UTR | 4 | 876 | tctttgattgggatagtgga | 55 | 100 | 1 |
| 298819 | 3'UTR | 4 | 883 | ctgtaattctttgattggga | 67 | 101 | 1 |
| 298820 | 3'UTR | 4 | 1157 | ctagcagccatcagcaagag | 84 | 102 | 1 |
| 298821 | 3'UTR | 4 | 1209 | ctgaaatcagaatcactaat | 67 | 103 | 1 |
| 298822 | 3'UTR | 4 | 1272 | gatccttcaccaatgttaca | 77 | 104 | 1 |
| 298823 | 3'UTR | 4 | 1277 | tcctggatccttcaccaatg | 88 | 105 | 1 |
| 298824 | 3'UTR | 4 | 1356 | aagctttgtagttacaaaaa | 35 | 106 | 1 |
| 298825 | 3'UTR | 4 | 1361 | tagcaaagctttgtagttac | 72 | 107 | 1 |
| 298826 | 3'UTR | 4 | 1376 | aaatgcataaatttgtagca | 37 | 108 | 1 |
| 298827 | 3'UTR | 4 | 1381 | gaatgaaatgcataaatttg | 36 | 109 | 1 |
| 298828 | 3'UTR | 4 | 1386 | gatttgaatgaaatgcataa | 52 | 110 | 1 |
| 298829 | 3'UTR | 4 | 1391 | tcactgatttgaatgaaatg | 64 | 111 | 1 |
| 298830 | 3'UTR | 4 | 1397 | catagatcactgatttgaat | 61 | 112 | 1 |
| 298831 | 3'UTR | 4 | 1466 | ctagtaggaatgtaattat | 49 | 113 | 1 |
| 298832 | 3'UTR | 4 | 1471 | taattctagttaggaatgta | 55 | 114 | 1 |

TABLE 1-continued

Inhibition of human eIF4E mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 298833 | 3'UTR | 4 | 1480 | cagacatactaattctagtt | 74 | 115 | 1 |
| 298834 | 3'UTR | 4 | 1564 | gcttttctacttgagccatt | 85 | 116 | 1 |
| 298835 | 3'UTR | 4 | 1593 | ttgtacactgtcttaatatg | 60 | 117 | 1 |
| 298836 | 3'UTR | 4 | 1598 | cagttttgtacactgtctta | 85 | 118 | 1 |
| 298837 | 3'UTR | 4 | 1603 | atttacagttttgtacactg | 74 | 119 | 1 |
| 298838 | 3'UTR | 4 | 1614 | gtacacattttatttacagt | 76 | 120 | 1 |
| 298839 | 3'UTR | 4 | 1649 | aaggacaaatctagttgtct | 46 | 121 | 1 |
| 298800 | Coding | 11 | 514 | tttcacactcagtagtccat | 34 | 122 | 1 |

As shown in Table 1, SEQ ID NOs 20, 21, 22, 23, 24, 25, 26, 28, 29, 30, 31, 32, 33, 34, 37, 38, 39, 40, 42, 43, 44, 46, 47, 51, 52, 54, 56, 57, 58, 59, 60, 63, 64, 65, 66, 67, 69, 70, 71, 72, 73, 74, 75, 76, 77, 78, 79, 80, 81, 82, 83, 84, 85, 86, 87, 88, 89, 91, 92, 93, 94, 95, 96, 97, 98, 99, 100, 101, 102, 103, 104, 105, 107, 110, 111, 112, 114, 115, 116, 117, 118, 119, 120 and 122 demonstrated at least 50% inhibition of human eIF4E expression in this assay and are therefore suitable. SEQ ID NOs 80, 65, 40, 97 and 105 are also suitable.

The target regions to which these suitable sequences are complementary are herein referred to as "suitable target segments" and are therefore suitable for targeting by compounds of the present invention. These suitable target segments are shown in Table 3. These sequences are shown to contain thymine (T) but one of skill in the art will appreciate that thymine (T) is generally replaced by uracil (U) in RNA sequences. The sequences represent the reverse complement of the suitable antisense compounds shown in Table 1. "Target site" indicates the first (5'-most) nucleotide number on the particular target nucleic acid to which the oligonucleotide binds. Also shown in Table 3 is the species in which each of the suitable target segments was found.

Example 16

Antisense Inhibition of Mouse eIF4E Expression by Chimeric Phosphorothioate Oligonucleotides Having 2'-MOE Wings and a Deoxy Gap In accordance with the present invention, the compounds in Table 1, which are complementary to both human and mouse eIF4E (for example mouse eIF4E GenBank accession number NM_007917.1, incorporated herein as SEQ ID NO:11) were further analyzed for their effect on mouse eIF4E mRNA levels by quantitative real-time PCR as described in other examples herein. In Table 2, "target site" indicates the first (5'-most) nucleotide number on the particular mouse eIF4E target nucleic acid to which the compound binds. Data, shown in Table 2, are averages from three experiments in which b.END cells were treated with the antisense oligonucleotides of the present invention. The positive control for each datapoint is identified in the table by sequence ID number. If present, "N.D." indicates "no data".

TABLE 2

Inhibition of mouse eIF4E mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 183731 | Coding | 11 | 601 | cgtgggactgataaccaatc | 83 | 21 | 1 |
| 183733 | Coding | 11 | 481 | caccttttagctctaacatta | 90 | 23 | 1 |
| 183734 | Coding | 11 | 644 | aacctattttttagtggtgga | 87 | 24 | 1 |
| 183739 | Stop Codon | 11 | 666 | gaaggtgtcttcttaaacaa | 81 | 29 | 1 |
| 183740 | Coding | 11 | 605 | tctgcgtgggactgataacc | 87 | 30 | 1 |
| 183746 | 3'UTR | 11 | 1764 | tcaatttattaaaaattgta | 0 | 36 | 1 |
| 183747 | 3'UTR | 11 | 1351 | ataaatttgtagcaaagctt | 62 | 37 | 1 |

TABLE 2-continued

Inhibition of mouse eIF4E mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 183750 | 3'UTR | 11 | 1267 | tgtcatattcctggatcctt | 90 | 40 | 1 |
| 183755 | 3'UTR | 11 | 1604 | aagacaattcactgtacaca | 73 | 45 | 1 |
| 183758 | 3'UTR | 11 | 1616 | ctagttgtctaaaagacaat | 43 | 48 | 1 |
| 298772 | Start Codon | 11 | 2 | atcttagatcgatctgatcg | 47 | 55 | 1 |
| 298773 | Start Codon | 11 | 11 | acagtcgccatcttagatcg | 67 | 56 | 1 |
| 298774 | Coding | 11 | 89 | ttagcaacctcctgattaga | 83 | 57 | 1 |
| 298775 | Coding | 11 | 95 | tctgggttagcaacctcctg | 83 | 58 | 1 |
| 298776 | Coding | 11 | 169 | gccaagttttgcttttatca | 76 | 59 | 1 |
| 298777 | Coding | 11 | 177 | gtttgcttgccaagttttgc | 77 | 60 | 1 |
| 298778 | Coding | 11 | 212 | tcttcaacagtatcaaactt | 59 | 61 | 1 |
| 298779 | Coding | 11 | 217 | aaaagtcttcaacagtatca | 69 | 62 | 1 |
| 298780 | Coding | 11 | 224 | agagcccaaaagtcttcaac | 55 | 63 | 1 |
| 298781 | Coding | 11 | 245 | gacaactggatatggttgta | 82 | 64 | 1 |
| 298782 | Coding | 11 | 250 | tactagacaactggatatgg | 85 | 65 | 1 |
| 298783 | Coding | 11 | 255 | taaattactagacaactgga | 78 | 66 | 1 |
| 298784 | Coding | 11 | 260 | ggcattaaattactagacaa | 81 | 67 | 1 |
| 298785 | Coding | 11 | 265 | agccaggcattaaattacta | 87 | 68 | 1 |
| 298786 | Coding | 11 | 270 | gtcacagccaggcattaaat | 87 | 69 | 1 |
| 298787 | Coding | 11 | 275 | gagtagtcacagccaggcat | 91 | 70 | 1 |
| 298788 | Coding | 11 | 280 | aaagtgagtagtcacagcca | 91 | 71 | 1 |
| 298789 | Coding | 11 | 287 | tccttaaaaagtgagtagtc | 83 | 72 | 1 |
| 298790 | Coding | 11 | 311 | tctcccacataggctcaat | 71 | 73 | 1 |
| 298791 | Coding | 11 | 316 | tctcatcttcccacataggc | 90 | 74 | 1 |
| 298792 | Coding | 11 | 321 | gtttttctcatcttcccaca | 83 | 75 | 1 |
| 298793 | Coding | 11 | 425 | aaagattctccaataaggca | 87 | 76 | 1 |
| 298794 | Coding | 11 | 446 | acatcatcactgtagtcatc | 86 | 77 | 1 |
| 298795 | Coding | 11 | 473 | gctctaacattaacaacagc | 80 | 78 | 1 |
| 298796 | Coding | 11 | 487 | tcttatcacctttagctcta | 90 | 79 | 1 |
| 298797 | Coding | 11 | 492 | tgctatcttatcacctttag | 87 | 80 | 1 |
| 298798 | Coding | 11 | 500 | gtccatattgctatcttatc | 89 | 81 | 1 |
| 298799 | Coding | 11 | 506 | tcagtagtccatattgctat | 87 | 82 | 1 |
| 298801 | Coding | 11 | 554 | tccttgtataccctccctat | 80 | 83 | 1 |
| 298802 | Coding | 11 | 559 | acctttccttgtataccctc | 86 | 84 | 1 |
| 298803 | Coding | 11 | 564 | tcctaacctttccttgtata | 83 | 85 | 1 |
| 298804 | Coding | 11 | 572 | ggaggaagtcctaacctttc | 88 | 86 | 1 |

TABLE 2-continued

Inhibition of mouse eIF4E mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 298805 | Coding | 11 | 593 | tgataaccaatcactatctt | 77 | 87 | 1 |
| 298806 | Coding | 11 | 614 | gtagctgtgtctgcgtggga | 87 | 88 | 1 |
| 298807 | Coding | 11 | 635 | ttagtggtggagccgctctt | 77 | 89 | 1 |
| 298808 | Coding | 11 | 650 | acaacaaacctattttagt | 47 | 90 | 1 |
| 298809 | Stop Codon | 11 | 660 | gtcttcttaaacaacaaacc | 64 | 91 | 1 |
| 298810 | 3'UTR | 11 | 673 | atactcagaaggtgtcttct | 70 | 92 | 1 |
| 298811 | 3'UTR | 11 | 678 | tgagaatactcagaaggtgt | 78 | 93 | 1 |
| 298812 | 3'UTR | 11 | 713 | agctcccaaatctcgattgc | 74 | 94 | 1 |
| 298813 | 3'UTR | 11 | 724 | ggctttggttcagctcccaa | 92 | 95 | 1 |
| 298814 | 3'UTR | 11 | 796 | atgagacttctcttatatct | 81 | 96 | 1 |
| 298815 | 3'UTR | 11 | 801 | ggcgaatgagacttctctta | 93 | 97 | 1 |
| 298816 | 3'UTR | 11 | 808 | agacaaaggcgaatgagact | 86 | 98 | 1 |
| 298817 | 3'UTR | 11 | 813 | gtacaagacaaaggcgaatg | 85 | 99 | 1 |
| 298818 | 3'UTR | 11 | 878 | tctttgattgggatagtgga | 86 | 100 | 1 |
| 298819 | 3'UTR | 11 | 885 | ctgtaattctttgattggga | 88 | 101 | 1 |
| 298820 | 3'UTR | 11 | 1149 | ctagcagccatcagcaagag | 87 | 102 | 1 |
| 298821 | 3'UTR | 11 | 1200 | ctgaaatcagaatcactaat | 66 | 103 | 1 |
| 298822 | 3'UTR | 11 | 1254 | gatccttcaccaatgttaca | 90 | 104 | 1 |
| 298823 | 3'UTR | 11 | 1259 | tcctggatccttcaccaatg | 95 | 105 | 1 |
| 298824 | 3'UTR | 11 | 1337 | aagctttgtagttacaaaaa | 72 | 106 | 1 |
| 298825 | 3'UTR | 11 | 1342 | tagcaaagctttgtagttac | 81 | 107 | 1 |
| 298826 | 3'UTR | 11 | 1357 | aaatgcataaatttgtagca | 80 | 108 | 1 |
| 298827 | 3'UTR | 11 | 1362 | gaatgaaatgcataaatttg | 43 | 109 | 1 |
| 298828 | 3'UTR | 11 | 1367 | gatttgaatgaaatgcataa | 49 | 110 | 1 |
| 298829 | 3'UTR | 11 | 1372 | tcactgatttgaatgaaatg | 70 | 111 | 1 |
| 298830 | 3'UTR | 11 | 1378 | catagatcactgatttgaat | 76 | 112 | 1 |
| 298831 | 3'UTR | 11 | 1445 | ctagttaggaatgtaattat | 65 | 113 | 1 |
| 298832 | 3'UTR | 11 | 1450 | taattctagttaggaatgta | 59 | 114 | 1 |
| 298833 | 3'UTR | 11 | 1459 | cagacatactaattctagtt | 82 | 115 | 1 |
| 298834 | 3'UTR | 11 | 1541 | gcttttctacttgagccatt | 87 | 116 | 1 |
| 298835 | 3'UTR | 11 | 1570 | ttgtacactgtcttaatatg | 72 | 117 | 1 |
| 298836 | 3'UTR | 11 | 1575 | cagttttgtacactgtctta | 83 | 118 | 1 |
| 298837 | 3'UTR | 11 | 1580 | atttacagttttgtacactg | 67 | 119 | 1 |
| 298838 | 3'UTR | 11 | 1591 | gtacacattttatttacagt | 79 | 120 | 1 |

TABLE 2-continued

Inhibition of mouse eIF4E mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 298839 | 3'UTR | 11 | 1626 | aaggacaaatctagttgtct | 56 | 121 | 1 |
| 298800 | Coding | 11 | 514 | tttcacactcagtagtccat | 84 | 122 | 1 |

As shown in Table 2, SEQ ID NOs 21, 23, 24, 29, 30, 40, 45, 57, 58, 59, 60, 64, 65, 66, 67, 68, 69, 70, 71, 72, 73, 74, 75, 76, 77, 78, 79, 80, 81, 82, 83, 84, 85, 86, 87, 88, 89, 92, 93, 94, 95, 96, 97, 98, 99, 100, 101, 102, 104, 105, 106, 107, 108, 111, 112, 115, 116, 117, 118, 120, 122 demonstrated at least 70% inhibition of mouse eIF4E expression in this experiment and is therefore suitable. SEQ ID NOs 105, 40, 97 and 80 are also suitable.

The target regions to which these suitable sequences are complementary are herein referred to as "suitable target segments" and are therefore suitable for targeting by compounds of the present invention. These suitable target segments are shown in Table 3. These sequences are shown to contain thymine (T) but one of skill in the art will appreciate that thymine (T) is generally replaced by uracil (U) in RNA sequences. The sequences represent the reverse complement of the suitable antisense compounds shown in Tables 1 and 2. "Target site" indicates the first (5'-most) nucleotide number on the particular target nucleic acid to which the oligonucleotide binds. Also shown in Table 3 is the species in which each of the suitable target segments was found.

TABLE 3

Sequence and position of suitable target segments identified in eIF4E

| SITE ID | TARGET SEQ ID NO | TARGET SITE | SITE SEQUENCE | REV COMP OF SEQ ID IN | AC- TIVE IN | SEQ ID NO |
|---|---|---|---|---|---|---|
| 99068 | 4 | 513 | atggactactgaatgtgaaa | 20 | H. sapiens | 123 |
| 99069 | 4 | 600 | gattggttatcagtcccacg | 21 | H. sapiens | 124 |
| 99070 | 4 | 1001 | gtcagaaaacaacttggcat | 22 | H. sapiens | 125 |
| 99071 | 4 | 480 | taatgttagagctaaaggtg | 23 | H. sapiens | 126 |
| 99072 | 4 | 643 | tccaccactaaaaataggtt | 24 | H. sapiens | 127 |
| 99073 | 4 | 1156 | actcttgctgatggctgcta | 25 | H. sapiens | 128 |
| 99074 | 4 | 1165 | gatggctgctagattttaat | 26 | H. sapiens | 129 |
| 99076 | 4 | 1583 | cagtcccattcatattaaga | 28 | H. sapiens | 130 |
| 99077 | 4 | 665 | ttgtttaagaagacaccttc | 29 | H. sapiens | 131 |
| 99078 | 4 | 604 | ggttatcagtcccacgcaga | 30 | H. sapiens | 132 |
| 99079 | 4 | 703 | actgcgtcaagcaatcgaga | 31 | H. sapiens | 133 |
| 99080 | 4 | 527 | gtgaaaacagagaagctgtt | 32 | H. sapiens | 134 |
| 99081 | 4 | 1162 | gctgatggctgctagatttt | 33 | H. sapiens | 135 |
| 99082 | 4 | 112 | gaacactatattaaacatcc | 34 | H. sapiens | 136 |
| 99085 | 4 | 1370 | aagctttgctacaaatttat | 37 | H. sapiens | 137 |
| 99086 | 4 | 1092 | attatgatgcatacagtttt | 38 | H. sapiens | 138 |
| 99087 | 4 | 387 | aagtgacctcgatcgctttt | 39 | H. sapiens | 139 |
| 99088 | 4 | 1285 | aaggatccaggaatatgaca | 40 | H. sapiens | 140 |
| 99090 | 4 | 1055 | ccatttatgcagaagcata | 42 | H. sapiens | 141 |

TABLE 3-continued

Sequence and position of suitable target segments identified in eIF4E

| SITE ID | TARGET SEQ ID NO | TARGET SITE SEQUENCE | | REV COMP OF SEQ ID NO | ACTIVE IN | SEQ ID NO |
|---|---|---|---|---|---|---|
| 99091 | 4 | 631 | actaagagcggctccaccac | 43 | H. sapiens | 142 |
| 99092 | 4 | 1094 | tatgatgcatacagttttct | 44 | H. sapiens | 143 |
| 99094 | 4 | 12 | atctaagatggcgactgtcg | 46 | H. sapiens | 144 |
| 99095 | 4 | 1021 | ttctatactttacaggaaaa | 47 | H. sapiens | 145 |
| 99099 | 4 | 1745 | tgtcttccatgtgaacagca | 51 | H. sapiens | 146 |
| 99100 | 4 | 1768 | gtttggagcactagtttgat | 52 | H. sapiens | 147 |
| 99102 | 4 | 621 | agacacagctactaagagcg | 54 | H. sapiens | 148 |
| 214540 | 4 | 10 | cgatctaagatggcgactgt | 56 | H. sapiens | 149 |
| 214541 | 4 | 88 | tctaatcaggaggttgctaa | 57 | H. sapiens | 150 |
| 214542 | 4 | 94 | caggaggttgctaacccaga | 58 | H. sapiens | 151 |
| 214543 | 4 | 168 | tgataaaagcaaaacttggc | 59 | H. sapiens | 152 |
| 214544 | 4 | 176 | gcaaaacttggcaagcaaac | 60 | H. sapiens | 153 |
| 214547 | 4 | 223 | gttgaagactttgggctct | 63 | H. sapiens | 154 |
| 214548 | 4 | 244 | tacaaccatatccagttgtc | 64 | H. sapiens | 155 |
| 214549 | 4 | 249 | ccatatccagttgtctagta | 65 | H. sapiens | 156 |
| 214550 | 4 | 254 | tccagttgtctagtaattta | 66 | H. sapiens | 157 |
| 214551 | 4 | 259 | ttgtctagtaatttaatgcc | 67 | H. sapiens | 158 |
| 214553 | 4 | 269 | atttaatgcctggctgtgac | 69 | H. sapiens | 159 |
| 214554 | 4 | 274 | atgcctggctgtgactactc | 70 | H. sapiens | 160 |
| 214555 | 4 | 279 | tggctgtgactactcacttt | 71 | H. sapiens | 161 |
| 214556 | 4 | 286 | gactactcactttttaagga | 72 | H. sapiens | 162 |
| 214557 | 4 | 310 | attgagcctatgtgggaaga | 73 | H. sapiens | 163 |
| 214558 | 4 | 315 | gcctatgtgggaagatgaga | 74 | H. sapiens | 164 |
| 214559 | 4 | 320 | tgtgggaagatgagaaaaac | 75 | H. sapiens | 165 |
| 214560 | 4 | 424 | tgccttattggagaatcttt | 76 | H. sapiens | 166 |
| 214561 | 4 | 445 | gatgactacagtgatgatgt | 77 | H. sapiens | 167 |
| 214562 | 4 | 472 | gctgttgttaatgttagagc | 78 | H. sapiens | 168 |
| 214563 | 4 | 486 | tagagctaaaggtgataaga | 79 | H. sapiens | 169 |
| 214564 | 4 | 491 | ctaaaggtgataagatagca | 80 | H. sapiens | 170 |
| 214565 | 4 | 499 | gataagatagcaatatggac | 81 | H. sapiens | 171 |
| 214566 | 4 | 505 | atagcaatatggactactga | 82 | H. sapiens | 172 |
| 214567 | 4 | 553 | atagggagggtatacaagga | 83 | H. sapiens | 173 |
| 214568 | 4 | 558 | gagggtatacaaggaaaggt | 84 | H. sapiens | 174 |
| 214569 | 4 | 563 | tatacaaggaaaggttagga | 85 | H. sapiens | 175 |

TABLE 3-continued

Sequence and position of suitable target segments identified in eIF4E

| SITE ID | TARGET SEQ ID NO | TARGET SITE SEQUENCE | REV COMP OF SEQ ID | ACTIVE IN | SEQ ID NO |
|---|---|---|---|---|---|
| 214570 | 4 | 571 gaaaggttaggacttcctcc | 86 | H. sapiens | 176 |
| 214571 | 4 | 592 aagatagtgattggttatca | 87 | H. sapiens | 177 |
| 214572 | 4 | 613 tcccacgcagacacagctac | 88 | H. sapiens | 178 |
| 214573 | 4 | 634 aagagcggctccaccactaa | 89 | H. sapiens | 179 |
| 214575 | 4 | 659 ggtttgttgtttaagaagac | 91 | H. sapiens | 180 |
| 214576 | 4 | 672 agaagacaccttctgagtat | 92 | H. sapiens | 181 |
| 214577 | 4 | 677 acaccttctgagtattctca | 93 | H. sapiens | 182 |
| 214578 | 4 | 713 gcaatcgagatttgggagct | 94 | H. sapiens | 183 |
| 214579 | 4 | 724 ttgggagctgaaccaaagcc | 95 | H. sapiens | 184 |
| 214580 | 4 | 800 agatataagagaagtctcat | 96 | H. sapiens | 185 |
| 214581 | 4 | 805 taagagaagtctcattcgcc | 97 | H. sapiens | 186 |
| 214582 | 4 | 812 agtctcattcgcctttgtct | 98 | H. sapiens | 187 |
| 214583 | 4 | 817 cattcgcctttgtcttgtac | 99 | H. sapiens | 188 |
| 214584 | 4 | 876 tccactatcccaatcaaaga | 100 | H. sapiens | 189 |
| 214585 | 4 | 883 tcccaatcaaagaattacag | 101 | H. sapiens | 190 |
| 214586 | 4 | 1157 ctcttgctgatggctgctag | 102 | H. sapiens | 191 |
| 214587 | 4 | 1209 attagtgattctgatttcag | 103 | H. sapiens | 192 |
| 214588 | 4 | 1272 tgtaacattggtgaaggatc | 104 | H. sapiens | 193 |
| 214589 | 4 | 1277 cattggtgaaggatccagga | 105 | H. sapiens | 194 |
| 214591 | 4 | 1361 gtaactacaaagcrttgcta | 107 | H. sapiens | 195 |
| 214594 | 4 | 1386 ttatgcatttcattcaaatc | 110 | H. sapiens | 196 |
| 214595 | 4 | 1391 catttcattcaaatcagtga | 111 | H. sapiens | 197 |
| 214596 | 4 | 1397 attcaaatcagtgatctatg | 112 | H. sapiens | 198 |
| 214598 | 4 | 1471 tacattcctaactagaatta | 114 | H. sapiens | 199 |
| 214599 | 4 | 1480 aactagaattagtatgtctg | 115 | H. sapiens | 200 |
| 214600 | 4 | 1564 aatggctcaagtagaaaagc | 116 | H. sapiens | 201 |
| 214601 | 4 | 1593 catattaagacagtgtacaa | 117 | H. sapiens | 202 |
| 214602 | 4 | 1598 taagacagtgtacaaaactg | 118 | H. sapiens | 203 |
| 214603 | 4 | 1603 cagtgtacaaaactgtaaat | 119 | H. sapiens | 204 |
| 214604 | 4 | 1614 actgtaaataaaatgtgtac | 120 | H. sapiens | 205 |
| 214433 | 11 | 514 atggactactgagtgtgaaa | 122 | M. musculus | 206 |

As these "suitable target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these suitable target segments and consequently inhibit the expression of eIF4E.

According to the present invention, antisense compounds include antisense oligonucleotides, ribozymes, external guide sequence (EGS) oligonucleotides, siRNA compounds, single- or double-stranded RNA interference (RNAi) compounds and other oligomeric compounds which hybridize to at least a portion of the target nucleic acid and modulate its function.

Example 17

Western Blot Analysis of eIF4E Protein Levels

Western blot analysis (immunoblot analysis) may be carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to eIF4E is used, with a radiolabeled or fluorescently labeled secondary antibody directed against the primary antibody species. Bands are visual using a PHOSPHORIMAGER™ (Molecular Dynamics, Sunnyvale Calif.).

Example 18

Effect of Antisense Inhibition of eIF4E Expression on Cell Proliferation

HeLa cells (American Type Culture Collection, Manassas Va.), $1 \times 10^6$ cells/100 µl, were electroporated with 3.25, 7.5, 15 and 30 µM oligonucleotide. Antisense inhibitors of eIF4E ISIS used were ISIS 183750 (SEQ ID NO: 40 and ISIS 298815 (SEQ ID NO:97). Control oligonucleotides used were ISIS 29848 (NNNNNNNNNNNNNNNNNNNN; SEQ ID NO:207, wherein N is a mixture of A, C, G and T) and an unrelated control oligonucleotide ISIS 129688 (TTCGCGGCTGGACGATTCAG; SEQ ID NO:208). A mock-transfected control was also used. Cell proliferation was measured in cells treated with 15 µM oligonucleotide using the CyQUANT Cell Proliferation Assay Kit (Molecular Probes, Inc., Eugene Oreg.). Antisense oligonucleotide inhibitors of human eIF4E ISIS 183750 and ISIS 298815 inhibited cell proliferation after 72 hr by 31% and 36%, respectively, compared to mock-treated controls. Cells treated with control oligonucleotides proliferated at rates at least as great as that of the mock treated controls.

eIF4A target mRNA reduction was also measured in this experiment. Both ISIS 183750 and ISIS 299815 yielded IC50s of less than 3 µM (concentration needed to inhibit eIF4E mRNA levels by 50%) and showed 70-80% inhibition at oligonucleotide concentrations of 7.5 µM and higher. Control oligonucleotides 29848 and 129688 yielded a maximum inhibition of 20% (7.5 µM 129688) but generally gave approximately 10% inhibition at other concentrations.

The effect of antisense inhibition of eIF4E on cell proliferation was also measured in U87-MG human glioblastoma cells. U87-MG cells (American Type Culture Collection, Manassas Va.), $1 \times 10^6$ cells/100 µl, were electroporated with ISIS 183750 (SEQ ID NO:40) and ISIS 298815 (SEQ ID NO:97) and an unrelated (control) oligonucleotide ISIS 129699 (GGATAGAACGCGAAAGCTTG; SEQ ID NO:209) at 7.5 µM. The two antisense inhibitors of eIF4E, ISIS 183750 and ISIS 298815, reduced U87-MG cell proliferation compared to control (ISIS 129699) by approximately 12% and 10%, respectively, after 96 hours. EIF4E target mRNA was measured at 48 hours after start of treatment and was reduced by approximately 31% by ISIS 183750 and 36% by ISIS 298815 when compared to untreated control. eIF4E mRNA levels were not reduced by control oligonucleotide ISIS 129699 and actually increased slightly.

Example 19

Effect of Antisense Inhibition of eIF4E Expression on Cell Cycle

The effect of eIF4E antisense compounds on the cell cycle was examined. HeLa cells were electroporated with 30 µM antisense oligonucleotide (ISIS 183750 or 299815) or control oligonucleotide (ISIS 29848 or ISIS 129688), or mock transfected. The fluorescent DNA intercalator propidium iodide (PI) was used to measure DNA content at 48 hours, using flow cytometry. Results (done in duplicate) are shown in Table 4.

TABLE 4

Cell cycle profile after antisense treatment

| Treatment | Approx. percentage of cells in each phase: | | | | |
|---|---|---|---|---|---|
| | SubG1 | G1 | S | G2M | Aneuploid |
| mock | 3.0 | 50.3 | 30.7 | 19.0 | 7.4 |
| 29848 | 2.4 | 45.8 | 33.0 | 21.2 | 8.2 |
| 129688 | 2.5 | 44.6 | 34.3 | 21.1 | 10.2 |
| 183750 | 8.3 | 46.1 | 32.9 | 21.0 | 12.7 |
| 298815 | 5.0 | 36.8 | 35.6 | 27.6 | 15.2 |

From the results shown in Table 4 it can be seen that treatment with both eIF4E antisense compounds (ISIS 183750 or ISIS 298815) increased the portion of cells in SubG1 phase, which is generally indicative of apoptosis. The portion of cells in G2M are also increased after ISIS 298815 treatment.

Example 20

Effect of Antisense Inhibition of eIF4E Expression on Angiogenesis/Tube Formation Angiogenesis is stimulated by numerous factors that promote interaction of endothelial cells with each other and with extracellular matrix molecules, resulting in the formation of capillary tubes. This process can be reproduced in tissue culture by the formation of tube-like structures by endothelial cells. Loss of tube formation in vitro has been correlated with the inhibition of angiogenesis in vivo (Carmeliet et al., Nature, 2000, 407, 249-257; and Zhang et al., Cancer Research, 2002, 62, 2034-42), which supports the use of in vitro tube formation as an endpoint for angiogenesis.

The tube formation assay is performed using an In vitro Angiogenesis Assay Kit (Chemicon International, Temecula, Calif.), or growth factor reduced Matrigel (BD Biosciences, Bedford, Mass.). HUVECs were plated at 4000 cells/well in 96-well plates. One day later, cells were transfected with antisense and control oligonucleotides according to standard published procedures (Monia et al., J. Biol. Chem., 1993, 268(19), 14514-22) using 75 nM oligonucleotide in lipofectin (Gibco, Grand Island, N.Y.). Approximately fifty hours post-transfection, cells were transferred to 96-well plates coated with ECMatrix™ (Chemicon International) or growth factor depleted Matrigel. Under these conditions, untreated HUVECs form tube-like structures. After an overnight incubation at 37° C., treated and untreated cells were inspected by light microscopy. Individual wells were assigned discrete scores from 1 to 5 depending on the extent of tube formation.

A score of 1 refers to a well with no tube formation while a score of 5 is given to wells where all cells are forming an extensive tubular network.

As calculated from the assigned discrete scores, cells treated with antisense inhibitors ISIS 183750 and ISIS 298815 had average tube formation scores of approximately 1.5 and 2.25, respectively. Cells treated with the random control oligonucleotide ISIS 29848 (NNNNNNNNNNNNNNNNNNNN; SEQ ID NO:207, wherein N is a mixture of A, C, G and T) had an average tube formation score of approximately 4.25 and cells treated with ISIS 334163 (TGTTACAGTCTTGTACCCTT; SEQ ID NO:210), a 6-base mismatch of ISIS 183750, had an average tube formation score of approximately 4.5. Thus, tube formation is specifically inhibited by 47-67% by eIF4E antisense oligonucleotides. Antisense inhibitors of eIF4E can, therefore, inhibit angiogenesis.

Example 21

Inhibition of eIF4E Expression in Mice

Eight-week old C57BL6 mice were injected intraperitoneally with oligonucleotide in saline twice weekly for 3 weeks (6 doses total) at an oligonucleotide concentration of 40 mg/kg. Compounds used were eIF4E antisense compounds ISIS 183750 (SEQ ID NO:40), ISIS 299815 (SEQ ID NO:97), ISIS 298797 (SEQ ID NO:80) and ISIS 298823 (SEQ ID NO:105). All are cross-species antisense oligonucleotides to both human and mouse eIF4E. ISIS 141923 is an unrelated (control) oligonucleotide (CCTTCCCTGAAG-GTTCCTCC; SEQ ID NO:211). A saline (vehicle) control was also used. Compared to saline control, ISIS 183750 reduced eIF4E mRNA levels in mouse liver to less than 20% of control (over 80% inhibition). ISIS 298815 also reduced eIF4E mRNA levels to approximately 20% of control. ISIS 298797 treatment reduced eIF4E mRNA levels to approximately 30% of control (70% inhibition) and ISIS 298823 treatment reduced eIF4E mRNA levels to approximately 37% of control (63% inhibition). In contrast, treatment with ISIS 141923 did not reduce eIF4E mRNA levels and actually increased them to approximately 140% of saline control.

EIF4E protein levels in mouse liver were also measured. Compared to saline control, treatment with ISIS 183750, ISIS 299815, ISIS 298797 and ISIS 298823 reduced eIF4E protein levels by 77%, 47%, 50% and 47% respectively; treatment with control oligonucleotide ISIS 141923 reduced eIF4E protein levels by 12%.

Mice treated with any one of the eIF4E antisense compounds showed essentially no changes in liver, spleen or total body weight. There was no significant change in liver enzyme levels (AST/ALT) and liver histology appeared the same as for saline-treated control mice.

Example 22

Effect of Antisense Inhibition of eIF4E Expression on Human Tumor Xenografts in Mice Male nude mice were injected subcutaneously in the flank with $5 \times 10^6$ PC-3 human prostate carcinoma cells (American Type Culture Collection, Manassas Va.). Antisense treatment began when the tumors reached a mean size of 100 mm$^3$, approximately 3 to 3.5 weeks after implantation. Mice were given 50 mg/kg by intravenous injection of antisense to eIF4E, ISIS 183750 (SEQ ID NO:40) or control oligonucleotide ISIS 141923 (SEQ ID NO:211) on the first dose and then 25 mg/kg every Monday, Wednesday and Friday thereafter. By day 54 after tumor implantation, tumors in mice treated with ISIS 183750 were approximately 450 mm$^3$ in size, approximately a 50% reduction compared to tumors in mice treated with control, ISIS 141923 (approximately 930 mm$^3$. This level of reduction continued until the end of study at day 57.

Xenografts were also done similarly using MDA-231 human breast cancer cells (American Type Culture Collection, Manassas Va.) in female mice. In this experiment both ISIS 183750 and ISIS 298815 were tested and gave nearly identical reduction in tumor cell growth of 55% and 50%, respectively, compared to saline control. eIF4E protein expression was measured in these MDA-231 xenografts by Western blot analysis (using antibody to eIF4E from Pharmingen, San Diego Calif.) and was found to be reduced by 45% in mice treated with ISIS 183750 (SEQ ID NO:40) and by 39% in mice treated with ISIS 298815 (SEQ ID NO:97), when compared to xenografts in mice treated with an unrelated control oligonucleotide (ISIS 141923, SEQ ID NO:211).

eIF4E can be phosphorylated in vivo at serine residue 209 of the human sequence. The phosphorylated form is often regarded as the active state of the protein, with increased phosphorylation often correlated with upregulation of rates of protein synthesis. Western blots using antibody specific for phosphorylated (pS209) eIF4E (BioSource, Camarillo Calif.) confirmed a decrease in the phosphorylated form of eIF4E after treatment with antisense compounds ISIS 183750 and 298815, but not an antisense control (ISIS 129699).

Cyclin D1 is an eIF4E target protein and cyclin D1 protein was also found to be reduced in MDA-231 xenografts in mice treated with antisense to eIF4E. Cyclin D1 was reduced by 40% after treatment with ISIS 183750 and by nearly 50% after treatment with ISIS 298815, when compared to cyclin D1 expression in xenografts in mice treated with unrelated control oligonucleotide ISIS 141923.

In a third similarly conducted xenograft study, female nude mice were injected subcutaneously into the flank with $5 \times 10^6$ H460 human non-small-cell lung cancer (NSCLC) cells (American Type Culture Collection, Manassas Va.). Intravenous dosing with oligonucleotides began once the tumors reached a mean size of 100 mm$^3$. The antisense treatment schedule began with a single dose of ISIS 141923 or ISIS 183750 at 50 mg/kg followed thereafter by 25 mg/kg every Monday, Wednesday and Friday for a total treatment time of 17 days. At the end of the study, the mean tumor volume of the ISIS 141923 control-treated group was approximately 2000 mm$^3$ vs. 550 mm$^3$ for ISIS 183750 ($p<0.001$).

Example 23

Inhibition of eIF-4E by Short Double Stranded RNA Oligonucleotides

Design and Synthesis of dsRNA Oligonucleotides

Human eIF-4E sequence Genbank #M15353 was queried for sequences. The G+C content of selected sequences range from 30% to 70%. Each of the dsRNA sequences specific to eIF-4E and depicted below contain two deoxythymidine nucleotides at the 3' terminal end of each strand of the RNA oligonucleotide duplex (not shown). Synthesis, duplex formation and purification of gene-specific siRNAs was performed by Dharmacon Research Inc. Three eIF-4E siRNA sequences were selected and tested, and are shown below:

```
eIF4E_1:
Position in gene sequence: 141-159

GC content: 53%
5'-CAGAUGGGCACUCUGGUUU-3'      SEQ ID NO: 212

3'-GUCUACCCGUGAGACCAAA-5'      SEQ ID NO: 213 eIF4E_2:
Position in gene sequence: 195-213

GC content: 63%
5'-CCUGCGGCUGAUCUCCAAG-3'      SEQ ID NO: 214

3'-GGACGCCGACUAGAGGUUC-5'      SEQ ID NO: 215 eIF4E_3:
Position in gene sequence: 1010-1028

GC content: 37%
5'-CAACUUGGCAUUUCUAUAC-3'      SEQ ID NO: 216

3'-GUUGAACCGUAAAGAUAUG-5'      SEQ ID NO: 217
```

A control dsRNA compound, also containing two deoxythymidine nucleotides at the 3' terminal end of each strand and complementary to pGL3 Luciferase, was purchased from Dharmacon Research Inc. and used in the assays below.

Control:

```
5'-CUUACGCUGAGUACUUCGA-3'      SEQ ID NO: 218

3'-GAAUGCGACUCAUGAAGCU-5'      SEQ ID NO: 219
```

Cell Culture

LNCaP, PC3, HCT116, MDA-231, MCF-7, T24, and CWR22RV1 cell lines are obtained through ATCC and are grown in RPMI Medium 1640 with L-glutamine, without phenol red (Gibco) containing 10% FBS (Hyclone).

Transfection of siRNA into Mammalian Cells

Mammalian cell lines are plated at $1 \times 10^5$ cells in 24-well plates, 24 hours prior to transfection. Transient transfections are performed using Oligofectamine (Invitrogen). Briefly, individual dsRNAs at a concentration between 5 to 500 nM (final volume) are diluted in OptiMEM (Invitrogen) while a separate solution of OptiMEM and Oligofectamine is incubated at room temperature for 5 min. The two solutions are mixed, followed by a 30-minute room temperature incubation. Serum-containing media is added to the transfection complex for a final volume of 0.5 ml/well. Existing cell media is aspirated and replaced with the transfection complex and incubated for 48-72 h at 37° C., 5% $CO_2$.

Immunoblotting

After 72 hours, the transfection mixture is gently aspirated, and cells are lysed in 150 ul ice-cold RIPA buffer (50 mM Tris-HCl, pH 7.4, 150 mM NaCl, 1% NP-40, 0.25% Na-deoxycholate, 1 mM EDTA) containing Complete tablet protease inhibitors (Roche Molecular Biochemicals), 1 mM activated $Na_3VO_5$ and incubated for 30 minutes at room temperature and stored at −20° C. for 1-24 h. Thirty µl of thawed lysate is added to 10 µl 4× NuPage sample buffer (Invitrogen) containing 0.2 M DTT. Samples are heated for 5 minutes at 85° C. and loaded onto 4-20% tris-glycine polyacrylamide gels (Invitrogen). Gels are transferred to Hybond-P PVDF membranes (Amersham Pharmacia Biotech) for 1100 mAH in 1× transfer buffer w/20% methanol. Membranes are blocked in PBS containing 5% non-fat milk for 1 hour. Primary antibodies, anti-eIF4E (BD Biosciences) and anti-actin (Sigma) are diluted in blocking buffer at 1:500 and 1:10,000, respectively and incubated 16 hours at 4° C. Membranes are washed 3× in PBS, followed by anti-mouse secondary antibody (Santa Cruz) incubation for 2 hours at room temperature. Blots are washed 3× in PBS and treated with SuperSignal West Pico chemiluminescent substrate (Pierce) for 1 minute. Captured signal is recorded on a Lumi-Imager F1 (Roche Molecular Biochemicals). Bands corresponding to both eIF4E and actin are quantitated using Lumi-Analyst software, and eIF4E expression levels are determined after normalizing to actin in order to control for gel loading and transfer.

In the LNCaP cell line, each of eIF4E-1, eIF4E-2, and eIF4E-3 inhibited eIF-4E protein levels by greater than 50% at concentrations of less than 50 nM. In the CWR22RV1 cell line, concentrations of less than 5 nM eIF4E-2 inhibited eIF-4E protein levels by greater than 50%. In each of the LNCaP, PC3, HCT116, MDA-231, and MCF-7 cell lines, concentrations of eIF4E-1 and eIF4E-2 less than 50 nM reduced eIF-4E protein expression by greater than 50%.

Cell Proliferation Assays

Cells are plated 24 hours prior to transfection at a cell density between $1.5-3.0 \times 10^3$ cells/well in poly-D-lysine coated 96-well plates (Becton Dickinson). Transfections of the eIF-4E and control siRNAs are performed in triplicate at siRNA concentrations ranging from 5 nM to 500 nM. Cells are harvested at 3, 6 and 8 days by addition of propidium iodide (Sigma) at 50 µg/ml final concentration, followed by a 30 minute room temperature incubation protected from light. Plates are measured pre- and post-freezing on a Victor$^2$ 1420 multi-label counter (Wallac). Corrected sums are obtained by subtracting the pre-from the post-freeze measurements.

In each of the LNCaP, PC3, and MDA-231 cell lines, concentrations of eIF4E-1 and eIF4E-2 less than 50 nM reduced cell proliferation by greater than 50%.

Example 24

Activity of siRNA Constructs Targeted to eIF4E in HeLa Cells

The duplexed oligomeric RNA (dsRNA) compounds shown in Table 5 below were prepared as described in previous examples and evaluated in HeLa cells (American Type Culture Collection, Manassas Va.). Culture methods used for HeLa cells are available from the ATCC and may be found, for example, at www.atcc.org. For comparison several single stranded chimeric antisense oligonucleotides were also tested.

Cells were plated in 96-well plates at a density of 5000 cells/well and grown in DMEM with high glucose, 10% FBS, 1% penicillin/streptomycin. Wells were washed once with 200 µL OPTI-MEM-1™ reduced-serum medium (Gibco BRL) and then treated with 130 µL of OPTI-MEM-1™ containing the desired dsRNA at a concentration of 25 nM and 2.5 ul/ml LIPOFECTIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples, normalized to Ribogreen. Human primer/probe set is SEQ ID NO:5, 6 and 7 used in previous examples.

The results are shown in Table 5. The siRNA constructs shown consist of one antisense strand and one sense strand. The antisense strand (AS) is shown first in Table 5 below, followed by the sense strand (S) in the next row. Unless otherwise indicated, all double-stranded constructs are unmodified RNA, i.e., ribose sugars with phosphate (P=O) backbones and 5'-terminal hydroxyl group, and are blunt-ended (no dTdT or other overhang) unless otherwise indicated. Unless otherwise indicated, single-stranded antisense molecules are chimeric gapped oligonucleotides with 2'-MOE at nucleotides 1-5 and 16-20 and 2'-deoxynucleotides at positions 6-15, with phosphorothioate (P=S) backbones and 5-methylcytosines at every C. It is understood in the art that, for RNA sequences, U (uracil) generally replaces T (thymine) which is normally found in DNA or DNA-like sequences.

TABLE 5 siRNA constructs targeted to eIF4E- activity in HeLa cells

| Strand | ISIS # | Sequence (5'→3') | SEQ ID NO | Target site | Target region | Species/note | % inhib |
|---|---|---|---|---|---|---|---|
| AS | 338910 | UGUCAUAUUCCUGGAUCCUU | 220 | 1285 | 3'UTR | h/m | 80.1 ± |
| S | 338935 | AAGGAUCCAGGAAUAUGACA | 221 | | | | 2.8 |
| AS | 338911 | GGAGGAAGUCCUAACCUUUC | 222 | 571 | coding | h/m/r | 27.5 ± |
| S | 338936 | GAAAGGUUAGGACUUCCUCC | 223 | | | | 1.4 |
| AS | 338912 | GGCUUUGGUUCAGCUCCCAA | 224 | 724 | 3'UTR | h/m/r | 55.8 ± |
| S | 338937 | UUGGGAGCUGAACCAAAGCC | 225 | | | | 3.5 |
| AS | 338913 | GGCGAAUGAGACUUCUCUUA | 226 | 805 | 3'UTR | h/m/r | 74.2 ± |
| S | 338938 | UAAGAGAAGUCUCAUUCGCC | 227 | | | | 0.2 |
| AS | 338914 | UCCUGGAUCCUUCACCAAUG | 228 | 1277 | 3'UTR | h/m/r | 76.1 ± |
| S | 338939 | CAUUGGUGAAGGAUCCAGGA | 229 | | | | 1.2 |
| AS | 338915 | GCUUUUCUACUUGAGCCAUU | 230 | 1564 | 3'UTR | h/m/r | 51.3 ± |
| S | 338940 | AAUGGCUCAAGUAGAAAAGC | 231 | | | | 1.6 |
| AS | 338916 | ACAUCAUCACUGUAGUCAUC | 232 | 445 | coding | h/m | 56.7 ± |
| S | 338941 | GAUGACUACAGUGAUGAUGU | 233 | | | | 0.9 |
| AS | 338917 | CACCUUUAGCUCUAACAUUA | 234 | 480 | coding | h/m | 42.3 ± |
| S | 338942 | UAAUGUUAGAGCUAAAGGUG | 235 | | | | 2.8 |
| AS | 338918 | UCUUAUCACCUUUAGCUCUA | 236 | 486 | coding | h/m/r | 77 ± |
| S | 338943 | UAGAGCUAAAGGUGAUAAGA | 237 | | | | 2.7 |
| AS | 338919 | UGCUAUCUUAUCACCUUUAG | 238 | 491 | coding | h/m/r | 52.4 ± |
| S | 338944 | CUAAAGGUGAUAAGAUAGCA | 239 | | | | 9 |
| AS | 338920 | GUCCAUAUUGCUAUCUUAUC | 240 | 499 | coding | h/m/r | 62.5 ± |
| S | 338945 | GAUAAGAUAGCAAUAUGGAC | 241 | | | | 4.4 |
| AS | 338921 | GCCAAGUUUUGCUUUUAUCA | 242 | 168 | coding | h/m/r | 32.3 ± |
| S | 338946 | UGAUAAAAGCAAAACUUGGC | 243 | | | | 12.1 |
| AS | 338922 | UCUUCAACAGUAUCAAACUU | 244 | 211 | coding | h/m/r | 16.6 ± |
| S | 338947 | AAGUUUGAUACUGUUGAAGA | 245 | | | | 0.6 |
| AS | 338923 | GUCACAGCCAGGCAUUAAAU | 246 | 269 | coding | h/m/r | 65.6 ± |
| S | 338948 | AUUUAAUGCCUGGCUGUGAC | 247 | | | | 0.3 |
| AS | 338924 | UCUCAUCUUCCCACAUAGGC | 248 | 315 | coding | h/m/r | 45 ± |
| S | 338949 | GCCUAUGUGGGAAGAUGAGA | 249 | | | | 1.3 |
| AS | 338925 | ACCUUUCCUUGUAUACCCUC | 250 | 558 | coding | h/m/r | 60.2 ± |
| S | 338950 | GAGGGUAUACAAGGAAAGGU | 251 | | | | 4.8 |

TABLE 5-continued siRNA constructs targeted to eIF4E- activity in HeLa cells

| Strand | ISIS # | Sequence (5'→3') | SEQ ID NO | Target site | Target region | Species/note | % inhib |
|---|---|---|---|---|---|---|---|
| AS | 338926 | GUAGCUGUGUCUGCGUGGGA | 252 | 613 | coding | h/m/r | 45.4 ± |
| S | 338951 | UCCCACGCAGACACAGCUAC | 253 | | | | 0.5 |
| AS | 338927 | AUACUCAGAAGGUGUCUUCU | 254 | 672 | 3'UTR | h/m/r | 83 ± |
| S | 338952 | AGAAGACACCUUCUGAGUAU | 255 | | | | 1.2 |
| AS | 338928 | CUGUAAUUCUUUGAUUGGGA | 256 | 883 | 3'UTR | h/m/r | 74 ± |
| S | 338953 | UCCCAAUCAAAGAAUUACAG | 257 | | | | 0.2 |
| AS | 338929 | GAAUGAAAUGCAUAAAUUUG | 258 | 1381 | 3'UTR | h/m/r | 5.6 ± |
| S | 338954 | CAAAUUUAUGCAUUUCAUUC | 259 | | | | 1.4 |
| AS | 338930 | UCACUGAUUUGAAUGAAAUG | 260 | 1391 | 3'UTR | h/m/r | 62.8 ± |
| S | 338955 | CAUUUCAUUCAAAUCAGUGA | 261 | | | | 0.7 |
| AS | 338931 | AUUUACAGUUUUGUACACUG | 262 | 1603 | 3'UTR | h/m/r | 63.8 ± |
| S | 338956 | CAGUGUACAAAACUGUAAAU | 263 | | | | 0.4 |
| AS | 338932 | AAAACCAGAGUGCCCAUCUG | 264 | 141 | Coding | h | 88.2 ± |
| S | 338957 | CAGAUGGGCACUCUGGUUUU | 265 | | | | 0.2 |
| AS | 338933 | ACUUGGAGAUCAGCCGCAGG | 266 | 195 | Coding | h | 42.1 ± |
| S | 338958 | CCUGCGGCUGAUCUCCAAGU | 267 | | | | 5.7 |
| AS | 338934 | AGUAUAGAAAUGCCAAGUUG | 268 | 1010 | 3'UTR | h | 69.3 ± |
| S | 338959 | CAACUUGGCAUUUCUAUACU | 269 | | | | 6.6 |
| AS | 341887 eIF4E_1 | AAACCAGAGUGCCCAUCUGTT | 270 | 141 | Coding | H Ribose except 3'dTdT | 69.5 ± 4.6 |
| S | 341886 | CAGAUGGGCACUCUGGUUUTT | 271 | | | | Ribose except 3'dTdT |
| AS | 341889 eIF4E_2 | CUUGGAGAUCAGCCGCAGGTT | 272 | 195 | Coding | h Ribose except 3'dTdT | 45.5 ± 16 |
| S | 341888 | CCUGCGGCUGAUCUCCAAGTT | 273 | | | | Ribose except 3'dTdT |
| AS | 341891 eIF4E_3 | GUAUAGAAAUGCCAAGUUGTT | 274 | 1010 | 3'UTR | h Ribose except 3'dTdT | 65 ± 14.8 |
| S | 341890 | CAACUUGGCAUUUCUAUACTT | 275 | | | | Ribose except 3'dTdT |
| AS | 335449 | UUUGUCUCUGGUCCUUACUU Control targeted to PTEN | 276 | — | | extra 5' UU; 5' phosphate | 31 ± 4 |
| S | 308746 | AAGUAAGGACCAGAGACAAA | 277 | | | | |
| AS | 263188 | CUUCUGGCAUCCGGUUUAGUU control; 6-mismatch to PTEN | 278 | — | | Ribose except 3'dTdT; | −5.7 ± 8.1 |

TABLE 5-continued siRNA constructs targeted to eIF4E- activity in HeLa cells

| Strand | ISIS # | Sequence (5'→3') | SEQ ID NO | Target site | Target region | Species/note | % inhib |
|---|---|---|---|---|---|---|---|
| | | | | | | alternating P = O/ P = S | |
| S | 263189 | CUAAACCGGAUGCCAGAAGUU | 279 | | | Ribose except 3'dTdT; alternating P = O/ P = S | |
| AS | 183750 | TGTCATATTCCTGGATCCTT | 40 | 1285 | 3'UTR | h/m MOE gapmer | 94 ± 0.5 |
| S | none | | | | | | |
| AS | 298815 | GGCGAATGAGACTTCTCTTA | 97 | 805 | 3'UTR | h/m/r MOE gapmer | 94.1 ± 1.6 |
| S | none | | | | | | |
| AS | 116847 | CTGCTAGCCTCTGGATTTGA control targeted to PTEN | 280 | — | | h/m/r/r ab MOE gapmer | -7.2 ± 3.3 |
| S | none | | | | | | |
| AS | 129686 | CGTTATTAACCTCCGTTGAA negative (scrambled) control | 281 | — | | MOE gapmer | 8.7 ± 17.6 |
| S | none | | | | | | |
| AS | 129691 | ATGCATACTACGAAAGGCCG negative (scrambled) control | 282 | — | | MOE gapmer | 4.9 ± 9.5 |
| S | none | | | | | | |

"% inhib" indicates % reduction of eIF4E RNA in cells treated with siRNA duplex (or other compound as shown) compared to untreated control cells. RNA quantitation is by RT-PCR. Where "% inhib" is negative, target RNA was increased.

"Target site" indicates the position of the 5'-most nucleotide of the target site on Genbank accession no. M15353.1 to which the compound is specifically hybridizable.

"Species" indicates whether the antisense sequence is perfectly complementary to human (h), rat (h), mouse (m) and/or rabbit (rab) eIF4E.

In this screen, the MOE gapmer leads to eIF4E were found to be slightly more active (94% inhibition) than the best siRNA (88% inhibition). Three out of five siRNA constructs at previously identified MOE gapmer lead sites are active. Eight eIF4E siRNA constructs show target reduction of 70% or more, and seven show reduction of 75% or more. This is consistent with the conclusions of Vickers et al. (J. Biol. Chem., 2003, 278, 7108-7118), i.e., in general, activity of siRNA oligonucleotide duplexes correlated with the activity of RNase H-dependent oligonucleotides (e.g, MOE gapmers) targeted to the same site, and optimized siRNA and RNase H-dependent oligonucleotides behave similarly in terms of potency, maximal effects, specificity and duration of action and efficiency.

The compounds in the above table were also tested for the ability to reduce PTEN RNA levels in HeLa cells. None of the eIF4E-targeted compounds (siRNA or single stranded MOE gapmers) reduced PTEN target RNA levels by more than about 20%. The siRNA positive control 335449 construct inhibited PTEN RNA by about 85% and the single stranded MOE gapmer positive control ISIS 116847 inhibited PTEN RNA by about 80%.

Example 25

Activity of siRNA Constructs Targeted to eIF4E in MH-S Cells

Nearly all of the siRNA compounds in the previous table are perfectly complementary to both mouse and human eIF4E mRNA. Here they are tested in the mouse MH-S murine alveolar macrophage cell line. Mouse MH-S cells were purchased from the American Type Culture Collection (Manassas, Va.). The cells were maintained in RPMI 1640 medium containing 10% heat-inactivated fetal calf serum (FCS) (Hyclone Laboratories, Logan, Utah). Cells were plated in 96-well plates at a density of 5000 cells/well and grown in DMEM with high glucose, 10% FBS, 1% penicillin/streptomycin. Wells were washed once with 200 µL OPTI-MEM-1™ reduced-serum medium (Gibco BRL) and then treated with 130 µL of OPTI-MEM-1™ containing the desired dsRNA at a concentration of 20 nM and 2.5 ul/ml LIPOFECTIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples.

The results are shown in Table 6. The siRNA constructs shown consist of one antisense strand and one sense strand. The antisense strand (AS) is shown first in Table 6 below, followed by the sense strand (S) in the next row. Unless otherwise indicated, all double-stranded constructs are unmodified RNA, i.e., ribose sugars with phosphate (P=O) backbones and 5'-terminal hydroxyl group. Unless otherwise indicated, single-stranded antisense molecules are chimeric gapped oligonucleotides with 2'-MOE at nucleotides 1-5 and 16-20 and 2'-deoxynucleotides at positions 6-15, with phosphorothioate (P=S) backbones and 5-methylcytosines at every C. It is understood in the art that, for RNA sequences, U (uracil) generally replaces T (thymine) which is normally found in DNA or DNA-like sequences.

Target sites, species, chemistry and sequences are as in previous tables.

TABLE 6

Activity of eIF4E siRNA constructs in mouse MH-S cells

| Strand | ISIS # | % inhib |
|---|---|---|
| AS | 338910 | 77.3 ± 4.6 |
| S | 338935 | |
| AS | 338911 | 37.9 ± 0.6 |
| S | 338936 | |
| AS | 338912 | 67.1 ± 0.3 |
| S | 338937 | |
| AS | 338913 | 77.3 ± 5.5 |
| S | 338938 | |
| AS | 338914 | 78.3 ± 1.8 |
| S | 338939 | |
| AS | 338915 | 52.5 ± 1.3 |
| S | 338940 | |
| AS | 338916 | 66.6 ± 3.2 |
| S | 338941 | |
| AS | 338917 | 54.8 ± 11.2 |
| S | 338942 | |
| AS | 338918 | 78.0 ± 2.4 |
| S | 338943 | |
| AS | 338919 | 59.8 ± 7.4 |
| S | 338944 | |
| AS | 338920 | 52.4 ± 2.7 |
| S | 338945 | |
| AS | 338921 | 61.6 ± 0.9 |
| S | 338946 | |
| AS | 338922 | 44.1 ± 2.1 |
| S | 338947 | |
| AS | 338923 | 66.8 ± 1.3 |
| S | 338948 | |
| AS | 338924 | 63.8 ± 2.7 |
| S | 338949 | |
| AS | 338925 | 65.0 ± 4.4 |
| S | 338950 | |
| AS | 338926 | 66.7 ± 2.3 |
| S | 338951 | |
| AS | 338927 | 81.6 ± 0.5 |
| S | 338952 | |
| AS | 338928 | 69.5 ± 2.4 |
| S | 338953 | |

TABLE 6-continued

Activity of eIF4E siRNA constructs in mouse MH-S cells

| Strand | ISIS # | % inhib |
|---|---|---|
| AS | 338929 | 3.0 ± 8.4 |
| S | 338954 | |
| AS | 338930 | 53.7 ± 0.0 |
| S | 338955 | |
| AS | 338931 | 58.2 ± 0.6 |
| S | 338956 | |
| AS | 338932 | 57.5 ± 4.5 |
| S | 338957 | |
| AS | 338933 | 38.7 ± 26.2 |
| S | 338958 | |
| AS | 338934 | 21.6 ± 5.3 |
| S | 338959 | |
| AS | 335449 | 7.4 ± 8.1 |
| S | 308746 | |
| AS | 263188 | 18.3 ± 3.8 |
| S | 263189 | |
| AS | 183750 | 84.1 ± 3.5 |
| | none | |
| AS | 298815 | 82.6 ± 3.6 |
| S | none | |
| AS | 116847 | 1.1 ± 4.9 |
| S | none | |
| AS | 129686 | 14.4 ± 7.4 |
| S | none | |
| AS | 341887 | 18.7 ± 14.2 |
| S | 341886 | |
| AS | 341889 | 21.7 ± 6.4 |
| S | 341888 | |
| AS | 341891 | 11.6 ± 7.2 |
| S | 341890 | |
| AS | 129691 | 6.3 ± 2.7 |
| S | none | |

Example 26

Additional siRNA Constructs Targeted to eIF4E and Activity in HeLa Cells

An additional gene walk was done to identify additional siRNAs that inhibit eIF4E. Constructs were screened in HeLa cells at a concentration of 50 nM.

The duplexed oligomeric RNA (dsRNA) compounds shown in Table 7 below were prepared as described in previous examples and evaluated in HeLa cells (American Type Culture Collection, Manassas Va.). Culture methods used for HeLa cells are available from the ATCC and may be found, for example, at www.atcc.org. For comparison several single stranded chimeric antisense oligonucleotides were also tested.

Cells were plated in 96-well plates at a density of 5000 cells/well and grown in DMEM with high glucose, 10% FBS, 1% penicillin/streptomycin. Wells were washed once with 200 µL OPTI-MEM-1™ reduced-serum medium (Gibco BRL) and then treated with 130 µL of OPTI-MEM-1™ containing the desired dsRNA at a concentration of 50 nM and 2.5 ul/ml LIPOFECTIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples. The results are shown in Table 7. The siRNA constructs shown consist of one antisense strand and one sense strand. The antisense strand (AS) is shown first in Table 7 below, followed by the sense strand (S) in the next row. Unless otherwise indicated, all double-stranded constructs are unmodified RNA, i.e., ribose sugars with phosphate (P=O) backbones and 5'-terminal hydroxyl group. Unless otherwise indicated, single-stranded antisense molecules are chimeric gapped oligonucleotides with 2'-MOE at nucleotides 1-5 and 16-20 and 2'-deoxynucleotides at positions 6-15, with phosphorothioate (P=S) backbones and 5-methylcytosines at every C. It is understood in the art that, for RNA sequences, U (uracil) generally replaces T (thymine) which is normally found in DNA or DNA-like sequences.

TABLE 7

Activity of eIF4E siRNA in HeLa cells

| Strand | ISIS # | Sequence | SEQ ID NO | Target site | Target region | Species | % inhib |
|---|---|---|---|---|---|---|---|
| AS | 342735 | UUAAAAAACCAGAGUGCCCA | 283 | 145 | coding | h/m/r | 75.7 ± |
| S | 342755 | UGGGCACUCUGGUUUUUUAA | 284 | | | | 5.7 |
| AS | 342736 | UUUAAAAAACCAGAGUGCCC | 285 | 146 | Coding | h/m/r | 56.6 ± |
| S | 342756 | GGGCACUCUGGUUUUUUAAA | 286 | | | | 8.8 |
| AS | 342737 | UUUUAAAAAACCAGAGUGCC | 287 | 147 | Coding | h/m/r | 75.4 ± |
| S | 342757 | GGCACUCUGGUUUUUUAAAA | 288 | | | | 1.6 |
| AS | 342738 | AUUUUUAAAAAACCAGAGUG | 289 | 149 | coding | h/m/r | 50.7 ± |
| S | 342758 | CACUCUGGUUUUUUAAAAAU | 290 | | | | 3.3 |
| AS | 342739 | AGAGCCCAAAAGUCUUCAAC | 291 | 223 | Coding | h/m/r | 58.0 ± |
| S | 342759 | GUUGAAGACUUUUGGGCUCU | 292 | | | | 7.5 |
| AS | 342740 | UACUAGACAACUGGAUAUGG | 293 | 249 | Coding | h/m/r | 86.1 ± |
| S | 342760 | CCAUAUCCAGUUGUCUAGUA | 294 | | | | 5.3 |
| AS | 342741 | GGCAUUAAAUUACUAGACAA | 295 | 259 | Coding | h/m/r | 6.2 ± |
| S | 342761 | UUGUCUAGUAAUUUAAUGCC | 296 | | | | 1.8 |
| AS | 342742 | AAAGUGAGUAGUCACAGCCA | 297 | 279 | Coding | h/m/r | 89.9 ± |
| S | 342762 | UGGCUGUGACUACUCACUUU | 298 | | | | 0.5 |
| AS | 342743 | GUUUUUCUCAUCUUCCCACA | 299 | 320 | Coding | h/m/r | 86.1 ± |
| S | 342763 | UGUGGGAAGAUGAGAAAAAC | 300 | | | | 5.6 |
| AS | 342744 | UCUUAUCACCUUUAGCUCU | 301 | 487 | Coding | h/m/r | 84.3 ± |
| S | 342764 | AGAGCUAAAGGUGAUAAGA | 302 | | | | 2.6 |
| AS | 342745 | UCCUUGUAUACCCUCCCUAU | 303 | 553 | Coding | h/m/r | 71.6 ± |
| S | 342765 | AUAGGGAGGGUAUACAAGGA | 304 | | | | 9.1 |
| AS | 342746 | UGAUAACCAAUCACUAUCUU | 305 | 592 | Coding | h/m/r | 88.7 ± |
| S | 342766 | AAGAUAGUGAUUGGUUAUCA | 306 | | | | 0.8 |
| AS | 342747 | ACAACAAACCUAUUUUUAGU | 307 | 649 | Coding | h/m/r | 10.8 ± |
| S | 342767 | ACUAAAAAUAGGUUUGUUGU | 308 | | | | 1.7 |
| AS | 342748 | AUGAGACUUCUCUUAUAUCU | 309 | 800 | 3'UTR | h/m/r | 86.3 ± |
| S | 342768 | AGAUAUAAGAGAAGUCUCAU | 310 | | | | 0.1 |
| AS | 342749 | GUACAAGACAAAGGCGAAUG | 311 | 817 | 3'UTR | h/m/r | 81.3 ± |
| S | 342769 | CAUUCGCCUUUGUCUUGUAC | 312 | | | | 2.6 |
| AS | 342750 | CUAGCAGCCAUCAGCAAGAG | 313 | 1157 | 3'UTR | h/m/r | 78.5 ± |
| S | 342770 | CUCUUGCUGAUGGCUGCUAG | 314 | | | | 0.6 |
| AS | 342751 | UAGCAAAGCUUUGUAGUUAC | 315 | 1361 | 3'UTR | h/m/r | 70.5 ± |

TABLE 7-continued

Activity of eIF4E siRNA in HeLa cells

| Strand | ISIS # | Sequence | SEQ ID NO | Target site | Target region | Species | % inhib |
|---|---|---|---|---|---|---|---|
| S | 342771 | GUAACUACAAAGCUUUGCUA | 316 | | | | 3.8 |
| AS | 342752 | CUAGUUAGGAAUGUAAUUAU | 317 | 1466 | 3'UTR | h/m/r | 62.1 ± |
| S | 342772 | AUAAUUACAUUCCUAACUAG | 318 | | | | 0.8 |
| AS | 342753 | UUGUACACUGUCUUAAUAUG | 319 | 1593 | 3'UTR | h/m/r | 58.0 ± |
| S | 342773 | CAUAUUAAGACAGUGUACAA | 320 | | | | 2.8 |
| AS | 342754 | GUACACAUUUUAUUUACAGU | 321 | 1614 | 3'UTR | h/m/r | 10.7 ± |
| S | 342774 | ACUGUAAAUAAAAUGUGUAC | 322 | | | | 4.3 |
| AS | 338910 | UGUCAUAUUCCUGGAUCCUU | 220 | 1285 | 3'UTR | h/m from screen 1 | 80.2 ± 2.3 |
| S | 338935 | AAGGAUCCAGGAAUAUGACA | 221 | | | | |
| AS | 338914 | UCCUGGAUCCUUCACCAAUG | 228 | 1277 | 3'UTR | h/m from screen 1 | 79.6 ± 2.2 |
| S | 338939 | CAUUGGUGAAGGAUCCAGGA | 229 | | | | |
| AS | 338918 | UCUUAUCACCUUUAGCUCUA | 236 | | coding | h/m/r from screen 1 | 84.7 ± 0.0 |
| S | 338943 | UAGAGCUAAAGGUGAUAAGA | 237 | | | | |
| AS | 338927 | AUACUCAGAAGGUGUCUUCU | 254 | 672 | 3'UTR | h/m/r from screen 1 | 88.6 ± 8.8 |
| S | 338952 | AGAAGACACCUUCUGAGUAU | 255 | | | | |
| AS | 338932 | AAAACCAGAGUGCCCAUCUG | 264 | 141 | Coding | h | 88.1 ± |
| S | 338957 | CAGAUGGGCACUCUGGUUUU | 265 | | | | 3.6 |
| AS | 341887 eIF4E_1 | AAACCAGAGUGCCCAUCUGU | 270 | 141 | coding | h Ribose except 3'dTdT | 56.5 |
| S | 341886 | CAGAUGGGCACUCUGGUUUUU | 271 | | | | |
| AS | 263188 | CUUCUGGCAUCCGGUUUAGUU control; 6-mismatch to PTEN | 278 | — | | Ribose except 3'dTdT; alternating P = O/ P = S | −5.6 ± 26.0 |
| S | 263189 | CUAAACCGGAUGCCAGAAGUU | 279 | | | | |
| AS | 335449 | UUUGUCUCUGGUCCUUACUU control targeted to PTEN | 276 | — | phos- phate | extra 3'- UU; 5' | −16.3 ± 6.1 |
| S | 308746 | AAGUAAGGACCAGAGACAAA | 277 | | | | |
| AS | 183750 | TGTCATATTCCTGGATCCTT | 40 | 1285 | 3'UTR | MOE gapmer h/m | 96.2 ± 0.6 |
| S | none | | | | | | |

TABLE 7-continued

Activity of eIF4E siRNA in HeLa cells

| Strand | ISIS # | Sequence | SEQ ID NO | Target site | Target region | Species | % inhib |
|---|---|---|---|---|---|---|---|
| AS | 129691 | ATGCATACTACGAAAGGCCG Negative (scrambled) control | 282 | — | | MOE gapmer | 1.7 ± 7.0 |
| S | none | | | | | | |
| AS | 116847 | CTGCTAGCCTCTGGATTTGA Control targeted to PTEN | 280 | — | | h/m/r/ rab MOE gapmer | -10.9 ± 9.7 |
| S | none | | | | | | |

"% inhib" indicates % reduction of eIF4E RNA in cells treated with siRNA duplex (or other compound as shown) compared to untreated control cells. Where "% inhib" is negative, target RNA is increased. RNA quantitation is by RT-PCR.

"Target site" indicates the position of the 5'-most nucleotide of the target site on Genbank accession no. M15353.1 to which the compound is specifically hybridizable.

"Species" indicates whether the antisense sequence is perfectly complementary to human (h), rat (h), mouse (m) and/or rabbit (rab) eIF4E.

Example 27

Activity of siRNA Constructs Targeted to eIF4E in MH-S Cells

Nearly all of the siRNA compounds in the previous table are perfectly complementary to both mouse and human eIF4E mRNA. Here they are tested in the mouse MH-S murine alveolar macrophage cell line. Mouse MH-S cells were purchased from the American Type Culture Collection (Manassas, Va.). The cells were maintained in RPMI 1640 medium containing 10% heat-inactivated fetal calf serum (FCS) (Hyclone Laboratories, Logan, Utah). Cells were plated in 96-well plates at a density of 5000 cells/well and grown in DMEM with high glucose, 10% FBS, 1% penicillin/streptomycin. Wells were washed once with 200 µL OPTI-MEM-1™ reduced-serum medium (Gibco BRL) and then treated with 130 µL of OPTI-MEM-1™ containing the desired dsRNA at a concentration of 50 nM and 2.5 ul/ml LIPOFECTIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples. The results are shown in Table 8. The siRNA constructs shown consist of one antisense strand and one sense strand. The antisense strand (AS) is shown; sense strand, target site, species, chemistry and sequence are as in previous tables. It is understood in the art that, for RNA sequences, U (uracil) generally replaces T (thymine) which is normally found in DNA or DNA-like sequences.

Unless otherwise indicated, all double-stranded constructs are unmodified RNA, i.e., ribose sugars with phosphate (P=O) backbones and 5'-terminal hydroxyl group. Unless otherwise indicated, single-stranded antisense molecules are chimeric gapped oligonucleotides with 2'-MOE at nucleotides 1-5 and 16-20 and 2'-deoxynucleotides at positions 6-15, with phosphorothioate (P=S) backbones and 5-methylcytosines at every C. Antisense strand identity is shown.

TABLE 8

Activity of eIF4E siRNA constructs in mouse MH-S cells

| Strand | ISIS # | % inhib |
|---|---|---|
| AS | 342735 | 63.1 ± 8.9 |
| AS | 342736 | 57.2 ± 8.0 |
| AS | 342737 | 42.2 ± 5.1 |
| AS | 342738 | 28.6 ± 4.3 |
| AS | 342739 | 23.9 ± 3.5 |
| AS | 342740 | 70.3 ± 9.3 |
| AS | 342741 | 7.2 ± 5.9 |
| AS | 342742 | 68.3 ± 7.3 |
| AS | 342743 | 59.2 ± 8.5 |
| AS | 342744 | 62.7 ± 10.5 |
| AS | 342745 | 58.1 ± 0.8 |
| AS | 342746 | 69.2 ± 5.7 |
| AS | 342747 | 8.8 ± 11.7 |
| AS | 342748 | 70.6 ± 3.1 |
| AS | 342749 | 58.7 ± 0.3 |
| AS | 342750 | 48.3 ± 7.9 |
| AS | 342751 | 32.0 ± 10.0 |
| AS | 342752 | 50.4 ± 3.2 |
| AS | 342753 | 38.5 ± 1.7 |
| AS | 342754 | -5.2 ± 8.2 |
| AS | 338910 | 60.9 ± 3.2 |
| AS | 338914 | 70.0 ± 14.1 |
| AS | 338918 | 69.0 ± 2.3 |
| AS | 338927 | 71.3 ± 5.3 |
| AS | 338932 | 46.4 ± 12.7 |
| AS | 341887 eIF4E_1 | 15.6 ± 1.0 |
| AS | 263188 | 6.5 ± 3.6 |
| AS | 335449 | -5.9 ± 4.3 |
| AS | 183750 | 47.8 ± 6.9 |
| AS | 129691 | -0.1 ± 2.5 |
| AS | 116847 | 1.6 ± 1.2 |

"% inhib" indicates % reduction of eIF4E RNA in cells treated with siRNA duplex (or other compound as shown) compared to untreated control cells. If "% inhib" is negative, target RNA increased. RNA quantitation is by RT-PCR.

"Target site" indicates the position of the 5'-most nucleotide of the target site on Genbank accession no. M15353.1 to which the compound is specifically hybridizable.

"Species" indicates whether the antisense sequence is perfectly complementary to human (h), rat (h), mouse (m) and/or rabbit (rab) eIF4E.

Example 28

Dose Response Experiment-IC50 of eiF4E siRNA Constructs in HeLa Cells

A dose-response experiment was done in HeLa cells using above treatment methods and siRNA concentrations of 0.1 nM, 1.0 nM, 10 nM and 100 nM, and an $IC_{50}$ (concentration of compound resulting in 50% inhibition of eIF4E compared to untreated control) was calculated for certain of the above compounds. The results are shown in Table 9. Antisense strand identity is shown. Sense strand, target site, species, chemistry and sequence are as in previous tables.

TABLE 9

$IC_{50}$s of siRNA compounds in HeLa cells

| ISIS # Antisense | $IC_{50}$ (nM) |
| --- | --- |
| 183750 | 3.0 |
| 338910 | 3.0 |
| 338914 | 1.9 |
| 338918 | 2.9 |
| 338927 | 6.0 |
| 338932 | 0.45 |
| 342740 | 1.3 |
| 342742 | 2.2 |
| 342743 | 6.6 |
| 342744 | 3.0 |
| 342746 | 5.2 |
| 342748 | 3.2 |
| 342749 | 3.6 |

Four of the above siRNA constructs were chosen for further evaluation and SAR (structure-activity-relationship) analysis. These parent constructs for siRNA SAR analysis are as shown here. It is understood in the art that, for RNA sequences, U (uracil) generally replaces T (thymine) which is normally found in DNA or DNA-like sequences.

```
"338918 construct"
                                    (SEQ ID NO: 237)
Sense:    5'-UAGAGCUAAAGGUGAUAAGA-3'    ISIS 338943

(SEQ ID NO: 236)
AS:       3'-AUCUCGAUUUCCACUAUUCU-5'    ISIS 338918
"338910 construct"

(SEQ ID NO: 221)
Sense:    5'-AAGGAUCCAGGAAUAUGACA-3'    ISIS 338935

(SEQ ID NO: 220)
AS:       3'-UUCCUAGGUCCUUAUACUGU-5'    ISIS 338910
"338927 construct"

(SEQ ID NO: 255)
Sense:    5'-AGAAGACACCUUCUGAGUAU-3'    ISIS 338952

(SEQ ID NO: 254)
AS:       3'-UCUUCUGUGGAAGACUCAUA-5'    ISIS 338927
"338914 construct"

(SEQ ID NO: 229)
Sense:    5'-CAUUGGUGAAGGAUCCAGGA-3'    ISIS 338939

(SEQ ID NO: 228)
AS:       3'-GUAACCACUUCCUAGGUCCU-5'    ISIS 338914
```

Example 29 eIF4E siRNA Constructs with Alternating 2' Modifications

The four siRNA constructs chosen in the previous example ("parent" constructs) were compared to siRNA constructs that have alternating 2'-O-methyl (2'-O—Me or 2'OMe) and 2'-fluoro (2'-F) modifications.

The duplexed oligomeric RNA (dsRNA) compounds shown in Table 10 below were prepared as described in previous examples and evaluated in HeLa cells (American Type Culture Collection, Manassas Va.). Culture methods used for HeLa cells are available from the ATCC and may be found, for example, at www.atcc.org. For comparison several single stranded chimeric antisense oligonucleotides were also tested. Cells were plated in 96-well plates at a density of 5000 cells/well and grown in DMEM with high glucose, 10% FBS, 1% penicillin/streptomycin. Wells were washed once with 200 μL OPTI-MEM-1™ reduced-serum medium (Gibco BRL) and then treated with 130 μL of OPTI-MEM-1™ containing the desired dsRNA at concentrations of 0.2, 2 and 20 nM and 2.5 μl/ml LIPOFECTIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples.

The results are shown in Table 10. The siRNA constructs shown consist of one antisense strand and one sense strand. For the alternating 2'-OMe/2'-F modified compounds, both the sense and antisense strands were modified, with the 5'-most nucleoside on the sense strand being a 2'-F and the 5'-most nucleoside on the antisense strand being a 2'-O—Me, so that the two kinds of modification are out of register in the duplexed molecule. It should be noted that the parent compounds are 20mers and the 2' modified compounds shown are 19mers, lacking the base pair corresponding to the 5' most pair of the sense strand (i.e., of the duplex as shown) These are shown in Table 10. 2'-O-methyl nucleosides are shown in bold; 2'-fluoro are underlined. Unmodified ribose is shown in plain UPPERCASE text. It is understood in the art that, for RNA sequences, U (uracil) generally replaces T (thymine) which is normally found in DNA or DNA-like sequences.

TABLE 10 eIF4E siRNA constructs with alternating 2'-O-Me and 2'-F modifications

| Strand | Isis No. | Sequence 5'→3' | SEQ ID NO | IC50 (nM) | % in-hib | Stability $t_{1/2}$ (h) |
| --- | --- | --- | --- | --- | --- | --- |
| AS | 338918 | UCUUAUCACCUUUAGCUCUA | 236 | 1.8 | 81 | 0.5 |
| S | 338943 | UAGAGCUAAAGGUGAUAAGA | 237 | | | |
| AS | 351831 | U<u>C</u>U<u>U</u>A<u>U</u>C<u>A</u>C<u>C</u>U<u>U</u>U<u>A</u>G<u>C</u>U<u>C</u>U | 301 | 1.1 | 88 | >4 |
| S | 351832 | <u>A</u>G<u>A</u>G<u>C</u>U<u>A</u>A<u>A</u>G<u>G</u>U<u>G</u>A<u>U</u>A<u>A</u>G<u>A</u> | 302 | | | |
| AS | 338910 | UGUCAUAUUCCUGGAUCCUU | 220 | 1.9 | 84 | |
| S | 338935 | AAGGAUCCAGGAAUAUGACA | 221 | | | |
| AS | 351827 | U<u>G</u>U<u>C</u>A<u>U</u>A<u>U</u>U<u>C</u>C<u>U</u>G<u>G</u>A<u>U</u>C<u>C</u>U | 323 | 7.3 | 65 | |

TABLE 10-continued eIF4E siRNA constructs with alternating 2'-O-Me and 2'-F modifications

| Strand | Isis No. | Sequence 5'→3' | SEQ ID NO | IC50 (nM) | % inhib | Stability t½ (h) |
|---|---|---|---|---|---|---|
| S | 351828 | AGGAUCCAGGAAUAUGACA | 324 | | | |
| AS | 338914 | UCCUGGAUCCUUCACCAAUG | 228 | 1.6 | 81 | |
| S | 338939 | CAUUGGUGAAGGAUCCAGGA | 229 | | | |
| AS | 351829 | UCCUGGAUCCUUCACCAAU | 325 | 5.8 | 63 | |
| S | 351830 | AUUGGUGAAGGAUCCAGGA | 326 | | | |
| AS | 338927 | AUACUCAGAAGGUGUCUUCU | 254 | 5.1 | 82 | |
| S | 338952 | AGAAGACACCUUCUGAGUAU | 255 | | | |
| AS | 351833 | AUACUCAGAAGGUGUCUUC | 327 | 6.5 | 61 | |
| S | 351834 | GAAGACACCUUCUGAGUAU | 328 | | | |

"% inhib" indicates % reduction of eIF4E RNA in cells treated with siRNA duplex (or other compound as shown) compared to untreated control cells.

NORMAL UYPE UPPER CASE=unmodified RNA with phosphate backbone.

2'-O-methyl nucleosides are shown in bold; 2'-fluoro are underlined.

For several of the constructs, the alternating 2'-O-methyl/2'-fluoro (2'-OMe/2'F) construct was shown to be comparable to or better than the parent (unmodified RNA) construct in efficacy of eIF4E mRNA reduction. Furthermore, the stability of the modified construct tested was more than 8-fold that of the unmodified compound (details in following example).

Example 30

Stability of Alternating 2'-O-methyl/2'-fluoro siRNA Constructs in Mouse Plasma

Intact duplex RNA was analyzed from diluted mouse-plasma using an extraction and capillary electrophoresis method similar to those previously described (Leeds et al., Anal. Biochem., 1996, 235, 36-43; Geary et al., Anal. Biochem., 1999, 274, 241-248). Heparin-treated mouse plasma, from 3-6 month old female Balb/c mice (Charles River Labs) was thawed from −80° C. and diluted to 25% (v/v) with phosphate buffered saline (140 mM NaCl, 3 mM KCl, 2 mM potassium phosphate, 10 mM sodium phosphate). Approximately 10 nmol of pre-annealed siRNA, at a concentration of 100 µM, was added to the 25% plasma and incubated at 37° C. for 0, 15, 30, 45, 60, 120, 180, 240, 360, and 420 minutes. Aliquots were removed at the indicated time, treated with EDTA to a final concentration of 2 mM, and placed on ice at 0° C. until analyzed by capillary gel electrophoresis (Beckman P/ACE MDQ-UV with eCap DNA Capillary tube). The area of the siRNA duplex peak was measured and used to calculate the percent of intact siRNA remaining. Adenosine triphosphate (ATP) was added at a concentration of 2.5 mM to each injection as an internal calibration standard. A zero time point was taken by diluting siRNA in phosphate buffered saline followed by capillary electrophoresis. Percent intact siRNA was plotted against time, allowing the calculation of a pseudo first-order half-life. Results are shown in Table 11.

TABLE 11

Stability of alternating 2'-O-methyl/2'-fluoro siRNA constructs in mouse plasma

| Construct | Time (minutes) | | | | | | | | |
|---|---|---|---|---|---|---|---|---|---|
| | 0 | 15 | 30 | 45 | 60 | 120 | 180 | 240 | 360 |
| 338918_338943 | 76.98 | 71.33 | 49.77 | 40.85 | 27.86 | 22.53 | 14.86 | 4.18 | 0 |
| 351831_351832 | 82.42 | 81.05 | 79.56 | 77.64 | 75.54 | 75.55 | 75.56 | 75.55 | 75 |

The parent (unmodified) construct is approximately 50% degraded after 30 minutes and nearly gone after 4 hours (completely gone at 6 hours). In contrast, the alternating 2'-O-methyl/2'-fluoro construct remains relatively unchanged and 75% remains even after 6 hours.

Example 31

Additional Modifications of eIF4E siRNA

Additional siRNA constructs with various modifications were prepared and tested as described in previous examples.

The duplexed oligomeric RNA (dsRNA) compounds shown in Table 12 below were prepared as described in previous examples and evaluated in HeLa cells (American Type Culture Collection, Manassas Va.). Culture methods used for HeLa cells are available from the ATCC and may be found, for example, at www.atcc.org. Cells were plated in 96-well plates at a density of 5000 cells/well and grown in DMEM with high glucose, 10% FBS, 1% penicillin/streptomycin. Wells were washed once with 200 µL OPTI-MEM-1™ reduced-serum medium (Gibco BRL) and then treated with 130 µL of OPTI-MEM-1™ containing the desired dsRNA at a range of concentrations and 2.5 µl/ml LIPOFECTIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples. For stability analysis, siRNA duplexes were incubated in 25% heparinized mouse plasma at 37° C. and analyzed by capillary gel electrophoresis with an internal reference standard.

The results are shown in Table 12. The siRNA constructs shown consist of one antisense strand and one sense strand. Unless otherwise indicated, all double-stranded constructs are unmodified RNA, i.e., ribose sugars with phosphate (P=O) backbones and 5'-terminal hydroxyl group. Unless otherwise indicated, single-stranded antisense molecules are chimeric gapped oligonucleotides with 2'-MOE at nucleotides 1-5 and 16-20 and 2'-deoxynucleotides at positions 6-15, with phosphorothioate (P=S) backbones and 5-methylcytosines at every C. It is understood in the art that, for RNA sequences, U (uracil) generally replaces T (thymine) which is normally found in DNA or DNA-like sequences. 2'-O-methyl nucleosides are shown in bold; 2'-fluoro are underlined, 4'-thio nucleosides are shown in lower case and unmodified ribose is shown in plain UPPERCASE text.

Compound 338918_338943 is unmodified (ribose, P=O backbone) parent construct. 349892_338943 has 2'F at positions 1-5, 8, 9, 12-17 and 2'Ome at pos. 6, 7, 10, 11, 18-20 of the antisense strand; the sense strand is unmodified (ribose, P=O backbone).

345847_345849 is a 19mer with alternating ribose and 2'OMe nucleosides (out of register) on both strands. The 5' most nucleoside of the sense strand is ribose and the 5' most nucleoside of the antisense strand is 2'OMe.

351831_351832 is a 19mer with alternating 2'-F and 2'OMe nucleosides (out of register) on both strands. The 5' most nucleoside of the sense strand is 2'-F and the 5' most nucleoside of the antisense strand is 2'OMe.

352824_342764 is a 19mer with three 4'-thio nucleosides at each terminus of the antisense strand (sense strand is unmodified).

352827_342764 is a 19mer with three 4'-thio nucleosides at the 5' terminus of the antisense strand and three 2'-OMe nucleosides at the 3' terminus of the antisense strand (sense strand is unmodified).

349890_338935 is a 20mer with mixed 2'-F/2'-OMe modifications of the antisense strand (sense strand is unmodified). The antisense strand has 2'-F at positions 1-5, 8, 9, and 12-17 and 2'-OMe at positions 6, 7, 10, 11, 18-20 (starting at the 5' end).

349891_338939 is a 20mer with mixed 2'-F/2'-OMe modifications of the antisense strand (sense strand is unmodified). The antisense strand has 2'-F at positions 1-5, 8, 9, and 12-17 and 2'-OMe at positions 6, 7, 10, 11, 18-20 (starting at the 5' end).

351097_338952 is a 20mer with mixed 2'-F/2'-OMe modifications of the antisense strand (sense strand is unmodified). The antisense strand has 2'-F at positions 1-5, 8, 9, and 12-17 and 2'-OMe at positions 6, 7, 10, 11, 18-20 (starting at the 5' end).

It should be noted that the parent compounds are 20mers and some of the 2' modified compounds shown are 19mers, lacking the base pair corresponding to the 5' most pair of the sense strand (i.e., of the duplex as shown) These are shown in Table 12. 2'-O-methyl nucleosides are shown in bold; 2'-fluoro are underlined, 4'-thio nucleosides are shown in lower case and unmodified ribose is shown in plain UPPERCASE text.

TABLE 12

Additional modifications of eIF4E siRNA and activity - summary

| Strand | Isis No. | Sequence 5'→3' | SEQ ID NO | IC50 (nM) | % inhib | Stability t½ (h) |
|---|---|---|---|---|---|---|
| AS | 338918 | UCUUAUCACCUUUAGCUCUA | 236 | 1.5 | 81 | 0.5 |
| S | 338943 | UAGAGCUAAAGGUGAUAAGA | 237 | | | |
| AS | 349892 | UCUUAUCACCUUUAGCUCUA | 236 | 0.4 | 85 | 0.3 |
| S | 338943 | UAGAGCUAAAGGUGAUAAGA | 237 | | | |
| AS | 345847 | UCUUAUCACCUUUAGCUCU | 301 | 2, | 80, | >4 |
| S | 345849 | AGAGCUAAAGGUGAUAAGA | 302 | 23 | 70 | |
| AS | 351831 | U_C_UUAU_C_A_C_CUUUA_C_CU_CU | 301 | 1.1 | 88 | >4 |
| S | 351832 | A_GAGC_UAAAGGUGAUAAGA | 302 | | | |
| AS | 352824 | ucuUAUCACCUUUAGCucu | 301~10 | | 50 | >4 |
| S | 342764 | AGAGCUAAAGGUGAUAAGA | 302 | | | |
| AS | 352827 | ucuUAUCACCUUUAGCUCU | 301 | 2 | 82 | n.d. |
| S | 342764 | AGAGCUAAAGGUGAUAAGA | 302 | | | |
| AS | 349890 | UGUCAUAUUCCUGGAUCCUU | 220 | | | |
| S | 338935 | AAGGAUCCAGGAAUAUGACA | 221 | | | |
| AS | 349891 | UCCUGGAUCCUUCACCAAUG | 228 | | | |
| S | 338939 | CAUUGGUGAAGGAUCCAGGA | 229 | | | |
| AS | 351097 | AUACUCAGAAGGUGUCUUCU | 254 | | | |
| S | 338952 | AGAAGACACCUUCUGAGUAU | 255 | | | |

NORMAL TYPE UPPER CASE=unmodified RNA with phosphate backbone

Bold=2'-O-methyl RNA with phosphate backbone;

Underline=2'-fluoro RNA with phosphate backbone

Lower case=4'-thio RNA with phosphate backbone

"% inhib" indicates % reduction of eIF4E RNA in cells treated with siRNA duplex (or other compound as shown) compared to untreated control cells.

2'-O-methyl nucleosides are shown in bold; 2'-fluoro are underlined.

The mixed (block) 2'-O-methyl/2'-fluoro (2'-OMe/2'F) construct 349892_338943 was shown to be comparable to or better than the parent (unmodified RNA) construct in efficacy of eIF4E mRNA reduction.

The alternating 2'-O-methyl/unmodified construct 345847_345849 construct was tested twice and was also shown to be comparable to or better than the parent (unmodified RNA) construct in efficacy of eIF4E mRNA reduction, with enhanced stability.

The 4'-thio block modified construct 352824_342764 was less active than the parent but highly stable.

The 4'-thio/2'-O-methyl construct 352827_342764 was comparable to the parent in efficacy. Stability data has not yet been obtained.

Example 32

Gapped Modified siRNA Constructs—Activity in HeLa Cells

Additional siRNA constructs were tested in HeLa cells. The duplexed oligomeric RNA (dsRNA) compounds shown in Table 13 below were prepared as described in previous examples and evaluated in HeLa cells (American Type Culture Collection, Manassas Va.). Culture methods used for HeLa cells are available from the ATCC and may be found, for example, at www.atcc.org. Cells were plated in 96-well plates at a density of 5000 cells/well and grown in DMEM with high glucose, 10% FBS, 1% penicillin/streptomycin. Wells were washed once with 200 µL OPTI-MEM-1™ reduced-serum medium (Gibco BRL) and then treated with 130 µL of OPTI-MEM-1™ containing the desired dsRNA at concentrations of 0.1, 1, 10 and 100 nM and 2.5 µl/ml LIPO-FECTIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples.

For stability analysis, siRNA duplexes were incubated in 25% heparinized mouse plasma at 37° C. and analyzed by capillary gel electrophoresis with an internal reference standard. The results are shown in Table 13. The siRNA constructs shown consist of one antisense strand and one sense strand. Unless otherwise indicated, all double-stranded constructs are unmodified RNA, i.e., ribose sugars with phosphate (P=O) backbones and 5'-terminal hydroxyl group. Unless otherwise indicated, single-stranded antisense molecules are chimeric gapped oligonucleotides with 2'-MOE at nucleotides 1-5 and 16-20 and 2'-deoxynucleotides at positions 6-15, with phosphorothioate (P=S) backbones and 5-methylcytosines at every C. It is understood in the art that, for RNA sequences, U (uracil) generally replaces T (thymine) which is normally found in DNA or DNA-like sequences.

Compound 338918_338943 is unmodified (ribose, P=O backbone) parent construct. 349892_338943 has 2'F at positions 1-5, 8, 9, 12-17 and 2'Ome at positions 6, 7, 10, 11, 18-20 of the antisense strand; the sense strand is unmodified (ribose, P=O backbone).

349896_338943 has 2'F at positions 1-5, ribose at positions 6-15, and 2'Ome at positions 16-20 of the antisense strand, counting from the 5' end of the AS strand; the sense strand is unmodified (ribose, P=O backbone).

349894_338935 has 2'F at positions 1-5, ribose at positions 6-15, and 2'Ome at positions 16-20 of the antisense strand, counting from the 5' end of the AS strand; the sense strand is unmodified (ribose, P=O backbone).

349895_338939 has 2'F at positions 1-5, ribose at positions 6-15, and 2'Ome at positions 16-20 of the antisense strand, counting from the 5' end of the AS strand; the sense strand is unmodified (ribose, P=O backbone).

349897_338952 has 2'F at positions 1-5, ribose at positions 6-15, and 2'Ome at positions 16-20 of the antisense strand, counting from the 5' end of the AS strand; the sense strand is unmodified (ribose, P=O backbone).

These are shown in Table 13. 2'-O-methyl nucleosides are shown in bold; 2'-fluoro are underlined, 4'-thio nucleosides are shown in lower case and unmodified ribose is shown in plain text. It is understood in the art that, for RNA sequences, U (uracil) generally replaces T (thymine) which is normally found in DNA or DNA-like sequences.

TABLE 13

Activity of Gapped Modified eIF4E siRNA

| Strand | Isis No. | Sequence 5'→3' | SEQ ID NO | IC50 (nM) | % inhib |
|---|---|---|---|---|---|
| AS | 338918 | UCUUAUCACCUUUAGCUCUA | 236 | 0.81 | 86.3 |
| S | 338943 | UAGAGCUAAAGGUGAUAAGA | 237 | | |
| AS | 349892 | UCUUAUCACCUUUAGCUCUA | 236 | 0.36 | 85.0 |
| S | 338943 | UAGAGCUAAAGGUGAUAAGA | 237 | | |
| AS | 349896 | UCUUAUCACCUUUAGCUCUA | 236 | 1.05 | 84.4 |
| S | 338943 | UAGAGCUAAAGGUGAUAAGA | 237 | | |
| AS | 349894 | UGUCAUAUUCCUGGAUCCUU | 220 | | |
| S | 338935 | AAGGAUCCAGGAAUAUGACA | 221 | | |
| AS | 349895 | UCCUGGAUCCUUCACCAAUG | 228 | | |
| S | 338939 | CAUUGGUGAAGGAUCCAGGA | 229 | | |
| AS | 349897 | AUACUCAGAAGGUGUCUUCU | 254 | | |
| S | 338952 | AGAAGACACCUUCUGAGUAU | 255 | | |

NORMAL TYPE UPPER CASE=unmodified RNA with phosphate backbone

Bold=2'-O-methyl RNA with phosphate backbone;

Underline=2'-fluoro RNA with phosphate backbone

Lower case=4'-thio RNA with phosphate backbone

"% inhib" indicates % reduction of eIF4E RNA in cells treated with siRNA duplex (or other compound as shown) compared to untreated control cells.

2'-O-methyl nucleosides are shown in bold; 2'-fluoro are underlined.

Example 33

Activity of Alternating 2'-Ome Modified Blunt End (No dT Overhang) 19mer siRNA in HeLa Cells—Microwalk Around eIF4E_1 (341887)

The duplexed oligomeric RNA (dsRNA) compounds shown in Table 14 below were prepared as described in previous examples and evaluated in HeLa cells (American Type Culture Collection, Manassas Va.). Cells were plated in 96-well plates at a density of 5000 cells/well and grown in DMEM with high glucose, 10% FBS, 1% penicillin/streptomycin. Wells were washed once with 200 µL OPTI-MEM-1™ reduced-serum medium (Gibco BRL) and then treated with 130 µL of OPTI-MEM-1™ containing the desired dsRNA at a concentration of 0.2, 2 and 20 nM plus 2.5 µl/ml LIPOFECTIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples.

The results are shown in Table 14. The siRNA constructs shown consist of one antisense strand and one sense strand. The antisense strand (AS) is shown first in Table 14 below, followed by the sense strand (S) in the next row. Unless otherwise indicated, all double-stranded constructs are unmodified RNA, i.e., ribose sugars with phosphate (P=O) backbones and 5'-terminal hydroxyl group. It is understood in the art that, for RNA sequences, U (uracil) generally replaces T (thymine) which is normally found in DNA or DNA-like sequences. 2'-O-methyl nucleosides are shown in bold.

338932 is an unmodified ribose 20mer with phosphate (P=O) backbone and 5' phosphate, targeted to the site of the eIF4E_1 (341887) 19mer.

338957 is an unmodified ribose 20mer with phosphate (P=O) backbone and 5' phosphate.

346658 is an unmodified ribose 19mer with phosphate (P=O) backbone and 5' phosphate targeted to the eIF4E_1 (341887) site (no dT)

346660 is an unmodified ribose 19mer with phosphate (P=O) backbone and 5' phosphate.

346661 is an alternating ribose and 2'-OMe 19mer with phosphate backbone and 5' terminal phosphate. 2'OMe on nucleosides 2, 4, 6, 8, 10, 12, 14, 16 and 18 starting from 5' end.

346659 is an alternating ribose and 2'-OMe 19mer with phosphate backbone and 5' terminal phosphate. 2'OMe on nucleosides 1, 3, 5, 7, 9, 11, 13, 15, 17 and 19 starting from 5' end.

346662 is an unmodified ribose 19mer with phosphate (P=O) backbone and 5' phosphate.

346664 is an unmodified ribose 19mer with phosphate (P=O) backbone and 5' phosphate.

346665 is an alternating ribose and 2'-OMe 19mer with phosphate backbone and 5' terminal phosphate. 2'OMe on nucleosides 2, 4, 6, 8, 10, 12, 14, 16 and 18 starting from 5' end.

346663 is an alternating ribose and 2'-OMe 19mer with phosphate backbone and 5' terminal phosphate. 2'OMe on nucleosides 1, 3, 5, 7, 9, 11, 13, 15, 17 and 19 starting from 5' end.

346666 is an unmodified ribose 19mer with phosphate (P=O) backbone and 5' phosphate.

346668 is an unmodified ribose 19mer with phosphate (P=O) backbone and 5' phosphate.

346669 is an alternating ribose and 2'-OMe 19mer with phosphate backbone and 5' terminal phosphate. 2'OMe on nucleosides 2, 4, 6, 8, 10, 12, 14, 16 and 18 starting from 5' end.

346667 is an alternating ribose and 2'-OMe 19mer with phosphate backbone and 5' terminal phosphate. 2'OMe on nucleosides 1, 3, 5, 7, 9, 11, 13, 15, 17 and 19 starting from 5' end.

TABLE 14

Alternating 2'-O-Me/ribose blunt-ended 19mers microwalk around eIF4E_1 (341887)

| Strand | ISIS # | Sequence (5'→3') | SEQ ID NO | % inhib | IC50 (nM) |
|---|---|---|---|---|---|
| AS | 338932 | AAACCAGAGUGCCCAUCUG | 264 | 88.6 | 0.52 |
| S | 338957 | CAGAUGGGCACUCUGGUUUU | 265 | | |
| AS | 346658 | AAACCAGAGUGCCCAUCUG | 329 | 39.5 | ~112 |
| S | 346660 | CAGAUGGGCACUCUGGUUU | 330 | | |
| AS | 346658 | AAACCAGAGUGCCCAUCUG | 329 | 48.9 | 21.1 |
| S | 346661 | CAGAUGGGCACUCUGGUUU | 330 | | |
| AS | 346659 | AAACCAGAGUGCCCAUCUG | 329 | 42.8 | ~72 |
| S | 346661 | CAGAUGGGCACUCUGGUUU | 330 | | |
| AS | 346659 | AAACCAGAGUGCCCAUCUG | 329 | 9.0 | N/A |
| S | 346660 | CAGAUGGGCACUCUGGUUU | 330 | | |
| AS | 346662 | AAAACCAGAGUGCCCAUCU | 331 | 66.2 | 4.98 |
| S | 346664 | AGAUGGGCACUCUGGUUUU | 332 | | |
| AS | 346662 | AAAACCAGAGUGCCCAUCU | 331 | 58.3 | 6.35 |
| S | 346665 | AGAUGGGCACUCUGGUUUU | 332 | | |
| AS | 346663 | AAAACCAGAGUGCCCAUCU | 331 | 76.4 | 1.25 |
| S | 346665 | AGAUGGGCACUCUGGUUUU | 332 | | |
| AS | 346663 | AAAACCAGAGUGCCCAUCU | 331 | 26.6 | n/a |
| S | 346664 | AGAUGGGCACUCUGGUUUU | 332 | | |
| AS | 346666 | AAAACCAGAGUGCCCAUC | 333 | 54.2 | 22.16 |
| S | 346668 | GAUGGGCACUCUGGUUUUU | 334 | | |
| AS | 346666 | AAAACCAGAGUGCCCAUC | 333 | 60.9 | 5.83 |
| S | 346669 | GAUGGGCACUCUGGUUUUU | 334 | | |
| AS | 346667 | AAAACCAGAGUGCCCAUC | 333 | 16.4 | n/a |
| S | 346668 | GAUGGGCACUCUGGUUUUU | 334 | | |
| AS | 346667 | AAAACCAGAGUGCCCAUC | 333 | 62.0 | 4.65 |
| S | 346669 | GAUGGGCACUCUGGUUUUU | 334 | | |

Example 34

Activity of Alternating 2'-Ome Modified Blunt End 21mer siRNA in HeLa Cells Microwalk Around eIF4E_1 (341887)

The duplexed oligomeric RNA (dsRNA) compounds shown in Table 15 below were prepared as described in previous examples and evaluated in HeLa cells (American Type Culture Collection, Manassas Va.). Culture methods used for HeLa cells are available from the ATCC and may be found, for example, at www.atcc.org. Cells were plated in 96-well plates at a density of 5000 cells/well and grown in DMEM with high glucose, 10% FBS, 1% penicillin/streptomycin. Wells were washed once with 200 μL OPTI-MEM-1™ reduced-serum medium (Gibco BRL) and then treated with 130 μL of OPTI-MEM-1™ containing the desired dsRNA at a concentration of 0.2, 2 and 20 nM plus 2.5 μl/ml LIPOFECTIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples.

The results are shown in Table 15. The siRNA constructs shown consist of one antisense strand and one sense strand. The antisense strand (AS) is shown first in Table 15 below, followed by the sense strand (S) in the next row. Unless otherwise indicated, all double-stranded constructs are unmodified RNA, i.e., ribose sugars with phosphate (P=O) backbones and 5'-terminal hydroxyl group. It is understood in the art that, for RNA sequences, U (uracil) generally replaces T (thymine) which is normally found in DNA or DNA-like sequences. 2'-O-methyl nucleosides are shown in bold.

338932 is an unmodified ribose 20mer with phosphate (P=O) backbone and 5' terminal phosphate, targeted to the eIF4E_1 site.

338957 is an unmodified ribose 20mer with phosphate (P=O) backbone and 5' terminal phosphate.

346674 is an unmodified ribose 21mer with phosphate (P=O) backbone and 5' terminal phosphate.

346676 is an unmodified ribose 21mer with phosphate (P=O) backbone and 5' terminal phosphate.

346675 is an alternating ribose and 2'-OMe 21mer with phosphate backbone and 5' terminal phosphate. 2'OMe on nucleosides 1, 3, 5, 7, 9, 11, 13, 15, 17, 19 and 21 starting from 5' end.

346677 is an alternating ribose and 2'-OMe 21mer with phosphate backbone and 5' terminal phosphate. 2'OMe on nucleosides 2, 4, 6, 8, 10, 12, 14, 16, 18 and 20 starting from 5' end.

346678 is an unmodified ribose 21mer with phosphate (P=O) backbone and 5' terminal phosphate.

346680 is an unmodified ribose 21mer with phosphate (P=O) backbone and 5' terminal phosphate.

346679 is an alternating ribose and 2'-OMe 21mer with phosphate backbone and 5' terminal phosphate. 2'OMe on nucleosides 1, 3, 5, 7, 9, 11, 13, 15, 17, 19 and 21 starting from 5' end.

346681 is an alternating ribose and 2'-OMe 21mer with phosphate backbone and 5' terminal phosphate. 2'OMe on nucleosides 2, 4, 6, 8, 10, 12, 14, 16, 18 and 20 starting from 5' end.

TABLE 15

Alternating 2'-Ome modified blunt end 21mer siRNA in HeLa cells -microwalk around eIF4E_1 (341887)

| Strand | ISIS # | Sequence (5'→3') | SEQ ID NO | % inhib | IC50 (nM) |
|---|---|---|---|---|---|
| AS | 338932 | AAAACCAGAGUGCCCAUCUG | 264 | 88.6 | 0.52 |
| S | 338957 | CAGAUGGGCACUCUGGUUUU | 265 | | |
| AS | 346674 | AAAACCAGAGUGCCCAUCUGU | 335 | 81.7 | 0.74 |
| S | 346676 | ACAGAUGGGCACUCUGGUUUU | 336 | | |
| AS | 346674 | AAAACCAGAGUGCCCAUCUGU | 335 | 82.5 | 0.43 |
| S | 346677 | ACAGAUGGGCACUCUGGUUUU | 336 | | |
| AS | 346675 | AAAACCAGAGUGCCCAUCUGU | 335 | 69.0 | 3.44 |
| S | 346676 | ACAGAUGGGCACUCUGGUUUU | 336 | | |
| AS | 346675 | AAAACCAGAGUGCCCAUCUGU | 335 | 84.5 | 0.19 |
| S | 346677 | ACAGAUGGGCACUCUGGUUUU | 336 | | |

TABLE 15-continued

Alternating 2'-Ome modified blunt end 21mer siRNA in HeLa cells -microwalk around eIF4E_1 (341887)

| Strand | ISIS # | Sequence (5'→3') | SEQ ID NO | % inhib | IC50 (nM) |
|---|---|---|---|---|---|
| AS | 346678 | AAAAACCAGAGUGCCCAUCUG | 337 | 82.5 | 0.13 |
| S | 346680 | CAGAUGGGCACUCUGGUUUUU | 338 | | |
| AS | 346678 | AAAAACCAGAGUGCCCAUCUG | 337 | 83.9 | 0.66 |
| S | 346681 | CAGAUGGGCACUCUGGUUUUU | 338 | | |
| AS | 346679 | AAAAACCAGAGUGCCCAUCUG | 337 | 66.8 | 2.39 |
| S | 346680 | CAGAUGGGCACUCUGGUUUUU | 338 | | |
| AS | 346679 | AAAAACCAGAGUGCCCAUCUC | 337 | 83.0 | 1.09 |
| S | 346681 | CAGAUGGGCACUCUGGUUUUU | 338 | | |

Example 35

Activity of 4'-thioribose Modified 19mer siRNA in HeLa Cells

The duplexed oligomeric RNA (dsRNA) compounds shown in Table 16 below were prepared as described in previous examples and evaluated in HeLa cells (American Type Culture Collection, Manassas Va.). Culture methods used for HeLa cells are available from the ATCC and may be found, for example, at www.atcc.org. Cells were plated in 96-well plates at a density of 5000 cells/well and grown in DMEM with high glucose, 10% FBS, 1% penicillin/streptomycin. Wells were washed once with 200 μL OPTI-MEM-1™ reduced-serum medium (Gibco BRL) and then treated with 130 μL of OPTI-MEM-1™ containing the desired dsRNA at a concentration of 0.02, 0.2, 2 and 20 nM with 2.5 μl/ml LIPOFECTIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples.

The results are shown in Table 16. The siRNA constructs shown consist of one antisense strand and one sense strand. The antisense strand (AS) is shown first in Table 16 below, followed by the sense strand (S) in the next row. Unless otherwise indicated, all double-stranded constructs are unmodified RNA, i.e., ribose sugars with phosphate (P=O) backbones and 5'-terminal hydroxyl group. It is understood in the art that, for RNA sequences, U (uracil) generally replaces T (thymine) which is normally found in DNA or DNA-like sequences. 2'-O-methyl nucleosides are shown in bold, unmodified ribose nucleosides are in PLAIN UPPERCASE and 4' thio are in lower case. All sequences in Table 16 are 19mers of SEQ ID NO: 301 (antisense strand)/SEQ ID NO: 302 (sense strand).

342744 is an unmodified ribose 19mer with phosphate (P=O) backbone and 5' terminal phosphate.

342764 is an unmodified ribose 19mer with phosphate (P=O) backbone and 5' terminal phosphate.

352824 has 4'-thio at nucleosides positions 1, 2, 3, 17, 18 and 19 (i.e., three at each terminus) with ribose at positions 4-16. Backbone is P=O, 5' terminal phosphate.

352819 has 4'-thio nucleosides at positions 1, 2, 3, 4, 16, 17, 18 and 19 (i.e., four at each terminus) with ribose at positions 5-14. Backbone is P=O, 5' terminal phosphate.

352827 has 4'-thio nucleosides at positions 1, 2, 3, and 2'-OMe at positions 17, 18 and 19 with ribose at positions 4-16. Backbone is P=O, 5' terminal phosphate.

352826 has 4'-thio nucleosides at positions 1, 2, 3, 10, 13 and 17-19 with ribose at positions 4-9, 11, 12 and 14-16. Backbone is P=O, 5' terminal phosphate.

352825 4'-thio nucleosides at positions 1, 2, 3, 7, 10, 13 and 17-19 with ribose at positions 4, 5, 6, 8, 9, 11, 12 and 14-16. Backbone is P=O, 5' terminal phosphate.

TABLE 16

Activity of 4'-thioribose modified 19mer siRNA

| Strand | ISIS # | Sequence (5'→3') | % inhib | IC50 (nM) |
|---|---|---|---|---|
| AS | 342744 | UCUUAUCACCUUUAGCUCU | 89.8 | 0.08 |
| S | 342764 | AGAGCUAAAGGUGAUAAGA | | |
| AS | 352824 | ucuUAUCACCUUUAGCucu | 49.3 | n/a |
| S | 342764 | AGAGCUAAAGGUGAUAAGA | | |
| AS | 352819 | ucuuAUCACCUUUAGcucu | 49.8 | n/a |
| S | 342764 | AGAGCUAAAGGUGAUAAGA | | |
| AS | 352827 | ucuUAUCACCUUUAGCUCU | 74.4 | 0.03 |
| S | 342764 | AGAGCUAAAGGUGAUAAGA | | |
| AS | 352826 | ucuUAUCACcUUuAGCucu | 31.3 | n/a |
| S | 342764 | AGAGCUAAAGGUGAUAAGA | | |
| AS | 352825 | ucuUAUcACcUUuAGCucu | 37.5 | n/a |
| S | 342764 | AGAGCUAAAGGUGAUAAGA | | |

Several of the 4'-thio constructs were shown to have IC$_{50}$s in the picomolar range.

Example 36

Activity of Additional eIF4E siRNAs with 2'-O-methyl Modifications—Based on 338914 Construct The duplexed oligomeric RNA (dsRNA) compounds shown in Table 17 below were prepared as described in previous examples and evaluated in HeLa cells (American Type Culture Collection, Manassas Va.). Culture methods used for HeLa cells are available from the ATCC and may be found, for example, at www.atcc.org. Cells were plated in 96-well plates at a density of 5000 cells/well and grown in DMEM with high glucose, 10% FBS, 1% penicillin/streptomycin. Wells were washed once with 200 μL OPTI-MEM-1™ reduced-serum medium (Gibco BRL) and then treated with 130 μL of OPTI-MEM-1™ containing the desired dsRNA at a concentration of 0.5, 5 and 50 nM with 2.5 μl/ml LIPOFECTIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples.

The results are shown in Table 17. The siRNA constructs shown consist of one antisense strand and one sense strand. The antisense strand (AS) is shown first in Table 17 below, followed by the sense strand (S) in the next row. Unless otherwise indicated, all double-stranded constructs are unmodified RNA, i.e., ribose sugars with phosphate (P=O) backbones and 5'-terminal hydroxyl group. It is understood in the art that, for RNA sequences, U (uracil) generally replaces T (thymine) which is normally found in DNA or DNA-like sequences. 2'-O-methyl nucleosides are shown in bold, unmodified ribose nucleosides are in PLAIN UPPERCASE.

338914 is an unmodified ribose 20mer with phosphate (P=O) backbone and 5' terminal phosphate.

338939 is an unmodified ribose 20mer with phosphate (P=O) backbone and 5' terminal phosphate.

345840 is a 19mer with alternating ribose and 2'-OMe with phosphate backbone and 5' terminal phosphate. 2'OMe on nucleosides 1, 3, 5, 7, 9, 11, 13, 15, 17 and 19 starting from 5' end.

345842 is a 19mer with alternating ribose and 2'-OMe with phosphate backbone and 5' terminal phosphate. 2'OMe on nucleosides 2, 4, 6, 8, 10, 12, 14, 16 and 18 starting from 5' end.

345735 is a 20mer with phosphate (P=O) backbone and 5' terminal phosphate, with 2'O-Me nucleosides at positions 16-20 and ribose at positions 1-15 starting from 5' end.

345843 is a 20mer with phosphate (P=O) backbone and 5' terminal phosphate, with 2'O-Me nucleosides at positions 2-19 and ribose at positions 1 and 20 starting from the 5' end.

345838 is a 20mer with phosphate (P=O) backbone and 5' terminal phosphate, with 2'O-Me nucleosides at positions 6, 12, 15 and 18-20 and ribose at positions 1-5, 7-11, 13, 14, 16, 17 and 20 starting from the 5' end.

345839 is a 20mer with phosphate (P=O) backbone and 5' terminal phosphate, with 2'O-Me nucleosides at positions 6, 7, 10, 11, 18-20 and ribose at positions 1-5, 8, 9, and 12-17 starting from the 5' end.

TABLE 17

Activity of additional eIF4E siRNAs with 2'-O-methyl modifications- based on 338914 construct

| Strand | ISIS # | Sequence (5'→3') | SEQ ID NO | % inhib | IC50 (nM) |
|---|---|---|---|---|---|
| AS | 338914 | UCCUGGAUCCUUCACCAAUG | 228 | 78.3 | 0.03 |
| S | 338939 | CAUUGGUGAAGGAUCCAGGA | 229 | | |
| AS | 345840 | UCCUGGAUCCUUCACCAAU | 325 | 23.9 | n/a |
| S | 345842 | AUUGGUGAACGAUCCAGGA | 326 | | |
| AS | 345735 | UCCUGGAUCCUUCACCAAUG | 228 | 77.9 | 1.4 |
| S | 338939 | CAUUGGUGAAGGAUCCAGGA | 229 | | |
| AS | 345735 | UCCUGGAUCCUUCACCAAUG | 228 | 75.5 | 8.2 |
| S | 345843 | CAUUGGUGAAGGAUCCACGA | 229 | | |
| AS | 345838 | UCCUGCAUCCUUCACCAAUG | 228 | 76.9 | 0.78 |
| S | 338939 | CAUUGGUGAAGGAUCCAGGA | 229 | | |
| AS | 345838 | UCCUGGAUCCUUCACCAAUG | 228 | 64.1 | 12.31 |

TABLE 17-continued

Activity of additional eIF4E siRNAs with 2'-O-methyl modifications- based on 338914 construct

| Strand | ISIS # | Sequence (5'→3') | SEQ ID NO | % inhib | IC50 (nM) |
|---|---|---|---|---|---|
| S | 345843 | CAUUGGUGAAGGAUCCAGGA | 229 | | |
| AS | 345839 | UCCUGGAUCCUUCACCAAUG | 228 | 80.3 | 1.64 |
| S | 338939 | CAUUGGUGAAGGAUCCAGGA | 229 | | |
| AS | 345839 | UCCUGGAUCCUUCACCAAUG | 228 | 71.3 | 12 |
| S | 345843 | CAUUGGUGAAGGAUCCAGGA | 229 | | |

Example 37

Additional eIF4E siRNAs with 2'-O-methyl Modifications—Based on 338910 Construct The duplexed oligomeric RNA (dsRNA) compounds shown in Table 18 below were prepared as described in previous examples and evaluated in HeLa cells (American Type Culture Collection, Manassas Va.). Culture methods used for HeLa cells are available from the ATCC and may be found, for example, at www.atcc.org. Cells were plated in 96-well plates at a density of 5000 cells/well and grown in DMEM with high glucose, 10% FBS, 1% penicillin/streptomycin. Wells were washed once with 200 μL OPTI-MEM-1™ reduced-serum medium (Gibco BRL) and then treated with 130 μL of OPTI-MEM-1™ containing the desired dsRNA at a concentration 0.5, 5 and 50 nM with 2.5 μl/ml LIPOFEC-TIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples.

The results are shown in Table 18. The siRNA constructs shown consist of one antisense strand and one sense strand. The antisense strand (AS) is shown first in Table 18 below, followed by the sense strand (S) in the next row. Unless otherwise indicated, all double-stranded constructs are unmodified RNA, i.e., ribose sugars with phosphate (P=O) backbones and 5'-terminal hydroxyl group. It is understood in the art that, for RNA sequences, U (uracil) generally replaces T (thymine) which is normally found in DNA or DNA-like sequences. 2'-β-methyl nucleosides are shown in bold.

338910 is an unmodified ribose 20mer with phosphate (P=O) backbone and 5' terminal phosphate.

338935 is an unmodified ribose 20mer with phosphate (P=O) backbone and 5' terminal phosphate.

345731 is a 19mer with alternating ribose and 2'-OMe with phosphate backbone and 5' terminal phosphate. 2'OMe on nucleosides 1, 3, 5, 7, 9, 11, 13, 15, 17 and 19 starting from the 5' end.

345733 is a 19mer with alternating ribose and 2'-OMe with phosphate backbone and 5' terminal phosphate. 2'OMe on nucleosides 2, 4, 6, 8, 10, 12, 14, 16 and 18 starting from 5' end.

345713 is a 20mer with phosphate backbone and 5' terminal phosphate. Ribose at nucleosides 1-15 and 2'OMe nucleosides at positions 16-20 starting from 5' end.

345734 is a 20mer with phosphate backbone and 5' terminal phosphate. Ribose at nucleosides 1 and 20 and 2'OMe nucleosides at positions 2-19 starting from 5' end.

345729 is a 20mer with phosphate backbone and 5' terminal phosphate. Ribose at nucleosides 1-5, 7, 8, 10, 11, 13, 14, 16 and 17 and 2'OMe nucleosides at positions 6, 9, 12, 15 and 18-20 starting from 5' end.

345730 is a 20mer with phosphate backbone and 5' terminal phosphate. Ribose at nucleosides 1-5, 8, 9, 12, 13, 14, 15, 16 and 17 and 2'OMe nucleosides at positions 6, 7, 10, 11 and 18-20 starting from 5' end.

TABLE 18

Additional eIF4E siRNAs with 2'-O-methyl modifications- based on 338910 construct

| Strand | ISIS # | Sequence (5'→3') | SEQ ID NO | % inhib | IC50 (nM) |
|---|---|---|---|---|---|
| AS | 338910 | UGUCAUAUUCCUGGAUCCUU | 220 | 81.5 | 3.21 |
| S | 338935 | AAGGAUCCAGGAAUAUGACA | 221 | | |
| AS | 345731 | UGUCAUAUUCCUGGAUCCU | 323 | 37.4 | 96.96 |
| S | 345733 | AAGGAUCCAGGAAUAUGACA | 324 | | |
| AS | 345713 | UGUCAUAUUCCUGGAUCCUU | 220 | 69.4 | 3.04 |
| S | 338935 | AAGGAUCCAGGAAUAUGACA | 221 | | |
| AS | 345713 | UGUCAUAUUCCUGGAUCCUU | 220 | 59.8 | 44.7 |
| S | 345734 | AAGGAUCCAGGAAUAUCACA | 221 | | |
| AS | 345729 | UGUCAUAUUCCUGGAUCCUU | 220 | 68.8 | 19.42 |
| S | 338935 | AAGGAUCCAGGAAUAUGACA | 221 | | |
| AS | 345729 | UGUCAUAUUCCUGGAUCCUU | 220 | 56.0 | 331 |
| S | 345734 | AAGGAUCCAGGAAUAUGACA | 221 | | |
| AS | 345730 | UGUCAUAUUCCUGGAUCCUU | 220 | 78.5 | 6.24 |
| S | 338935 | AAGGAUCCAGGAAUAUGACA | 221 | | |
| AS | 345730 | UGUCAUAUUCCUGGAUCCUU | 220 | 81.8 | 23.5 |
| S | 345734 | AAGGAUCCAGGAAUAUGACA | 221 | | |

Example 38

Additional eIF4E siRNAs with 2'-O-methyl Modifications—Based on 338927 Construct The duplexed oligomeric RNA (dsRNA) compounds shown in Table 19 below were prepared as described in previous examples and evaluated in HeLa cells (American Type Culture Collection, Manassas Va.). Culture methods used for HeLa cells are available from the ATCC and may be found, for example, at www.atcc.org. Cells were plated in 96-well plates at a density of 5000 cells/well and grown in DMEM with high glucose, 10% FBS, 1% penicillin/streptomycin. Wells were washed once with 200 μL OPTI-MEM-1™ reduced-serum medium (Gibco BRL) and then treated with 130 μL of OPTI-MEM-1™ containing the desired dsRNA at a concentration 0.5, 5 and 50 nM with 2.5 μl/ml LIPOFEC-TIN™ (Gibco BRL) per strand of oligomeric compound. Treatments were done in duplicate. After 4 or 5 hours of treatment, the medium was replaced with fresh medium.

Cells were harvested 16 or 18 hours after dsRNA treatment, at which time RNA was isolated and target reduction measured by RT-PCR as described in previous examples.

The results are shown in Table 19. The siRNA constructs shown consist of one antisense strand and one sense strand. The antisense strand (AS) is shown first in Table 19 below, followed by the sense strand (S) in the next row. Unless otherwise indicated, all double-stranded constructs are unmodified RNA, i.e., ribose sugars with phosphate (P=O) backbones and 5'-terminal hydroxyl group It is understood in the art that, for RNA sequences, U (uracil) generally replaces T (thymine) which is normally found in DNA or DNA-like sequences. 2'-O-methyl nucleosides are shown in bold.

338927 is an unmodified ribose 20mer with phosphate (P=O) backbone and 5' terminal phosphate.

338952 is an unmodified ribose 20mer with phosphate (P=O) backbone and 5' terminal phosphate.

345854 is a 19mer with alternating ribose and 2'-OMe with phosphate backbone and 5' terminal phosphate. 2'OMe on nucleosides 1, 3, 5, 7, 9, 11, 13, 15, 17 and 19 starting from the 5' end.

345856 is a 19mer with alternating ribose and 2'-OMe with phosphate backbone and 5' terminal phosphate. 2'OMe on nucleosides 2, 4, 6, 8, 10, 12, 14, 16 and 18 starting from 5' end.

345851 is a 20mer with phosphate backbone and 5' terminal phosphate. Ribose at nucleosides 1-15 and 2'OMe nucleosides at positions 16-20 starting from 5' end.

345857 is a 20mer with phosphate backbone and 5' terminal phosphate. Ribose at nucleosides 1 and 20 and 2'OMe nucleosides at positions 2-19 starting from 5' end.

345852 is a 20mer with phosphate backbone and 5' terminal phosphate. Ribose at nucleosides 1-5, 7, 8, 10, 11, 13, 14, 16 and 17 and 2'OMe nucleosides at positions 6, 9, 12, 15 and 18-20 starting from 5' end.

345853 is a 20mer with phosphate backbone and 5' terminal phosphate. Ribose at nucleosides 1-5, 8, 9, 12, 13, 14, 15, 16 and 17 and 2'OMe nucleosides at positions 6, 7, 10, 11 and 18-20 starting from 5' end.

TABLE 19

Additional eIF4E siRNAs with 2'-O-methyl modifications based on 338927 construct

| Strand | ISIS # | Sequence (5'→3') | SEQ ID NO | % inhib | IC50 (nM) |
|---|---|---|---|---|---|
| AS | 338927 | AUACUCAGAAGGUGUCUUCU | 254 | 69.7 | 6.5 |
| S | 338952 | AGAAGACACCUUCUGAGUAU | 255 | | |
| AS | 345854 | AUACUCAGAAGGUGUCUUC | 327 | 59.8 | 20.77 |
| S | 345856 | GAAGACACCUUCUGAGUAU | 328 | | |
| AS | 345851 | AUACUCAGAAGGUGUCUUCU | 254 | 70.8 | 5.43 |
| S | 338952 | AGAAGACACCUUCUGAGUAU | 255 | | |
| AS | 345851 | AUACUCAGAAGGUGUCUUCU | 254 | 65.5 | 24.48 |
| S | 345857 | AGAAGACACCUUCUGAGUAU | 255 | | |
| AS | 345852 | AUACUCAGAAGGUGUCUUCU | 254 | 70.0 | 4.98 |
| S | 338952 | AGAAGACACCUUCUGAGUAU | 255 | | |
| AS | 345852 | AUACUCAGAAGGUGUCUUCU | 254 | 69.2 | 17.04 |
| S | 345857 | AGAAGACACCUUCUGAGUAU | 255 | | |
| AS | 345853 | AUACUCAGAAGGUGUCUUCU | 254 | 85.6 | 2.2 |
| S | 338952 | AGAAGACACCUUCUGAGUAU | 255 | | |
| AS | 345853 | AUACUCAGAAGGUGUCUUCU | 254 | 94.9 | 4.28 |
| S | 345857 | AGAAGACACCUUCUGAGUAU | 255 | | |

Example 39

Additional eIF4E siRNAs with 2'-O-methyl Modifications—Based on 338918 Construct The duplexed oligomeric RNA (dsRNA) compounds shown in Table 20 below were prepared as described in previous examples and evaluated in HeLa cells (American Type Culture Collection, Manassas Va.). Culture methods used for HeLa cells are available from the ATCC and may be found, for example, at www.atcc.org. Cells were plated in 96-well plates at a density of 5000 cells/well and grown in DMEM with high glucose, 10% FBS, 1% penicillin/streptomycin. Wells were washed once with 200 μL OPTI-MEM-1™ reduced-serum medium (Gibco BRL) and then treated with 130 μL of OPTI-MEM-1™ containing the desired dsRNA at a concentration 0.5, 5 and 50 nM with 2.5 μl/ml LIPOFEC-TIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples.

The results are shown in Table 20. The siRNA constructs shown consist of one antisense strand and one sense strand. The antisense strand (AS) is shown first in Table 20 below, followed by the sense strand (S) in the next row. Unless otherwise indicated, all double-stranded constructs are unmodified RNA, i.e., ribose sugars with phosphate (P=O) backbones and 5'-terminal hydroxyl group. It is understood in the art that, for RNA sequences, U (uracil) generally replaces T (thymine) which is normally found in DNA or DNA-like sequences. 2'-O-methyl nucleosides are shown in bold.

338918 is an unmodified ribose 20mer with phosphate (P=O) backbone and 5' terminal phosphate.

338943 is an unmodified ribose 20mer with phosphate (P=O) backbone and 5' terminal phosphate.

345847 is a 19mer with alternating ribose and 2'-OMe with phosphate backbone and 5' terminal phosphate. 2'OMe on nucleosides 1, 3, 5, 7, 9, 11, 13, 15, 17 and 19 starting from the 5' end.

345849 is a 19mer with alternating ribose and 2'-OMe with phosphate backbone and 5' terminal phosphate. 2'OMe on nucleosides 2, 4, 6, 8, 10, 12, 14, 16 and 18 starting from 5' end.

345844 is a 20mer with phosphate backbone and 5' terminal phosphate. Ribose at nucleosides 1-15 and 2'OMe nucleosides at positions 16-20 starting from 5' end.

345850 is a 20mer with phosphate backbone and 5′ terminal phosphate. Ribose at nucleosides 1 and 20 and 2′OMe nucleosides at positions 2-19 starting from 5′ end.

345845 is a 20mer with phosphate backbone and 5′ terminal phosphate. Ribose at nucleosides 1-5, 7, 8, 10, 11, 13, 14, 16 and 17 and 2′OMe nucleosides at positions 6, 9, 12, 15 and 18-20 starting from 5′ end.

345846 is a 20mer with phosphate backbone and 5′ terminal phosphate. Ribose at nucleosides 1-5, 8, 9, 12, 13, 14, 15, 16 and 17 and 2′OMe nucleosides at positions 6, 7, 10, 11 and 18-20 starting from 5′ end.

TABLE 20

Additional eIF4E siRNAs with 2'-O-methyl modifications- based on 338918 construct

| Strand | ISIS # | Sequence (5'→3') | SEQ ID NO | % inhib | IC50 (nM) |
|---|---|---|---|---|---|
| AS | 338918 | UCUUAUCACCUUUAGCUCUA | 236 | 77.9 | 4.92 |
| S | 338943 | UAGAGCUAAAGGUGAUAAGA | 237 | | |
| AS | 345847 | UCUUAUCACCUUUAGCUCU | 301 | 69.3 | 23.39 |
| S | 345849 | AGAGCUAAAGGUGAUAAGA | 302 | | |
| AS | 345844 | UCUUAUCACCUUUAGCUCUA | 236 | 67.2 | 17.7 |
| S | 338943 | UAGAGCUAAAGGUGAUAAGA | 237 | | |
| AS | 345844 | UCUUAUCACCUUUAGCUCUA | 236 | 83.0 | 8.85 |
| S | 345850 | UAGAGCUAAAGGUGAUAAGA | 237 | | |
| AS | 345845 | UCUUAUCACCUUUAGCUCUA | 236 | 30.9 | n/a |
| S | 338943 | UAGAGCUAAAGGUGAUAAGA | 237 | | |
| AS | 345845 | UCUUAUCACCUUUAGCUCUA | 236 | 61.5 | 48.22 |
| S | 345850 | UAGAGCUAAAGGUGAUAAGA | 237 | | |
| AS | 345846 | UCUUAUCACCUUUAGCUCUA | 236 | 79.6 | 9.6 |
| S | 338943 | UAGAGCUAAAGGUGAUAAGA | 237 | | |
| AS | 345846 | UCUUAUCACCUUUAGCUCUA | 236 | 89.6 | 4.77 |
| S | 345850 | UAGAGCUAAAGGUGAUAAGA | 237 | | |

Example 40

Activity of 4′-thioribose Modified and Mixed 19mer siRNA in HeLa Cells

The duplexed oligomeric RNA (dsRNA) compounds shown in Table 21 below were prepared as described in previous examples and evaluated in HeLa cells (American Type Culture Collection, Manassas Va.). Culture methods used for HeLa cells are available from the ATCC and may be found, for example, at www.atcc.org. Cells were plated in 96-well plates at a density of 5000 cells/well and grown in DMEM with high glucose, 10% FBS, 1% penicillin/streptomycin. Wells were washed once with 200 μL OPTI-MEM-1™ reduced-serum medium (Gibco BRL) and then treated with 130 μL of OPTI-MEM-1™ containing the desired dsRNA at a concentration of 0.02, 0.2, 2 and 20 nM with 2.5 μl/ml LIPOFECTIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples.

The results are shown in Table 21. The siRNA constructs shown consist of one antisense strand and one sense strand. The antisense strand (AS) is shown first in Table 21 below, followed by the sense strand (S) in the next row. Unless otherwise indicated, all double-stranded constructs are unmodified RNA, i.e., ribose sugars with phosphate (P=O) backbones and 5′-terminal hydroxyl group. It is understood in the art that, for RNA sequences, U (uracil) generally replaces T (thymine) which is normally found in DNA or DNA-like sequences. 2′-O-methyl nucleosides are shown in bold. All are 19mers of SEQ ID NO: 301 (antisense strand)/SEQ ID NO: 302 (sense strand).

342744 is an unmodified ribose 19mer with phosphate (P=O) backbone and 5′ terminal phosphate.

342764 is an unmodified ribose 19mer with phosphate (P=O) backbone and 5′ terminal phosphate.

352824 has 4′-thio at nucleosides positions 1, 2, 3, 17, 18 and 19 (i.e., three at each terminus) with ribose at positions 4-16. Backbone is P=O, 5′ terminal phosphate.

352819 has 4′-thio nucleosides at positions 1, 2, 3, 4, 16, 17, 18 and 19 (i.e., four at each terminus) with ribose at positions 5-14. Backbone is P=O, 5′ terminal phosphate.

352827 has 4′-thio nucleosides at positions 1, 2, 3, and 2′-OMe at positions 17, 18 and 19 with ribose at positions 4-16. Backbone is P=O, 5′ terminal phosphate.

352826 has 4′-thio nucleosides at positions 1, 2, 3, 10, 13 and 17-19 with ribose at positions 4-9, 11, 12 and 14-16. Backbone is P=O, 5′ terminal phosphate.

352825 has 4′-thio nucleosides at positions 1, 2, 3, 7, 10, 13 and 17-19 with ribose at positions 4, 5, 6, 8, 9, 11, 12 and 14-16. Backbone is P=O, 5′ terminal phosphate.

354604 has 4′-thio nucleosides at positions 1, 2, 3, and 2′-OMe at positions 17, 18 and 19 with ribose at positions 4-16. Backbone is P=O, 5′ terminal phosphate.

TABLE 21

Activity of 4'-thioribose modified and mixed 19mer siRNA in HeLa cells

| Strand | ISIS # | Sequence (5'→3') | IC50 (nM) |
|---|---|---|---|
| AS | 342744 | UCUUAUCACCUUUAGCUCU | 1.4 |
| S | 342764 | AGAGCUAAAGGUGAUAAGA | |
| AS | 352824 | ucuUAUCACCUUUAGCucu | n/a |
| S | 342764 | AGAGCUAAAGGUGAUAAGA | |
| AS | 352819 | ucuuAUCACCUUUAGcucu | n/a |
| S | 342764 | AGAGCUAAAGGUGAUAAGA | |
| AS | 352827 | ucuUAUCACCUUUAGCUCU | 3.7 |
| S | 342764 | AGAGCUAAAGGUGAUAAGA | |
| AS | 352826 | ucuUAUCAcCUUuAGCucu | n/a |
| S | 342764 | AGAGCUAAAGGUGAUAAGA | |
| AS | 352825 | ucuUAUcACcUUuAGCucu | n/a |
| S | 342764 | AGAGCUAAAGGUGAUAAGA | |

TABLE 21-continued

Activity of 4'-thioribose modified and mixed 19mer siRNA in HeLa cells

| Strand | ISIS # | Sequence (5'→3') | IC50 (nM) |
|---|---|---|---|
| AS | 354604 | ucuUAUCACCUUUAGCUCU | 2.7 |
| S | 342764 | AGAGCUAAAGGUGAUAAGA | |

Several of the 4'-thio constructs were shown to have IC$_{50}$s in the picomolar range.

Example 41

Activity of siRNA Constructs Targeted to eIF4E in U-87 MG Glioblastoma Cells The modified or unmodified siRNA constructs shown in previous tables are tested for their ability to reduce levels of human eIF4E mRNA in U-87 MG cells using the methods described above. The U-87 human glioblastoma cell line is obtained from the ATCC (Rockville Md.) and maintained in Iscove's DMEM medium supplemented with heat-inactivated 10% fetal calf serum. Dose response experiments are performed as described in previous examples to obtain IC50 values.

Example 42

Additional siRNAs Targeted to Human eIF4E

Additional siRNAs were designed to human eIF4E mRNA (Genbank accession no. M15353.1, SEQ ID NO: 4) All are alternating 2'-O-methyl/2'-OH on antisense strand and alternating 2'-OH/2'-O-methyl on sense strand. The backbone is phosphate (P=O) and the 5' terminus is 5'-OH, although it will be understood that these and other siRNA constructs shown herein may also be synthesized with a 5'-phosphate group.

The antisense strands are shown in Table 22; sense strands are fully complementary and are not shown.

"Target site" refers to the 5'-most position of the target region on the M15353.1 human eIF4E sequence (SEQ ID NO: 4) to which the oligonucleotide is targeted.

TABLE 22

Additional siRNAs targeted to human eIF4E

| Isis # | SEQ ID NO | Antisense strand 5'→3' | Target site |
|---|---|---|---|
| 357532 | 339 | GCUUUGGUUCAGCUCCCAA | 724 |
| 357533 | 340 | GGCGAAUGAGACUUCUCUU | 806 |
| 357534 | 341 | CUUUUCUACUUGAGCCAUU | 1564 |
| 357535 | 342 | CAUCAUCACUGUAGUCAUC | 445 |
| 357536 | 343 | UGCUAUCUUAUCACCUUUA | 492 |
| 357537 | 344 | UCCAUAUUGCUAUCUUAUC | 499 |
| 357538 | 345 | UCACAGCCAGGCAUUAAAU | 269 |
| 357539 | 346 | ACCUUUCCUUGUAUACCCU | 559 |

TABLE 22-continued

Additional siRNAs targeted to human eIF4E

| Isis # | SEQ ID NO | Antisense strand 5'→3' | Target site |
|---|---|---|---|
| 357540 | 347 | UGUAAUUCUUUGAUUGGGA | 883 |
| 357541 | 348 | UCACUGAUUUGAAUGAAAU | 1392 |
| 357542 | 349 | UUUACAGUUUUGUACACUG | 1603 |
| 357543 | 350 | UUAAAAAACCAGAGUGCCC | 146 |
| 357544 | 351 | UUUAAAAAACCAGAGUGCC | 147 |
| 357545 | 352 | UUUUAAAAACCAGAGUGC | 148 |
| 357546 | 353 | AUUUUUAAAAAACCAGAGU | 150 |
| 357547 | 354 | AGAGCCCAAAAGUCUUCAA | 224 |
| 357548 | 355 | UACUAGACAACUGGAUAUG | 250 |
| 357549 | 356 | AAAGUGAGUAGUCACAGCC | 280 |
| 357550 | 357 | UUUUUCUCAUCUUCCCACA | 320 |
| 357551 | 358 | UCCUUGUAUACCCUCCCUA | 554 |
| 357552 | 359 | UGAUAACCAAUCACUAUCU | 593 |
| 357553 | 360 | AUGAGACUUCUCUUAUAUC | 801 |
| 357554 | 361 | UACAAGACAAAGGCGAAUG | 817 |
| 357555 | 362 | UAGCAGCCAUCAGCAAGAG | 1157 |
| 357556 | 363 | UAGCAAAGCUUUGUAGUUA | 1362 |
| 357557 | 364 | UAGUUAGGAAUGUAAUUAU | 1466 |
| 357558 | 365 | UUGUACACUGUCUUAUAU | 1594 |
| 346659 | 329 | AAACCAGAGUGCCCAUCUG | 141 |
| 357559 | 366 | UUAUCACCUUUAGCUCUAA | 485 |
| 357560 | 367 | UUUAGCUCUAACAUUAACA | 477 |
| 357561 | 368 | CUUUAGCUCUAACAUUAAC | 478 |
| 357562 | 369 | CUCUAACAUUAACAACAGC | 472 |
| 357563 | 370 | UUACUAGACAACUGGAUAU | 251 |
| 357564 | 371 | CUAGACAACUGGAUAUGGU | 248 |
| 357565 | 372 | UUAAAUUACUAGACAACUG | 256 |
| 357566 | 373 | AUUAAAUUACUAGACAACU | 257 |
| 357567 | 374 | AAAAAGUGAGUAGUCACAG | 282 |
| 357568 | 375 | UUAAAAGUGAGUAGUCAC | 284 |
| 357569 | 376 | UGAGUAGUCACAGCCAGGC | 276 |
| 357570 | 377 | AAGUGAGUAGUCACAGCCA | 279 |
| 357571 | 378 | UUUUGCUUUUAUCAUUUUU | 163 |
| 357572 | 379 | GUUUUGCUUUUAUCAUUUU | 164 |
| 357573 | 380 | UUUUAUUUACAGUUUUGUA | 1608 |
| 357574 | 381 | CAUUUUAUUUACAGUUUUG | 1610 |
| 357575 | 382 | UUAAAAAUUGUAAUAAACA | 1793 |

TABLE 22-continued

Additional siRNAs targeted to human eIF4E

| Isis # | SEQ ID NO | Antisense strand 5'→3' | Target site |
|---|---|---|---|
| 357576 | 383 | UUUAUUAAAAAUUGUAAUA | 1797 |
| 357577 | 384 | UUUGUUUUUCUCAUCUUCC | 324 |
| 357578 | 385 | AAAAAAUUACCAAAGAAUG | 1333 |
| 357579 | 386 | AAUGAAAUGCAUAAAUUUG | 1381 |
| 357580 | 387 | AAACUGAAAUCAGAAUCAC | 1213 |
| 357630 | 388 | UUAAUGUUUAUUCCACCUU | 1307 |
| 357631 | 389 | UAAAUUUGUAGCAAAGCUU | 1370 |
| 357632 | 390 | UAAUUCUAGUUAGGAAUGU | 1472 |
| 357633 | 391 | UAACCAAAGCAAAAUAACC | 1543 |
| 357634 | 392 | UGUACACAUUUUAUUUACA | 1616 |
| 357635 | 393 | UAGUUGUCUAAAAGACAAU | 1639 |
| 357636 | 394 | UCAAUUUAUUAAAAAUUGU | 1801 |

Example 43

Additional Antisense Compounds Targeted to eIF4E

A set of uniform 2'-O-methoxyethyl (2'-MOE) phosphorothioate oligonucleotides were synthesized, all targeted to the 5' cap region of the eIF4E mRNA, i.e, the extreme 5' end of the mRNA adjacent to the 5' cap. These are shown in Table 23. All cytokines are 5-methylcytosines. While not wishing to be bound by theory, fully 2'-MOE oligonucleotides are not believed to be substrates for RNAse H and thus are believed to interfere with protein translation via an occupancy-only or steric hindrance mechanism rather than via degradation of the mRNA target. "Target site" refers to the position on the eIF4E mRNA (SEQ ID NO: 4 or 11 as indicated).

TABLE 23

2'-O-methoxyethyl antisense oligonucleotides targeted to the 5' cap region of eIF4E mRNA

| ISIS # | SEQUENCE | REGION | TARGET SEQ ID NO | TARGET SITE | SEQ ID NO |
|---|---|---|---|---|---|
| 335022 | GATCGATCTGATCGC | 5' UTR | 11 | 1 | 395 |
| 335023 | AGATCGATCTGATCG | 5' UTR | 4 | 1 | 396 |
| 335024 | TAGATCGATCTGATC | 5' UTR | 4 | 2 | 397 |
| 335025 | TTAGATCGATCTGAT | 5' UTR | 4 | 3 | 398 |

A series of PNA oligomers was also synthesized which are targeted to the same sites as the oligonucleotides in Table 23. These are shown in Table 24. Each has a lysine on the 3' end of the oligomer. As with the fully modified 2' MOE compounds, PNA oligomers are not believed to be substrates for RNAse H.

TABLE 24

PNA antisense oligomers targeted to the 5' cap region of eIF4E mRNA

| ISIS # | SEQUENCE | REGION | TARGET SEQ ID NO | TARGET SITE | SEQ ID NO |
|---|---|---|---|---|---|
| 333879 | GATCGATCTGATCGC | 5' UTR | 11 | 1 | 395 |
| 333880 | AGATCGATCTGATCG | 5' UTR | 4 | 1 | 396 |
| 333881 | TAGATCGATCTGATC | 5' UTR | 4 | 2 | 397 |
| 333882 | TTAGATCGATCTGAT | 5' UTR | 4 | 3 | 398 |

Example 44

LNA and 2'-OMe Modified siRNA

The duplexed oligomeric RNA (dsRNA) compounds shown in Table 14 below were prepared as described in previous examples and evaluated in HeLa cells (American Type Culture Collection, Manassas Va.). Cells were plated in 96-well plates at a density of 5000 cells/well and grown in DMEM with high glucose, 10% FBS, 1% penicillin/streptomycin. Wells were washed once with 200 µL OPTI-MEM-1™ reduced-serum medium (Gibco BRL) and then treated with 130 µL of OPTI-MEM-1™ containing the desired dsRNA at a concentration of 0.2, 2 and 20 nM plus 2.5 µl/ml LIPOFECTIN™ (Gibco BRL) per strand of oligomeric compound. Treatments were done in duplicate. After 4 or 5 hours of treatment, the medium was replaced with fresh medium. Cells were harvested 16 or 18 hours after dsRNA treatment, at which time RNA was isolated and target reduction measured by RT-PCR as described in previous examples.

The results are shown in Table 25. The siRNA constructs shown consist of one antisense strand and one sense strand. The antisense strand (AS) is shown first in Table 25 below, followed by the sense strand (S) in the next row. Unless otherwise indicated, all double-stranded constructs are unmodified RNA, i.e., ribose sugars with phosphate (P=O) backbones and 5'-terminal hydroxyl group. It is understood in the art that, for RNA sequences, U (uracil) generally replaces T (thymine) which is normally found in DNA or DNA-like sequences. 2'-O-methyl nucleosides are shown in bold. LNA nucleosides are in italics.

338910 is an unmodified ribose 20mer with phosphate (P=O) backbone and 5' terminal phosphate.

338935 is an unmodified ribose 20mer with phosphate (P=O) backbone and 5' terminal phosphate.

352493 is a 20mer with LNA at positions 6, 9, 12 and 15 (italics), 2'-O-methyl at positions 18-20 (bold) and ribose at remaining positions.

338914 is an unmodified ribose 20mer with phosphate (P=O) backbone and 5' terminal phosphate.

338939 is an unmodified ribose 20mer with phosphate (P=O) backbone and 5' terminal phosphate.

352494 is a 20mer with LNA at positions 6, 9, 12 and 15 (italics), 2'-O-methyl at positions 18-20 (bold) and ribose at remaining positions.

338918 is an unmodified ribose 20mer with phosphate (P=O) backbone and 5' terminal phosphate.

338943 is an unmodified ribose 20mer with phosphate (P=O) backbone and 5' terminal phosphate.

352495 is a 20mer with LNA at positions 6, 9, 12 and 15 (italics), 2'-O-methyl at positions 18-20 (bold) and ribose at remaining positions.

338927 is an unmodified ribose 20mer with phosphate (P=O) backbone and 5' terminal phosphate.

338952 is an unmodified ribose 20mer with phosphate (P=O) backbone and 5' terminal phosphate.

352496 is a 20mer with LNA at positions 6, 9, 12 and 15 (italics), 2'-O-methyl at positions 18-20 (bold) and ribose at remaining positions.

TABLE 25

LNA and 2'-OMe modified siRNA

| Strand | ISIS # | Construct 5'→3' | SEQ ID NO | IC50 (nM) | % inhib |
|---|---|---|---|---|---|
| AS | 338910 | UGUCAUAUUCCUGGAUCCUU | 220 | 1.42 | 72 |
| S | 338935 | AAGGAUCCAGGAAUAUGACA | 221 | | |
| AS | 352493 | UGUCA*UAU*U*CC*UGGAUCCUU | 220 | – | 18 |
| S | 338935 | AAGGAUCCAGGAAUAUGACA | 228 | | |
| AS | 338914 | UCCUGGAUCCUUCACCAAUG | 228 | 2.29 | 72 |
| S | 338939 | CAUUGGUGAAGGAUCCAGGA | 229 | | |
| AS | 352494 | UCCUGGAUCC*UU*CACCAAUG | 228 | – | 9 |
| S | 338939 | CAUUGGUGAAGGAUCCAGGA | 229 | | |
| AS | 338918 | UCUUAUCACCUUUAGCUCUA | 236 | 1.96 | 66 |
| S | 338943 | UAGAGCUAAAGGUGAUAAGA | 237 | | |
| AS | 352495 | UCUUA*U*CACC*UU*UAGCUCUA | 236 | – | 13 |
| S | 338943 | UAGAGCUAAAGGUGAUAAGA | 237 | | |
| AS | 338927 | AUACUCAGAAGGUGUCUUCU | 254 | 5.78 | 62 |
| S | 338952 | AGAAGACACCUUCUGAGUAU | 255 | | |
| AS | 352496 | AUACUCAGAAGGU*GU*CUUCU | 254 | – | 25 |
| S | 338952 | AGAAGACACCUUCUGAGUAU | 255 | | |

Example 45

Activity of Additional siRNAs Targeted to Human eIF4E siRNAs from Table 22 were tested for ability to reduce eIF4E RNA levels in HeLa cells. These compounds were designed to human eIF4E mRNA (Genbank accession no. M15353.1, SEQ ID NO:4). Unless noted, antisense strands are alternating 2'-O-methyl/ribose starting with 2'-O-methyl at position 1 (i.e., odd-numbered positions are 2'-O-methyl and even-numbered positions are ribose) and sense strands are alternating ribose/2'-O-methyl starting with ribose at position 1 (i.e., odd-numbered positions are ribose and even-numbered positions are 2'-O-methyl). The backbone is phosphate (P=O) and the 5' terminus is 5'-OH, although it will be understood that these and other siRNA constructs shown herein may also be synthesized with a 5'-phosphate group. Note that the ISIS 351831_351832 construct has the same sequence as the 345847_345849 construct but the former is alternating 2'-O-methyl/2'-fluoro (antisense strand has 2'-O-methyl on odd numbered positions and 2'-fluoro on evens; sense strand has 2'F on odd numbered positions and 2'-O-methyl on evens).

The compounds shown in Table 26 were tested at low dose of 5 nM in HeLa cells as in above examples. The results are shown in Table 26. The siRNA constructs shown consist of one antisense strand and one sense strand. The antisense strand (AS) is shown first in the table below, followed by the sense strand in the next row. It is understood in the art that, for RNA sequences, U (uracil) generally replaces T (thymine) which is normally found in DNA or DNA-like sequences. Results are shown as percent reduction of eIF4E RNA ("% inhib") in Table 26. "Target site" refers to the 5'-most position of the target region on the M15353.1 human eIF4E sequence (SEQ ID NO: 4) to which the oligonucleotide is targeted.

TABLE 26

Activity of additional siRNAs targeted to human eIF4E

| Strand | Isis# | Sequence 5'→3' | SEQ ID NO | Target site | Target region | Note | % inhib |
|---|---|---|---|---|---|---|---|
| AS | 183750 | TGTCATATTCCTGGATCCTT | 40 | 1285 | 3' UTR | MOE gapmer | 40 ± 11 |
| S | none | | | | | | |
| AS | 338918 | UCUUAUCACCUUUAGCUCUA | 236 | 486 | Coding | All ribose | 42 ± 8 |
| S | 338943 | UAGAGCUAAAGGUGAUAAGA | 237 | | | All ribose | |
| AS | 345847 | UCUUAUCACCUUUAGCUCU | 301 | 487 | Coding | | 0 |
| S | 345849 | AGAGCUAAAGGUGAUAAGA | 302 | | | | |
| AS | 351831 | UCUUAUCACCUUUAGCUCU | 301 | 487 | Coding | Alternating 2'-OMe/2'F | 42 ± 28 |
| S | 351832 | AGAGCUAAAGGUGAUAAGA | 302 | | | Alternating | |

TABLE 26-continued

Activity of additional siRNAs targeted to human eIF4E

| Strand | Isis# | Sequence 5'→3' | SEQ ID NO | Target site | Target region | Note 2'F/2'-OMe | % inhib |
|---|---|---|---|---|---|---|---|
| AS | 357532 | GCUUUGGUUCAGCUCCCAA | 339 | 724 | 3' UTR | | 0 |
| S | 357581 | UUGGGAGCUGAACCAAAGC | 399 | | | | |
| AS | 357533 | GGCGAAUGAGACUUCUCUU | 340 | 806 | 3' UTR | | 4 ± 17 |
| S | 357582 | AAGAGAAGUCUCAUUCGCC | 400 | | | | |
| AS | 357534 | CUUUUCUACUUGAGCCAUU | 341 | 1564 | 3' UTR | | 0 |
| S | 357583 | AAUGGCUCAAGUAGAAAAG | 401 | | | | |
| AS | 357535 | CAUCAUCACUGUAGUCAUC | 342 | 445 | Coding | | 0 |
| S | 357584 | GAUGACUACAGUGAUGAUG | 402 | | | | |
| AS | 357536 | UGCUAUCUUAUCACCUUUA | 343 | 492 | Coding | | 27 ± 41 |
| S | 357585 | UAAAGGUGAUAAGAUAGCA | 403 | | | | |
| AS | 357537 | UCCAUAUUGCUAUCUUAUC | 344 | 499 | Coding | | 0 |
| S | 357586 | GAUAAGAUAGCAAUAUGGA | 404 | | | | |
| AS | 357538 | UCACAGCCAGGCAUUAAAU | 345 | 269 | Coding | | 0 |
| S | 357587 | AUUUAAUGCCUGGCUGUGA | 405 | | | | |
| AS | 357539 | ACCUUUCCUUGUAUACCCU | 346 | 559 | Coding | | 0 |
| S | 357588 | AGGGUAUACAAGGAAAGGU | 406 | | | | |
| AS | 357540 | UGUAAUUCUUUGAUUGGGA | 347 | 883 | 3' UTR | | 24 ± 5 |
| S | 357589 | UCCCAAUCAAAGAAUUACA | 407 | | | | |
| AS | 357541 | UCACUGAUUUGAAUGAAAU | 348 | 1392 | 3' UTR | | 1 ± 5 |
| S | 357590 | AUUUCAUUCAAAUCAGUGA | 408 | | | | |
| AS | 357542 | UUUACAGUUUUGUACACUG | 349 | 1603 | 3' UTR | | 0 |
| S | 357591 | CAGUGUACAAAACUGUAAA | 409 | | | | |
| AS | 357543 | UUAAAAAACCAGAGUGCCC | 350 | 146 | Coding | | 4 ± 9 |
| S | 357592 | GGGCACUCUGGUUUUUUAA | 410 | | | | |
| AS | 357544 | UUUAAAAAACCAGAGUGCC | 351 | 147 | Coding | | 7 ± 29 |
| S | 357593 | GGCACUCUGGUUUUUUAAA | 411 | | | | |
| AS | 357545 | UUUUAAAAAACCAGAGUGC | 352 | 148 | Coding | | 7 ± 11 |
| S | 357594 | GCACUCUGGUUUUUUAAAA | 412 | | | | |
| AS | 357546 | AUUUUUAAAAAACCAGAGU | 353 | 150 | Coding | | 0 |
| S | 357595 | ACUCUGGUUUUUUAAAAAU | 413 | | | | |
| AS | 357547 | AGAGCCCAAAAGUCUUCAA | 354 | 224 | Coding | | 0 |
| S | 357596 | UUGAAGACUUUUGGGCUCU | 414 | | | | |
| AS | 357548 | UACUAGACAACUGGAUAUG | 355 | 250 | Coding | | 30 ± 4 |
| S | 357597 | CAUAUCCAGUUGUCUAGUA | 415 | | | | |
| AS | 357549 | AAAGUGAGUAGUCACAGCC | 356 | 280 | Coding | | 0 |
| S | 357598 | GGCUGUGACUACUCACUUU | 416 | | | | |

TABLE 26-continued

Activity of additional siRNAs targeted to human eIF4E

| Strand | Isis# | Sequence 5'→3' | SEQ ID NO | Target site | Target region | Note | % inhib |
|---|---|---|---|---|---|---|---|
| AS | 357550 | UUUUUCUCAUCUUCCCACA | 357 | 320 | Coding | | 0 |
| S | 357599 | UGUGGGAAGAUGAGAAAAA | 417 | | | | |
| AS | 357551 | UCCUUGUAUACCCUCCCUA | 358 | 554 | Coding | | 0 |
| S | 357600 | UAGGGAGGGUAUACAAGGA | 418 | | | | |
| AS | 357552 | UGAUAACCAAUCACUAUCU | 359 | 593 | Coding | | 38 ± 6 |
| S | 357601 | AGAUAGUGAUUGGUUAUCA | 419 | | | | |
| AS | 357553 | AUGAGACUUCUCUUAUAUC | 360 | 801 | 3' UTR | | 10 ± 12 |
| S | 357602 | GAUAUAAGAGAAGUCUCAU | 420 | | | | |
| AS | 357554 | UACAAGACAAAGGCGAAUG | 361 | 817 | 3' UTR | | 26 ± 8 |
| S | 357603 | CAUUCGCCUUUGUCUUGUA | 421 | | | | |
| AS | 357555 | UAGCAGCCAUCAGCAAGAG | 362 | 1157 | 3' UTR | | 0 |
| S | 357604 | CUCUUGCUGAUGGCUGCUA | 422 | | | | |
| AS | 357556 | UAGCAAAGCUUUGUAGUUA | 363 | 1362 | 3' UTR | | 13 ± 5 |
| S | 357605 | UAACUACAAAGCUUUGCUA | 423 | | | | |
| AS | 357557 | UAGUUAGGAAUGUAAUUAU | 364 | 1466 | 3' UTR | | 16 ± 3 |
| S | 357606 | AUAAUUACAUUCCUAACUA | 424 | | | | |
| AS | 357558 | UUGUACACUGUCUUAAUAU | 365 | 1594 | 3' UTR | | 21 ± 15 |
| S | 357607 | AUAUUAAGACAGUGUACAA | 425 | | | | |
| AS | 357559 | UUAUCACCUUUAGCUCUAA | 366 | 485 | Coding | | 0 |
| S | 357608 | UUAGAGCUAAAGGUGAUAA | 426 | | | | |
| AS | 357560 | UUUAGCUCUAACAUUAACA | 367 | 477 | Coding | | 48 ± 12 |
| S | 357609 | UGUUAAUGUUAGAGCUAAA | 427 | | | | |
| AS | 357561 | CUUUAGCUCUAACAUUAAC | 368 | 478 | Coding | | 0 |
| S | 357610 | GUUAAUGUUAGAGCUAAAG | 428 | | | | |
| AS | 357562 | CUCUAACAUUAACAACAGC | 369 | 472 | Coding | | 4 ± 31 |
| S | 357611 | GCUGUUGUUAAUGUUAGAG | 429 | | | | |
| AS | 357563 | UUACUAGACAACUGGAUAU | 370 | 251 | Coding | | 55 ± 18 |
| S | 357612 | AUAUCCAGUUGUCUAGUAA | 430 | | | | |
| AS | 357564 | CUAGACAACUGGAUAUGGU | 371 | 248 | Coding | | 0 |
| S | 357613 | ACCAUAUCCAGUUGUCUAG | 431 | | | | |
| AS | 357565 | UUAAAUUACUAGACAACUG | 372 | 256 | Coding | | 20 ± 13 |
| S | 357614 | CAGUUGUCUAGUAAUUUAA | 432 | | | | |
| AS | 357566 | AUUAAAUUACUAGACAACU | 373 | 257 | Coding | | 20 ± 12 |
| S | 357615 | AGUUGUCUAGUAAUUUAAU | 433 | | | | |
| AS | 357567 | AAAAGUGAGUAGUCACAG | 374 | 282 | Coding | | 35 ± 20 |
| S | 357616 | CUGUGACUACUCACUUUUU | 434 | | | | |

TABLE 26-continued

Activity of additional siRNAs targeted to human eIF4E

| Strand | Isis# | Sequence 5'→3' | SEQ ID NO | Target site | Target region | Note | % inhib |
|---|---|---|---|---|---|---|---|
| AS | 357568 | UUAAAAAGUGAGUAGUCAC | 375 | 284 | Coding | | 51 ± 4 |
| S | 357617 | GUGACUACUCACUUUUUAA | 435 | | | | |
| AS | 357569 | UGAGUAGUCACAGCCAGGC | 376 | 276 | Coding | | 21 ± 6 |
| S | 357618 | GCCUGGCUGUGACUACUCA | 436 | | | | |
| AS | 357570 | AAGUGAGUAGUCACAGCCA | 377 | 279 | Coding | | 0 |
| S | 357619 | UGGCUGUGACUACUCACUU | 437 | | | | |
| AS | 357571 | UUUUGCUUUUAUCAUUUUU | 378 | 163 | Coding | | 0 |
| S | 357620 | AAAAAUGAUAAAAGCAAAA | 438 | | | | |
| AS | 357572 | GUUUUGCUUUUAUCAUUUU | 379 | 164 | Coding | | 0 |
| S | 357621 | AAAAUGAUAAAAGCAAAAC | 439 | | | | |
| AS | 357573 | UUUUAUUUACAGUUUUGUA | 380 | 1608 | 3' UTR | | 2 ± 3 |
| S | 357622 | UACAAAACUGUAAAUAAAA | 440 | | | | |
| AS | 357574 | CAUUUUAUUUACAGUUUUG | 381 | 1610 | 3' UTR | | 0 |
| S | 357623 | CAAAACUGUAAAUAAAAUG | 441 | | | | |
| AS | 357575 | UUAAAAAUUGUAAUAAACA | 382 | 1793 | 3' UTR | | 7 ± 5 |
| S | 357624 | UGUUUAUUACAAUUUUUAA | 442 | | | | |
| AS | 357576 | UUUAUUAAAAAUUGUAAUA | 383 | 1797 | 3' UTR | | 0 |
| S | 357625 | UAUUACAAUUUUUAAUAAA | 443 | | | | |
| AS | 357577 | UUUGUUUUUCUCAUCUUCC | 384 | 324 | Coding | | 34 ± 3 |
| S | 357626 | GGAAGAUGAGAAAAACAAA | 444 | | | | |
| AS | 357578 | AAAAAAUUACCAAAGAAUG | 385 | 1333 | 3' UTR | | 0 |
| S | 357627 | CAUUCUUUGGUAAUUUUUU | 445 | | | | |
| AS | 357579 | AAUGAAAUGCAUAAAUUUG | 386 | 1381 | 3' UTR | | 0 |
| S | 357628 | CAAAUUUAUGCAUUUCAUU | 446 | | | | |
| AS | 357580 | AAACUGAAAUCAGAAUCAC | 387 | 1213 | 3' UTR | | 56 ± 14 |
| S | 357629 | GUGAUUCUGAUUUCAGUUU | 447 | | | | |
| AS | 357631 | UAAAUUUGUAGCAAAGCUU | 389 | 1370 | 3' UTR | | 0 |
| S | 358638 | UUGUCCUCAACCAUGGUCAG | 448 | | | | |
| AS | 357632 | UAAUUCUAGUUAGGAAUGU | 390 | 1472 | 3' UTR | | 4 ± 9 |
| S | 357639 | CUGCCCUAGGCUGGCAGGGC | 449 | | | | |
| AS | 357633 | UAACCAAAGCAAAAUAACC | 391 | 1543 | 3' UTR | | 13 |
| S | 357640 | UUGGCAUGGAGGUGGGAGAG | 450 | | | | |
| AS | 357634 | UGUACACAUUUUAUUUACA | 392 | 1616 | 3' UTR | | 0 |
| S | 357641 | GGCAUUCCAAAACAUUCUUU | 451 | | | | |
| AS | 357635 | UAGUUGUCUAAAAGACAAU | 393 | 1639 | 3' UTR | | 0 |
| S | 357642 | UGCGCCCUCAGGAGUUCCGG | 452 | | | | |

TABLE 26-continued

Activity of additional siRNAs targeted to human eIF4E

| Strand | Isis# | Sequence 5'→3' | SEQ ID NO | Target site | Target region | Note | % inhib |
|---|---|---|---|---|---|---|---|
| AS | 357636 | UCAAUUUAUUAAAAAUUGU | 394 | 1801 | 3' UTR | | 0 |
| S | 357643 | AUUGUCACAGGGUCUCACAG | 453 | | | | |

The siRNA duplexes whose antisense strands have SEQ ID NO: 236, 301, 343, 347, 355, 359, 360, 361, 363, 364, 365, 367, 370, 372, 373, 374, 375, 376, 384, 387, or 391 inhibited eIF4E in this assay by at least 10%.

Example 46

Single-Stranded Antisense RNA (asRNA) Targeted to eIF4E

A series of single-stranded RNA antisense oligonucleotides targeted to human eIF4E (SEQ ID NO: 4) were synthesized. All are RNA (ribose sugars) with phosphorothioate backbone linkages throughout and a 5' phosphate cap. The human umbilical vein endothilial cell line HuVEC is obtained from the American Type Culture Collection (Manassas, Va.). HuVEC cells are routinely cultured in EBM (Clonetics Corporation Walkersville, Md.) supplemented with SingleQuots supplements (Clonetics Corporation, Walkersville, Md.). Cells are routinely passaged by trypsinization and dilution when they reach 90% confluence and are maintained for up to 15 passages. Cells are seeded into 96-well plates (Falcon-Primaria #3872) at a density of 10000 cells/well for treatment with RNA oligonucleotides (30 nM oligonucleotide concentration). Sequences and results of treatment (reduction of eIF4E RNA levels) are shown in Table 27. It is understood in the art that, for RNA sequences, U (uracil) generally replaces T (thymine) which is normally found in DNA or DNA-like sequences. As in above examples, "Target site" refers to the 5'-most position of the target region on the M15353.1 human eIF4E sequence (SEQ ID NO: 4) to which the oligonucleotide is targeted. "% inhib" refers to percent reduction in eIF4E RNA (shown ± standard deviation).

TABLE 27

Activity of single-stranded antisense RNA targeted to eIF4E in HuVEC cells

| Isis # | Sequence 5'→3' | SEQ ID NO: | Target site | Target region | % inhib |
|---|---|---|---|---|---|
| 347398 | UGUCAUAUUCCUGGAUCCUU | 220 | 1285 | 3' UTR | 16 ± 14 |
| 347399 | GGAGGAAGUCCUAACCUUUC | 222 | 571 | Coding | 29 ± 16 |
| 347400 | GGCUUUGGUUCAGCUCCCAA | 224 | 724 | 3' UTR | 18 ± 22 |
| 347401 | GGCGAAUGAGACUUCUCUUA | 226 | 805 | 3' UTR | 18 ± 4 |
| 347402 | UCCUGGAUCCUUCACCAAUG | 228 | 1277 | 3' UTR | 59 ± 1 |
| 347403 | GCUUUUCUACUUGAGCCAUU | 230 | 1564 | 3' UTR | 21 ± 1 |
| 347404 | ACAUCAUCACUGUAGUCAUC | 232 | 445 | Coding | 24 ± 1 |
| 347405 | CACCUUUAGCUCUAACAUUA | 234 | 480 | Coding | 22 ± 3 |
| 347406 | UCUUAUCACCUUUAGCUCUA | 236 | 486 | Coding | 27 ± 4 |
| 347407 | UGCUAUCUUAUCACCUUUAG | 238 | 491 | Coding | 24 ± 3 |
| 347408 | GUCCAUAUUGCUAUCUUAUC | 240 | 499 | Coding | 26 ± 7 |
| 347409 | GCCAAGUUUUGCUUUUAUCA | 242 | 168 | Coding | 24 ± 6 |
| 347410 | UCUUCAACAGUAUCAAACUU | 244 | 211 | Coding | 11 ± 9 |
| 347411 | GUCACAGCCAGGCAUUAAAU | 246 | 269 | Coding | 48 ± 11 |
| 347412 | UCUCAUCUUCCCACAUAGGC | 148 | 315 | Coding | 17 ± 10 |
| 347413 | ACCUUUCCUUGUAUACCCUC | 250 | 558 | Coding | 17 ± 2 |
| 347414 | GUAGCUGUGUCUGCGUGGGA | 252 | 613 | Coding | 43 ± 5 |
| 347415 | AUACUCAGAAGGUGUCUUCU | 254 | 672 | Stop | 12 ± 10 |
| 347416 | CUGUAAUUCUUUGAUUGGGA | 256 | 883 | 3' UTR | 27 ± 2 |
| 347417 | GAAUGAAAUGCAUAAAUUUG | 258 | 1381 | 3' UTR | 22 ± 8 |
| 347418 | UCACUGAUUUGAAUGAAAUG | 260 | 1391 | 3' UTR | 22 ± 7 |
| 347419 | AUUUACAGUUUUGUACACUG | 262 | 1603 | 3' UTR | 11 ± 20 |
| 347420 | AAAACCAGAGUGCCCAUCUG | 264 | 141 | Coding | 33 ± 7 |
| 347421 | ACUUGGAGAUCAGCCGCAGG | 266 | 195 | Coding | 31 ± 2 |

As shown in the table above, all of the single-stranded antisense RNA compounds were able to reduce human eIF4E RNA levels by at least 10%. Compounds that reduced eIF4E RNA levels by at least 20%, at least 30%, at least 40% or at least 50% are especially suitable for use as inhibitors of eIF4E expression.

ISIS 347402 (SEQ ID NO: 228) gave the greatest reduction in eIF4E expression in this experiment. A dose-response analysis of this single-stranded antisense RNA compound was done in HeLa cells using antisense RNA concentrations of 1 nM, 10 nM and 100 nM. ISIS 347402 gave a dose-dependent inhibition of eIF4E expression, with 41% reduction of eIF4E expression at 10 nM and 67% reduction at 100 nM (no effect was observed at 1 nM dose in this experiment).

Example 47

Activity of Double-Stranded siRNA Compounds with Antisense Strand Sequences Corresponding to Single Stranded Antisense RNA Compounds Double-stranded RNA compounds were prepared as in previous examples. The antisense strands of the duplexes are identical in sequence to the single-stranded antisense RNA compounds used in the previous example, but were made with a phosphodiester (P=O) backbone. The sense strand is fully complementary to the antisense strand (thus forming a blunt ended 20mer duplex) and also has a P=O backbone. Both strands are unmodified RNA. The siRNA duplexes were used at a concentration of 25 nM to treat HeLa cells as described in previous siRNA examples. Effect of treatment on eIF4E RNA levels in HeLa cells is as shown in Table 28. "% inhib" refers to percent reduction in eIF4E RNA (shown±standard deviation). Only the sequence of the antisense strand is shown in Table 28. It is understood in the art that, for RNA sequences, U (uracil) generally replaces T (thymine) which is normally found in DNA or DNA-like sequences.

TABLE 28

Activity of double-stranded siRNA compounds corresponding to single stranded antisense RNA compounds

| Sequence (antisense strand) | SEQ ID NO | % inhib |
|---|---|---|
| UGUCAUAUUCCUGGAUCCUU | 220 | 80 ± 3 |
| GGAGGAAGUCCUAACCUUUC | 222 | 28 ± 1 |
| GGCUUUGGUUCAGCUCCCAA | 224 | 56 ± 4 |
| GGCGAAUGAGACUUCUCUUA | 226 | 74 ± 0 |
| UCCUGGAUCCUUCACCAAUG | 228 | 76 ± 1 |
| GCUUUUCUACUUGAGCCAUU | 230 | 51 ± 2 |
| ACAUCAUCACUGUAGUCAUC | 232 | 57 ± 1 |
| CACCUUUAGCUCUAACAUUA | 234 | 42 ± 3 |
| UCUUAUCACCUUUAGCUCUA | 236 | 77 ± 3 |
| UGCUAUCUUAUCACCUUUAG | 238 | 52 ± 9 |
| GUCCAUAUUGCUAUCUUAUC | 240 | 62 ± 4 |
| GCCAAGUUUUGCUUUUAUCA | 242 | 32 ± 12 |
| UCUUCAACAGUAUCAAACUU | 244 | 17 ± 1 |
| GUCACAGCCAGGCAUUAAAU | 246 | 66 ± 0 |
| UCUCAUCUUCCCACAUAGGC | 248 | 45 ± 1 |

TABLE 28-continued

Activity of double-stranded siRNA compounds corresponding to single stranded antisense RNA compounds

| Sequence (antisense strand) | SEQ ID NO | % inhib |
|---|---|---|
| ACCUUUCCUUGUAUACCCUC | 250 | 60 ± 5 |
| GUAGCUGUGUCUGCGUGGGA | 252 | 45 ± 1 |
| AUACUCAGAAGGUGUCUUCU | 254 | 83 ± 1 |
| CUGUAAUUCUUUGAUUGGGA | 256 | 74 ± 0 |
| GAAUGAAAUGCAUAAAUUUG | 258 | 6 ± 1 |
| UCACUGAUUUGAAUGAAAUG | 260 | 63 ± 1 |
| AUUUACAGUUUUGUACACUG | 262 | 64 ± 0 |
| AAAACCAGAGUGCCCAUCUG | 264 | 88 ± 0 |
| ACUGGAGAUCAGCCGCAGG | 266 | 42 ± 6 |
| AGUAUAGAAAUGCCAAGUUG | 268 | 69 ± 7 |

Double-stranded RNA antisense compounds whose antisense strands have SEQ ID NO: 220, 222, 224, 226, 228, 230, 232, 234, 236, 238, 240, 242, 244, 246, 248, 250, 252, 254, 256, 260, 262, 264, 266 or 268 gave at least 10% inhibition of eIF4E RNA levels. Double-stranded RNA antisense compounds whose antisense strands have SEQ ID NO: 220, 224, 226, 228, 230, 232, 236, 238, 240, 246, 250, 254, 256, 260, 262, 264, or 268 gave at least 50% inhibition of eIF4E RNA levels and are therefore particularly suitable inhibitors of eIF4E expression.

Thus both single and double-stranded antisense RNA compounds are able to cause inhibition of eIF4E RNA levels. Compounds which are active in both single- and double-stranded versions (i.e, the active antisense strand with or without a complementary sense strand) are believed to be particularly useful.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety. U.S. provisional application Ser. No. 60/504,110 filed Sep. 18, 2004 and U.S. provisional application Ser. No. 60/576,534 filed Jun. 3, 2004, are each incorporated herein by reference in its entirety.

What is claimed is:

1. A modified antisense oligonucleotide, comprising the nucleotide sequence shown in SEQ ID NO:40, having at least one chemically modified internucleoside linkage, sugar moiety, or nucleobase, or a pharmaceutically acceptable salt thereof.

2. The modified antisense oligonucleotide or pharmaceutically acceptable salt thereof of claim 1, which consists of 20 to 30 nucleotides.

3. The modified antisense oligonucleotide or pharmaceutically acceptable salt thereof of claim 1, having at least one 2'-O-(2-methoxyethyl) sugar moiety.

4. The modified antisense oligonucleotide or pharmaceutically acceptable salt thereof of claim 1, having at least one phosphorothioate internucleoside linkage.

5. The modified antisense oligonucleotide or pharmaceutically acceptable salt thereof of claim 1, wherein at least one cytosine is a 5-methylcytosine.

6. The modified antisense oligonucleotide or pharmaceutically acceptable salt thereof of claim 1, wherein every internucleoside linkage is a phosphorothioate linkage, nucleotides 1-5 and 16-20 reading from the 5' end to the 3' end of SEQ ID NO:40 each comprise a 2'-O-(2-methoxyethyl) sugar, nucleotides 6-15 are 2'-deoxynucleotides, and every cytosine residue is a 5-methylcytosine.

7. The modified antisense oligonucleotide or pharmaceutically acceptable salt thereof of claim 1, which is in the form of a sodium salt.

8. A modified antisense oligonucleotide, consisting of the nucleotide sequence shown in SEQ ID NO:40, wherein every internucleoside linkage is a phosphorothioate linkage, nucleotides 1-5 and 16-20 reading from the 5' end to the 3' end each comprise a 2'-O-(2-methoxyethyl) sugar, nucleotides 6-15 are 2'-deoxynucleotides, and every cytosine residue is a 5-methylcytosine, which modified antisense oligonucleotide is in the form of a sodium salt.

9. A pharmaceutical or veterinary composition, comprising said sodium salt of said modified antisense oligonucleotide of claim 8, and a pharmaceutically or physiologically acceptable carrier, diluent, or excipient.

10. A method of treating a condition or disease associated with eIF4E expression or overexpression in a mammal in need thereof, comprising administering to said mammal an effective amount of said sodium salt of said modified antisense oligonucleotide of claim 8.

11. The method of claim 10, wherein said condition or disease associated with eIF4E expression or overexpression is a hyperproliferative condition or disease.

12. The method of claim 11, wherein said hyperproliferative condition or disease is a susceptible cancer, tumor, or condition characterized by aberrant angiogenesis.

13. The method of claim 11, wherein said hyperproliferative condition or disease associated with eIF4E expression or overexpression is selected from the group consisting of breast cancer, head and neck cancer, colorectal cancer, prostate cancer, lung cancer, bladder cancer, ovarian cancer, renal cancer, and glioblastoma.

14. The method of claim 10, wherein said mammal is a human.

15. A modified antisense oligonucleotide, consisting of the nucleotide sequence shown in SEQ ID NO:40, having at least one chemically modified internucleoside linkage, sugar moiety, or nucleobase, which modified antisense oligonucleotide is in the form of a sodium salt.

16. A The modified antisense oligonucleotide of claim 15, wherein every internucleoside linkage is a phosphorothioate linkage, nucleotides 1-5 and 16-20 reading from the 5' end to the 3' end each comprise a 2' -O-(2-methoxyethyl) sugar, nucleotides 6-15 are 2'-deoxynucleotides, and at least one cytosine is a 5-methylcytosine, and which modified antisense oligonucleotide is in the form of a sodium salt.

* * * * *